US012473303B2

(12) United States Patent
Ainscow et al.

(10) Patent No.: US 12,473,303 B2
(45) Date of Patent: Nov. 18, 2025

(54) 4-[[(7-AMINOPYRAZOLO[1,5-A]PYRIMIDIN-5-YL)AMINO METHYL]PIPERIDIN-3-OL COMPOUNDS AND THEIR THERAPEUTIC USE

(71) Applicant: CARRICK THERAPEUTICS LIMITED, Dublin (IE)

(72) Inventors: Edward Ainscow, Dublin (IE); Ashwani Bahl, Dublin (IE); Mihiro Sunose, Nottingham (GB); Damien Francis Philippe Crepin, Nottingham (GB); Kamaldeep Kaur Chohan, Nottingham (GB); Brett Stevenson, Nottingham (GB); Jason John Shiers, Nottingham (GB)

(73) Assignee: Carrick Therapeutics Limited, Belfield (IE)

( * ) Notice: Subject to any disclaimer, the term of this patent is extended or adjusted under 35 U.S.C. 154(b) by 751 days.

(21) Appl. No.: 17/785,511

(22) PCT Filed: Dec. 16, 2020

(86) PCT No.: PCT/EP2020/086419
§ 371 (c)(1),
(2) Date: Jun. 15, 2022

(87) PCT Pub. No.: WO2021/122745
PCT Pub. Date: Jun. 24, 2021

(65) Prior Publication Data

US 2023/0144197 A1 May 11, 2023

(30) Foreign Application Priority Data

Dec. 16, 2019 (GB) ..................................... 1918541

(51) Int. Cl.
*C07D 519/00* (2006.01)
*A61K 31/138* (2006.01)
(Continued)

(52) U.S. Cl.
CPC .......... *C07D 519/00* (2013.01); *A61K 31/138* (2013.01); *A61K 31/167* (2013.01);
(Continued)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 8,067,424 B2 | 11/2011 | Jogalekar | |
| 9,932,344 B2 | 4/2018 | Bondke | |

(Continued)

FOREIGN PATENT DOCUMENTS

| | | |
|---|---|---|
| WO | WO 2001/047897 A1 | 7/2001 |
| WO | WO 2004/022561 A1 | 3/2004 |

(Continued)

OTHER PUBLICATIONS

Lui et al. J. Clin. Pathol. 2018;71:957-962 (Year: 2018).*
Alarcon et al., 2009, Cell, vol. 139, pp. 757 769, "Nuclear CDKs Drive Smad Transcriptional Activation and Turnover in BMP and TGF-b Pathways".
Ali et al., 1993, The EMBO Journal, vol. 12, No. 3, pp. 1153 1160, "Modulation of transcriptional activation by ligand dependent phosphorylation of the human oestrogen receptor A/B region".
Ali et al., 2002, Nat. Rev. Cancer, vol. 2, pp. 101 112, "Endocrine-Responsive Breast Cancer and Strategies for Combating Resistance".
Ali et al., 2011, Annu. Rev. Med., vol. 62 pp. 217-232, "Antiestrogens and their Therapeutic Applications in Breast Cancer and Other Diseases".

(Continued)

*Primary Examiner* — James D. Anderson
(74) *Attorney, Agent, or Firm* — Fish & Richardson P.C.

(57) ABSTRACT

The present invention pertains generally to the field of therapeutic compounds. More specifically the present invention pertains to certain H-APPAMP compounds (referred to herein as "H-APPAMP compounds") that, inter alia, inhibit cyclin-dependent protein kinases (CDKs), especially CDK12 and/or CDK13, and are selective, for example, for CDK12 and/or CDK13 as compared to CDK7. In addition to selectively inhibiting CDK12 and/or CDK13, the compounds also act as selective Cyclin K degraders thereby removing the key signaling mechanism required for CDK12 and/or CDK13 activation; this confers additional cellular potency and selectivity. The present invention also pertains to pharmaceutical compositions comprising such compounds, and the use of such compounds and compositions, both in vitro and in vivo, to inhibit CDK, especially CDK12 and/or CDK13; and to treat disorders including: disorders that are associated with CDK, especially CDK12 and/or CDK13; disorders that result from an inappropriate activity of a CDK, especially CDK12 and/or CDK13; disorders that are associated with CDK mutation, especially CDK12 and/or CDK13 mutation; disorders that are associated with CDK overexpression, especially CDK12 and/or CDK13 overexpression; disorders that are associated with upstream pathway activation of CDK, especially CDK12 and/or CDK13; disorders that are ameliorated by the inhibition of CDK, especially CDK12 and/or CDK13; proliferative disorders; cancer; viral infections (including HIV); neurodegenerative disorders (including Alzheimer's disease and Parkinson's disease); ischaemia; renal diseases; cardiovascular disorders (including atherosclerosis); autoimmune disorders (including rheumatoid arthritis); and disorders caused by dysfunction of translation in cells (including muscular dystrophy). Optionally, the treatment further comprises treatment (e.g., simultaneous or sequential treatment) with a further active agent which is, e.g., an aromatase inhibitor, an anti estrogen, an anti-androgen, a Her2 blocker, a cytotoxic chemotherapeutic agent, an agent stimulating the immune system, a checkpoint inhibitor, a DNA repair inhibitor, etc.

20 Claims, No Drawings

(51) Int. Cl.

| | |
|---|---|
| ***A61K 31/167*** | (2006.01) |
| ***A61K 31/282*** | (2006.01) |
| ***A61K 31/337*** | (2006.01) |
| ***A61K 31/4166*** | (2006.01) |
| ***A61K 31/4184*** | (2006.01) |
| ***A61K 31/4196*** | (2006.01) |
| ***A61K 31/513*** | (2006.01) |
| ***A61K 31/517*** | (2006.01) |
| ***A61K 31/519*** | (2006.01) |
| ***A61K 31/568*** | (2006.01) |
| ***A61K 31/5685*** | (2006.01) |
| ***A61K 31/664*** | (2006.01) |
| ***A61K 31/704*** | (2006.01) |
| ***A61K 31/7068*** | (2006.01) |
| ***A61K 39/395*** | (2006.01) |
| ***C07D 487/04*** | (2006.01) |
| ***C07K 16/32*** | (2006.01) |

(52) U.S. Cl.

CPC .......... *A61K 31/282* (2013.01); *A61K 31/337* (2013.01); *A61K 31/4166* (2013.01); *A61K 31/4184* (2013.01); *A61K 31/4196* (2013.01); *A61K 31/513* (2013.01); *A61K 31/517* (2013.01); *A61K 31/519* (2013.01); *A61K 31/568* (2013.01); *A61K 31/5685* (2013.01); *A61K 31/664* (2013.01); *A61K 31/704* (2013.01); *A61K 31/7068* (2013.01); *A61K 39/39558* (2013.01); *C07D 487/04* (2013.01); *C07K 16/32* (2013.01)

(56) References Cited

U.S. PATENT DOCUMENTS

| | | | |
|---|---|---|---|
| 10,414,772 | B2 | 9/2019 | Bondke |
| 10,927,119 | B2 | 2/2021 | Bondke |
| 2010/0261683 | A1 | 10/2010 | Jogalekar |
| 2016/0362410 | A1 | 12/2016 | Bondke |
| 2018/0273540 | A1 | 9/2018 | Bondke |
| 2020/0055862 | A1 | 2/2020 | Bondke |

FOREIGN PATENT DOCUMENTS

| | | | |
|---|---|---|---|
| WO | WO 2004/069162 | A2 | 8/2004 |
| WO | WO 2004/076458 | A1 | 9/2004 |
| WO | WO 2004/087707 | A1 | 10/2004 |
| WO | WO 2005/000838 | A1 | 1/2005 |
| WO | WO 2008/151304 | A1 | 12/2008 |
| WO | WO 2010/118207 | A1 | 10/2010 |
| WO | WO 2011/068667 | A1 | 6/2011 |
| WO | WO 2012/059932 | A1 | 5/2012 |
| WO | WO 2013/128028 | A1 | 9/2013 |
| WO | WO 2013/128029 | A1 | 9/2013 |
| WO | WO 2015/124941 | A1 | 8/2015 |
| WO | WO 2019/035866 | A1 | 2/2019 |
| WO | WO 2019/057825 | A1 | 3/2019 |
| WO | WO 2019/144149 | A2 | 7/2019 |
| WO | WO 2019/197546 | A1 | 10/2019 |
| WO | WO 2019/197549 | A1 | 10/2019 |
| WO | WO 2019/217421 | A1 | 11/2019 |

OTHER PUBLICATIONS

Bacher et al., 2004, "The NF-kB Pathway as a Potential Target for Autoimmune Disease Therapy", Curr. Pharm. Des., vol. 10, No. 23, pp. 2827-2837.

Bartkowiak et al., 2010, Gene Dev., vol. 24, pp. 2303 2316, "CDK12 is a transcription elongation associated CTD kinase, the metazoan ortholog of yeast Ctk1".

Bastien et al., 2000, J. Biol. Chem., vol. 275, No. 29, pp. 21896 21904, "TFIIH Interacts with the Retinoic Acid Receptor γ and Phosphorylates Its AF-1-activating Domain through cdk7*".

Blazek et al., 2011, Gene Dev., vol. 25, pp. 2158 2172, "The Cyclin K/Cdk12 complex maintains genomic stability via regulation of expression of DNA damage response genes".

Borg et al., 2000, JNCI, vol. 92, No. 15, pp. 1260 1266, "High Frequency of Multiple Melanomas and Breast and Pancreas Carcinomas in CDKN2A Mutation-Positive Melanoma Families".

Chen et al., 2000, Molecular Cell, vol. 6, pp. 127 137, "Activation of Estrogen Receptor α by S118 Phosphorylation Involves a Ligand-Dependent Interaction with TFIIH and Participation of CDK7".

Chen et al., 2002, Oncogene, vol. 21, pp. 4921 4931, "Phosphorylation of human estrogen receptor α at serine 118 by two distinct signal transduction pathways revealed by phosphorylation-specific antisera".

Chen et al., 2006, "Identification and Characterization of the CDK12/Cyclin L1 Complex Involved in Alternative Splicing Regulation," Mol Cell Biol., vol. 26, No. 7, pp. 2736-2745.

Cheng et al., 2012, Mol. Cell. Biol., vol. 32, No. 22, p. 4691 4704. "Interaction of Cyclin-Dependent Kinase 12/CrkRS with Cyclin K1 is Required for the Phosphorylation of the C-Terminal Domain of RNA Polymerase II".

Choi et al., 2019, "CDK12 drives breast tumor initiation and trastuzumab resistance via WNT and IRS1-ErbB-PI3K signalling", EMBO Rep, vol. 20, No. 10, e48058.

Chymkowitch et al., 2011, EMBO J., vol. 30, No. 3, pp. 468 479, "The phosphorylation of the androgen receptor by TFIIH directs the ubiquitin/proteasome process".

Claudio et al., 2006, J. Cell. Physiol., vol. 208, pp. 602 612, "Cdk9 Phosphorylates p53 on Serine 392 Independently of CKII".

Corlu et al., 2012, Int. J. Hepatol., Article ID 689324, 17 pages, "Regulation of the G1/S Transition in Hepatocytes: Involvement of the Cyclin-Dependent Kinase Cdk1 in the DNA Replication".

Cuzick et al., 2010, Lancet Oncol., vol. 11, pp. 1135 1141, "Effect of anastrozole and tamoxifen as adjuvant treatment for early-stage breast cancer: 10-year analysis of the ATAC Trial".

Drogat et al., 2012, Cell Rep., vol. 2, pp. 1068 1076, "Cdk11-CyclinL Controls the Assembly of the RNA Polymerase II Mediator Complex".

Dhariwala et al., 2008, Cell. Mol. Neurobiol., vol. 28, pp. 351 369, "An Unusual Member of the Cdk Family: Cdk5".

Fisher et al., 1994, Cell, vol. 78, pp. 713 724, "A Novel Cyclin Associates with MO15/CDK7 to Form the CDK-Activating Kinase".

GB Search Report for GB 1403093.6, dated Sep. 12, 2014.

GB Search Report for GB 1715194.5, dated Jun. 5, 2018.

GB Search Report for GB1918541.2, dated Jun. 8, 2020.

Ganuza et al., 2012, EMBO J., vol. 31, pp. 2498 2510, "Genetic inactivation of Cdk7 leads to cell cycle arrest and induces premature aging due to adult stem cell exhaustion".

Gijsen et al., 2008, Tetrahedron, vol. 64, pp. 2456 2464, "Development of two diastereoselective routes towards trans-4-aminomethyl-piperidin-3-ol building blocks".

Gordon et al., 2010, Mol. Endocrinol., vol. 24, No. 12, pp. 2267 2280, "CDK9 Regulates AR Promoter Selectivity and Cell Growth through Serine 81 Phosphorylation".

Greifenberg et al., 2016, "Structural and Functional Analysis of the CDK13/Cyclin K Complex," Cell Rep., vol. 14, No. 2, pp. 320-331.

Hamada et al., 1996, Biochim. Biophys. Acta., vol. 1310, pp. 149-156, "Protein kinase C inhibits the CAK-CDK2 cyclin-dependent kinase cascade and G1/S cell cycle progression in human diploid fibroblasts".

Hansson, 2008, Surg. Clin. North Am., vol. 88, pp. 897-916, "Familial Melanoma".

Hansson, 2010, Adv. Exp. Med. Biol., vol. 685, Chapter 13, pp. 134 145, "Familial Cutaneous Melanoma".

Hazel et al., 2017, "Inhibitor Selectivity for Cyclin-Dependent Kinase 7: A Structural, Thermodynamic, and Modelling Study", Chem Med Chem, vol. 12, pp. 372-380.

Hong et al., 1997, Tetrahedron Lett., vol. 38, No. 32, pp. 5607 5610, "Palladium Catalyzed Amination of 2-Chloro-1,3-Azole Derivatives: Mild Entry to Potent H1-Antihistaminic Norastemizole".

Hong et al., 2018, J. Cell. Mol. Med., vol. 22, No. 2, pp. 1292-1301, "CDK7 inhibition suppresses rheumatoid arthritis inflammation via blockage of NF-κB activation and IL-1β/IL-6 secretion".

(56) References Cited

OTHER PUBLICATIONS

Iniguez et al., 2018, Cancer Cell, vol. 33, No. 2, pp. 202-216, "EWS/FLI Confers Tumor Cell Synthetic Lethality to CDK12 Inhibition in Ewing Sarcoma".
International Search Report and Written Opinion of the International Searching Authority for PCT/GB2015/050494 dated Apr. 14, 2015, 9 pages.
International Preliminary Report on Patentability for PCT/GB2015/050494 dated Aug. 23, 2016, 6 pages.
International Search Report and Written Opinion of the International Searching Authority for PCT/EP2018/075482 dated Nov. 20, 2018, 12 pages.
International Search Report (ISR) for International patent application No. PCT/EP2020/086419 dated Mar. 11, 2021, 3 pages.
International Preliminary Report on Patentability (IPRP) for International patent application No. PCT/EP2020/086419 dated May 17, 2022, 6 pages.
Lorns et al., 2008, Cancer Cell, vol. 13, pp. 91 104, "Identification of CDK10 as an Important Determinant of Resistance to Endocrine Therapy for Breast Cancer".
Johannes et al., 2018, Chem Med Chem, vol. 13, pp. 231-235, "Structure-Based Design of Selective Noncovalent CDK12 Inhibitors".
Johnson et al., 2016, Cell Rep, vol. 17, No. 9, pp. 2367-2381, "CDK12 Inhibition Reverses De Novo and Acquired PARP Inhibitor Resistance in BRCA Wild-Type and Mutated Models of Triple-Negative Breast Cancer".
Johnston et al., 2003, Nat. Rev. Cancer, vol. 3, pp. 821 831, "Aromatase Inhibitors For Breast Cancer: Lessons From The Laboratory".
Jones et al., 2007, Cell, vol. 128, pp. 683 692, "The Epigenomics of Cancer".
Knockaert et al., 2002, Trends Pharmacol. Sci., vol. 23, No. 9, pp. 417 425, "Pharmacological inhibitors of cyclin-dependent kinases".
Ko et al., 1997, Mol. Cell. Biol., vol. 17, No. 12, pp. 7220 7229 "p53 is Phosphorylated by CDK7-Cyclin H in a $p36^{MAT1}$-Dependent Manner".
Kolb et al., 1994, Chem. Rev., vol. 94, pp. 2483 2547, "Catalytic Asymmetric Dihydroxylation".
Kosugi et al., 2012, J. Med. Chem., 55(15):6700-6715, "Mitogen-Activated Protein Kinase- Activated Protein Kinase 2 (MAPKAP-K2) as an Antiinflammatory Target: Discovery and In Vivo Activity of Selective Pyrazolo[1,5-α]pyrimidine Inhibitors Using a Focused Library and Structure-Based Optimization Approach".
Larochelle et al., 2007, Mol. Cell, vol. 25, pp. 839 850, "Requirements for Cdk7 in the Assembly of Cdk1/Cyclin B and Activation of Cdk2 Revealed by Chemical Genetics in Human Cells".
Larochelle et al., 2012, Nat. Struct. Mol. Biol., vol. 19, No. 11, pp. 1108 1115, "Cyclin-dependent kinase control of the initiation-to-elongation switch of RNA polymerase II".
Lei et al., 2018, Nature Communications, vol. 9, Article 1876, "Cyclin K regulates prereplicative complex assembly to promote mammalian cell proliferation".
Li et al., 2016, Sci Rep, vol. 6, 21455, "CDK12 is a gene-selective RNA polymerase II kinase that regulates a subset of the transcriptome, including Nrf2 target genes".
Lord et al., 2016, Nat Rev Cancer, vol. 16, No. 2, pp. 110-120, "BRCAness revisited".
Lu et al., 1992, Nature, pp. 358, pp. 641 645, "Human general transcription factor 11H phosphorylates the C-terminal domain of RNA polymerase II".
Lu et al., 1997, Mol. Cell. Biol., vol. 17, No. 10, pp. 5923 5934, "The CDK7-cycH-p36 Complex of Transcription Factor IIH Phosphorylates p53, Enhancing Its Sequence-Specific DNA Binding Activity In Vitro".
Lui et al., 2018, J Clin Pathol, vol. 71, No. 11, pp. 957-962, "CDK12: an emerging therapeutic target for cancer".
Lv et al., 2020, eLife 2020; 9:e59994, "Discovery of a molecular glue promoting CDK12-DDB1 interaction to trigger cyclin K degradation".
Malumbres et al., 2001, Nat. Rev. Cancer, vol. 1, pp. 222 231, "To Cycle or Not to Cycle: A Critical Decision in Cancer".
Malumbres et al., 2009, Nat. Cell Biology, vol. 11, pp. 1275 1276, "Cyclin-dependent kinases: a family portrait".
Malumbres et al., 2009, Nat. Rev. Cancer, vol. 9, pp. 153 166, "Cell cycle, CDKs and cancer: a changing paradigm".
Marshall et al., 2006, Nephron. Exp. Nephrol., vol. 102, No. 2, pp. e39 e48, "Cell Cycle and Glomerular Disease: A Minireview".
Monaco et al., 2005, Front. Biosci., vol. 10, No. 1, pp. 143 159, "Role of Protein Kinases In Neurodegenerative Disease: Cyclin-Dependent Kinases in Alzheimer's Disease".
Morgan, 1995, Nature, vol. 374, pp. 131 134, "Principles of CDK regulation".
Nagel et al., 1984, Angew. Chem. Int. Ed. Eng. vol. 23, No. 6, pp. 435-436 (corresponding to Angew. Chem., vol. 96, No. 6, pp. 425 426), "Asymmetric Hydrogenation of a-(Acetylamino)cinnamic Acid with a Novel Rhodium Complex; the Design of an Optimal Ligand**".
Ortega et al., 2002, Biochim. Biophys. Acta., vol. 1602, pp. 73 87, "Cyclin D-dependent kinases, INK4 inhibitors and cancer".
Osborne et al., 2011, Annu. Rev. Med., vol. 62, pp. 233 247, "Mechanisms of Endocrine Resistance in Breast Cancer".
Osborne, 1998, N. Engl. J. Med., vol. 339, No. 22, pp. 1609 1618, "Tamoxifen in the Treatment of Breast Cancer".
Patel et al., 2018, Mol Cancer Ther, vol. 17, No. 6, pp. 1156-1166, "ICEC0942, an Orally Bioavailable Selective Inhibitor of CDK7 for Cancer Treatment".
Peterson et al., 1991, J. Med. Chem., vol. 34, pp. 2787 2797, "Synthesis and Biological Evaluation of 4-Purinylpyrrolidine Nucleosides".
Pines, 1995, Biochem. J., vol. 308, pp. 697 711, "Cyclins and cyclin-dependent kinases: a biochemical view".
Radhakrishnan et al., 2006, Cell Cycle, vol. 5, No. 5, pp. 519 521, "CDK9 Phosphorylates p53 on Serine Residues 33, 315 and 392".
Remuzon, 1996, Tetrahedron, vol. 52, No. 44, 13803-13835, "Trans-4-Hydroxy.L-Proline, a Useful and Versatile Chiral Starting Block".
Rochette-Egly et al., 1997, Cell, vol. 90, pp. 97 107. "Stimulation of RARα Activation Function AF-1 through Binding to the General Transcription Factor TFIIH and Phosphorylation by CDK7".
Serizawa et al., 1995, Nature, vol. 374, pp. 280-282, "Association of Cdk-activating kinase subunits with transcription factor TFIIH".
Sherr et al., 1995, Genes Dev., vol. 9 pp. 1149-1163, "Inhibitors of mammalian G1 cyclin-dependent kinases".
Shiekattar et al., 1995, Nature, vol. 374, pp. 283-287, "Cdk-activating kinase complex is a component of human transcription factor TFIIH".
Skehan et al., 1990, J. Natl. Cancer Inst., vol. 82, No. 13, pp. 1107-1112, "New Colorimetric Cytotoxicity Assay for Anticancer-Drug Screening".
Słabicki et al., 2020, Nature, vol. 585, pp. 293-297, "The CDK inhibitor CR8 acts as a molecular glue degrader that depletes cyclin K".
Wang et al., 2008, Trends Pharmacol. Sci., vol. 29, No. 6, pp. 302-313, "Cyclin-dependent kinase 9: a key transcriptional regulator and potential drug target in oncology, virology and cardiology".
Written Opinion of the International Search Authority (WOISA) for International patent application No. PCT/EP2020/086419 dated Mar. 11, 2021, 5 pages.
Xu et al., 2011, J. Genet. Genomics, vol. 38, pp. 439-452, "Dysregulation of CDK8 and Cyclin C in tumorigenesis".
Xu et al., 2011, Tetrahedron Lett., vol. 52, pp. 3266-3270, "An improved synthesis of 2-oxa-7-azaspiro[3,5]nonane and analogs as novel reagents in medicinal chemistry".
Yankulov et al., 1995, J. Biol. Chem., vol. 270, No. 41 pp. 23922-23925, "The Transcriptional Elongation Inhibitor 5,6-Dichloro-1-β-D-ribofuranosylbenzimidazole Inhibits Transcription Factor IIH-associated Protein Kinase*".
Yu et al., 2012, Oncol. Rep., vol. 27, pp. 1266-1276, "CDK10 functions as a tumor suppressor gene and regulates survivability of biliary tract cancer cells".
Zhang et al., 2016, "Covalent targeting of remote cysteine residues to develop CDK12 and CDK13 inhibitors", Nat. Chem. Biol., vol. 12, No. 10, pp. 876-884.

(56) References Cited

OTHER PUBLICATIONS

Zuo et al., 1996, Nat Genet., vol. 12 pp. 97-99, "Germline mutations in the p16INK4a binding domain of CDK4 in familial melanoma".

* cited by examiner

4-[[(7-AMINOPYRAZOLO[1,5-A]PYRIMIDIN-5-YL)AMINO METHYL]PIPERIDIN-3-OL COMPOUNDS AND THEIR THERAPEUTIC USE

RELATED APPLICATION

This application claims priority to and is a 35 U.S.C. § 371 national phase application of PCT/EP2020/086419 (WO2021/122745), filed on Dec. 16, 2020. PCT/EP2020/086419 is related to, and claims priority of, Great Britain patent application number GB 1918541.2, filed Dec. 16, 2019, the contents of which are incorporated herein by reference in their entirety.

TECHNICAL FIELD

The present invention pertains generally to the field of therapeutic compounds. More specifically the present invention pertains to certain H-APPAMP compounds (referred to herein as "H-APPAMP compounds") that, inter alia, inhibit cyclin-dependent protein kinases (CDKs), especially CDK12 and/or CDK13, and are selective, for example, for CDK12 and/or CDK13 as compared to CDK7. In addition to selectively inhibiting CDK12 and/or CDK13, the compounds also act as selective Cyclin K degraders thereby removing the key signaling mechanism required for CDK12 and/or CDK13 activation; this confers additional cellular potency and selectivity. The present invention also pertains to pharmaceutical compositions comprising such compounds, and the use of such compounds and compositions, both in vitro and in vivo, to inhibit CDK, especially CDK12 and/or CDK13; and to treat disorders including: disorders that are associated with CDK, especially CDK12 and/or CDK13; disorders that result from an inappropriate activity of a CDK, especially CDK12 and/or CDK13; disorders that are associated with CDK mutation, especially CDK12 and/or CDK13mutation; disorders that are associated with CDK overexpression, especially CDK12 and/or CDK13 overexpression; disorders that are associated with upstream pathway activation of CDK, especially CDK12 and/or CDK13; disorders that are ameliorated by the inhibition of CDK, especially CDK12 and/or CDK13; proliferative disorders; cancer; viral infections (including HIV); neurodegenerative disorders (including Alzheimer's disease and Parkinson's disease); ischaemia; renal diseases; cardiovascular disorders (including atherosclerosis); autoimmune disorders (including rheumatoid arthritis); and disorders caused by dysfunction of translation in cells (including muscular dystrophy). Optionally, the treatment further comprises treatment (e.g., simultaneous or sequential treatment) with a further active agent which is, e.g., an aromatase inhibitor, an anti estrogen, an anti-androgen, a Her2 blocker, a cytotoxic chemotherapeutic agent, an agent stimulating the immune system, a checkpoint inhibitor, a DNA repair inhibitor, etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cyclin-Dependent Protein Kinase (CDK)

Cyclin-dependent protein kinases (CDK) are the catalytic subunits of a family of 21 serine/threonine protein kinases (see, e.g., Malumbres et al., 2009), some of which control progression of the cell through the stages of growth, DNA replication and mitosis (see, e.g., Pines, 1995; Morgan, 1995). Activation of specific CDKs is required for appropriate progression through the different stages of the cell cycle and entry into the next stage of the cell cycle.

Cyclin-dependent kinase 12 (CDK12) and its orthologue 13 (CDK13) belong to the cyclin-dependent kinase (CDK) family of serine/threonine protein kinases that regulate transcriptional and posttranscriptional processes, thereby modulating multiple cellular functions. Studies have characterised CDK12 and CDK13 as a transcriptional CDK that complexes with cyclin K to mediate gene transcription by phosphorylating RNA polymerase II (see, e.g., Li et al., 2016; Greifenberg et al., 2016). The CDK12/cyclin K and CDK13/cyclin K complexes phosphorylate RNA Pol II at Ser2 (Ser2p-RNA Pol II), which is thought to be a critical step in transition from transcriptional initiation to elongation. Additionally, CDK12 can form a complex with cyclins L1 and L2 to regulate alternative splicing of mRNA transcripts (see, e.g., Chen et al., 2016). CDK12 has been demonstrated to specifically upregulate the expression of genes involved in response to DNA damage, stress and heat shock (see, e.g., Blazek et al., 2011; Lord et al., 2016). CDK13 regulates a different set of genes to CDK12, with CDK3 activity mostly involved in growth signaling pathways, including tyrosine kinase signalling (Greifenberg et al., 2016). Studies have also implicated CDK12 in regulating mRNA splicing, 3'-end processing, pre-replication complex assembly, and genomic stability. Genomic alterations in CDK12 have been detected in oesophageal, stomach, breast, endometrial, uterine, ovarian, bladder, colorectal and pancreatic cancers (see, e.g., Gyl et al., 2018). A number of studies point to CDK12 inhibition as an effective strategy to inhibit tumour growth, and synthetic lethal interactions have been described with a number of pathways relevant for cancer survival and progression (see, e.g., Johnson et al., 2016; Choi et al., 2019).

Cyclin K degradation is a property of some, but not all inhibitors of CDK12 (see, e.g., Slabicki et al., 2020). Upon binding of an inhibitor with a degrader activity, CDK12 acts as a surrogate substrate receptor for the CUL4-DDB1 ubiquitin ligase complex, presenting Cyclin K for ubiquitination by CRL4 and resulting in proteosomal degradation. Interaction between CDK12 and DDB1 is driven, in part, due to interactions of the inhibitor with DDB1. Therefore, only CDK12 inhibitors that simultaneously occupy the kinase active site and fill the hydrophobic pocket of DDB1 can promote Cyclin K degradation. For example, the pan-CDK inhibitor CR8 was found to cause Cyclin K degradation by this mechanism, whereas the CDK12 selective covalent inhibitor THZ-531 did not cause cyclin K degradation.

Cyclin K degradation can complement the direct inhibition of CDK12 and/or 13 in cells. This is advantageous for a number of reasons. Firstly, degradation can lead to enhanced potency over kinase inhibition alone, as shown by the increased potency of molecules in cell killing assays. Enhanced cellular potency can lead to reduced off-target interactions and effects between the inhibitor and other kinases than CDK12 and/or CDK13. Secondly, Cyclin K is the obligate partner for both CDK12 and CDK13 and is needed for their activity. Cyclin K degraders will therefore cause impaired activity of both kinases, even if the compound shows differential selectivity between CDK12 and CDK13. Finally, Cyclin K has been shown to have a half-life in cells in excess of 12 hours (see, e.g., Lei et al., 2018). Hence degraders may have effects in cells and tumours that may extend beyond the duration of exposure to the compound.

Known Compounds

Bondke et al., 2015, describes certain pyrazolo[1,5-a] pyrimidine-5,7-diamine compounds as CDK inhibitors, including, for example, the following compound (referred to therein as PPDA-001):

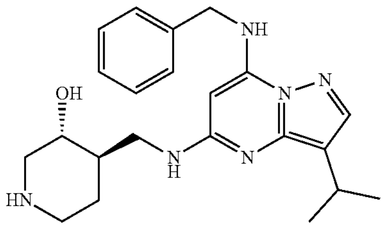

PPDA-001

Hazel et al., 2017, describes studies of the selectivity of inhibitors of CDK7, including ICEC0942 (shown below). Patel et al., 2018, describes studies of the CDK7 inhibitor ICEC0942 in the treatment of cancer.

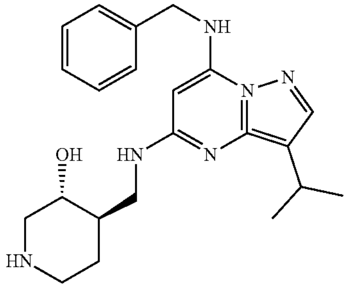

Johannes et al., 2018, describes studies used it identify a class of selective CDK12 inhibitors, including the lead compound, denoted "Compound 7" therein, shown below.

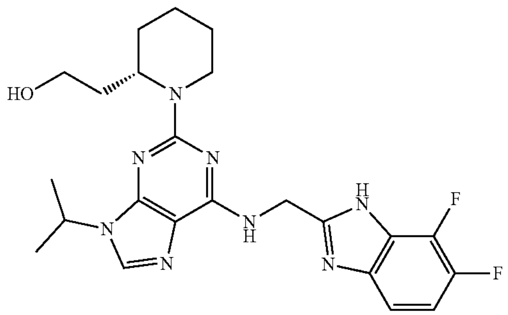 [SMILES: CC(C)n1cnc2c(NCc3nc4ccc(F)c(F)c4[nH]3)nc(N3CCCC[C@H]3CCO)nc21]

Bahl et al., 2019, describes four specific pyrazolo[1,5-a] pyrimidine-5,7-diamine compounds as CDK inhibitors, including, for example, the following compound (referred to therein as APPAMP-001):

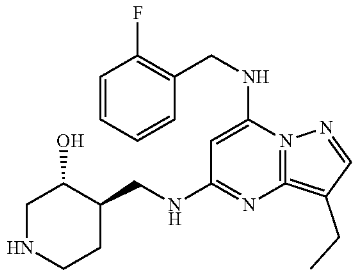

APPAMP-001

Kugel, 2019, describes the use of CDK7, generally, in the treatment of certain sub-types of pancreatic cancer. A range of known CDK7 inhibitors are shown on pages 26-30 therein.

Kwiatkowski et al., 2019, use of CDK7, generally, in the treatment of tuberous sclerosis complex. A range of known CDK7 inhibitors are shown on pages 25-55 therein.

Roush et al., 2019, describes certain small molecule inhibitors of CDK12/CDK13 which allegedly are useful in the treatment of cancers, such as breast cancer, brain cancer, and ovarian cancer. The compounds have the following formula, wherein $R^1$ is aryl or heteroaryl. Examples therein include Compounds 6 and 7, shown below.

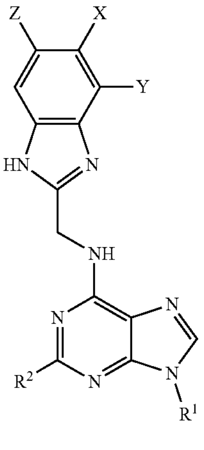

-continued

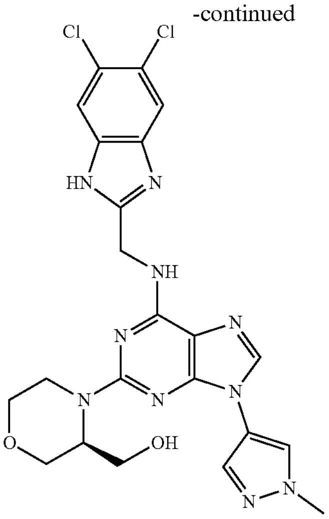

Compound 6

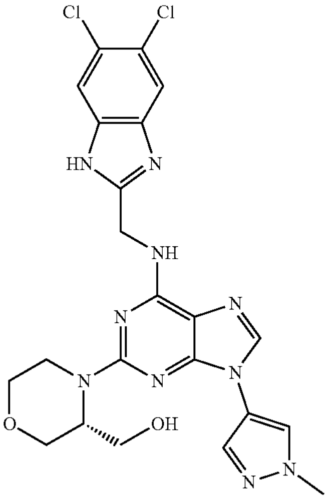

Compound 7

Potency/Selectivity

The H-APPAMP compounds described herein are potent CDK12 and/or CDK13 inhibitors that are also highly selective for CDK12 and/or CDK13, for example, as compared to CDK7.

In addition to selectively inhibiting CDK12 and/or CDK13, the H-APPAMP compounds described herein may also act as selective Cyclin K degraders thereby removing the key signaling mechanism required for CDK12 and/or CDK13 activation; this confers additional cellular potency and selectivity.

SUMMARY OF THE INVENTION

One aspect of the invention pertains to certain 4-[[(7-aminopyrazolo[1,5-a]pyrimidin-5-yl)amino]methyl]piperidin-3-ol compounds (referred to herein as "H-APPAMP compounds"), as described herein.

Another aspect of the invention pertains to a composition (e.g., a pharmaceutical composition) comprising an H-APPAMP compound, as described herein, and a pharmaceutically acceptable carrier or diluent.

Another aspect of the invention pertains to a method of preparing a composition (e.g., a pharmaceutical composition) comprising the step of mixing an H-APPAMP compound, as described herein, and a pharmaceutically acceptable carrier or diluent.

Another aspect of the present invention pertains to a method of inhibiting CDK12 and/or CDK13 (function (e.g., in a cell), in vitro or in vivo, comprising contacting the cell with an effective amount of an H-APPAMP compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an H-APPAMP compound, as described herein.

Another aspect of the present invention pertains to an H-APPAMP compound as described herein for use in a method of treatment of the human or animal body by therapy, for example, for use a method of treatment of a disorder (e.g., a disease) as described herein.

Another aspect of the present invention pertains to use of an H-APPAMP compound, as described herein, in the manufacture of a medicament, for example, for use in a method of treatment, for example, for use a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of an H-APPAMP compound, as described herein, preferably in the form of a pharmaceutical composition.

In one embodiment, the treatment further comprises treatment (e.g., simultaneous or sequential treatment) with a further active agent which is, e.g., an aromatase inhibitor, an anti-estrogen, an anti-androgen, a Her2 blocker, a cytotoxic chemotherapeutic agent, an agent stimulating the immune system, a checkpoint inhibitor, a DNA repair inhibitor, etc., as described herein.

Another aspect of the present invention pertains to a kit comprising (a) an H-APPAMP compound, as described herein, preferably provided as a pharmaceutical composition and in a suitable container and/or with suitable packaging; and (b) instructions for use, for example, written instructions on how to administer the compound.

Another aspect of the present invention pertains to an H-APPAMP compound obtainable by a method of synthesis as described herein, or a method comprising a method of synthesis as described herein.

Another aspect of the present invention pertains to an H-APPAMP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which are related to pyrazolo[1,5-a]pyrimidine-5,7-diamine ("PPDA"):

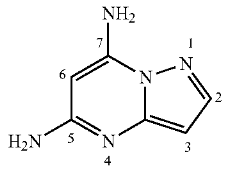 [SMILES: Nc1cc(N)n2nccc2n1]

More specifically, the compounds are related to (3R,4R)-4-[[(7-aminopyrazolo[1,5-a]pyrimidin-5-yl)amino]methyl] piperidin-3-ol ("APPAMP"):

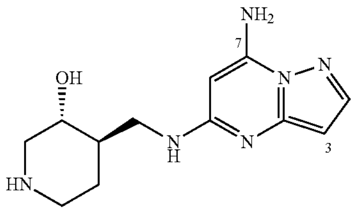

Furthermore, all of the compounds of the present invention have:

(a) a substituted amino group at the 7-position (denoted herein as —NH-$L^7$-$R^7$); and (b) an alkyl or cycloalkyl group at the 3-position (denoted herein as —$R^3$).

More specifically, the group —$R^7$ is a fused bicyclic $C_{8-10}$heteroaryl group having exactly 1, 2, or 3 ring heteroatoms, wherein each ring heteroatom is N, S, or O.

For the avoidance of doubt, the fused bicyclic $C_{8-10}$heteroaryl group has a 6/6, 6/5, 5/6, or 5/5 fused ring structure; that is, a 6-membered aromatic ring fused to a 6-membered aromatic ring; a 6-membered aromatic ring fused to a 5-membered aromatic ring; a 5-membered aromatic ring fused to a 6-membered aromatic ring; or a 5-membered aromatic ring fused to a 5-membered aromatic ring; respectively.

Thus, one aspect of the present invention is a compound of the following formula, or a pharmaceutically acceptable salt, hydrate, or solvate thereof, wherein —$R^7$, -$L^7$-, and —$R^3$ are as defined herein (for convenience, collectively referred to herein as "H-APPAMP" compounds"):

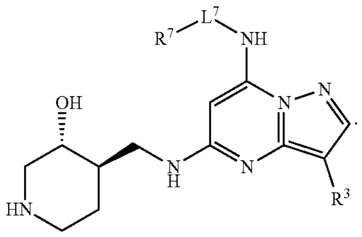

Some embodiments include the following:

(1) A compound of the following formula:

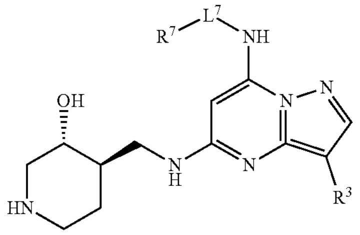

or a pharmaceutically acceptable salt or solvate thereof; wherein:

—$R^7$ is a fused bicyclic $C_{8-10}$heteroaryl group having exactly 1, 2, or 3 ring heteroatoms, wherein each ring heteroatom is N, S, or O;

and wherein —$R^7$ is:

optionally substituted on carbon with one or more groups —$R^{SC}$; and optionally substituted on secondary nitrogen, if present, with a group —$R^{SN}$;

wherein:

each —$R^{SC}$ is independently:

—$R^{TT}$,

—F, —Cl, —Br, —I,

—OH, —$OR^{TT}$,

-$L^T$-OH, -$L^T$-$OR^{TT}$,

—$CF_3$, —$CHF_2$, —$OCF_3$, —$OCHF_2$,

—$NH_2$, —$NHR^{TT}$, —$NR^{TT}_2$, —$R^{TM}$,

-$L^T$-$NH_2$, -$L^T$-$NHR^{TT}$, -$L^T$-$NR^{TT}_2$, -$L^T$-$R^{TM}$,

—C(═O)OH, —C(═O)$OR^{TT}$,

—OC(═O)$R^{TT}$,

—C(═O)$NH_2$, —C(═O)$NHR^{TT}$, —C(═O)$NR^{TT}_2$, —C(═O)$R^{TM}$,

—NHC(═O)$R^{TT}$, —$NR^{TN}$C(═O)$R^{TT}$,

—NHC(═O)$NH_2$, —NHC(═O)$NHR^{TT}$, —NHC(═O)$NR^{TT}_2$, —NHC(═O)$R^{TM}$,

—$NR^{TN}$C(═O)$NH_2$, —$NR^{TN}$C(═O)$NHR^{TT}$, —$NR^{TN}$C(═O)$NR^{TT}_2$, —$NR^{TN}$C(═O)$R^{TM}$,

—NHC(═O)$OR^{TT}$, —$NR^{TN}$C(═O)$OR^{TT}$,

—OC(═O)$NH_2$, —OC(═O)$NHR^{TT}$, —OC(═O)$NR^{TT}_2$, —OC(═O)$R^{TM}$,

—C(═O)$R^{TT}$,

—$SR^{TT}$, —S(═O)$R^{TT}$, —S(═O)$_2R^{TT}$,

—S(═O)$NH_2$, —S(═O)$NHR^{TT}$, —S(═O)$NR^{TT}_2$, —S(═O)$R^{TM}$,

—S(═O)$_2NH_2$, —S(═O)$_2NHR^{TT}$, —S(═O)$_2NR^{TT}_2$, —S(═O)$_2R^{TM}$,

—NHS(═O)$_2R^{TT}$, —$NR^{TN}$S(═O)$_2R^{TT}$,

—CN, or —$NO_2$;

each —$R^{SN}$ is independently:

—$R^{TT}$,

-$L^T$-OH, -$L^T$-$OR^{TT}$,

-$L^T$-$NH_2$, -$L^T$-$NHR^{TT}$, -$L^T$-$NR^{TT}_2$, -$L^T$-$R^{TM}$,

—C(═O)$R^{TT}$,

—C(═O)$OR^{TT}$,

—C(═O)$NH_2$, —C(═O)$NHR^{TT}$, —C(═O)$NR^{TT}_2$, —C(═O)$R^{TM}$, or

—S(═O)$_2R^{TT}$;

wherein:

each $-L^{T}-$ is independently linear or branched saturated $C_{1-4}$alkylene;

each $—R^{TT}$ is independently $—R^{TT1}$, $—R^{TT2}$, $-L^{TT}-R^{TT2}$, $—R^{TT3}$ or $-L^{TT}-R^{TT3}$;

each $—R^{TT1}$ is independently linear or branched saturated $C_{1-6}$alkyl, and is optionally substituted with one or more groups selected from —F, —OH, and $—OR^{TTT}$;

each $—R^{TT2}$ is saturated $C_{3-6}$cycloalkyl, and is optionally substituted with one or more groups selected from —F, $—R^{TTT}$, —OH, and $—OR^{TTT}$;

each $—R^{TT3}$ is independently phenyl or naphthyl, and is optionally substituted with one or more groups selected from —F, —Cl, —Br, —I, $—R^{TTT}$, OH, $—OR^{TTT}$, $—OCF_3$, $—NH_2$, $—NHR^{TTT}$, and $—NR^{TTT}_2$;

each $-L^{TT}-$ is independently linear or branched saturated $C_{1-4}$alkylene;

each $—R^{TN}$ is linear or branched saturated $C_{1-4}$alkyl, phenyl, or benzyl;

each $—R^{TM}$ is independently azetidino, pyrrolidino, piperidino, piperazino, morpholino, azepano, or diazepano, and is:

optionally substituted on carbon with one or more groups selected from: $—R^{TMM}$, $—C(=O)R^{TMM}$, $—S(=O)_2R^{TMM}$, —F, $—NH_2$, $—NHR^{TMM}$, $—NR^{TMM}_2$, —OH, and $—OR^{TMM}$; and optionally substituted on secondary nitrogen, if present, with a group selected from: $—R^{TMM}$, $—C(=O)R^{TMM}$, $—C(=O)OR^{TMM}$ and $—S(=O)_2R^{TMM}$;

each $—R^{TTT}$ is independently linear or branched saturated $C_{1-4}$alkyl, phenyl, or benzyl; and each $—R^{TMM}$ is independently linear or branched saturated $C_{1-4}$alkyl, phenyl, or benzyl;

and wherein:

$-L^{7}-$ is independently linear or branched saturated $C_{1-3}$alkylene, and is optionally substituted with one or more groups selected from —F, —OH, and —OMe;

$—R^{3}$ is independently $—R^{3A}$ or $—R^{3B}$;

$—R^{3A}$ is independently linear or branched saturated $C_{1-6}$alkyl, and is optionally substituted with one or more groups selected from —F, —OH, and —OMe; and $—R^{3B}$ is independently saturated $C_{3-7}$cycloalkyl, and is optionally substituted with one or more groups selected from —F, —OH, and —OMe.

For the avoidance of doubt:

The index "$C_{x-y}$" in terms such as "$C_{9-10}$heteroaryl", "$C_{3-7}$heterocyclyl", and the like, refers to the number of ring atoms, which may be carbon atoms or heteroatoms (e.g., N, O, S, as the case may be). For example, pyridyl is an example of a $C_6$heteroaryl group, and piperidino is an example of a $C_6$heterocyclyl group.

The term "heteroaryl" refers to a group that is attached to the rest of the molecule by an atom that is part of an aromatic ring, wherein the aromatic ring is part of an aromatic ring system, and the aromatic ring system has one or more heteroatoms (e.g., N, O, S, as the case may be). For example, pyridyl is an example of a $C_6$heteroaryl group, and quinolyl is an example of a $C_{10}$heteroaryl group.

The phrase "substituent on carbon" is intended to refer to a substituent which is attached to a carbon ring atom. Similarly, the phrase "substituent on secondary nitrogen" is intended to refer to a substituent which is attached to a nitrogen ring atom which, in the absence of the substituent, would be a secondary nitrogen ring atom (i.e., —NH—). Consequently, a pyridyl group may only have "substituents on carbon", whereas 1H-pyrrole may have both "substituents on carbon" and a "substituent on secondary nitrogen", as illustrated below.

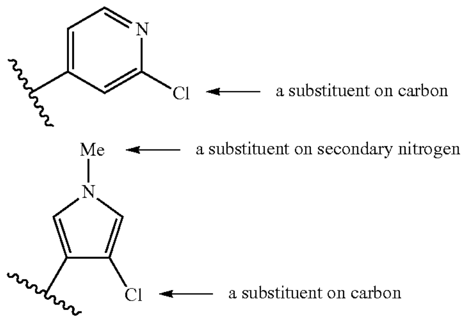

Similarly, a piperidino group may only have "substituents on carbon", whereas piperizino may have both "substituents on carbon" and a "substituent on secondary nitrogen", as illustrated below.

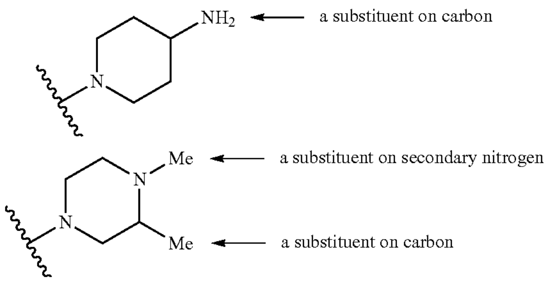

Unless otherwise indicated, where a compound is shown or described which has one or more chiral centres, and two or more stereoisomers are possible, all such stereoisomers are disclosed and encompassed, both individually (e.g., as isolated from the other stereoisomer(s)) and as mixtures (e.g., as equimolar or non-equimolar mixtures of two or more stereoisomers). For example, unless otherwise indicated, where a compound has one chiral centre, each of the (R) and (S) enantiomers are disclosed and encompassed, both individually (e.g., as isolated from the other enantiomer) and as a mixture (e.g., as equimolar or non-equimolar mixtures of the two enantiomers). For example, the initial carbon atom of a pendant sec-butyl group, $—CH(CH_3)CH_2CH_3$ is usually chiral, and so gives rise to stereoisomers, e.g., (R) and (S) enantiomers if it is the only chiral centre, each of which is disclosed and encompassed.

The Group $—R^{7}$ (2) A compound according to (1), wherein $—R^{7}$ is a fused bicyclic $C_{9-10}$heteroaryl group having exactly 1, 2, or 3 ring heteroatoms, wherein each ring heteroatom is N.

$C_9$Heteroaryl Groups:

(3) A compound according to (1), wherein $—R^{7}$ is a fused bicyclic $C_9$heteroaryl group having exactly 1, 2, or 3 ring heteroatoms, wherein each ring heteroatom is N.

(4) A compound according to (1), wherein $—R^{7}$ is a fused bicyclic $C_9$heteroaryl group having exactly 2 or 3 ring heteroatoms, wherein each ring heteroatom is N.

(5) A compound according to (1), wherein $—R^{7}$ is a fused bicyclic $C_9$heteroaryl group having exactly 1 ring heteroatom, wherein the ring heteroatom is N.

(6) A compound according to (1), wherein —$R^7$ is independently:

indolyl; indolizinyl; 2H-isoindolyl; 2H-cyclopenta[c]pyridinyl; or 1H-cyclopenta[b]pyridinyl.

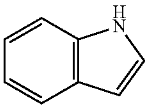 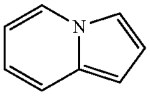 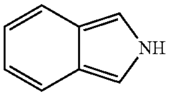

indole indolizine 2H-isoindole

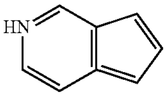 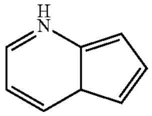

2H-cyclopenta[c]pyridine 1H-cyclopenta[b]pyridine (7) A compound according to (1), wherein —$R^7$ is a fused bicyclic $C_9$heteroaryl group having exactly 2 ring heteroatoms, wherein each ring heteroatom is N.

(8) A compound according to (1), wherein —$R^7$ is independently;

1H-indazolyl, benzimidazolyl; 1H-pyrrolo[3,2-b]pyridinyl; 1H-pyrrolo[3,2-c]pyridinyl; 1H-pyrrolo[2,3-c]pyridinyl; 1H-pyrrolo[2,3-b]pyridinly; pyrazolo[1,5-a]pyridinyl; imidazo[1,5-a]pyridinyl; imidazo[1,2-a]pyridinyl; pyrrolo[1,2-a]pyrimidinyl; pyrrolo[1,2-a]pyrazinyl; pyrrolo[1,2-c]pyrimidinyl; pyrrolo[1,2-b]pyridazinyl; 2H-pyrrolo[3,4-c]pyridinyl; or 6H-pyrrolo[3,4-b]pyridinyl.

1H-indazole

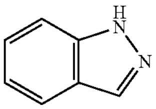

benzimidazole

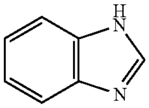

1H-pyrrolo[3,2-b]pyridine

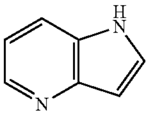

1H-pyrrolo[3,2-c]pyridine

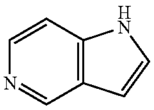

1H-pyrrolo[2,3-c]pyridine

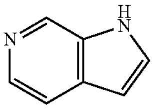

1H-pyrrolo[2,3-b]pyridine

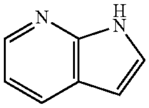

-continued pyrazolo[1,5-a]pyridine

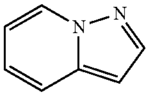

imidazo[1,5-a]pyridine

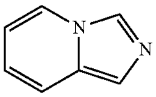

imidazo[1,2-a]pyridine

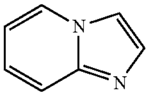

pyrrolo[1,2-a]pyrimidine

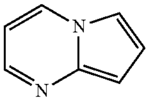

pyrrolo[1,2-a]pyrazine

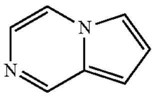

pyrrolo[1,2-c]pyrimidine

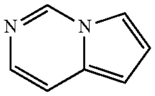

pyrrolo[1,2-b]pyridazine

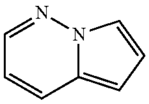

2H-pyrrolo[3,4-c]pyridine

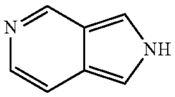

6H-pyrrolo[3,4-b]pyridine

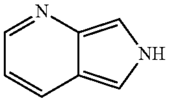

(9) A compound according to (1), wherein —$R^7$ is a fused bicyclic $C_9$heteroaryl group having exactly 3 ring heteroatoms, wherein each ring heteroatom is N.

(10) A compound according to (1), wherein —$R^7$ is independently: 1H-pyrazolo[4,3-b]pyridinyl; 1H-pyrazolo[4,3-c]pyridinyl; 1H-pyrazolo[3,4-c]pyridinyl; 1H-pyrazolo[3,4-b]pyridinyl; 1H-imidazo[4,5-b]pyridinyl; 1H-imidazo[4,5-c]pyridinyl; 3H-imidazo[4,5-c]pyridinyl; 3H-imidazo[4,5-b]pyridinyl; 5H-pyrrolo[3,2-c]pyridazinyl; 5H-pyrrolo[3,2-d]pyrimidinyl; 5H-pyrrolo[2,3-b]pyrazinyl; 1H-pyrrolo[2,3-d]pyridazinyl; 7H-pyrrolo[2,3-d]pyrimidinyl; 7H-pyrrolo[2,3-c]pyridazinyl; 6H-pyrrolo[3,4-d]pyridazinyl; 6H-pyrrolo[3,4-d]pyrimidinyl; 6H-pyrrolo[3,4-c]pyridazinyl; 6H-pyrrolo[3,4-b]pyrazinyl; triazolo[1,5-a]pyridinyl; [1,2,4]triazolo[1,5-a]pyridinyl; pyrazolo[1,5-a]pyrimidinyl; pyrazolo[1,5-a]pyrazinyl; pyrazolo[1,5-c]pyrimidinyl; pyrazolo[1,5-b]pyridazinyl; [1,2,4]triazolo[4,3-a]pyridinyl; imidazo[1,5-a]pyrimidinyl; imidazo[1,5-a]pyrazinyl; imidazo[1,5-c]pyrimidinyl; imidazo[1,5-b]pyridazinyl; imidazo[1,2-a]pyrimidinyl; imidazo[1,2-a]pyrazinyl; imidazo[1,2-c]pyrimidinyl; imidazo[1,2-b]pyridazinyl; pyrrolo[2,1-c][1,2,4]triazinyl; pyrrolo[1,2-a][1,3,5]triazinyl; pyrrolo[1,2-b][1,2,4]triazinyl; pyrrolo[1,2-d][1,2,4]triazinyl; pyrrolo[2,1-f][1,2,4]triazinyl; or pyrrolo[1,2-c]triazinyl.

1H-benzotriazole

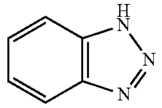

1H-pyrazolo[4,3-b]pyridine

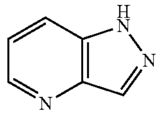

1H-pyrazolo[4,3-c]pyridine

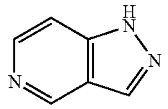

1H-pyrazolo[3,4-b]pyridine

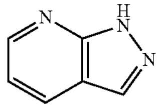

1H-imidazo[4,5-b]pyridine

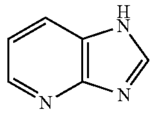

1H-imidazo[4,5-c]pyridine

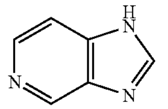

3H-imidazo[4,5-c]pyridine

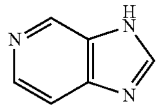

3H-imidazo[4,5-b]pyridine

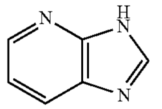

5H-pyrrolo[3,2-c]pyridine

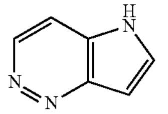

5H-pyrrolo[3,2-d]pyrimidine

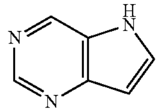

5H-pyrrolo[2,3-b]pyrazine

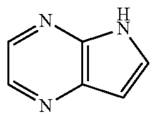

1H-pyrrolo[2,3-d]pyridazine

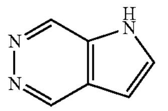

7H-pyrrolo[2,3-d]pyrimidine

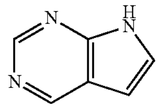

-continued 7H-pyrrolo[2,3-c]pyridazine

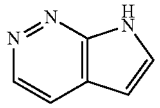

6H-pyrrolo[3,4-d]pyridazine

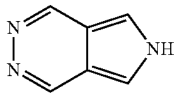

6H-pyrrolo[3,4-d]pyrimidine

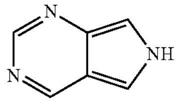

6H-pyrrolo[3,4-c]pyridazine

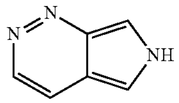

6H-pyrrolo[3,4-b]pyrazine

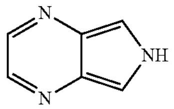

triazolo[1,5-a]pyridine

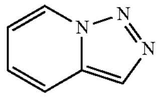

[1,2,4]triazolo[1,5-a]pyridine

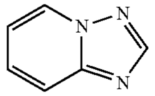

pyrazolo[1,5-a]pyrimidine

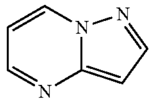

pyrazolo[1,5-a]pyrazine

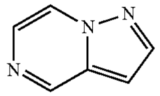

pyrazolo[1,5-c]pyrimidine

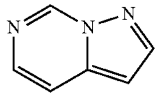

pyrazolo[1,5-b]pyridazine

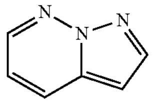

[1,2,4]triazolo[4,3-a]pyridine

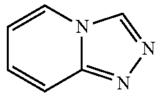

imidazo[1,5-a]pyrimidine

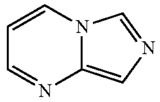

imidazo[1,5-a]pyrazine

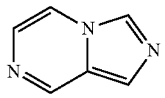

-continued imidazo[1,5-c]pyrimidine

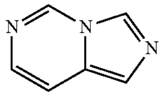

imidazo[1,5-b]pyridazine

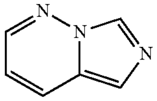

imidazo[1,2-a]pyrimidine

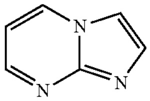

imidazo[1,2-a]pyrazine

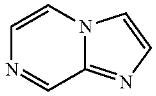

imidazo[1,2-c]pyrimidine

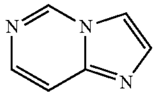

imidazo[1,2-b]pyridazine

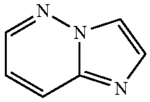

pyrrolo[2,1-c][1,2,4]triazine

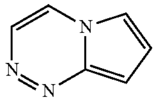

pyrrolo[1,2-a][1,3,5]triazine

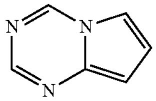

pyrrolo[1,2-b][1,2,4]triazine

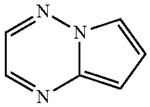

pyrrolo[1,2-d][1,2,4]triazine

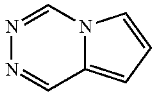

pyrrolo[2,1-f][1,2,4]triazine

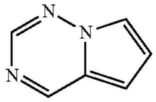

pyrrolo[1,2-c]triazine

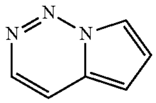

(11) A compound according to (1), wherein —$R^7$ is independently: imidazo[1,2-a]pyridinyl; imidazo[1,2-a]pyrimidinyl; benzimidazolyl; imidazo[1,2-b]pyridazinyl; or [1,2,4]triazolo[1,5-a]pyridinyl.

(12) A compound according to (1), wherein —$R^7$ is independently: imidazo[1,2-a]pyridinyl; imidazo[1,2-a]pyrimidinyl; or benzimidazolyl.

(13) A compound according to (1), wherein —$R^7$ is imidazo[1,2-a]pyridinyl.

(14) A compound according to (1), wherein —$R^7$ is independently: 2-imidazo[1,2-a]pyridinyl; or 3-imidazo[1,2-a]pyridinyl.

(15) A compound according to (1), wherein —$R^7$ is 2-imidazo[1,2-a]pyridinyl (shown below).

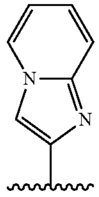 [SMILES: *c1cn2ccccc2n1]

(16) A compound according to (1), wherein —$R^7$ is 3-imidazo[1,2-a]pyridinyl (shown below).

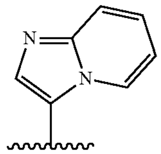 [SMILES: *c1cnc2ccccn12]

(17) A compound according to (1), wherein —$R^7$ is imidazo[1,2-a]pyrimidinyl.

(18) A compound according to (1), wherein —$R^7$ is 2-imidazo[1,2-a]pyrimidinyl (shown below).

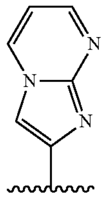 [SMILES: *c1cn2cccnc2n1]

(19) A compound according to (1), wherein —$R^7$ is imidazo[1,2-b]pyridazinyl.

(20) A compound according to (1), wherein —$R^7$ is 2-imidazo[1,2-b]pyridazinyl (shown below).

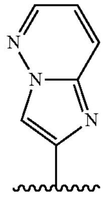 [SMILES: *c1cn2ncccc2n1]

(21) A compound according to (1), wherein —$R^7$ is [1,2,4]triazolo[1,5-a]pyridinyl.

(22) A compound according to (1), wherein —$R^7$ is 2-[1,2,4]triazolo[1,5-a]pyridinyl (shown below).

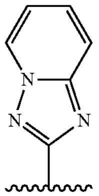 [SMILES: *c1nc2ccccn2n1]

(23) A compound according to (1), wherein —$R^7$ is benzimidazolyl.

(24) A compound according to (1), wherein —$R^7$ is independently: 2-benzimidazolyl or 5-benzimidazolyl.

(25) A compound according to (1), wherein —$R^7$ is 2-benzimidazolyl (shown below).

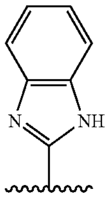 [SMILES: *c1nc2ccccc2[nH]1]

(26) A compound according to (1), wherein —$R^7$ is 5-benzimidazolyl (shown below).

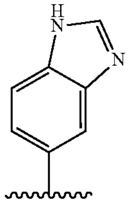 [SMILES: *c1ccc2[nH]cnc2c1]

(27) A compound according to (1), wherein —$R^7$ is a fused bicyclic $C_9$heteroaryl group having exactly 1 or 2 ring heteroatoms, wherein each ring heteroatom is independently N or O.

(28) A compound according to (1), wherein —$R^7$ is a fused bicyclic $C_9$heteroaryl group having exactly 1 ring heteroatom, wherein the ring heteroatom is O.

(29) A compound according to (1), wherein —$R^7$ is benzofuranyl.

(30) A compound according to (1), wherein —$R^7$ is independently: 2-benzofuranyl or 3-benzofuranyl.

(31) A compound according to (1), wherein —$R^7$ is 2-benzofuranyl (shown below).

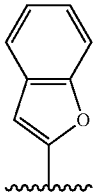 [SMILES: *c1cc2ccccc2o1]

(32) A compound according to (1), wherein —$R^7$ is 3-benzofuranyl (shown below).

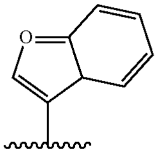

$C_8$Heteroaryl Groups:

(33) A compound according to (1), wherein —$R^7$ is a fused bicyclic $C_8$heteroaryl group having exactly 1, 2, or 3 ring heteroatoms, wherein each ring heteroatom is N, S, or O.

(34) A compound according to (1), wherein —$R^7$ is a fused bicyclic $C_8$heteroaryl group having exactly 1, 2, or 3 ring heteroatoms, wherein each ring heteroatom is N or S.

(35) A compound according to (1), wherein —$R^7$ is a fused bicyclic $C_8$heteroaryl group having exactly 2 or 3 ring heteroatoms, wherein each ring heteroatom is N, S, or O.

(36) A compound according to (1), wherein —$R^7$ is a fused bicyclic $C_8$heteroaryl group having exactly 2 or 3 ring heteroatoms, wherein each ring heteroatom is N or S.

(37) A compound according to (1), wherein —$R^7$ is a fused bicyclic $C_8$heteroaryl group having exactly 2 ring heteroatoms, wherein each ring heteroatom is N, S, or O.

(38) A compound according to (1), wherein —$R^7$ is a fused bicyclic $C_8$heteroaryl group having exactly 2 ring heteroatoms, wherein each ring heteroatom is N or S.

(39) A compound according to (1), wherein —$R^7$ is a fused bicyclic $C_8$heteroaryl group having exactly 2 ring heteroatoms, wherein 1 of said ring heteroatoms is N and 1 of said ring heteroatoms is S or O.

(40) A compound according to (1), wherein —$R^7$ is a fused bicyclic $C_8$heteroaryl group having exactly 2 ring heteroatoms, wherein 1 of said ring heteroatoms is N and 1 of said ring heteroatoms is S.

(41) A compound according to (1), wherein —$R^7$ is a fused bicyclic $C_8$heteroaryl group having exactly 3 ring heteroatoms, wherein each ring heteroatom is N, S, or O.

(42) A compound according to (1), wherein —$R^7$ is a fused bicyclic $C_8$heteroaryl group having exactly 3 ring heteroatoms, wherein each ring heteroatom is N or S.

(43) A compound according to (1), wherein —$R^7$ is a fused bicyclic $C_8$heteroaryl group having exactly 3 ring heteroatoms, wherein 2 of said ring heteroatoms are N and 1 of said ring heteroatoms is S or O.

(44) A compound according to (1), wherein —$R^7$ is a fused bicyclic $C_8$heteroaryl group having exactly 3 ring heteroatoms, wherein 2 of said ring heteroatoms are N and 1 of said ring heteroatoms is S.

(45) A compound according to (1), wherein —$R^7$ is independently: imidazo[2,1-b]thiazolyl or imidazo[2,1-b]thiazolyl or imidazo[2,1-b]oxazolyl.

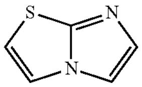

imidazo[2, 1-b]thiazole

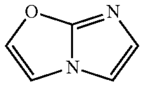

imidazo[2, 1-b]oxazole

(46) A compound according to (1), wherein —$R^7$ is imidazo[2,1-b]thiazolyl.

(47) A compound according to (1), wherein —$R^7$ is 6-imidazo[2,1-b]thiazolyl (shown below).

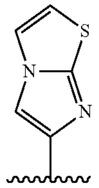 [SMILES: *c1cn2ccsc2n1]

$C_{10}$Heteroaryl Groups:

(48) A compound according to (1), wherein —$R^7$ is a fused bicyclic $C_{10}$heteroaryl group having exactly 1, 2, or 3 ring heteroatoms, wherein each ring heteroatom is N.

(49) A compound according to (1), wherein —$R^7$ is a fused bicyclic $C_{10}$heteroaryl group having exactly 1 or 2 ring heteroatoms, wherein each ring heteroatom is N.

(50) A compound according to (1), wherein —$R^7$ is a fused bicyclic $C_{10}$heteroaryl group having exactly 1 ring heteroatom, wherein the ring heteroatom is N.

(51) A compound according to (1), wherein —$R^7$ is independently: quinolinyl or isoquinolinyl.

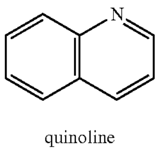

quinoline

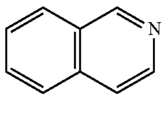

isoquinoline

(52) A compound according to (1), wherein —$R^7$ is quinolinyl.

(53) A compound according to (1), wherein —$R^7$ is 2-quinolinyl (shown below).

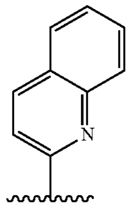 [SMILES: *c1ccc2ccccc2n1]

(54) A compound according to (1), wherein —$R^7$ is 3-quinolinyl (shown below).

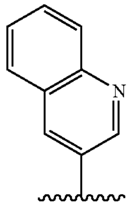 [SMILES: *c1cnc2ccccc2c1]

(55) A compound according to (1), wherein —$R^7$ is isoquinolinyl.

(56) A compound according to (1), wherein —$R^7$ is a fused bicyclic $C_{10}$heteroaryl group having exactly 2 ring heteroatoms, wherein each ring heteroatom is N.

(57) A compound according to (1), wherein —$R^7$ is independently: cinnolinyl; quinazolinyl; quinoxalinyl; 1,5-naphthyridinyl; 1,6-naphthyridinyl; 1,7-naphthyridinyl; 1,8-naphthyridinyl; phthalazinyl; 2,6-naphthyridinyl; or 2,7-naphthyridinyl.

cinnoline

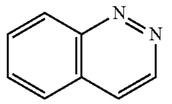

quinazoline

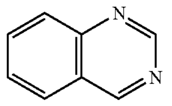

quinoxaline

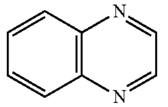

1,5-naphthyridine

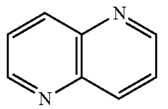

1,6-naphthyridine

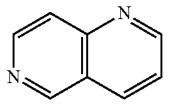

1,7-naphthyridine

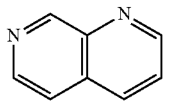

1,8-naphthyridine

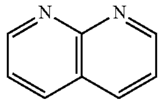

phthalazine

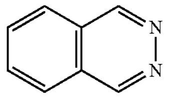

2,6-naphthyridine

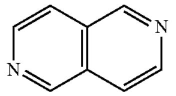

2,7-naphthyridine

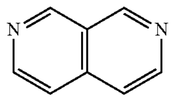

The Group —$R^7$: Point of Attachment

(58) A compound according to any one of (1) to (57), wherein —$R^7$ is attached to -$L^7$- via a ring carbon atom of —$R^7$ (e.g., a non-bridging ring carbon atom of —$R^7$).

(59) A compound according to any one of (1) to (57), wherein —$R^7$ is attached to -$L^7$- via a ring nitrogen atom of —$R^7$ (e.g., a non-bridging ring nitrogen atom of —$R^7$).

An example of benzimidazolyl attached via a non-bridging ring carbon atom is shown below.

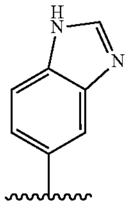 [SMILES: *c1ccc2[nH]cnc2c1]

Similarly, an example of benzimidazolyl attached via a non-bridging ring nitrogen atom is shown below.

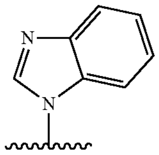 [SMILES: *n1cnc2ccccc21]

The Substituents —$R^{SC}$

(60) A compound according to any one of (1) to (59), wherein each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$,
—$CF_3$, —$CHF_2$, —$OCF_3$, —$OCHF_2$,
—$NH_2$, —$NHR^{TT}$, —$NR^{TT}{}_2$, —$R^{TM}$,
-$L^{T}$-$NH_2$, -$L^{T}$-$NHR^{TT}$, -$L^{T}$-$NR^{TT}{}_2$, -$L^{T}$-$R^{TM}$,
—C(=O)OH, —C(=O)$OR^{TT}$
—OC(=O)$R^{TT}$,
—C(=O)$NH_2$, —C(=O)$NHR^{TT}$, —C(=O)$NR^{TT}{}_2$, —C(=O)$R^{TM}$,
—NHC(=O)$R^{TT}$
—NHC(=O)$NH_2$, —NHC(=O)$NHR^{TT}$, —NHC(=O)$NR^{TT}{}_2$, —NHC(=O)$R^{TM}$,
—NHC(=O)$OR^{TT}$,
—OC(=O)$NH_2$, —OC(=O)$NHR^{TT}$, —OC(=O)$NR^{TT}{}_2$, —OC(=O)$R^{TM}$,
—C(=O)$R^{TT}$,
—$S(=O)_2R^{TT}$,
—$S(=O)_2NH_2$, —$S(=O)_2NHR^{TT}$, —$S(=O)_2NR^{TT}{}_2$, —$S(=O)_2R^{TM}$,
—$NHS(=O)_2R^{TT}$,
—CN, or —$NO_2$.

(61) A compound according to any one of (1) to (59), wherein each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$,
—$CF_3$, —$CHF_2$, —$OCF_3$, —$OCHF_2$,
—$NH_2$, —$NHR^{TT}$, —$NR^{TT}{}_2$, —$R^{TM}$,
-$L^{T}$-$NH_2$, -$L^{T}$-$NHR^{TT}$, -$L^{T}$-$NR^{TT}{}_2$, -$L^{T}$-$R^{TM}$,
—C(=O)OH, —C(=O)$OR^{TT}$,
—OC(=O)$R^{TT}$,
—C(=O)$NH_2$, —C(=O)$NHR^{TT}$, —C(=O)$NR^{TT}{}_2$, —C(=O)$R^{TM}$,
—NHC(=O)$R^{TT}$
—C(=O)$R^{TT}$
—$S(=O)_2NH_2$, —$S(=O)_2NHR^{TT}$, —$S(=O)_2NR^{TT}{}_2$, —$S(=O)_2R^{TM}$,
—$NHS(=O)_2R^{TT}$,
—CN, or —$NO_2$.

(62) A compound according to any one of (1) to (59), wherein each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$,
—$CF_3$, —$CHF_2$, —$OCF_3$, —$OCHF_2$,
—$NH_2$, —$NHR^{TT}$, —$NR^{TT}{}_2$, —$R^{TM}$,
-$L^{T}$-$NH_2$, -$L^{T}$-$NHR^{TT}$, -$L^{T}$-$NR^{TT}{}_2$, -$L^{T}$-$R^{TM}$,
—C(=O)OH, —C(=O)$OR^{TT}$
—OC(=O)$R^{TT}$,
—C(=O)$NH_2$, —C(=O)$NHR^{TT}$, —C(=O)$NR^{TT}{}_2$, —C(=O)$R^{TM}$,
—NHC(=O)$R^{TT}$,
—C(=O)$R^{TT}$,
—$S(=O)_2NH_2$, —$S(=O)_2NHR^{TT}$, —$S(=O)_2NR^{TT}{}_2$, —$S(=O)_2R^{TM}$
—$NHS(=O)_2R^{TT}$,
—CN, or —$NO_2$.

(63) A compound according to any one of (1) to (59), wherein each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$,
—$CF_3$, —$CHF_2$, —$OCF_3$, —$OCHF_2$,
—$NH_2$, —$NHR^{TT}$, —$NR^{TT}{}_2$, —$R^{TM}$,
-$L^{T}$-$NH_2$, -$L^{T}$-$NHR^{TT}$, -$L^{T}$-$NR^{TT}{}_2$, or -$L^{T}$-$R^{TM}$.

(64) A compound according to any one of (1) to (59), wherein each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$.
—$CF_3$, —$CHF_2$, —$OCF_3$, or —$OCHF_2$.

(65) A compound according to any one of (1) to (59), wherein each —$R^{SC}$, if present, is independently:
$R^{TT}$,
—F, —Cl, —Br, —I,
—OH, —$OR^{TT}$,
—$CF_3$, —$CHF_2$, —$OCF_3$, or —$OCHF_2$.

(66) A compound according to any one of (1) to (59), wherein each —$R^{SC}$, if present, is independently:
—$R^{TT}$,
—F, —Cl, —Br, or —I.

(67) A compound according to any one of (1) to (59), wherein each —$R^{SC}$, if present, is independently:
—$R^{TT}$.

The Substituents —$R^{SN}$

(68) A compound according to any one of (1) to (67), wherein each —$R^{SN}$, if present, is independently:
—$R^{TT}$,
—C(=O)$R^{TT}$,
—C(=O)$OR^{TT}$,
—C(=O)$NH_2$, —C(=O)$NHR^{TT}$, —C(=O)$NR^{TT}{}_2$, —C(=O)$R^{TM}$ or
—$S(=O)_2R^{TT}$.

(69) A compound according to any one of (1) to (67), wherein each —$R^{SN}$, if present, is independently:
—$R^{TT}$,
—C(=O)$R^{TT}$, or
—C(=O)$OR^{TT}$.

(70) A compound according to any one of (1) to (67), wherein each —$R^{SN}$, if present, is:

—$R^{TT}$.

The Group -$L^{T}$-

(71) A compound according to any one of (1) to (70), wherein each -$L^{T}$-, if present, is independently linear or branched saturated $C_{1-3}$alkylene.

(72) A compound according to any one of (1) to (70), wherein each -$L^{T}$-, if present, is independently —$CH_2$—, —$CH_2CH_2$—, —$CH_2CH_2CH_2$—, —$CH(CH_3)$—, —$C(CH_3)_2$—, —$CH(CH_2CH_3)$—, —$CH(CH_3)CH_2$—, or —$CH_2CH(CH_3)$—.

(73) A compound according to any one of (1) to (70), wherein each -$L^{T}$-, if present, is independently —$CH_2$—, —$CH_2CH_2$—, or —$CH_2CH_2CH_2$—.

(74) A compound according to any one of (1) to (70), wherein each -$L^{T}$-, if present, is —$CH_2$—.

The Group —$R^{TT}$

(75) A compound according to any one of (1) to (74), wherein each —$R^{TT}$, if present, is independently —$R^{TT1}$, —$R^{TT2}$, —$R^{TT3}$ or -$L^{TT}$-$R^{TT3}$.

(76) A compound according to any one of (1) to (74), wherein each —$R^{TT}$, if present, is independently —$R^{TT1}$, —$R^{TT3}$ or -$L^{TT}$-$R^{TT3}$.

(77) A compound according to any one of (1) to (74), wherein each —$R^{TT}$, if present, is —$R^{TT1}$.

The Group —$R^{TT1}$

(78) A compound according to any one of (1) to (77), wherein each —$R^{TT1}$, if present, is independently linear or branched saturated $C_{1-6}$alkyl.

(79) A compound according to any one of (1) to (77), wherein each —$R^{TT1}$, if present, is independently linear or branched saturated $C_{1-4}$alkyl, and is optionally substituted with one or more groups selected from —F, —OH, and —$OR^{TTT}$.

(80) A compound according to any one of (1) to (77), wherein each —$R^{TT1}$, if present, is independently linear or branched saturated $C_{1-4}$alkyl.

(81) A compound according to any one of (1) to (77), wherein each —$R^{TT1}$, if present, is independently -Me, -Et, -nPr, -iPr, -nBu, -sBu, -iBu, or -tBu.

(82) A compound according to any one of (1) to (77), wherein each —$R^{TT1}$, if present, is independently -Me, -Et, -nPr, or -iPr.

(83) A compound according to any one of (1) to (77), wherein each —$R^{TT1}$, if present, is -Me.

The Group —$R^{TT2}$

(84) A compound according to any one of (1) to (83), wherein each —$R^{TT2}$, if present, is saturated $C_{3-6}$cycloalkyl, and is optionally substituted with one or more groups selected from —F, —OH, and —$OR^{TTT}$.

(85) A compound according to any one of (1) to (83), wherein each —$R^{TT2}$, if present, is saturated $C_{3-6}$cycloalkyl.

(86) A compound according to any one of (1) to (83), wherein each —$R^{TT2}$, if present, is independently cyclopropyl, cyclobutyl, cyclopentyl, or cyclohexyl.

(87) A compound according to any one of (1) to (83), wherein each —$R^{TT2}$, if present, is cyclopropyl.

The Group —$R^{TT3}$

(88) A compound according to any one of (1) to (87), wherein each —$R^{TT3}$, if present, is phenyl, and is optionally substituted with one or more groups selected from —F, —Cl, —Br, —I, —$R^{TTT}$, OH, —$OR^{TTT}$, —$OCF_3$, —$NH_2$, —$NHR^{TTT}$, and —$NR^{TTT}_2$;

(89) A compound according to any one of (1) to (87), wherein each —$R^{TT3}$, if present, is phenyl, and is optionally substituted with one or more groups selected from —F, —Cl, —Br, —I, —$R^{TTT}$, OH, —$OR^{TTT}$, and —$OCF_3$.

(90) A compound according to any one of (1) to (87), wherein each —$R^{TT3}$, if present, is phenyl, and is optionally substituted with one or more groups selected from —F, —Cl, —Br, —I, and —$R^{TTT}$.

(91) A compound according to any one of (1) to (87), wherein each —$R^{TT3}$, if present, is phenyl.

The Group -$L^{TT}$-

(92) A compound according to any one of (1) to (91), wherein each -$L^{TT}$-, if present, is independently linear or branched saturated $C_{1-3}$alkylene.

(93) A compound according to any one of (1) to (91), wherein each -$L^{TT}$-, if present, is independently —$CH_2$—, —$CH_2CH_2$—, —$CH_2CH_2CH_2$—, —$CH(CH_3)$—, —$C(CH_3)_2$—, —$CH(CH_2CH_3)$—, —$CH(CH_3)CH_2$—, or —$CH_2CH(CH_3)$—.

(94) A compound according to any one of (1) to (91), wherein each -$L^{TT}$-, if present, is independently —$CH_2$—, —$CH_2CH_2$—, or —$CH_2CH_2CH_2$—.

(95) A compound according to any one of (1) to (91), wherein each -$L^{TT}$-, if present, is —$CH_2$—.

The Group —$R^{TN}$

(96) A compound according to any one of (1) to (95), wherein each —$R^{TN}$, if present, is independently linear or branched saturated $C_{1-4}$alkyl.

(97) A compound according to any one of (1) to (95), wherein each —$R^{TN}$, if present, is -Me.

The Group —$R^{TM}$

(98) A compound according to any one of (1) to (97), wherein each —$R^{TM}$, if present, is independently azetidino, pyrrolidino, piperidino, piperazino, morpholino, azepano, or diazepano, and is:

optionally substituted on carbon with one or more groups selected from: —$R^{TMM}$, —F, —OH, and —$OR^{TMM}$; and optionally substituted on secondary nitrogen, if present, with a group selected from: —$R^{TMM}$, —$C(=O)R^{TMM}$ and —$C(=O)OR^{TMM}$.

(99) A compound according to any one of (1) to (97), wherein each —$R^{TM}$, if present, is independently pyrrolidino, piperidino, piperazino, or morpholino, and is:

optionally substituted on carbon with one or more groups selected from: —$R^{TMM}$, —F, —OH, and —$OR^{TMM}$; and optionally substituted on secondary nitrogen, if present, with a group selected from: —$R^{TMM}$, —$C(=O)R^{TMM}$ and —$C(=O)OR^{TMM}$.

(100) A compound according to any one of (1) to (97), wherein each —$R^{TM}$, if present, is independently pyrrolidino, piperidino, piperazino, or morpholino, and is:

optionally substituted on carbon with one or more groups selected from: —$R^{TMM}$; and optionally substituted on secondary nitrogen, if present, with a group selected from: —$R^{TMM}$, —$C(=O)R^{TMM}$ and —$C(=O)OR^{TMM}$.

(101) A compound according to any one of (1) to (97), wherein each —$R^{TM}$, if present, is independently pyrrolidino, piperidino, piperazino, or morpholino, and is:

optionally substituted on carbon with one or more groups selected from: —$R^{TMM}$; and optionally substituted on secondary nitrogen, if present, with a group selected from: —$R^{TMM}$.

The Group —$R^{TTT}$ (102) A compound according to any one of (1) to (101), wherein each —$R^{TTT}$, if present, is independently linear or branched saturated $C_{1-4}$alkyl.

(103) A compound according to any one of (1) to (101), wherein each $—R^{TTT}$, if present, is -Me.

The Group $—R^{TMM}$ (104) A compound according to any one of (1) to (103), wherein each $—R^{TMM}$, if present, is independently linear or branched saturated $C_{1-4}$alkyl.

(105) A compound according to any one of (1) to (103), wherein each $—R^{TMM}$, if present, is -Me.

The Group $-L^7-$ (106) A compound according to any one of (1) to (105), wherein $-L^7-$ is independently linear or branched saturated $C_{1-3}$alkylene.

(107) A compound according to any one of (1) to (105), wherein $-L^7-$ is independently $—CH_2—$, $—CH_2CH_2—$, $—CH_2CH_2CH_2—$, $—CH(CH_3)—$, $—C(CH_3)_2—$, $—CH(CH_2CH_3)—$, $—CH(CH_3)CH_2—$, or $—CH_2CH(CH_3)—$.

(108) A compound according to any one of (1) to (105), wherein $-L^7-$ is independently $—CH_2—$, $—CH_2CH_2—$, or $—CH_2CH_2CH_2—$.

(109) A compound according to any one of (1) to (105), wherein $-L^7-$ is independently $—CH_2—$, $—CH(CH_3)—$, $—C(CH_3)_2—$, or $—CH(CH_2CH_3)—$.

(110) A compound according to any one of (1) to (105), wherein $-L^7-$ is independently $—CH_2—$ or $—CH(CH_3)—$.

(111) A compound according to any one of (1) to (105), wherein $-L^7-$ is $—CH_2—$.

(112) A compound according to any one of (1) to (105), wherein $-L^7-$ is $—CH_2—$, and further wherein $-L^7-$ is $—CD_2-$.

The Group $—R^3$ (113) A compound according to any one of (1) to (112), wherein $—R^3$ is $—R^{3A}$.

(114) A compound according to any one of (1) to (112), wherein $—R^3$ is $—R^{3B}$.

The Group $—R^{3A}$ (115) A compound according to any one of (1) to (114), wherein $—R^{3A}$, if present, is independently linear or branched saturated $C_{1-6}$alkyl.

(116) A compound according to any one of (1) to (114), wherein $—R^{3A}$, if present, is independently -Me, -Et, -nPr, -iPr, -nBu, -iBu, -sBu, or -tBu, n-pentyl, t-pentyl, neo-pentyl, iso-pentyl, sec-pentyl, 3-pentyl, 1-hexyl, 2-hexyl, 3-hexyl, 3-methyl-1-pentyl, 4-methyl-1-pentyl, 4-methyl-2-pentyl, 4-methyl-3-pentyl, 2-methyl-2-pentyl, 2-methyl-1-pentyl, 2-methyl-2-pentyl, 3,3-dimethyl-1-butyl, 3,3-dimethyl-2-butyl, 3-methyl-1-pentyl, 3-methyl-2-pentyl, 3-methyl-3-pentyl, 2,2-dimethyl-1-butyl, 2,3-dimethyl-1-butyl, or 2,3-dimethyl-2-butyl.

(117) A compound according to any one of (1) to (114), wherein $—R^{3A}$, if present, is independently linear or branched saturated $C_{1-4}$alkyl.

(118) A compound according to any one of (1) to (114), wherein $—R^{3A}$, if present, is independently -Me, -Et, -nPr, -iPr, -nBu, -iBu, -sBu, or -tBu.

(119) A compound according to any one of (1) to (114), wherein $—R^{3A}$, if present, is independently -Me, -Et, -nPr, or -iPr.

(120) A compound according to any one of (1) to (114), wherein $—R^{3A}$, if present, is independently -Et, -nPr, or -iPr.

(121) A compound according to any one of (1) to (114), wherein $—R^{3A}$, if present, is -iPr.

The Group $—R^{3B}$ (122) A compound according to any one of (1) to (121), wherein $—R^{3B}$, if present, is saturated $C_{3-7}$cycloalkyl.

(123) A compound according to any one of (1) to (121), wherein $—R^{3B}$, if present, is independently cyclopropyl, cyclobutyl, cyclopentyl, or cyclohexyl.

(124) A compound according to any one of (1) to (121), wherein $—R^{3B}$, if present, is independently cyclopropyl or cyclobutyl.

(125) A compound according to any one of (1) to (121), wherein $—R^{3B}$, if present, is cyclopropyl.

(126) A compound according to any one of (1) to (121), wherein $—R^{3B}$, if present, is cyclobutyl.

Some Preferred Combinations (127) A compound according to (1), wherein:

$—R^7$ is independently:
- imidazo[1,2-a]pyridinyl;
- imidazo[1,2-a]pyrimidinyl;
- benzimidazolyl;
- imidazo[2,1-b]thiazolyl;
- imidazo[1,2-b]pyridazinyl;
- [1,2,4]triazolo[1,5-a]pyridinyl;
- quinolinyl; or
- benzofuranyl;
- and is optionally substituted as described herein;

$-L^7-$ is $—CH_2—$ or $—CH(CH_3)—$;

$—R^3$ is $—R^{3A}$ or $—R^{3B}$;

$—R^{3A}$ is -iPr; and $—R^{3B}$ is cyclopropyl.

(128) A compound according to (1), wherein:

$—R^7$ is independently:
- 2-imidazo[1,2-a]pyridinyl;
- 3-imidazo[1,2-a]pyridinyl;
- 2-imidazo[1,2-a]pyrimidinyl;
- 2-benzimidazolyl;
- 5-benzimidazolyl;
- 6-imidazo[2,1-b]thiazolyl;
- 2-imidazo[1,2-b]pyridazinyl;
- 2-[1,2,4]triazolo[1,5-a]pyridinyl;
- 2-quinolinyl;
- 3-quinolinyl; or
- 2-benzofuranyl;
- and is optionally substituted as described herein;

$-L^7-$ is $—CH_2—$ or $—CH(CH_3)—$;

$—R^3$ is $—R^{3A}$ or $—R^{3B}$;

$—R^{3A}$ is -iPr; and $—R^{3B}$ is cyclopropyl.

(129) A compound according to (1), wherein:

$—R^7$ is independently:
- imidazo[1,2-a]pyridinyl; or
- imidazo[1,2-a]pyrimidinyl;
- and is optionally substituted as described herein;
- $-L^7-$ is $—CH_2—$ or $—CH(CH_3)—$;
- $—R^3$ is $—R^{3A}$ or $—R^{3B}$;
- $—R^{3A}$ is -iPr; and
- $—R^{3B}$ is cyclopropyl.

(130) A compound according to (1), wherein:

$—R^7$ is independently:
- 2-imidazo[1,2-a]pyridinyl;
- 2-imidazo[1,2-a]pyrimidinyl;
- and is optionally substituted as described herein;

$-L^7-$ is $—CH_2—$ or $—CH(CH_3)—$;

$—R^3$ is $—R^{3A}$ or $—R^{3B}$;

$—R^{3A}$ is -iPr; and $—R^{3B}$ is cyclopropyl.

(131) A compound according to (1), wherein:

$—R^7$ is independently:
- imidazo[1,2-a]pyridinyl;
- imidazo[1,2-a]pyrimidinyl;
- benzimidazolyl; or
- imidazo[2,1-b]thiazolyl;
- and is optionally substituted as described herein;

$-L^7-$ is $—CH_2—$;

$—R^3$ is $—R^{3A}$; and $R^{3A}$ is iPr.

(132) A compound according to (1), wherein:

—$R^7$ is independently:

imidazo[1,2-a]pyridinyl;

imidazo[1,2-a]pyrimidinyl; or benzimidazolyl;

and is optionally substituted as described herein;

-$L^7$- is —$CH_2$—;

—$R^3$ is —$R^{3A}$; and

—$R^{3A}$ is -iPr.

(133) A compound according to (1), wherein:

—$R^7$ is independently:

3-imidazo[1,2-a]pyridinyl;

2-imidazo[1,2-a]pyridinyl;

2-imidazo[1,2-a]pyrimidinyl;

2-benzimidazolyl;

5-benzimidazolyl; or imidazo[2,1-b]thiazol-6-yl;

and is optionally substituted as described herein;

-$L^7$- is —$CH_2$—;

—$R^3$ is —$R^{3A}$; and

—$R^{3A}$ is -iPr.

(134) A compound according to (1), wherein:

—$R^7$ is independently:

3-imidazo[1,2-a]pyridinyl;

2-imidazo[1,2-a]pyridinyl;

2-imidazo[1,2-a]pyrimidinyl;

2-benzimidazolyl; or 5-benzimidazolyl;

and is optionally substituted as described herein;

-$L^7$- is —$CH_2$—;

—$R^3$ is —$R^{3A}$; and

—$R^{3A}$ is -iPr.

Specific Compounds (135) A compound according to (1), selected from compounds of the following formulae and pharmaceutically acceptable salts, hydrates, and solvates thereof:

| Cmpd No. | Structure |
|---|---|
| H-APPAMP-001 | 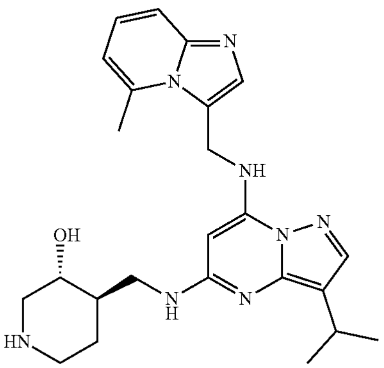 [SMILES: Cc1cccc2ncc(CNc3cc(NC[C@H]4CCNC[C@@H]4O)nc4c(C(C)C)cnn34)n12] |

-continued

| Cmpd No. | Structure |
|---|---|
| H-APPAMP-002 | 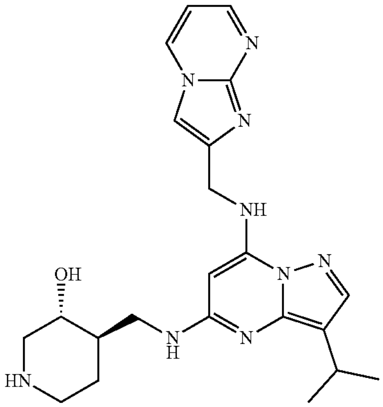 [SMILES: CC(C)c1cnn2c(NCc3cn4cccnc4n3)cc(NC[C@H]3CCNC[C@@H]3O)nc12] |
| H-APPAMP-003 | 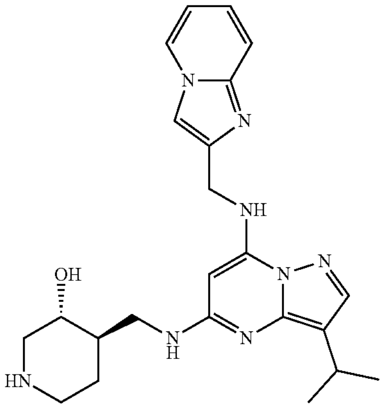 [SMILES: CC(C)c1cnn2c(NCc3cn4ccccc4n3)cc(NC[C@H]3CCNC[C@@H]3O)nc12] |
| H-APPAMP-004 | 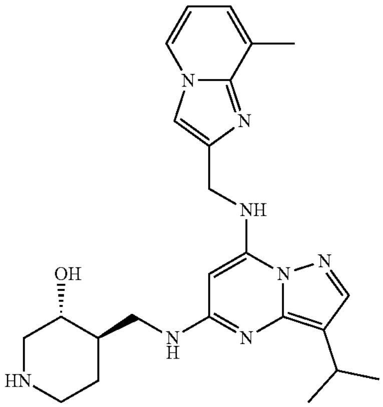 [SMILES: Cc1cccn2cc(CNc3cc(NC[C@H]4CCNC[C@@H]4O)nc4c(C(C)C)cnn34)nc12] |

-continued
| Cmpd No. | Structure |
| --- | --- |
| H-APPAMP-005 | 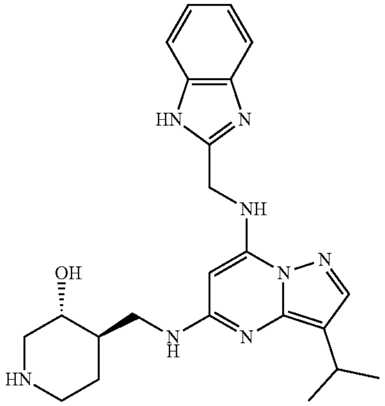 [SMILES: CC(C)c1cnn2c(NCc3nc4ccccc4[nH]3)cc(NC[C@H]3CCNC[C@@H]3O)nc12] |
| H-APPAMP-006 | 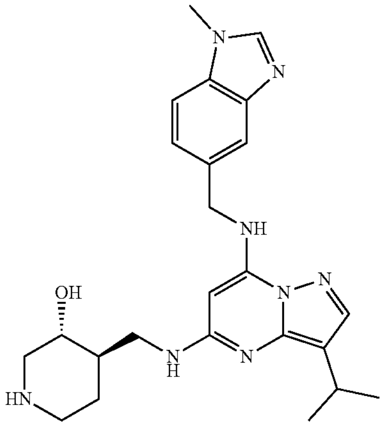 [SMILES: CC(C)c1cnn2c(NCc3ccc4c(c3)ncn4C)cc(NC[C@H]3CCNC[C@@H]3O)nc12] |
| H-APPAMP-007 | 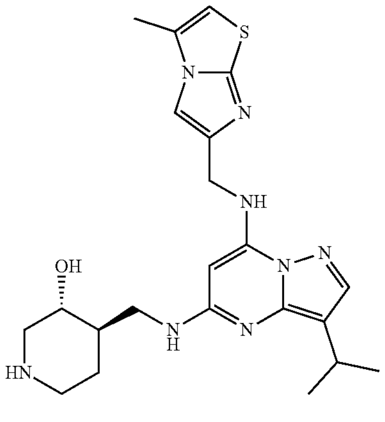 [SMILES: Cc1csc2nc(CNc3cc(NC[C@H]4CCNC[C@@H]4O)nc4c(C(C)C)cnn34)cn12] |
-continued
| Cmpd No. | Structure |
| --- | --- |
| H-APPAMP-008 | 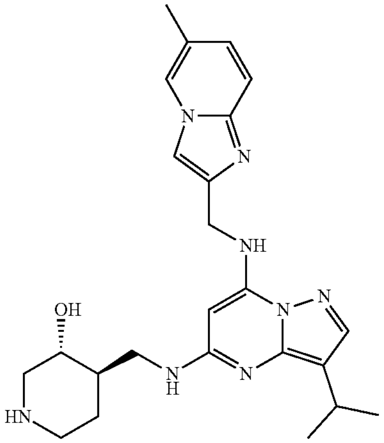 [SMILES: Cc1ccc2nc(CNc3cc(NC[C@H]4CCNC[C@@H]4O)nc4c(C(C)C)cnn34)cn2c1] |
| H-APPAMP-009 | 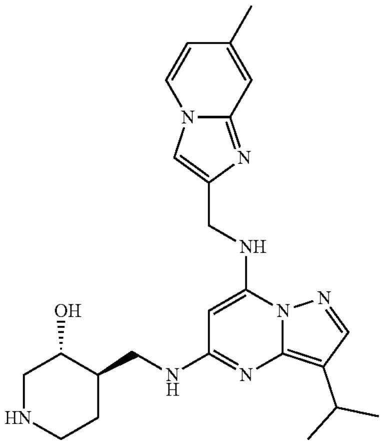 [SMILES: Cc1ccn2cc(CNc3cc(NC[C@H]4CCNC[C@@H]4O)nc4c(C(C)C)cnn34)nc2c1] |
| H-APPAMP-010 | 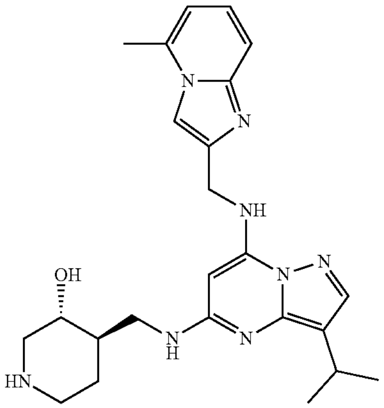 [SMILES: Cc1cccc2nc(CNc3cc(NC[C@H]4CCNC[C@@H]4O)nc4c(C(C)C)cnn34)cn12] |

-continued
| Cmpd No. | Structure |
|---|---|
| H-APPAMP-011 | 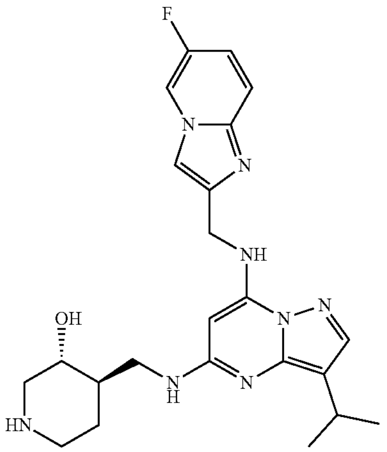 [SMILES: CC(C)c1cnn2c(NCc3cn4cc(F)ccc4n3)cc(NC[C@H]3CCNC[C@@H]3O)nc12] |
| H-APPAMP-012 | 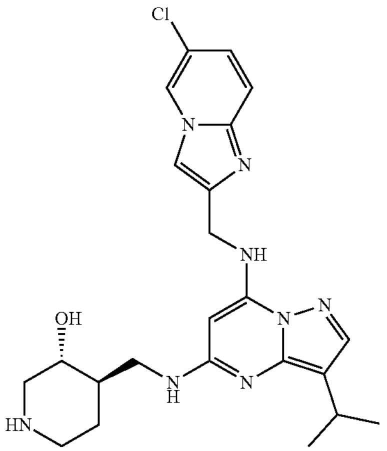 [SMILES: CC(C)c1cnn2c(NCc3cn4cc(Cl)ccc4n3)cc(NC[C@H]3CCNC[C@@H]3O)nc12] |
| H-APPAMP-013 | 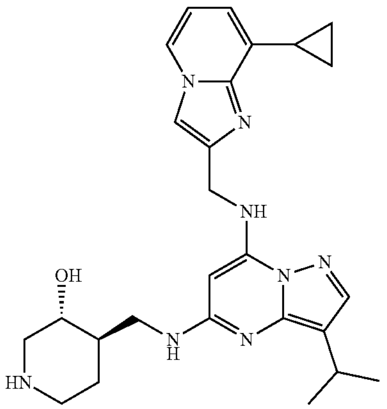 [SMILES: CC(C)c1cnn2c(NCc3cn4cccc(C5CC5)c4n3)cc(NC[C@H]3CCNC[C@@H]3O)nc12] |
-continued
| Cmpd No. | Structure |
|---|---|
| H-APPAMP-014 | 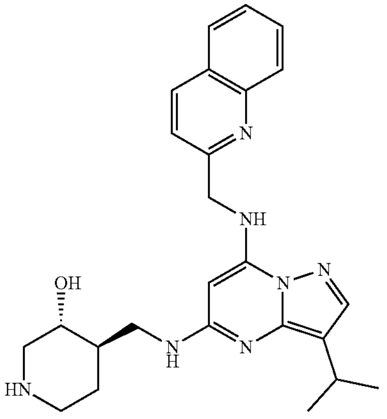 [SMILES: CC(C)c1cnn2c(NCc3ccc4ccccc4n3)cc(NC[C@H]3CCNC[C@@H]3O)nc12] |
| H-APPAMP-015 | 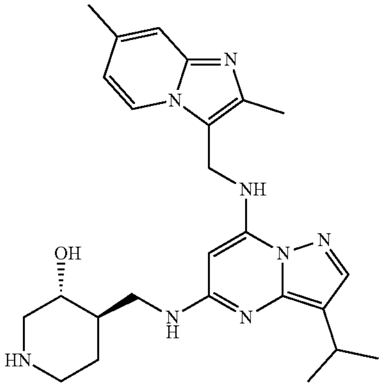 [SMILES: Cc1ccn2c(CNc3cc(NC[C@H]4CCNC[C@@H]4O)nc4c(C(C)C)cnn34)c(C)nc2c1] |
| H-APPAMP-016 | 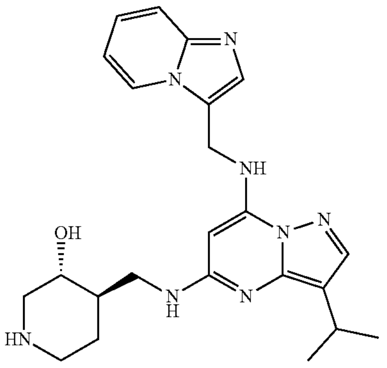 [SMILES: CC(C)c1cnn2c(NCc3cnc4ccccn34)cc(NC[C@H]3CCNC[C@@H]3O)nc12] |
| H-APPAMP-017 | 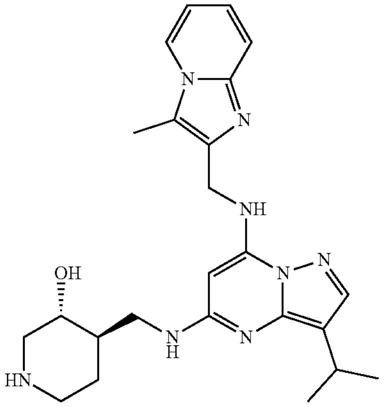 [SMILES: Cc1c(CNc2cc(NC[C@H]3CCNC[C@@H]3O)nc3c(C(C)C)cnn23)nc2ccccn12] |

-continued
| Cmpd No. | Structure |
| --- | --- |
| H-APPAMP-018 | 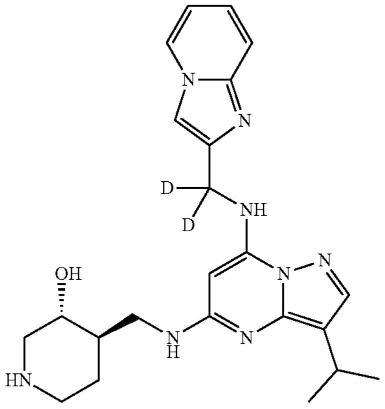 [SMILES: [2H]C([2H])(Nc1cc(NC[C@H]2CCNC[C@@H]2O)nc2c(C(C)C)cnn12)c1cn2ccccc2n1] |
| H-APPAMP-019 | 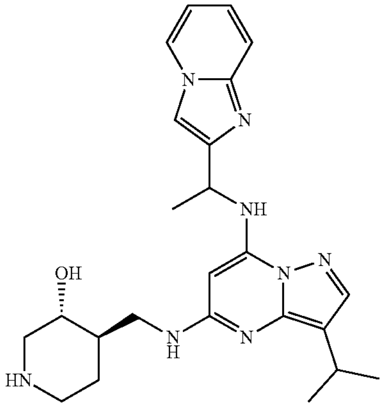 [SMILES: CC(C)c1cnn2c(NC(C)c3cn4ccccc4n3)cc(NC[C@H]3CCNC[C@@H]3O)nc12] |
| H-APPAMP-020 | 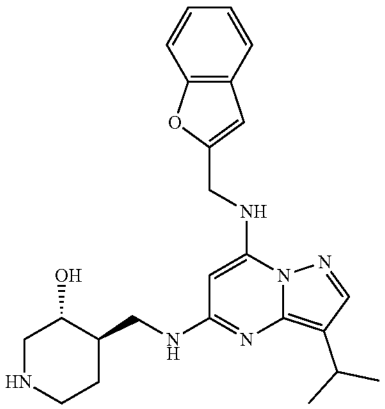 [SMILES: CC(C)c1cnn2c(NCc3cc4ccccc4o3)cc(NC[C@H]3CCNC[C@@H]3O)nc12] |
-continued
| Cmpd No. | Structure |
| --- | --- |
| H-APPAMP-021 | 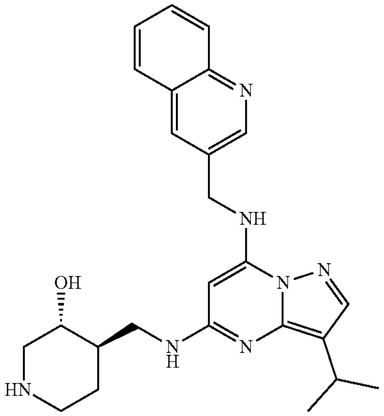 [SMILES: CC(C)c1cnn2c(NCc3cnc4ccccc4c3)cc(NC[C@H]3CCNC[C@@H]3O)nc12] |
| H-APPAMP-022 | 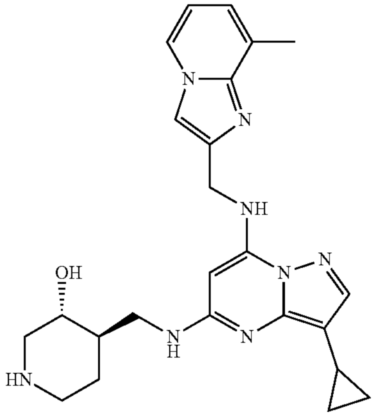 [SMILES: Cc1cccn2cc(CNc3cc(NC[C@H]4CCNC[C@@H]4O)nc4c(C5CC5)cnn34)nc12] |
| H-APPAMP-023 | 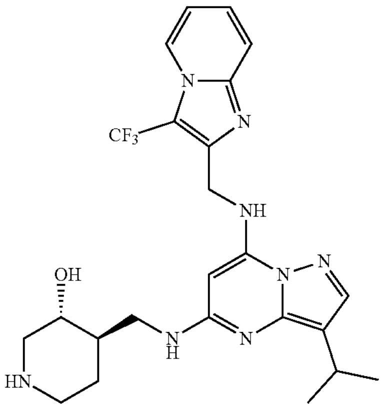 [SMILES: CC(C)c1cnn2c(NCc3nc4ccccn4c3C(F)(F)F)cc(NC[C@H]3CCNC[C@@H]3O)nc12] |

-continued
| Cmpd No. | Structure |
|---|---|
| H-APPAMP-024 | 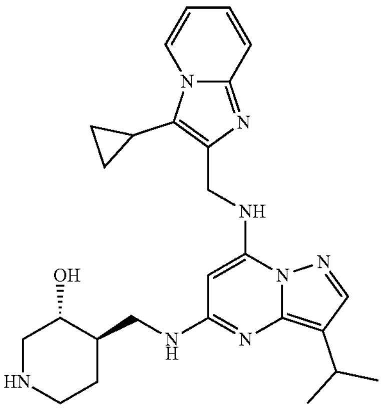 [SMILES: CC(C)c1cnn2c(NCc3nc4ccccn4c3C3CC3)cc(NC[C@H]3CCNC[C@@H]3O)nc12] |
| H-APPAMP-025 | 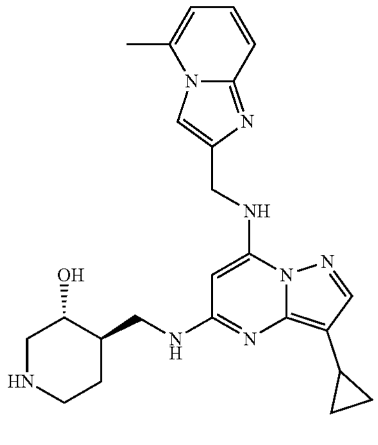 [SMILES: Cc1cccc2nc(CNc3cc(NC[C@H]4CCNC[C@@H]4O)nc4c(C5CC5)cnn34)cn12] |
| H-APPAMP-026 | 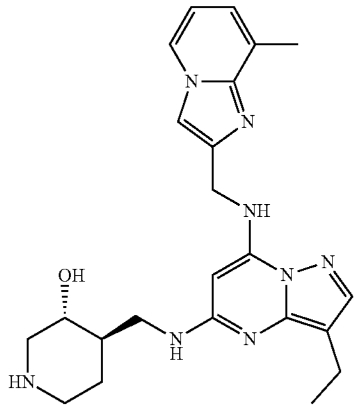 [SMILES: CCc1cnn2c(NCc3cn4cccc(C)c4n3)cc(NC[C@H]3CCNC[C@@H]3O)nc12] |
-continued
| Cmpd No. | Structure |
|---|---|
| H-APPAMP-027 | 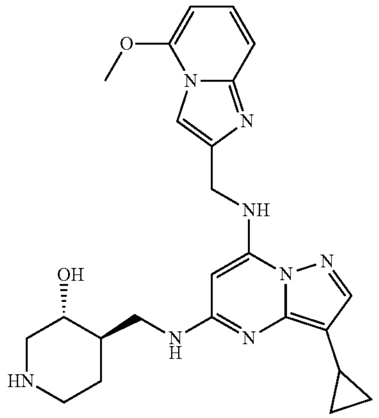 [SMILES: COc1cccc2nc(CNc3cc(NC[C@H]4CCNC[C@@H]4O)nc4c(C5CC5)cnn34)cn12] |
| H-APPAMP-028 | 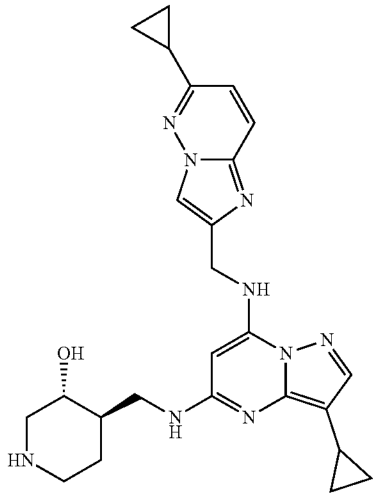 [SMILES: O[C@H]1CNCC[C@@H]1CNc1cc(NCc2cn3nc(C4CC4)ccc3n2)n2ncc(C3CC3)c2n1] |
| H-APPAMP-029 | 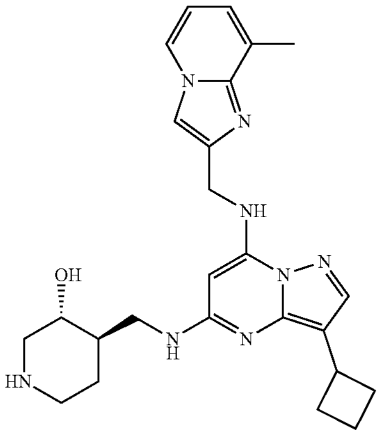 [SMILES: Cc1cccn2cc(CNc3cc(NC[C@H]4CCNC[C@@H]4O)nc4c(C5CCC5)cnn34)nc12] |

-continued
| Cmpd No. | Structure |
|---|---|
| H-APPAMP-030 | 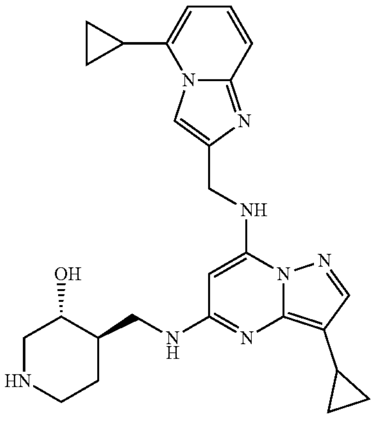 [SMILES: O[C@H]1CNCC[C@@H]1CNc1cc(NCc2cn3c(C4CC4)cccc3n2)n2ncc(C3CC3)c2n1] |
| H-APPAMP-031 | 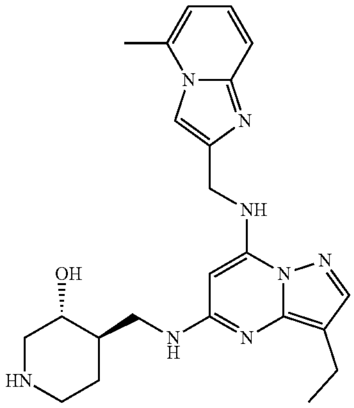 [SMILES: CCc1cnn2c(NCc3cn4c(C)cccc4n3)cc(NC[C@H]3CCNC[C@@H]3O)nc12] |
| H-APPAMP-032 | 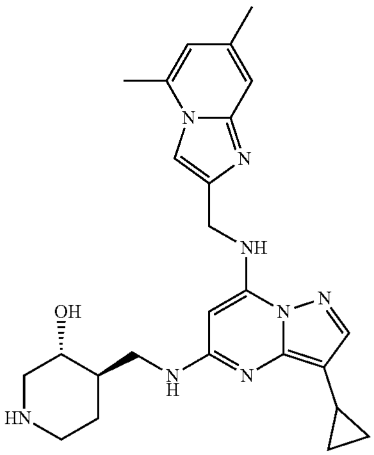 [SMILES: Cc1cc(C)n2cc(CNc3cc(NC[C@H]4CCNC[C@@H]4O)nc4c(C5CC5)cnn34)nc2c1] |
-continued
| Cmpd No. | Structure |
|---|---|
| H-APPAMP-033 | 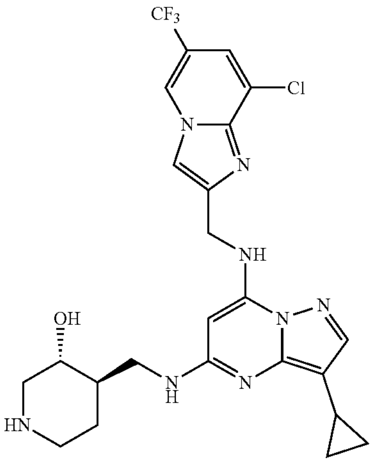 [SMILES: O[C@H]1CNCC[C@@H]1CNc1cc(NCc2cn3cc(C(F)(F)F)cc(Cl)c3n2)n2ncc(C3CC3)c2n1] |
| H-APPAMP-034 | 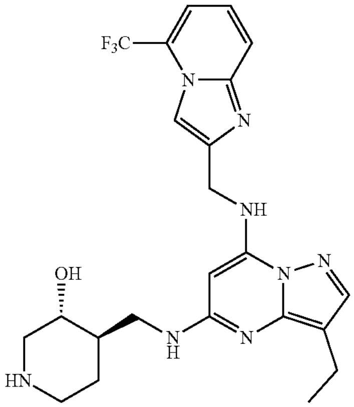 [SMILES: CCc1cnn2c(NCc3cn4c(C(F)(F)F)cccc4n3)cc(NC[C@H]3CCNC[C@@H]3O)nc12] |
| H-APPAMP-035 | 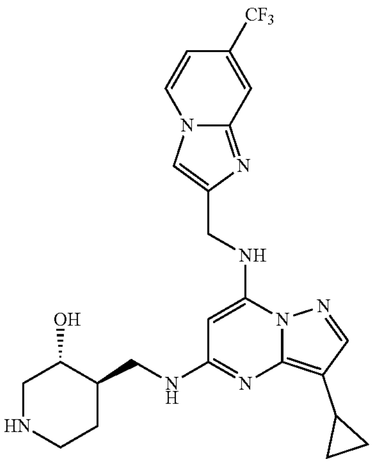 [SMILES: O[C@H]1CNCC[C@@H]1CNc1cc(NCc2cn3ccc(C(F)(F)F)cc3n2)n2ncc(C3CC3)c2n1] |

-continued
| Cmpd No. | Structure |
| --- | --- |
| H-APPAMP-036 | 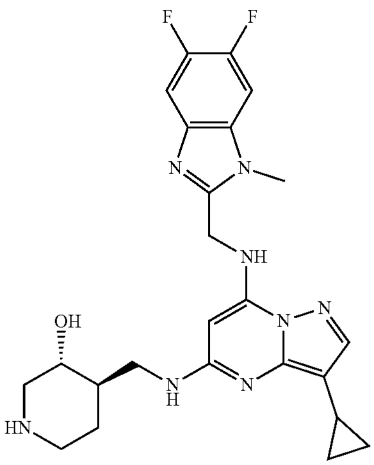 [SMILES: Cn1c(CNc2cc(NC[C@H]3CCNC[C@@H]3O)nc3c(C4CC4)cnn23)nc2cc(F)c(F)cc21] |
| H-APPAMP-037 | 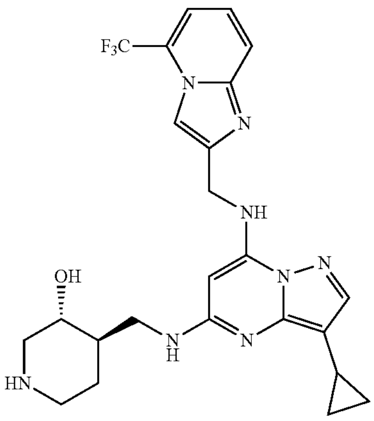 [SMILES: O[C@H]1CNCC[C@@H]1CNc1cc(NCc2cn3c(C(F)(F)F)cccc3n2)n2ncc(C3CC3)c2n1] |
| H-APPAMP-038 | 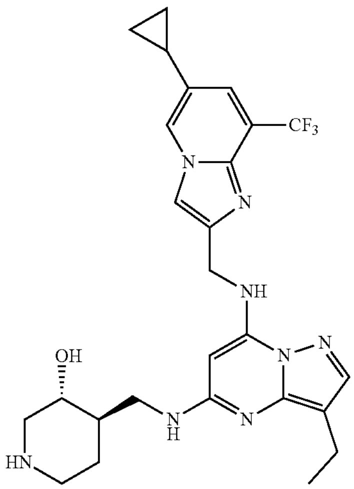 [SMILES: CCc1cnn2c(NCc3cn4cc(C5CC5)cc(C(F)(F)F)c4n3)cc(NC[C@H]3CCNC[C@@H]3O)nc12] |
-continued
| Cmpd No. | Structure |
| --- | --- |
| H-APPAMP-039 | 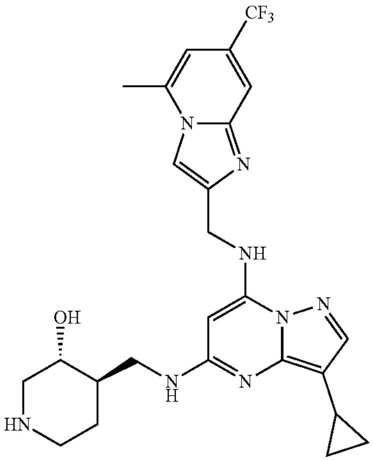 |
| H-APPAMP-040 | 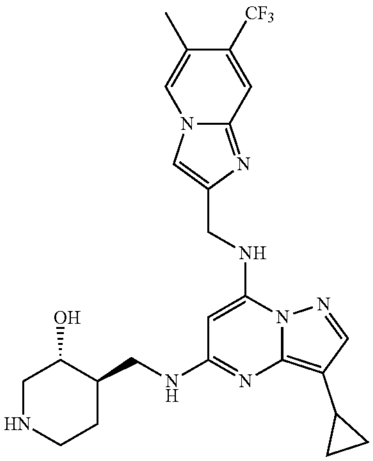 [SMILES: Cc1cn2cc(CNc3cc(NC[C@H]4CCNC[C@@H]4O)nc4c(C5CC5)cnn34)nc2cc1C(F)(F)F] |
| H-APPAMP-041 | 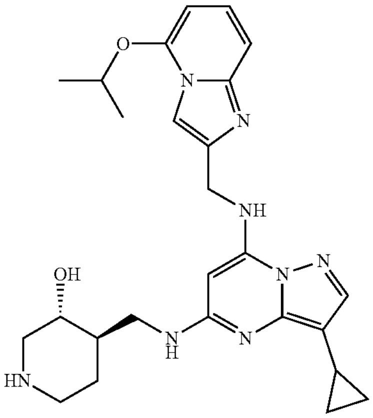 [SMILES: CC(C)Oc1cccc2nc(CNc3cc(NC[C@H]4CCNC[C@@H]4O)nc4c(C5CC5)cnn34)cn12] |

-continued

| Cmpd No. | Structure |
| --- | --- |
| H-APPAMP-042 | 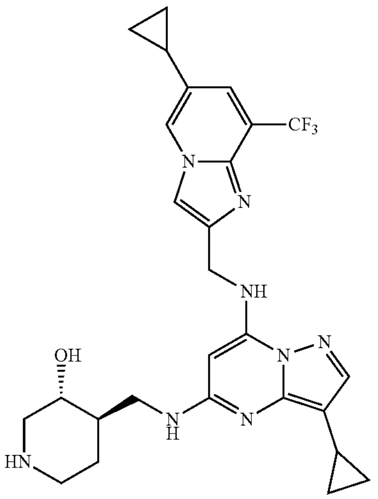 [SMILES: O[C@H]1CNCC[C@@H]1CNc1cc(NCc2cn3cc(C4CC4)cc(C(F)(F)F)c3n2)n2ncc(C3CC3)c2n1] |
| H-APPAMP-043 | 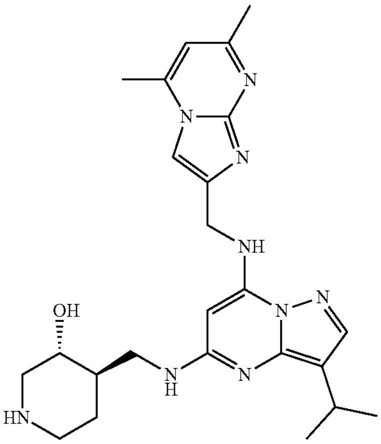 [SMILES: Cc1cc(C)n2cc(CNc3cc(NC[C@H]4CCNC[C@@H]4O)nc4c(C(C)C)cnn34)nc2n1] |
| H-APPAMP-044 | 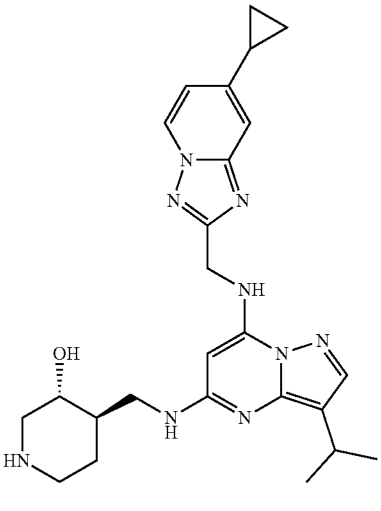 [SMILES: CC(C)c1cnn2c(NCc3nc4cc(C5CC5)ccn4n3)cc(NC[C@H]3CCNC[C@@H]3O)nc12] |

-continued

| Cmpd No. | Structure |
| --- | --- |
| H-APPAMP-045 | 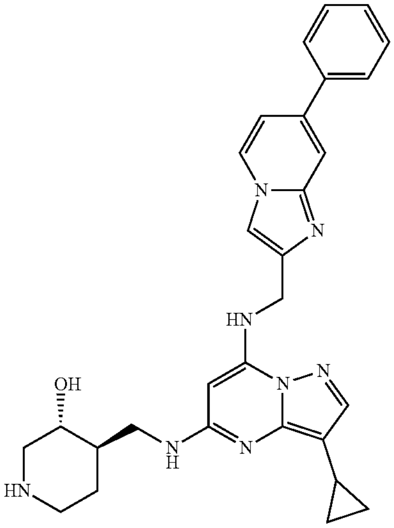 [SMILES: O[C@H]1CNCC[C@@H]1CNc1cc(NCc2cn3ccc(-c4ccccc4)cc3n2)n2ncc(C3CC3)c2n1] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $—R^7$, $-L^3-$, $—R^3$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In this context, the skilled person will readily appreciate that certain combinations of groups (e.g., substituents) may give rise to compounds which may not be readily synthesized and/or are chemically unstable. In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to H-APPAMP compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless otherwise specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, $—OCH_3$, is not to be construed as a reference to its structural isomer, a hydroxymethyl group, $—CH_2OH$. Similarly, a reference specifically to ortho-chlorophenyl is not to be construed as a reference to its structural isomer, meta-chlorophenyl.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro. A reference herein to one tautomer is intended to encompass both tautomers.

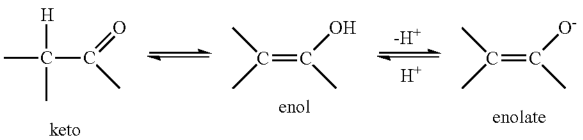

keto enol enolate

For example, 1H-pyridin-2-one-5-yl and 2-hydroxyl-pyridin-5-yl (shown below) are tautomers of one another. A reference herein to one is intended to encompass both.

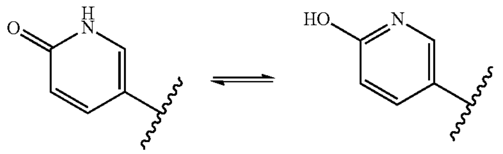

1H-pyridin-2-one-5-yl 2-hydroxyl-pyridin-5-yl

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group, which may be anionic (e.g., —COOH may be $—COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$ as well as the ammonium ion (i.e., $NH_4^+$). Examples of suitable organic cations include, but are not limited to substituted ammonium ions (e.g., $NH_3R^+$, $NH_2R_2^+$, $NHR_3^+$, $NR_4^+$), for example, where each R is independently linear or branched saturated $C_{1-18}$alkyl, $C_{3-8}$cycloalkyl, $C_{3-8}$cycloalkyl-$C_{1-6}$alkyl, and phenyl-$C_{1-6}$alkyl, wherein the phenyl group is optionally substituted. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group, which upon protonation may become cationic (e.g., $—NH_2$ may become $—NH_3^+$), then a salt may be formed with a suitable anion.

For example, if a parent structure contains a cationic group (e.g., $—NMe_2^+$), or has a functional group, which upon protonation may become cationic (e.g., $—NH_2$ may become $—NH_3^+$), then a salt may be formed with a suitable anion. In the case of a quaternary ammonium compound a counter-anion is generally always present in order to balance the positive charge. If, in addition to a cationic group (e.g., $—NMe_2^+$, $—NH_3^+$), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyloxybenzoic, acetic, trifluoroacetic, ascorbic, aspartic, benzoic, camphorsulfonic, cinnamic, citric, edetic, 1,2-ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Examples of suitable counter-ions which are especially suitable for quaternary ammonium compounds (e.g., those with a $—NMe_2^+$ group) include 1-adamantanesulfonate, benzenesulfonate, bisulfate, bromide, chloride, iodide, methanesulfonate, methylsulfate, 1,5-napthalene-bis-sulfonate, 4-nitrobenzenesulfonate, formate, tartrate, tosylate, trifluoroacetate, trifluoromethylsulfonate, sulphate. Again, if the compound also contains a group capable of forming an anion (e.g., —COOH), then an inner salt may be formed.

Unless otherwise specified, a reference to a particular compound also includes salt forms thereof.

Solvates and Hydrates

It may be convenient or desirable to prepare, purify, and/or handle a corresponding solvate of the compound. The term “solvate” is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term “chemically protected form” is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (alternatively as a masked or masking group or a blocked or blocking group). By protecting a reactive functional group, reactions involving other unprotected reactive functional groups can be performed, without affecting the protected group; the protecting group may be removed or the masking group transformed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such “protecting,” “blocking,” or “masking” methods are widely used and well known in organic synthesis. For example, a compound which has two nonequivalent reactive functional groups, both of which would be reactive under specified conditions, may be derivatized to render one of the functional groups “protected,” and therefore unreactive, under the specified conditions; so protected, the compound may be used as a reactant which has effectively only one reactive functional group. After the desired reaction (involving the other functional group) is complete, the protected group may be “deprotected” to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester ($—OC(=O)CH_3$, —OAc).

For example, an aldehyde or ketone group may be protected as an acetal ($R—CH(OR)_2$) or ketal ($R_2C(OR)_2$), respectively, in which the carbonyl group (>C=O) is converted to a 1,1-diether ($>C(OR)_2$), by reaction with, for example, a primary alcohol in the presence of an acid. The aldehyde or ketone group is readily regenerated, for example, by hydrolysis using water in the presence of acid.

For example, an amine group may be protected, for example, as an amide (—NRCO—R) or a urethane (—NRCO—OR), for example, as: an acetamide ($—NHCO—CH_3$); a benzyloxy amide ($—NHCO—OCH_2C_6H_5$, —NH-Cbz); as a t-butoxy amide ($—NHCO—OC(CH_3)_3$, —NH-Boc); a 2-biphenyl-2-propoxy amide ($—NHCO—OC(CH_3)_2C_6H_4C_6H_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O•).

For example, a carboxylic acid group may be protected as an ester for example, as: an $C_{1-7}$alkyl ester (e.g., a methyl ester; a t-butyl ester); a $C_{1-7}$haloalkyl ester (e.g., a 2,2,2-trihaloethyl ester); a 2-tri($C_{1-7}$alkyl)silyl-ethyl ester; or a $C_{5-20}$aryl-$C_{1-7}$alkyl ester (e.g., a benzyl ester; a nitrobenzyl ester); or as an amide or hydrazide, for example, as acetamide or a N,N,N-trimethylhydrazide.

For example, a thiol group may be protected as a thioether (—SR), for example, as: a benzyl thioether; an acetamidomethyl ether ($—S—CH_2NHC(=O)CH_3$).

Prodrugs

It may be convenient or desirable to prepare, purify, and/or handle the compound in the form of a prodrug. The term “prodrug,” as used herein, pertains to a compound, which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound, which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

Compositions

One aspect of the present invention pertains to a composition (e.g., a pharmaceutical composition) comprising an H-APPAMP compound, as described herein, and a pharmaceutically acceptable carrier, diluent, or excipient.

Another aspect of the present invention pertains to a method of preparing a composition (e.g., a pharmaceutical composition) comprising mixing an H-APPAMP compound, as described herein, and a pharmaceutically acceptable carrier, diluent, or excipient.

Uses

The H-APPAMP compounds described herein are useful in the treatment of, for example, proliferative disorders (as “anti-proliferative agents”), cancer (as “anti-cancer agents”), viral infections (as “anti-viral agents”), neurodegenerative diseases (as “anti-neurodegenerative agents”), etc.

Use in Methods of Inhibiting CDK

One aspect of the present invention pertains to a method of inhibiting CDK (e.g., CDK12 and/or CDK13) function (e.g., in a cell), in vitro or in vivo, comprising contacting the cell with an effective amount of an H-APPAMP compound, as described herein.

One of ordinary skill in the art is readily able to determine whether or not a candidate compound inhibits CDK (e.g., CDK12 and/or CDK13). For example, suitable assays are described herein or are known in the art.

In one embodiment, the method is performed in vitro.

In one embodiment, the method is performed in vivo.

In one embodiment, the H-APPAMP compound is provided in the form of a pharmaceutically acceptable composition.

Any type of cell may be treated, including adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of “effect,” the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Cell Proliferation, Etc.

The H-APPAMP compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an H-APPAMP compound, as described herein.

In one embodiment, the method is a method of regulating (e.g., inhibiting) cell proliferation (e.g., proliferation of a cell), in vitro or in vivo, comprising contacting a cell with an effective amount of an H-APPAMP compound, as described herein.

In one embodiment, the method is performed in vitro.

In one embodiment, the method is performed in vivo.

In one embodiment, the H-APPAMP compound is provided in the form of a pharmaceutically acceptable composition.

Any type of cell may be treated, including lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays, which may conveniently be used to assess the activity offered by a particular compound are described herein.

For example, a sample of cells (e.g., from a tumour) may be grown in vitro and a compound brought into contact with said cells, and the effect of the compound on those cells observed. As an example of “effect,” the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an H-APPAMP compound, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of an H-APPAMP compound, as described herein, in the manufacture of a medicament, for example, for use in a method of treatment, for example, for use a method of treatment of a disorder (e.g., a disease) as described herein.

In one embodiment, the medicament comprises the H-APPAMP compound.

Methods of Treatment

Another aspect of the present invention pertains to a method of treatment, for example, a method of treatment of a disorder (e.g., a disease) as described herein, comprising administering to a subject in need of treatment a therapeutically-effective amount of an H-APPAMP compound, as described herein, preferably in the form of a pharmaceutical composition.

Disorders Treated—Disorders Associated with CDK

In one embodiment (e.g., for use in methods of therapy, of use in the manufacture of medicaments, of methods of treatment), the treatment is treatment of: a disorder (e.g., a disease) that is associated with CDK, especially CDK12 and/or CDK13; a disorder (e.g., a disease) resulting from an inappropriate activity of a CDK, especially CDK12 and/or CDK13; a disorder (e.g., a disease) that is associated with CDK mutation, especially CDK12 and/or CDK13 mutation; a disorder (e.g., a disease) that is associated with CDK overexpression, especially CDK12 and/or CDK13 overexpression; a disorder (e.g., a disease) that is associated with upstream pathway activation of CDK, especially CDK12 and/or CDK13; a disorder (e.g., a disease) that is ameliorated by the inhibition (e.g., selective inhibition) of CDK, especially CDK12 and/or CDK13.

In one embodiment (e.g., for use in methods of therapy, of use in the manufacture of medicaments, of methods of treatment), the treatment is treatment of a disorder (e.g., a disease) that is associated with CDK, especially CDK12 and/or CDK13.

In one embodiment, the treatment is treatment of: a disorder (e.g., a disease) resulting from an inappropriate activity of CDK, especially CDK12 and/or CDK13.

In one embodiment, the treatment is treatment of: a disorder (e.g., a disease) that is associated with CDK mutation, especially CDK12 mutation; CDK overexpression, especially CDK12 and/or CDK13 overexpression (e.g., as compared to corresponding normal cells; e.g., wherein the overexpression is by a factor of 1.5, 2, 3, 5, 10, 20 or 50); or upstream pathway activation of CDK, especially CDK12 and/or CDK13.

In one embodiment, the treatment is treatment of a disorder (e.g., a disease) that is ameliorated by the inhibition (e.g., selective inhibition) of CDK, especially CDK12 and/or CDK13.

Disorders Treated

In one embodiment (e.g., for use in methods of therapy, of use in the manufacture of medicaments, of methods of treatment), the treatment is treatment of: a proliferative disorder; cancer; a viral infection (e.g., HIV); a neurodegenerative disorder (e.g., Alzheimer's disease, Parkinson's disease); ischaemia; a renal disease; a cardiovascular disorder (e.g., atherosclerosis); or an autoimmune disorder (e.g., rheumatoid arthritis).

In one embodiment (e.g., for use in methods of therapy, of use in the manufacture of medicaments, of methods of treatment), the treatment is treatment of: a disorder (e.g., a disease) caused by dysfunction of translation in cells, for example, muscular dystrophy, amyotrophic lateral sclerosis, spinal muscular atrophy, and Fragile X syndrome.

In one embodiment (e.g., for use in methods of therapy, of use in the manufacture of medicaments, of methods of treatment), the treatment is treatment of: a disorder (e.g., a disease) in a patient who has received prior therapeutic treatments, but who receives little or no further clinical benefit from those treatments. This includes, for example, patients who have received prior therapeutic treatments with PARP inhibitors, CDK inhibitors, and/or HER2 directed therapies (see, e.g., Johnson et al., 2016; Choi et al., 2019).

Disorders Treated—Proliferative Disorders

In one embodiment (e.g., for use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as neoplastic or hyperplastic growth.

In one embodiment, the treatment is treatment of: a proliferative disorder characterised by benign, pre-malignant, or malignant cellular proliferation.

In one embodiment, the treatment is treatment of: hyperplasia; a neoplasm; a tumour (e.g., a histocytoma, a glioma, an astrocyoma, an osteoma); cancer; psoriasis; a bone disease; a fibroproliferative disorder (e.g., of connective tissues); pulmonary fibrosis; atherosclerosis; or smooth muscle cell proliferation in the blood vessels (e.g., stenosis or restenosis following angioplasty).

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer metastasis.

Included among cancers are:

(1) Carcinomas, including tumours derived from stratified squamous epithelia (squamous cell carcinomas) and tumours arising within organs or glands (adenocarcinomas). Examples include breast, colon, lung, prostate, ovary.

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and haemangioendothelioma (blood vessels); liposarcoma (adipose tissue); glioma and astrocytoma (neurogenic connective tissue found in the brain); myxosarcoma (primitive embryonic connective tissue); mesenchymous and mixed mesodermal tumour (mixed connective tissue types).

(3) Myeloma.

(4) Haematopoietic tumours, including: myelogenous and granulocytic leukaemia (malignancy of the myeloid and granulocytic white blood cell series), e.g., chronic myeloid leukemia (CML), acute myeloid leukemia (AML); lymphatic, lymphocytic, and lymphoblastic leukaemia (malignancy of the lymphoid and lymphocytic blood cell series), e.g., acute lymphoblastic leukemia (ALL), chronic lymphocytic leukemia (CLL); polycythaemia vera (malignancy of various blood cell products, but with red cells predominating).

(5) Lymphomas, including: Hodgkin and Non-Hodgkin lymphomas.

(6) Mixed Types, including, e.g., adenosquamous carcinoma; mixed mesodermal tumour; carcinosarcoma; teratocarcinoma.

For example, in one embodiment, the treatment is treatment of breast cancer.

In one embodiment, the cancer is associated with CDK, especially CDK12 and/or CDK13.

In one embodiment, the cancer is characterised by, or further characterised by, inappropriate activity of CDK, especially CDK12 and/or CDK13.

In one embodiment, the cancer is characterised by, or further characterised by, overexpression of CDK, especially CDK12 and/or CDK13.

In one embodiment, the cancer is characterised by, or further characterised by, an amplification of the CDK12 and/or CDK13 gene, including, for example, cancers overexpressing the protein HER2 where the 17q12-q21 locus is amplified (see, e.g., Choi et al., 2019).

In one embodiment, the cancer is characterised by, or further characterised by, a fusion of genes that cause cancers to appear, including, for example, cancers that have gene fusions of EWS-FLI (see, e.g., Inigues et al., 2018), BCR-ABL, EML4-ALK, FGFR3-TACC3, KIF5B-RET, ETV6-RUNX1, or TMPRSS2-ERG.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), the promotion of apoptosis (programmed cell death), death by necrosis, or induction of death by autophagy. The compounds described herein may be used in the treatment of the cancers described herein, independent of the mechanisms discussed herein.

Disorders Treated—DNA Repair

In one embodiment (e.g., of use in methods of therapy, of use in the manufacture of medicaments, of methods of treatment), the treatment is treatment of a disorder (e.g., a disease) in a patient having under-expression, defects, and/or mutations in the genes of proteins that are involved in DNA repair, including, e.g., BRCA1, BRCA2, ATM, ATR, BAP1, CDK12, CDK13, CHK1, CHK2, FANCA, FANCC, FANCD2, FANCE, FANCF, FANCI, PALB2, NBS1, WRN, RAD51B, RAD51C, RAD51D, MRE11A, BLM, BRIP1. This includes, for example, cancer patients whose tumours display "BRCAness" (see, e.g., Lord et al., 2019).

In one embodiment (e.g., of use in methods of therapy, of use in the manufacture of medicaments, of methods of treatment), the treatment is treatment of a disorder (e.g., a disease) in a patient having under-expression, defects, and/or mutations in the genes of proteins that are involved in non-homologous DNA repair, including, e.g. XLF, RAD50, NBS1, MRE11, LIG4, XRCC4, POLL, POLM.

Disorders Treated—Viral Infections

In one embodiment (e.g., for use in methods of therapy, of use in the manufacture of medicaments, of methods of treatment), the treatment is treatment of a viral infection.

In one embodiment, the treatment is treatment of a viral infection by:

(Group I:) a dsDNA virus, e.g., an adenovirus, a herpesvirus, a poxvirus;
(Group II:) a ssDNA virus, e.g., a parvovirus;
(Group III:) a dsRNA virus, e.g., a reovirus;
(Group IV:) a (+)ssRNA virus, e.g., a picornavirus, a togavirus;
(Group V:) a (−)ssRNA virus, e.g., an orthomyxovirus, a rhabdovirus;
(Group VI:) a ssRNA-RT virus, e.g., a retrovirus; or
(Group VII:) a dsDNA-RT virus, e.g., a hepadnavirus.

As used above: ds: double strand; ss: +strand; (+)ssRNA: +strand RNA; (−)ssRNA: −strand RNA; ssRNA-RT: (+strand)RNA with DNA intermediate in life-cycle.

In one embodiment, the treatment is treatment of: human immunodeficiency virus (HIV); hepatitis B virus (HBV); hepatitis C virus (HCV); human papilloma virus (HPV); cytomegalovirus (CMV); or Epstein-Barr virus (EBV); human herpesvirus 8 (HHV) associated with Kaposi sarcoma; Coxsackievirus B3; Borna virus; influenza virus.

Disorders Treated—Autoimmune Disorders

In one embodiment (e.g., for use in methods of therapy, of use in the manufacture of medicaments, of methods of treatment), the treatment is treatment of an autoimmune disorder.

In one embodiment, the treatment is treatment of: an autoimmune disorder associated with connective tissue, joints, skin, or the eye.

In one embodiment, the treatment is treatment of: rheumatoid arthritis, systemic lupus erythematosus, psoriasis, or Sjogren's syndrome.

Disorders Treated—Disorders caused by Dysfunction of Translation in Cells

In one embodiment (e.g., for use in methods of therapy, of use in the manufacture of medicaments, of methods of treatment), the treatment is treatment of a disorder caused by dysfunction of translation in cells.

In one embodiment, the treatment is treatment of: muscular dystrophy, myotonic dystrophy, amyotrophic lateral sclerosis, spinal muscular atrophy, or Fragile X syndrome.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include chemotherapy (the administration of active agents, including, e.g., drugs, antibodies (e.g., as in immunotherapy), prodrugs (including, e.g., as in photodynamic therapy, GDEPT, ADEPT, etc.)); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the H-APPAMP compounds described herein include the following:

- an aromatase inhibitor, for example, exemestane (also known as Aromasin), letrozole (also known as Femara), anastrozole (also known as Arimidex), etc.;
- an anti-estrogen, for example, faslodex (also known as Fulvestrant and ICI182780), tamoxifen (also known as Nolvadex), hydroxytamoxifen, etc.;
- an anti-androgen, for example, an anti-androgen used in the treatment of prostate cancer, for example, flutamide, enzalutamide, apalutamide, bicalutamide, nilutamide, etc.;
- a Her2 blocker, for example, herceptin, pertuzumab, lapatinib, etc.;

a cytotoxic chemotherapeutic agent, for example, a taxane (e.g., paclitaxel also known as Taxol; docetaxel also known as Taxotere), cyclophosphamide, an antimetabolite (e.g., carboplatin, capecitabine, gemcitabine, doxorubicin, epirubicin, 5-fluorouracil, etc.), an agent stimulating the immune system, for example, a Toll-like receptor (TLR1-13) agonist, a Stimulator of Interferon Genes (STING) agonist, etc.;

a checkpoint inhibitor, for example, an inhibitor of PD1, PD1L, CTLA4, etc., for example, pembrolizumab, atezolizumab, ipilimumab, etc.;

a DNA repair inhibitor, for example, a PARP inhibitor, for example, Olaparib, Niraparib, etc.

Thus, in one embodiment, the treatment further comprises treatment (e.g., simultaneous or sequential treatment) with a further active agent which is, e.g., an aromatase inhibitor, an anti-estrogen, an anti-androgen, a Her2 blocker, a cytotoxic chemotherapeutic agent, an agent stimulating the immune system, a checkpoint inhibitor, a DNA repair inhibitor, etc.

Other Uses

The H-APPAMP compounds described herein may also be used as cell culture additives to inhibit CDK (e.g., CDK12 and/or CDK13).

The H-APPAMP compounds described herein may also be used as part of an in vitro assay, for example, in order to determine whether a candidate host is likely to benefit from treatment with the compound in question.

The H-APPAMP compounds described herein may also be used as a standard, for example, in an assay, in order to identify other active compounds, other CDK12 and/or CDK13 inhibitors, etc.

Kits

One aspect of the invention pertains to a kit comprising (a) an H-APPAMP compound as described herein, or a composition comprising an H-APPAMP compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The H-APPAMP compound or pharmaceutical composition comprising the H-APPAMP compound may be administered to a subject by any convenient route of administration, whether systemically/peripherally or topically (i.e., at the site of desired action).

Examples of routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for an H-APPAMP compound to be administered alone, it is preferable to present it as a pharmaceutical formulation (e.g., composition, preparation, medicament) comprising at least one H-APPAMP compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one H-APPAMP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier, which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection) include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes, which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the H-APPAMP compounds, and compositions comprising the H-APPAMP compounds, can vary from patient to patient. Determining the optimal dosage will generally involve the balancing of the level of therapeutic benefit against any risk or deleterious side effects. The selected dosage level will depend on a variety of factors including the activity of the particular H-APPAMP compound, the route of administration, the time of administration, the rate of excretion of the H-APPAMP compound, the duration of the treatment, other drugs, compounds, and/or materials used in combination, the severity of the disorder, and the species, sex, age, weight, condition, general health, and prior medical history of the patient. The amount of H-APPAMP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the H-APPAMP compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Synthesis

Abbreviations aq: aqueous;
Boc: tert-butoxycarbonyl;
$Boc_2O$: di-tert-butyl dicarbonate;
br: broad;
ca.: circa;
d: doublet;
$^t$BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate;
DCM: dichloromethane;
DCE: 1,2-dichloroethane;
dioxane: 1,4-dioxane;
DIPEA: diisopropylethylamine;
DMAP: 4-(Dimethylamino)pyridine;
EtOAc: ethyl acetate;
EtOH: ethanol;
h: hours;
HPLC: high performance liquid chromatography;
IPA: isopropanol;
LCMS: liquid chromatography—mass spectrometry;
LiHMDS: lithium hexamethyldisilazide;
m: multiplet;
M: molar, molecular ion;
mCPBA: 3-chloroperbenzoic acid;
MeCN: actetonitrile;
MeOH: methanol;
min: minutes;
MS: mass spectrometry;
NCS: N-chlorosuccinimide;
NIS: N-iodosuccinimide;
NMR: nuclear magnetic resonance;
$PdCl_2$(dppf)-DCM: [1,1'-Bis(diphenylphosphino)ferrocene]dichloropalladium(II), complex with dichloromethane;
q: quartet;
RT: room temperature (ca. 20° C.);
$R_T$: retention time;
s: singlet, solid;
SCX: strong cation exchange;
t: triplet;
TBME: tert-butyl methyl ether;
TFA: trifluoroacetic acid;
THF: tetrahydrofuran;
UPLC/MS: ultra performance liquid chromatography—mass spectrometry.

Other abbreviations are intended to convey their generally accepted meaning.

Nomenclature of structures was generated using 'Structure to Name' conversion from ChemDraw® Professional 17 (PerkinElmer).

General Synthetic Methods

Methods for the chemical synthesis of the H-APPAMP compounds are described herein. These and/or other well-known methods may be modified and/or adapted in known ways in order to provide alternative or improved methods of synthesis of the H-APPAMP compounds.

In a first method, the synthesis starts with the 5,7-dichloro-3-pyrazolo[1,5-a]pyrimidine derivative I-1. Nucleophilic aromatic substitution with amine affords the corresponding 5-amino-pyrazolopyrimidine I-2. Boc-protection of the amino group affords the intermediate I-3. The latter is used in a Buchwald-Hartwig cross-coupling to yield the intermediate I-4. Final global Boc-deprotection yields the target compounds.

This method is illustrated in the following chemical scheme. In one embodiment, R' is isopropyl.

Scheme 1

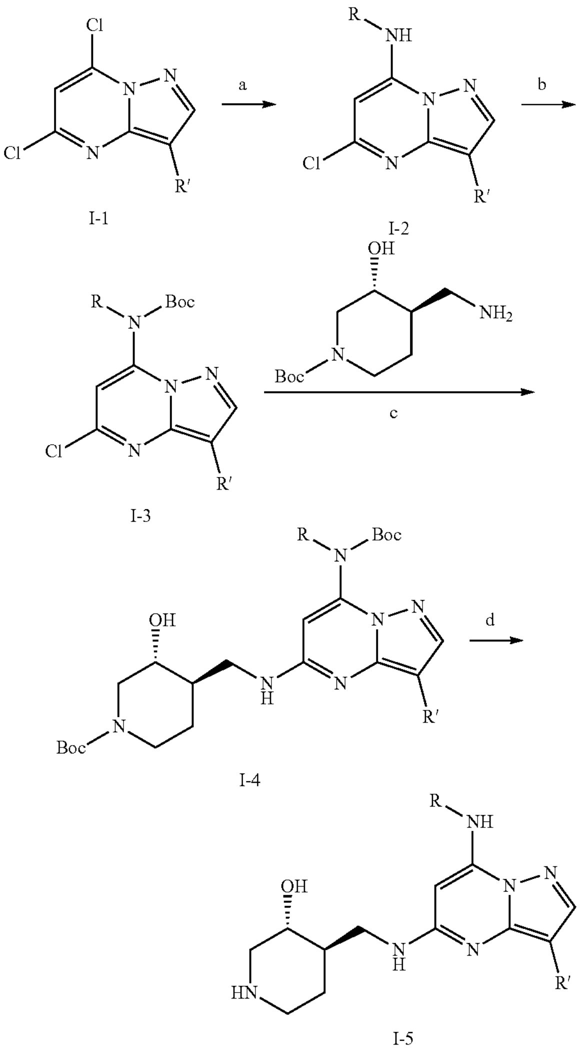

I-1
I-2
I-3
I-4
I-5

Representative reactions conditions for the above scheme are as follows: (a) $RNH_2$, DIPEA, EtOH, 50° C. to 90° C.; (b) $Boc_2O$, DMAP, THF, RT to 60° C.; (c) $^{t}$BuXPhos-Pd-G3, LiHMDS, THF, 60° C.; (d) TFA, DCM, RT; or HCl, dioxane, RT to 40° C.; for example:

(a) $RNH_2$, DIPEA, EtOH, 90° C.; (b) $Boc_2O$, DMAP, THF, RT; (c) $^{t}$BuXPhos-Pd-G3, LiHMDS, THF, 60° C.; (d) HCl, dioxane, RT.

In a second method, the synthesis starts with the 5,7-dichloro-3-pyrazolo[1,5-a]pyrimidine derivative I-1. Nucleophilic aromatic substitution with sodium thiomethoxide affords the thioether intermediate I-6. Buchwald-Hartwig cross-coupling leads to the formation of the intermediate I-7, which can be converted into sulfoxide intermediate I-8 by oxidation of the thioether. Nucleophilic aromatic substitution yields the 5-amino-pyrazolopyrimidine intermediate I-9. Final Boc-deprotection yields the target compounds.

This method is illustrated in the following chemical scheme. In one embodiment, R' is isopropyl.

Scheme 2

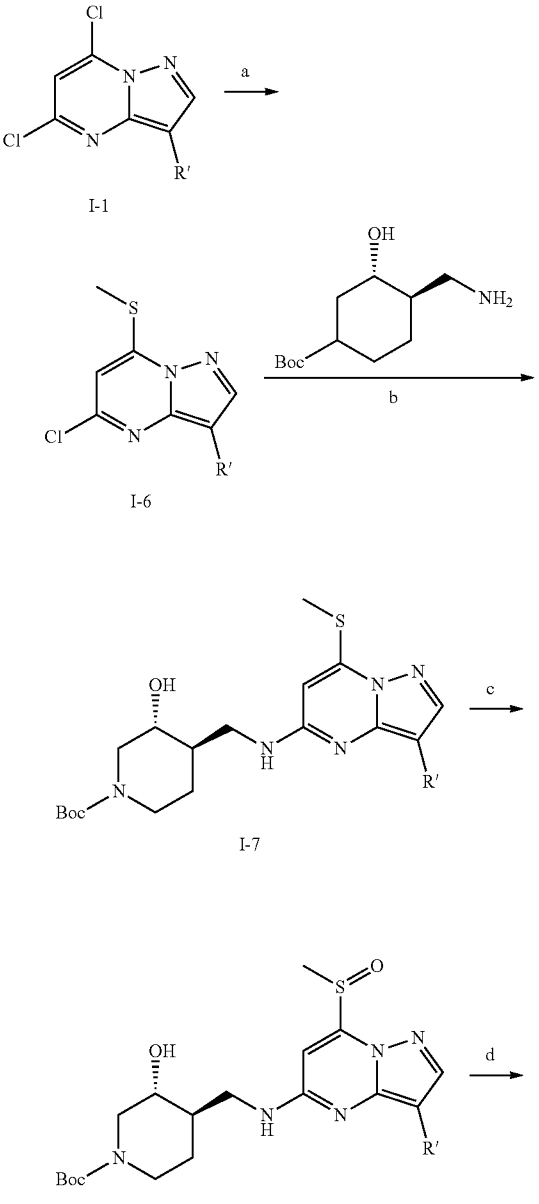

I-1
I-6
I-7
I-8

-continued

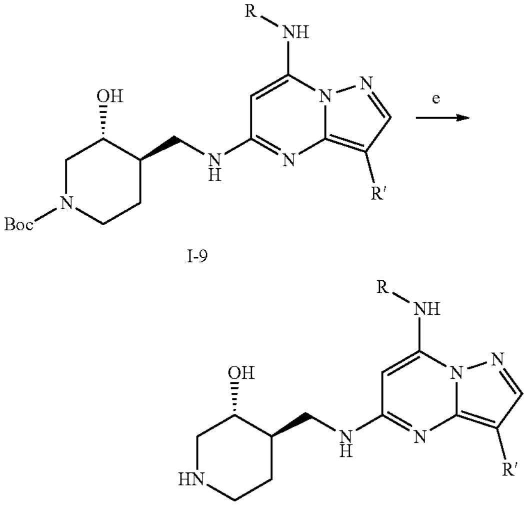

I-9

I-5

Representative reactions conditions for the above scheme are as follows: (a) MeSNa, THF, RT; (b) $^t$BuXPhos-Pd-G3, LiHMDS, THF, 60° C.; (c) mCPBA, DCM, RT; (d) $RNH_2$, DIPEA, dioxane, 110° C.; (e) TFA, DCM, RT; or HCl, dioxane, RT to 40° C.; for example:

(a) MeSNa, THF, RT; (b) $^t$BuXPhos-Pd-G3, LiHMDS, THF, 60° C.; (c) mCPBA, DCM, RT;

(d) $RNH_2$, DIPEA, dioxane, 110° C.; (e) TFA, DCM, RT; or HCl, dioxane, RT.

In a third method, the synthesis starts with the 5,7-dichloro-3-pyrazolo[1,5-a]pyrimidine derivative I-1. Nucleophilic aromatic substitution with ammonium hydroxide affords the corresponding 5-amino-pyrazolopyrimidine I-10. Boc-protection of the amino group affords the intermediate I-11. Substitution with alkyl halide RX affords intermediate I-3. The latter is used in a Buchwald-Hartwig cross-coupling to yield the intermediate I-4. Final global Boc-deprotection yields the target compounds.

This method is illustrated in the following chemical scheme. In one embodiment, R' is isopropyl.

Scheme 3

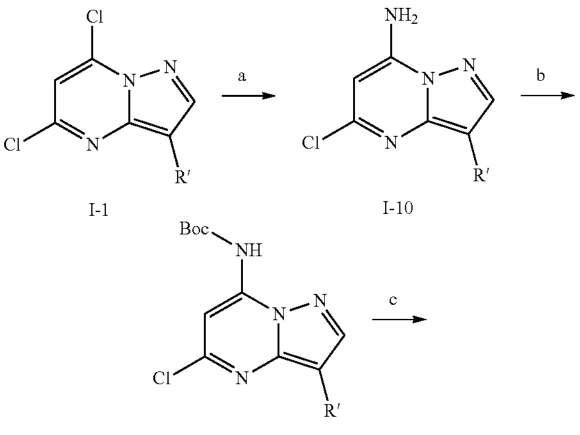

I-1 I-10

I-11

-continued

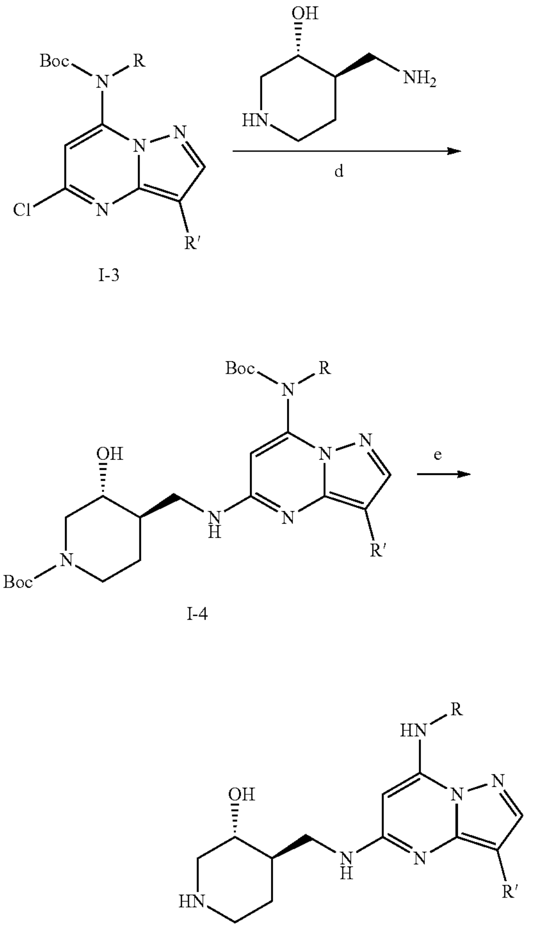

I-3

I-4

I-5

Representative reactions conditions for the above scheme are as follows: (a) $NH_4OH$, 85° C.; (b) $Boc_2O$, DMAP, THF, RT to 60° C.; (c) RCl, K2CO3 DMF, 70° C. (d) $^t$BuXPhos-Pd-G3, LiHMDS, THF, 60° C.; (e) TFA, DCM, RT; or HCl, dioxane, RT to 40° C.

In a fourth method, the synthesis starts with the 5,7-dichloro-3-pyrazolo[1,5-a]pyrimidine derivative I-1. Nucleophilic aromatic substitution with amine affords the corresponding 5-amino-pyrazolopyrimidine I-2. That is followed by a second nucleophilic aromatic substitution with amine to afford the intermediate I-4. Final Boc-deprotection yields the target compounds.

This method is illustrated in the following chemical scheme. In one embodiment, R' is isopropyl.

Scheme 4

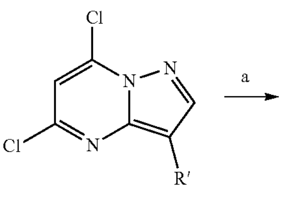

I-1

-continued

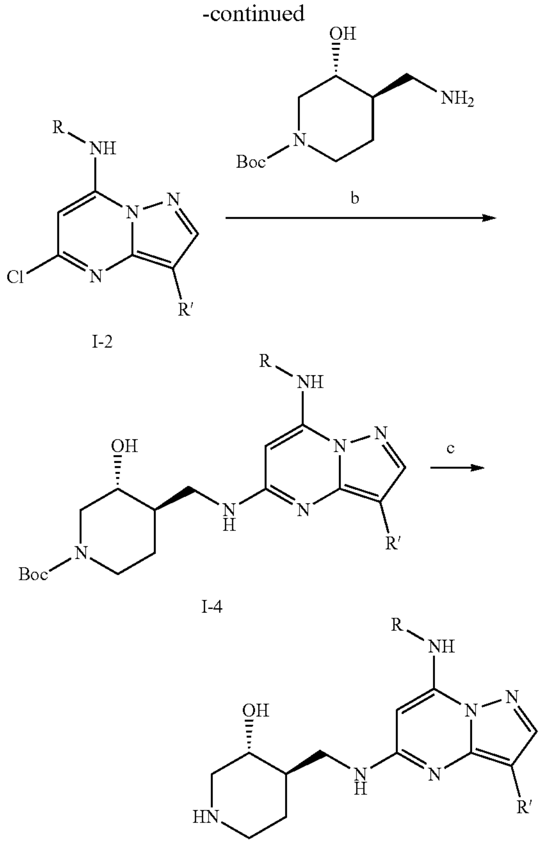

I-2

I-4

I-5

Representative reactions conditions for the above scheme are as follows: (a) $RNH_2$, DIPEA, EtOH, 50° C.; (b) DIPEA, NMP, 150° C., microwave; (c) $^t$BuXPhos-Pd-G3, LiHMDS, THF, 60° C.; (d) HCl, dioxane, 35° C.

Chemical Synthesis Examples

The following examples are provided solely to illustrate the present invention and are not intended to limit the scope of the invention, as described herein.

General Experimental Conditions

All starting materials and solvents were obtained either from commercial sources or prepared according to the literature citation. Reaction mixtures were magnetically stirred unless otherwise indicated.

Column chromatography was performed on an automated flash chromatography system, such as a CombiFlash Rf system, using Grace™ GraceResolv™ pre-packed silica (40 μm) cartridges, unless otherwise indicated.

$^1$H NMR spectra were recorded using a Bruker Avance III spectrometer (400 MHz) or Bruker (500 MHz). Chemical shifts are expressed in parts per million using either the central peaks of the residual protic solvent or an internal standard of tetramethylsilane as references. The spectra were recorded at ambient temperature unless otherwise stated.

Analytical LCMS experiments to determine retention times and associated mass ions were performed using an Agilent 1200 series HPLC system coupled to an Agilent 6110 or 6120 series single quadrupole mass spectrometer running Method 1 or Method 2 described below.

Preparative HPLC purifications were performed using a Waters X-Bridge BEH C18, 5 μm, 19×50 mm column using a gradient of MeCN and 10 mM ammonium bicarbonate (aq).

Fractions were collected following detection by UV at a single wavelength measured by a variable wavelength detector.

SCX resin was purchased from Sigma Aldrich or Silicycle and washed with MeOH prior to use.

Analytical Methods

Method 1—LCMS Acidic 4 Min Method:

Column: Waters X-Select CSH C18, 2.5 μm, 4.6×30 mm
Detection: UV at 254 nm unless otherwise indicated
MS ionisation: Electrospray
Solvent A: Water/0.1% Formic acid
Solvent B: MeCN/0.1% Formic acid

| Method 1-Gradient | | | |
|---|---|---|---|
| Time | % A | % B | Flow rate (ml/min) |
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 2—LCMS Basic 4 Min Method:

Column: Waters X-Bridge BEH C18, 2.5 μm, 4.6×30 mm
Solvent A: Water/10 mM ammonium bicarbonate
Solvent B: MeCN
(other parameters are the same as for Method 1)

Method 3—UPLC/MS Acidic 3 Min Method:

Column: Waters Acquity CSH C18 (2.1×30 mm)
Detection: Waters Acquity PDA detector between 210 and 400 nm
MS ionisation: Electrospray
Solvent A: Water/0.1% Formic acid
Solvent B: MeCN/0.1% Formic acid
Column maintained at a temperature of 40° C. and eluted with a linear acetonitrile gradient from 95.0% A to 5.0% B over 3 min and at a constant flow rate of 0.77 mL/min.

Method 4—UPLC/MS Basic 3 Min Method:

Column: Waters Acquity BEH C18 column (2.1×30 mm)
Detection: Waters Acquity PDA detector between 210 and 400 nm
MS ionisation: Electrospray
Solvent A: Water/10 mM ammonium bicarbonate
Solvent B: MeCN
(other parameters are the same as for Method 3)

Method 5—UPLC/MS Basic 3 Min Method:

Column: Waters Acquity BEH C18 column (2.1×30 mm)
Detection: Waters Acquity PDA detector between 210 and 400 nm
MS ionisation: Electrospray
Solvent A: Water/10 mM ammonium hydroxide
Solvent B: MeCN
(other parameters are the same as for Method 3)

Method 6—UPLC/MS Basic 1 Min Method:

Column: Waters Acquity BEH C18 column (2.1×30 mm)
Detection: Waters Acquity PDA detector between 210 and 400 nm
MS ionisation: Electrospray
Solvent A: Water/10 mM ammonium bicarbonate
Solvent B: MeCN Column maintained at a temperature of 40° C. and eluted with a linear acetonitrile gradient from 95.0% A to 5.0% B over 1 min and at a constant flow rate of 0.77 mL/min.

Synthesis 1

(3R,4R)-4-(((7-((imidazo[1,2-a]pyridin-2-ylmethyl)amino)-3-isopropylpyrazolo[1,5-a]pyrimidin-5-yl)amino)methyl)piperidin-3-ol (H-APPAMP-003)

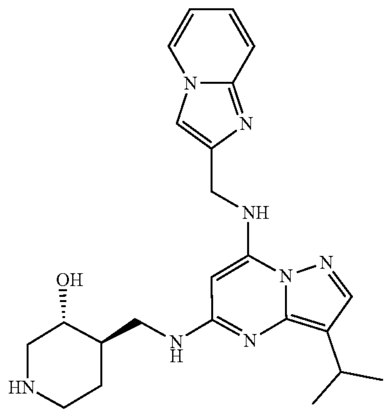 [SMILES: CC(C)c1cnn2c(NCc3cn4ccccc4n3)cc(NC[C@H]3CCNC[C@@H]3O)nc12]

Step 1

5-Chloro-N-(imidazo[1,2-a]pyridin-2-ylmethyl)-3-isopropylpyrazolo[1,5-a]pyrimidin-7-amine Imidazo[1,2-a]pyridin-2-ylmethanamine, 2HCl (0.175 g, 0.80 mmol) was added to a solution of 5,7-dichloro-3-isopropylpyrazolo[1,5-a]pyrimidine (0.122 g, 0.53 mmol) and DIPEA (0.74 ml, 4.24 mmol) in EtOH (10 mL). The reaction mixture was heated at 90° C. for 6 h. The reaction mixture was concentrated in vacuo and the residue was partitioned between EtOAc (50 mL) and water (50 mL). The aq layer was extracted with EtOAc (3×50 mL) and the combined organic layers were dried over $Na_2SO_4$ and concentrated under reduced pressure to give the title compound (0.160 g, 0.42 mmol, 80% yield, 90% purity) as a white solid.

UPLC/MS (Method 4): m/z 341 (M+H)+, $R_T$ 1.38 min.

Step 2 tert-Butyl (5-chloro-3-isopropylpyrazolo[1,5-a]pyrimidin-7-yl)(imidazo[1,2-a]pyridin-2-ylmethyl)carbamate BOC-anhydride (0.14 mL, 0.61 mmol) was added to a solution of 5-chloro-N-(imidazo[1,2-a]pyridin-2-ylmethyl)-3-isopropylpyrazolo[1,5-a]pyrimidin-7-amine (0.160 g, 0.47 mmol) and DMAP (0.011 g, 0.09 mmol) in THE (10 mL). The reaction mixture was stirred at RT for 16 h. The reaction mixture was concentrated under reduced pressure and the residue partitioned between DCM (20 mL) and water (30 mL). The aq layer was extracted with DCM (2×10 mL) and the combined organic layers were washed with brine (30 mL), dried over $Na_2SO_4$ and concentrated under reduced pressure. Purification by column chromatography (80 g cartridge, 0-10% MeOH/DCM) gave the title compound (0.170 g, 0.37 mmol, 78% yield, 95% purity) as a cream solid.

UPLC/MS (Method 4): m/z 441 (M+H)+, $R_T$ 1.73 min.

Step 3 tert-Butyl (3R,4R)-4-(((7-((tert-butoxycarbonyl)(imidazo[1,2-a]pyridin-2-ylmethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(imidazo[1,2-a]pyridin-2-ylmethyl)carbamate (0.150 g, 0.34 mmol), (3R,4R)-tert-butyl 4-(aminomethyl)-3-hydroxypiperidine-1-carboxylate (0.094 g, 0.41 mmol) and $^t$BuBrettPhos Pd G3 (0.029 g, 0.03 mmol) in THE (3 mL) was degassed with $N_2$ for 10 minutes. LiHMDS (1 M in THF) (0.51 ml, 0.51 mmol) was added in one portion under bubbling $N_2$. Bubbling was ceased and the reaction mixture was heated to 60° C. for 1 h. The reaction was quenched with water (5 mL) and extracted with EtOAc (3×10 mL). The combined organic layers were dried over $Na_2SO_4$ and concentrated under reduced pressure. Purification by column chromatography (12 g cartridge, 0-10% MeOH/DCM) gave the title compound (0.075 g, 0.12 mmol, 34% yield, 98% purity) as a white solid.

UPLC/MS (Method 4): m/z 635 (M+H)+, $R_T$ 1.65 min.

Step 4

(3R,4R)-4-(((7-((imidazo[1,2-a]pyridin-2-ylmethyl)amino)-3-isopropylpyrazolo[1,5-a]pyrimidin-5-yl)amino)methyl)piperidin-3-ol Hydrogen chloride (4 M in dioxane) (0.44 mL, 1.77 mmol) was added to a solution of tert-butyl (3R,4R)-4-(((7-((tert-butoxycarbonyl)(imidazo[1,2-a]pyridin-2-ylmethyl)amino)-3-isopropylpyrazolo[1,5-a]pyrimidin-5-yl)amino)methyl)-3-hydroxypiperidine-1-carboxylate (0.075 g, 0.12 mmol) in DCM (10 mL). The reaction mixture was stirred for 16 h at RT and concentrated in vacuo. The residue was diluted in MeOH (5 mL) and loaded onto a SCX cartridge, washed with MeOH (ca. 5 mL) and eluted with 0.7 M ammonia in MeOH (ca. 5 mL). The ammoniacal methanol solution was concentrated under reduced pressure. Purification by column chromatography (4 g cartridge, 0-10% MeOH (containing 0.7M $NH_3$)/DCM) gave the title compound (0.030 g, 0.07 mmol, 57% yield, 95% purity) as a clear glass solid.

UPLC/MS (Method 4): m/z 435 (M+H)+, $R_T$ 0.96 min.

$^1$H NMR (500 MHz, DMSO-$d_6$) δ 8.50-8.46 (m, 1H), 7.78 (s, 1H), 7.65 (t, J=6.3 Hz, 1H), 7.63 (s, 1H), 7.50 (d, J=9.1 Hz, 1H), 7.24-7.16 (m, 1H), 6.85 (td, J=6.8, 1.2 Hz, 1H), 6.76-6.70 (m, 1H), 5.35-5.30 (m, 1H), 5.28 (s, 1H), 4.56 (d, J=5.9 Hz, 2H), 4.12-4.05 (m, 1H), 3.60-3.48 (m, 1H), 3.17 (d, J=4.2 Hz, 1H), 3.06-2.99 (m, 1H), 2.98-2.92 (m, 1H), 2.92 (dd, J=11.6, 4.8 Hz, 1H), 2.81-2.74 (m, 1H), 2.30 (td, J=12.2, 2.7 Hz, 1H), 2.16 (dd, J=11.6, 9.9 Hz, 1H), 1.58-1.51 (m, 1H), 1.38-1.28 (m, 1H), 1.23 (t, J=6.5 Hz, 6H), 1.19-1.10 (m, 1H).

Synthesis 2

(3R,4R)-4-(((7-((imidazo[1,2-a]pyrimidin-2-ylmethyl)amino)-3-isopropylpyrazolo[1,5-a]pyrimidin-5-yl)amino)methyl)piperidin-3-ol (H-APPAMP-002)

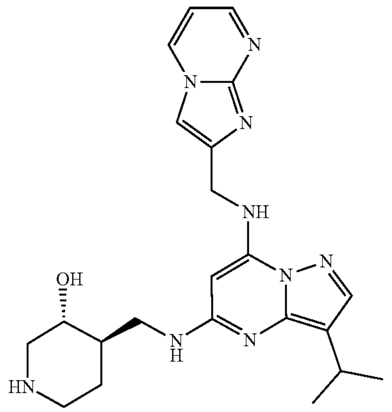 [SMILES: CC(C)c1cnn2c(NCc3cn4cccnc4n3)cc(NC[C@H]3CCNC[C@@H]3O)nc12]

Step 1

5-Chloro-N-(imidazo[1,2-a]pyrimidin-2-ylmethyl)-3-isopropylpyrazolo[1,5-a]pyrimidin-7-amine Imidazo[1,2-a]pyrimidin-2-ylmethanamine, 2HCl (5.04 g, 22.82 mmol) was added to a solution of 5,7-dichloro-3-isopropylpyrazolo[1,5-a]pyrimidine (3.50 g, 15.21 mmol) and DIPEA (21.3 ml, 122.0 mmol) in EtOH (80 mL). The reaction mixture was heated at 90° C. for 5 h. The reaction mixture was concentrated in vacuo and the residue was partitioned between EtOAc (50 mL) and water (50 mL). The aq layer was extracted with EtOAc (3×50 mL) and the combined organic layers were dried over $Na_2SO_4$ and concentrated under reduced pressure to give the title compound (5.10 g, 14.62 mmol, 96% yield, 98% purity) as a white solid.

UPLC/MS (Method 3): m/z 342 (M+H)+, $R_T$ 1.06 min

Step 2 tert-Butyl (5-chloro-3-isopropylpyrazolo[1,5-a]pyrimidin-7-yl)(imidazo[1,2-a]pyrimidin-2-ylmethyl)carbamate BOC-Anhydride (3.2 ml, 13.69 mmol) was added to a solution of 5-chloro-N-(imidazo[1,2-a]pyrimidin-2-ylmethyl)-3-isopropylpyrazolo[1,5-a]pyrimidin-7-amine (3.60 g, 10.53 mmol) and DMAP (0.26 g, 2.11 mmol) in THE (10 mL). The reaction mixture was stirred at RT for 16 h. The reaction mixture was concentrated under reduced pressure and the residue partitioned between DCM (20 mL) and water (30 mL). The aq layer was extracted with DCM (2×30 mL) and the combined organic layers were washed with brine (30 mL), dried over $Na_2SO_4$ and concentrated under reduced pressure. Purification by column chromatography (80 g cartridge, 0-10% MeOH/DCM) gave the title compound (4 g, 8.60 mmol, 82% yield, 95% purity) as a cream solid.

UPLC/MS (Method 3): m/z 442 (M+H)+, $R_T$ 1.44 min.

Step 3 tert-Butyl (3R,4R)-4-(((7-((tert-butoxycarbonyl)(imidazo[1,2-a]pyrimidin-2-ylmethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(imidazo[1,2-a]pyrimidin-2-ylmethyl)carbamate (3.19, 7.22 mmol), (3R,4R)-tert-butyl 4-(aminomethyl)-3-hydroxypiperidine-1-carboxylate (1.75 g, 7.58 mmol) and $^t$BuBrettPhos Pd G3 (0.62 g, 0.72 mmol) in THE (30 mL) was degassed with $N_2$ for 10 min. LiHMDS (1M in THF) (10.8 ml, 10.8 mmol) was added in one portion under bubbling $N_2$. Bubbling was ceased and the reaction mixture heated to 60° C. for 1 h. The reaction was quenched with water (50 mL) and extracted with EtOAc (3×30 mL). The combined organic layers were dried over $Na_2SO_4$ and concentrated under reduced pressure. Purification by column chromatography (80 g cartridge, 0-10% MeOH/DCM) gave the title compound (2.10 g, 3.24 mmol, 44% yield, 98% purity) as an orange solid.

UPLC/MS (Method 4): m/z 636 (M+H)+, $R_T$ 1.50 min.

Step 4

(3R,4R)-4-(((7-((imidazo[1,2-a]pyrimidin-2-ylmethyl)amino)-3-isopropylpyrazolo[1,5-a]pyrimidin-5-yl)amino)methyl)piperidin-3-ol Hydrogen chloride (4 M in dioxane) (12.4 mL, 49.5 mmol) was added to a suspension of tert-butyl (3R,4R)-4-(((7-((tert-butoxycarbonyl)(imidazo[1,2-a]pyrimidin-2-ylmethyl)amino)-3-isopropylpyrazolo[1,5-a]pyrimidin-5-yl)amino)methyl)-3-hydroxypiperidine-1-carboxylate (2.10 g, 3.30 mmol) in DCM (10 mL). The reaction mixture was stirred at RT for 1 h and concentrated in vacuo. The residue was loaded onto a column of SCX. The column was washed with MeOH (30 mL) and the product eluted with 0.7 M ammonia in MeOH (30 mL). The ammoniacal methanol solution was concentrated in vacuo to give a yellow solid. Further purification by column chromatography (24 g cartridge, 0-20% MeOH (containing 0.7M $NH_3$)/DCM) gave a yellow solid. The solid was dissolved in DCM (20 mL) and MeOH (ca. 1 mL). Diethyl ether (100 mL) was added. A tan solid formed and was collected by filtration to give the title compound (0.700 g, 1.56 mmol, 47% yield, 98% purity).

UPLC/MS (Method 4): m/z 436 (M+H)+, $R_T$ 0.85 min.

$^1$H NMR (500 MHz, DMSO-$d_6$) δ 8.89 (dd, J=6.8, 2.1 Hz, 1H), 8.49 (dd, J=4.1, 2.0 Hz, 1H), 7.78-7.72 (m, 2H), 7.64 (s, 1H), 7.02 (dd, J=6.7, 4.1 Hz, 1H), 6.76 (d, J=5.0 Hz, 1H), 5.47 (s, 1H), 5.27 (s, 1H), 4.60 (d, J=6.0 Hz, 2H), 3.58-3.48 (m, 1H), 3.45-3.25 (m, 2H), 3.25-3.19 (m, 1H), 3.14-3.07 (m, 1H), 3.00-2.95 (m, 1H), 2.85 (d, J=12.2 Hz, 1H), 2.39 (td, J=12.3, 2.9 Hz, 1H), 2.25 (d, J=11.0 Hz, 1H), 1.63-1.57 (m, 1H), 1.37 (d, J=11.7 Hz, 1H), 1.24 (t, J=6.5 Hz, 6H), 1.21-1.17 (m, 1H).

Synthesis 3

(3R,4R)-4-(((3-isopropyl-7-(((1-methyl-1H-benzo[d]imidazol-5-yl)methyl)amino)pyrazolo[1,5-a]pyrimidin-5-yl)amino)methyl)piperidin-3-ol (H-APPAMP-006)

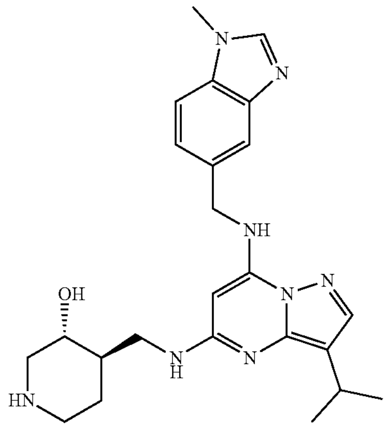 [SMILES: CC(C)c1cnn2c(NCc3ccc4c(c3)ncn4C)cc(NC[C@H]3CCNC[C@@H]3O)nc12]

Step 1

5-chloro-3-isopropyl-7-(methylthio)pyrazolo[1,5-a]pyrimidine

A solution of 5,7-dichloro-3-isopropylpyrazolo[1,5-a]pyrimidine (8.00 g, 34.8 mmol) in THE (100 mL) was cooled to −5° C. and sodium thiomethoxide (2.44 g, 34.8 mmol) was added. The reaction mixture was allowed to warm to RT and stirred overnight. The reaction mixture was diluted with EtOAc (400 ml) and washed with aq. saturated $NaHCO_3$ (500 mL). The aq layer was extracted with EtOAc (260 mL) and the combined organic layers were washed with brine (160 mL), dried over $MgSO_4$ and concentrated in vacuo. Purification by column chromatography (40 g cartridge, 0-20% EtOAc/isohexane) gave the title compound (6.00 g, 24.6 mmol, 71% yield, 99% purity) as a pale yellow oil which solidified on standing.

LCMS (Method 1): m/z 242 (M+H)+, $R_T$ 2.40 min.

Step 2 tert-Butyl (3R,4R)-3-hydroxy-4-(((3-isopropyl-7-(methylthio)pyrazolo[1,5-a]pyrimidin-5-yl)amino)methyl)piperidine-1-carboxylate A solution of 5-chloro-3-isopropyl-7-(methylthio)pyrazolo[1,5-a]pyrimidine (1.70 g, 7.03 mmol), (3R,4R)-tert-butyl 4-(aminomethyl)-3-hydroxypiperidine-1-carboxylate (1.62 g, 7.03 mmol) and $^{t}$BuBrettPhos Pd G3 (300 mg, 0.35 mmol) in THE (10 mL) was degassed for 5 min. LiHMDS (1 M in THF) (7.8 mL, 7.74 mmol) was added and the mixture degassed for a further 5 min. The reaction mixture was heated to 60° C. and stirred for 0.5 h. The solvent was evaporated and the residue was redissolved in EtOAc, washed with 1:1 water/brine (50 mL) and the aq layer was extracted with EtOAc (3×50 mL). The combined organic layer was dried over $Na_2SO_4$, filtered and the solvent was evaporated. Purification by column chromatography (80 g cartridge, 0-100% EtOAc/isohexane) gave the title compound (2.30 g, 5.12 mmol, 66% yield, 97% purity) as yellow solid.

LCMS (Method 1): m/z 436 (M+H)+, $R_T$ 2.25 min.

Step 3 tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate tert-Butyl (3R,4R)-3-hydroxy-4-(((3-isopropyl-7-(methylthio)pyrazolo[1,5-a]pyrimidin-5-yl)amino)methyl)piperidine-1-carboxylate (1.70 g, 3.90 mmol) was dissolved in DCM (30 mL). The solution was cooled to 0° C. and mCPBA (1.35 g, 5.85 mmol) was added in one portion. The reaction mixture stirred at 0° C. for 1 h. The reaction mixture was worked up by addition of DCM (30 mL) and washed with aq saturated $NaHCO_3$ (2×30 mL). The aq layer was extracted with DCM (3×20 mL). The organic layer was washed with brine, dried over $Na_2SO_4$ and the solvent was evaporated to afford the title compound (1.50 g, 3.16 mmol, 81% yield, 95% purity).

UPLC/MS (Method 4): m/z 452 (M+H)+, $R_T$ 1.43 min.

Step 4 tert-butyl (3R,4R)-3-hydroxy-4-(((3-isopropyl-7-(((1-methyl-1H-benzo[d]imidazol-5-yl)methyl)amino)pyrazolo[1,5-a]pyrimidin-5-yl)amino)methyl)piperidine-1-carboxylate tert-butyl (3R,4R)-3-hydroxy-4-(((3-isopropyl-7-(methylsulfinyl)pyrazolo[1,5-a]pyrimidin-5-yl)amino)methyl)piperidine-1-carboxylate (90 mg, 0.149 mmol) in dioxane (0.5 mL) was added to a solution of (1-methyl-1H-benzo[d]imidazol-5-yl)methanamine (72 mg, 0.448 mmol) and DIPEA (0.25 mL, 1.431 mmol) in dioxane (0.5 mL). The resultant mixture was heated at 100° C. for 3 days. The reaction mixture was cooled to RT and concentrated in vacuo. Purification by column chromatography (4 g cartridge, 0-100% EtOAc/isohexane then 0 to 5% MeOH/DCM) gave the title compound (28 mg, 0.046 mmol, 31% yield, 90% purity) as a pale yellow glass.

UPLC/MS (Method 4): m/z 549 (M+H)+, $R_T$ 1.44 min.

Step 5

(3R,4R)-4-(((3-Isopropyl-7-(((1-methyl-1H-benzo[d]imidazol-5-yl)methyl)amino)pyrazolo[1,5-a]pyrimidin-5-yl)amino)methyl)piperidin-3-ol tert-Butyl (3R,4R)-3-hydroxy-4-(((3-isopropyl-7-(((1-methyl-1H-benzo[d]imidazol-5-yl)methyl)amino)pyrazolo[1,5-a]pyrimidin-5-yl)amino)methyl)piperidine-1-carboxylate (28 mg, 0.051 mmol) was treated with a mixture of TFA (50 μL, 0.649 mmol) in DCM (0.5 mL). The resultant mixture was stirred for 3 h. The mixture was concentrated then partitioned between EtOAc (5 mL) and aq saturated $NaHCO_3$ (3 mL) and the phases separated. The organic phase was washed with water (2 mL) and brine (2 mL), dried over $MgSO_4$, filtered and concentrated in vacuo to give the title compound (10 mg, 0.021 mmol, 41% yield, 95% purity) as a white powder.

UPLC/MS (Method 4): m/z 449 (M+H)+, $R_T$ 0.97 min.

$^{1}H$ NMR (500 MHz, DMSO-$d_6$) δ 8.14 (s, 1H), 7.88 (t, J=6.5 Hz, 1H), 7.65-7.62 (m, 2H), 7.51 (d, J=8.3 Hz, 1H), 7.31 (dd, J=8.3, 1.6 Hz, 1H), 6.73-6.66 (m, 1H), 5.35-5.29 (m, 1H), 5.22 (s, 1H), 4.53 (d, J=6.4 Hz, 2H), 3.81 (s, 3H), 3.57-3.47 (m, 1H), 3.19-3.12 (m, 1H), 3.05-2.96 (m, 1H), 2.96-2.91 (m, 1H), 2.89 (dd, J=12.0, 4.3 Hz, 1H), 2.79-2.73 (m, 1H), 2.34-2.25 (m, 1H), 2.15 (dd, J=11.6, 10.0 Hz, 1H), 1.55-1.49 (m, 1H), 1.34-1.27 (m, 1H), 1.22 (t, J=7.0 Hz, 6H), 1.15-1.07 (m, 1H), 1H under water.

Synthesis 4

(3R,4R)-4-(((7-(((1H-benzo[d]imidazol-2-yl)methyl)amino)-3-isopropylpyrazolo[1,5-a]pyrimidin-5-yl)amino)methyl)piperidin-3-ol (H-APPAMP-005)

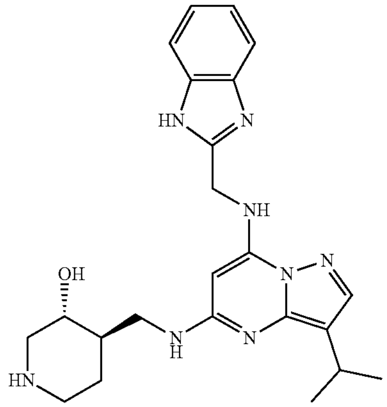 [SMILES: CC(C)c1cnn2c(NCc3nc4ccccc4[nH]3)cc(NC[C@H]3CCNC[C@@H]3O)nc12]

Step 4: tert-Butyl (3R,4R)-4-(((7-(((1H-benzo[d]imidazol-2-yl)methyl)amino)-3-isopropylpyrazolo[1,5-a]pyrimidin-5-yl)amino)methyl)-3-hydroxypiperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (80% purity) (0.467 g, 0.827 mmol) and (1H-benzo[d]imidazol-2-yl)methanamine (0.146 g, 0.993 mmol) in dioxane (1 mL) were heated to 105° C. for 16 h. The reaction mixture was cooled to RT and concentrated in vacuo. Purification by column chromatography (4 g cartridge, 0-20% MeOH (containing 0.7M $NH_3$)/DCM) gave the title compound (26 mg, 0.041 mmol, 5% yield, 85% purity) as a brown solid.

UPLC/MS (Method 4): m/z 535 (M+H)+, $R_T$ 1.45 min.

Step 5

(3R,4R)-4-(((7-(((1H-benzo[d]imidazol-2-yl)methyl)amino)-3-isopropylpyrazolo[1,5-a]pyrimidin-5-yl)amino)methyl)piperidin-3-ol Hydrogen chloride (4 M in dioxane) (0.15 mL, 0.61 mmol) was added to a solution of tert-butyl (3R,4R)-4-(((7-(((1H-benzo[d]imidazol-2-yl)methyl)amino)-3-isopropylpyrazolo[1,5-a]pyrimidin-5-yl)amino)methyl)-3-hydroxypiperidine-1-carboxylate (30 mg, 0.040 mmol) in DCM (10 mL). The reaction was stirred 16 h and concentrated in vacuo. The residue was diluted in MeOH (5 mL) and loaded onto a SCX cartridge, washing with MeOH (3× column volumes) and eluting with 0.7 M ammonia in MeOH (3× column volumes). The ammoniacal methanol solution was concentrated under reduced pressure. Purification by column chromatography (4 g cartridge, 0-20% MeOH (containing 0.7M $NH_3$)/DCM) gave the title compound (5 mg, 10.9 μmol, 27% yield, 95% purity) as a yellow solid.

UPLC/MS (same method as Method 4, but run length was 10 min): m/z 435 (M+H)+, $R_T$3.87 min.

$^1$H NMR (500 MHz, DMSO-$d_6$) δ 12.30 (s, 1H), 7.71 (t, J=6.2 Hz, 1H), 7.66 (s, 1H), 7.55 (s, 1H), 7.44 (s, 1H), 7.14 (dd, J=6.1, 3.0 Hz, 2H), 6.81-6.71 (m, 1H), 5.29 (s, 1H), 5.22 (s, 1H), 4.69 (d, J=5.8 Hz, 2H), 3.59-3.44 (m, 1H), 3.23-3.14 (m, 2H), 3.06-2.99 (m, 1H), 2.96 (p, J=6.9 Hz, 1H), 2.89 (dd, J=11.7, 4.6 Hz, 1H), 2.79-2.73 (m, 1H), 2.32-2.24 (m, 1H), 2.15 (dd, J=11.6, 9.9 Hz, 1H), 1.53 (dd, J=13.0, 3.4 Hz, 1H), 1.32 (s, 1H), 1.24 (t, J=6.5 Hz, 6H), 1.18-1.07 (m, 1H).

Synthesis 5

(3R,4R)-4-(((3-isopropyl-7-(((8-methylimidazo[1,2-a]pyridin-2-yl)methyl)amino)pyrazolo[1,5-a]pyrimidin-5-yl)amino)methyl)piperidin-3-ol (H-APPAMP-004)

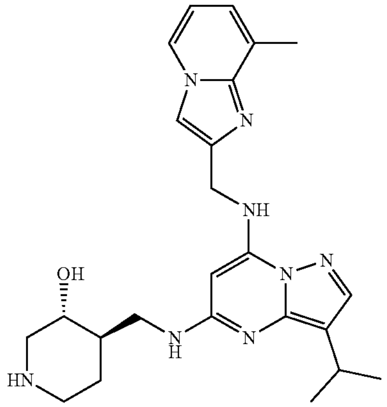 [SMILES: Cc1cccn2cc(CNc3cc(NC[C@H]4CCNC[C@@H]4O)nc4c(C(C)C)cnn34)nc12]

Step 4 tert-Butyl (3R,4R)-3-hydroxy-4-(((3-isopropyl-7-(((8-methylimidazo[1,2-a]pyridin-2-yl)methyl)amino)pyrazolo[1,5-a]pyrimidin-5-yl)amino)methyl)piperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (0.100 g, 0.221 mmol) and (8-methylimidazo[1,2-a]pyridin-2-yl)methanamine (0.107 g, 0.666 mmol) in dioxane (0.5 mL) was heated to 105° C. for 4 days. The reaction mixture was allowed to cool to RT and concentrated. Purification by column chromatography (12 g cartridge, 0-10% MeOH/DCM) gave the title compound (48 mg, 0.041 mmol, 38% yield, 95% purity) as an orange glass solid.

UPLC/MS (Method 1): m/z 549 (M+H)+, $R_T$ 1.32 min.

Step 5

(3R,4R)-4-(((3-isopropyl-7-(((8-methylimidazo[1,2-a]pyridin-2-yl)methyl)amino)pyrazolo[1,5-a]pyrimidin-5-yl)amino)methyl)piperidin-3-ol Hydrogen chloride (4 M in dioxane) (0.40 mL, 1.51 mmol) was added to a suspension of tert-butyl (3R,4R)-3-hydroxy-4-(((3-isopropyl-7-(((8-methylimidazo[1,2-a]pyridin-2-yl)methyl)amino)pyrazolo[1,5-a]pyrimidin-5-yl) amino)methyl)piperidine-1-carboxylate (48 mg, 0.083 mmol) in dioxane (3 mL). The reaction mixture was stirred at 40° C. for 4 h. The solvent was removed in vacuo. The residue was diluted in MeOH (1 mL) and loaded onto a SCX cartridge, washing with MeOH (ca. 5 mL) and eluting with 0.7 M ammonia in MeOH (ca. 5 mL). The ammoniacal methanol solution was concentrated under reduced pressure. Purification by column chromatography (4 g cartridge, 0-10% MeOH (containing 0.7M $NH_3$)/DCM) gave the title compound (24 mg, 0.052 mmol, 63% yield, 98% purity) as a tan glass solid.

LCMS (Method 2): m/z 449 (M+H)+, $R_T$ 1.67 min.

$^1$H NMR (400 MHz, DMSO-$d_6$) δ 8.32 (dt, J=6.8, 1.1 Hz, 1H), 7.74 (s, 1H), 7.66 (t, J=6.2 Hz, 1H), 7.63 (s, 1H), 7.01 (dt, J=6.8, 1.2 Hz, 1H), 6.75 (t, J=6.8 Hz, 1H), 6.72-6.68 (m, 1H), 5.35-5.29 (m, 1H), 5.27 (s, 1H), 4.57 (d, J=6.1 Hz, 2H), 3.59-3.46 (m, 1H), 3.24-3.14 (m, 1H), 3.08-2.99 (m, 1H), 2.96 (p, J=6.8 Hz, 1H), 2.90 (dd, J=11.9, 4.3 Hz, 1H), 2.82-2.73 (m, 1H), 2.47 (s, 3H), 2.35-2.26 (m, 1H), 2.16 (dd, J=11.6, 9.9 Hz, 1H), 1.59-1.51 (m, 1H), 1.39-1.28 (m, 1H), 1.23 (dd, J=6.9, 4.8 Hz, 6H), 1.20-1.08 (m, 1H), 1H under water.

Synthesis 6

(3R,4R)-4-(((3-isopropyl-7-(((5-methylimidazo[1,2-a]pyridin-3-yl)methyl)amino)pyrazolo[1,5-a]pyrimidin-5-yl)amino)methyl)piperidin-3-ol (H-APPAMP-001)

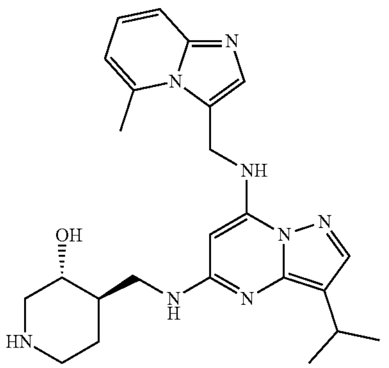 [SMILES: Cc1cccc2ncc(CNc3cc(NC[C@H]4CCNC[C@@H]4O)nc4c(C(C)C)cnn34)n12]

Steps 4 and 5

(3R,4R)-4-(((3-Isopropyl-7-(((5-methylimidazo[1,2-a]pyridin-3-yl)methyl)amino)pyrazolo[1,5-a]pyrimidin-5-yl)amino)methyl)piperidin-3-ol Step 4: tert-Butyl (3R,4R)-3-hydroxy-4-(((3-isopropyl-7-(methylsulfinyl)pyrazolo[1,5-a]pyrimidin-5-yl)amino) methyl)piperidine-1-carboxylate (0.100 g, 0.221 mmol) and (8-methylimidazo[1,2-a]pyridin-2-yl)methanamine (0.107 g, 0.666 mmol) in dioxane (0.5 mL) was heated to 105° C. for 4 days. The reaction mixture was allowed to cool to RT and concentrated. Purification by column chromatography (12 g cartridge, 0-10% MeOH (containing 0.7M $NH_3$)/DCM) gave the corresponding Boc intermediate (40 mg).

Step 5: A solution of tert-butyl (3R,4R)-3-hydroxy-4-(((3-isopropyl-7-(((5-methylimidazo[1,2-a]pyridin-3-yl)methyl)

amino)pyrazolo[1,5-a]pyrimidin-5-yl)amino)methyl)piperidine-1-carboxylate (40 mg, 0.073 mmol) and HCl (4 M in dioxane) (505 μL, 16.6 mmol) was stirred at RT for 16 h. The solvent was evaporated. Purification by column chromatography (12 g cartridge, 0-10% MeOH (containing 0.7M $NH_3$)/DCM) gave the title compound (15 mg, 45% yield, 95% purity) as a brown solid.

LCMS (Method 2): m/z 449 (M+H)+, $R_T$ 1.64 min.

$^1$H NMR (500 MHz, DMSO-$d_6$) δ 7.61 (s, 1H), 7.58 (t, J=5.3 Hz, 1H), 7.51 (s, 1H), 7.40 (d, J=9.0 Hz, 1H), 7.13 (dd, J=9.0, 6.8 Hz, 1H), 6.81-6.74 (m, 1H), 6.68 (d, J=6.9 Hz, 1H), 5.42 (s, 1H), 5.31 (s, 1H), 4.96 (d, J=5.0 Hz, 2H), 3.60-3.49 (m, 1H), 3.28-3.21 (m, 1H), 3.11-3.03 (m, 1H), 2.98-2.91 (m, 2H), 2.89 (s, 3H), 2.84-2.79 (m, 1H), 2.38-2.31 (m, 1H), 2.23-2.16 (m, 1H), 1.64-1.57 (m, 1H), 1.42-1.32 (m, 1H), 1.23 (dd, J=6.9, 5.2 Hz, 6H), 1.20-1.13 (m, 1H), 1H under water.

Synthesis 7

(3R,4R)-4-[[[3-isopropyl-7-[(3-methylimidazo[2,1-b]thiazol-6-yl)methylamino]pyrazolo[1,5-a]pyrimidin-5-yl]amino]methyl]piperidin-3-ol (H-APPAMP-007)

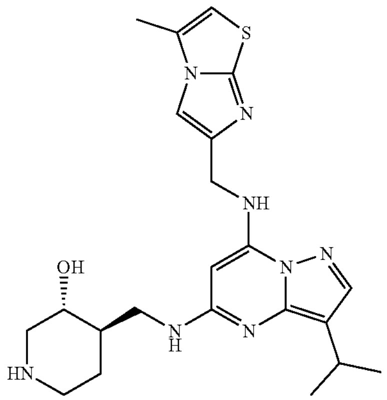 [SMILES: Cc1csc2nc(CNc3cc(NC[C@H]4CCNC[C@@H]4O)nc4c(C(C)C)cnn34)cn12]

Step 4: tert-butyl (3R,4R)-3-hydroxy-4-(((3-isopropyl-7-(((3-methylimidazo[2,1-b]thiazol-6-yl)methyl) amino)pyrazolo[1,5-a]pyrimidin-5-yl)amino)methyl) piperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (80.0 mg, 0.145 mmol), (3-methylimidazo[2,1-b]thiazol-6-yl)methanamine, 2HCl, hydrate (74.9 mg, 0.290 mmol) and DIPEA (0.228 mL, 1.305 mmol) in Ethanol (2 mL) was heated at 140° C. under microwave irradiation for 4 hours. The reaction mixture was allowed to cool to RT and concentrated. Purification by column chromatography (4 g cartridge, 0-10% MeOH (containing 0.7M $NH_3$)/DCM) followed by purification by reverse phase C18 chromatography (4 g cartridge, 15-75% MeCN/10 mM Ammonium Bicarbonate) gave the title compound (40 mg, 0.071 mmol, 49% yield, 97% purity) as a tan solid.

UPLC/MS (Method 4): m/z 555 (M+H)+, $R_T$ 0.52 min.

Step 5: (3R,4R)-4-[[[3-isopropyl-7-[(3-methylimidazo[2,1-b]thiazol-6-yl)methylamino]pyrazolo[1,5-a]pyrimidin-5-yl]amino]methyl]piperidin-3-ol Hydrogen chloride (4M in dioxane) (0.169 ml, 0.676 mmol) was added to a solution of tert-butyl (3R,4R)-3-hydroxy-4-(((3-isopropyl-7-(((3-methylimidazo[2,1-b]thiazol-6-yl)methyl)amino)pyrazolo[1,5-a]pyrimidin-5-yl)amino)methyl)piperidine-1-carboxylate (25 mg, 0.045 mmol) in dioxane (2 mL). The reaction mixture was stirred at 35° C. for 1 h. The solvent was evaporated. The residue was diluted in MeOH (1 mL) and loaded onto a SCX cartridge, washing with MeOH (ca. 5 mL) and eluting with 0.7M ammonia in MeOH (ca. 5 mL). The ammoniacal methanol solution was concentrated under reduced pressure to afford the title compound (18 mg, 0.038 mmol, 84% yield, 96% purity) as a tan solid after trituration in $Et_2O$ then drying under vacuum at 50° C. overnight.

UPLC/MS (Method 4): m/z 455 (M+H)+, $R_T$ 1.03 min.

$^1H$ NMR (500 MHz, DMSO-d6) δ 7.62 (s, 1H), 7.59 (s, 1H), 7.49 (t, J=6.1 Hz, 1H), 6.85 (q, J=1.3 Hz, 1H), 6.79-6.73 (m, 1H), 5.38-5.35 (m, 1H), 5.35 (s, 1H), 4.47-4.43 (m, 2H), 3.25-3.19 (m, 1H), 3.10-3.02 (m, 1H), 2.98-2.90 (m, 2H), 2.85-2.79 (m, 2H), 2.36 (d, J=1.3 Hz, 3H), 2.35-2.30 (m, 1H), 2.23-2.16 (m, 1H), 1.63-1.56 (m, 1H), 1.40-1.32 (m, 1H), 1.23 (dd, J=6.9, 6.0 Hz, 6H), 1.21-1.13 (m, 1H), 1H under water.

Synthesis 8 tert-butyl (3R,4R)-3-hydroxy-4-(((3-isopropyl-7-(((7-methylimidazo[1,2-a]pyridin-2-yl)methyl)amino)pyrazolo[1,5-a]pyrimidin-5-yl)amino)methyl)piperidine-1-carboxylate (H-APPAMP-008)

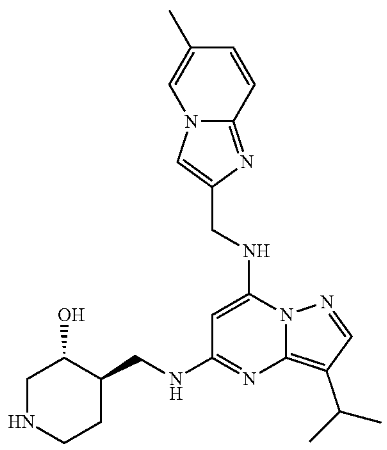 [SMILES: Cc1ccc2nc(CNc3cc(NC[C@H]4CCNC[C@@H]4O)nc4c(C(C)C)cnn34)cn2c1]

Step 4: tert-butyl (3R,4R)-3-hydroxy-4-(((3-isopropyl-7-(((7-methylimidazo[1,2-a]pyridin-2-yl)methyl)amino)pyrazolo[1,5-a]pyrimidin-5-yl)amino)methyl)piperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (80 mg, 0.145 mmol) was added to a solution of (6-methylimidazo[1,2-a]pyridin-2-yl)methanamine, 2HCl (102 mg, 0.435 mmol) and DIPEA (0.23 mL, 1.305 mmoRPI) in EtOH (2.0 mL). The resultant mixture was heated at 140° C. under microwave irradiation for 4 h. The reaction mixture was cooled to RT and concentrated in vacuo. Purification by column chromatography (4 g cartridge, 0-10% MeOH (containing 0.7 M $NH_3$)/DCM) gave the title compound (67 mg, 0.112 mmol, 77% yield, 92% purity) as a yellow oil.

UPLC/MS (Method 3): m/z 549 (M+H)+, $R_T$ 0.84 min.

Step 5: tert-butyl (3R,4R)-3-hydroxy-4-(((3-isopropyl-7-(((7-methylimidazo[1,2-a]pyridin-2-yl)methyl)amino)pyrazolo[1,5-a]pyrimidin-5-yl)amino)methyl)piperidine-1-carboxylate A solution of tert-butyl (3R,4R)-3-hydroxy-4-(((3-isopropyl-7-(((7-methylimidazo[1,2-a]pyridin-2-yl)methyl)amino)pyrazolo[1,5-a]pyrimidin-5-yl)amino)methyl)piperidine-1-carboxylate (67 mg, 0.122 mmol) in 1,4-dioxane (2.0 mL) was treated with HCl (4M in 1,4-dioxane) (458 μL, 1.832 mmol). The reaction mixture was stirred at RT overnight and concentrated to dryness. Purification by column chromatography (4 g cartridge, 0-15% MeOH (containing 0.7 M $NH_3$)/DCM) gave the title compound (32 mg, 0.068 mmol, 55% yield, 95% purity) as an off-white solid after drying under vacuum at 50° C. overnight.

UPLC/MS (Method 4): m/z 449 (M+H)+, $R_T$ 1.08 min.

$^1H$ NMR (500 MHz, DMSO-$d_6$) δ 8.93-8.82 (m, 1H), 8.65-8.52 (m, 1H), 8.32 (s, 1H), 7.73 (s, 1H), 7.67 (s, 1H), 7.44 (d, J=9.2 Hz, 1H), 7.13 (d, J=9.3 Hz, 1H), 6.99-6.86 (m, 1H), 6.12-6.03 (m, 1H), 5.27 (s, 1H), 4.56 (d, J=6.0 Hz, 2H), 3.60-3.50 (m, 1H), 3.47-3.39 (m, 1H), 3.25-3.13 (m, 2H), 3.01-2.92 (m, 1H), 2.84-2.72 (m, 1H), 2.66-2.59 (m, 1H), 2.53-2.52 (m, 1H), 2.26 (s, 3H), 1.85-1.76 (m, 1H), 1.68-1.56 (m, 1H), 1.52-1.41 (m, 1H), 1.24 (t, J=6.6 Hz, 6H).

Synthesis 9

(3R,4R)-4-(((3-isopropyl-7-(((7-methylimidazo[1,2-a]pyridin-2-yl)methyl)amino)pyrazolo[1,5-a]pyrimidin-5-yl)amino)methyl)piperidin-3-ol (H-APPAMP-009)

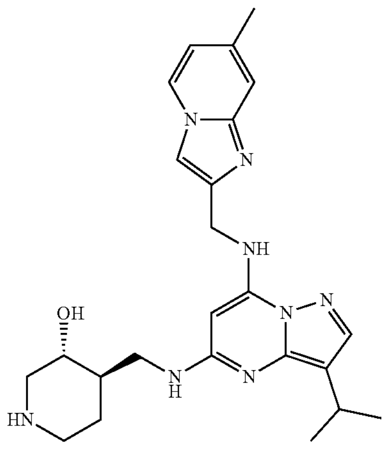 [SMILES: Cc1ccn2cc(CNc3cc(NC[C@H]4CCNC[C@@H]4O)nc4c(C(C)C)cnn34)nc2c1]

Step 4: tert-butyl (3R,4R)-3-hydroxy-4-(((3-isopropyl-7-(((6-methylimidazo[1,2-a]pyridin-2-yl)methyl)amino)pyrazolo[1,5-a]pyrimidin-5-yl)amino)methyl)piperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (80 mg, 0.145 mmol) was added to a solution of (7-methylimidazo[1,2-a]pyridin-2-yl)methanamine, 2HCl (102 mg, 0.435 mmol) and DIPEA (0.228 mL, 1.305 mmol) in EtOH (2.0 mL). The resultant mixture was heated at 140° C. under microwave irradiation for 3.5 h. The reaction mixture was cooled to RT and concentrated in vacuo. Purification by column chromatography (4 g cartridge, 0-10% MeOH (containing 0.7 M $NH_3$)/DCM) gave the title compound (60 mg, 0.093 mmol, 64% yield, 85% purity) as a brown oil.

UPLC/MS (Method 3): m/z 549 (M+H)+, $R_T$ 0.83 min.

Step 5: (3R,4R)-4-(((3-isopropyl-7-(((7-methylimidazo[1,2-a]pyridin-2-yl)methyl)amino)pyrazolo[1,5-a]pyrimidin-5-yl)amino)methyl)piperidin-3-ol A solution of tert-butyl (3R,4R)-3-hydroxy-4-(((3-isopropyl-7-(((6-methylimidazo[1,2-a]pyridin-2-yl)methyl)amino)pyrazolo[1,5-a]pyrimidin-5-yl)amino)methyl)piperidine-1-carboxylate (60 mg, 0.104 mmol) in 1,4-dioxane (2.0 mL) was treated with HCl (4M in 1,4-dioxane) (0.390 mL, 1.558 mmol). The reaction mixture was stirred at RT overnight and concentrated to dryness. Purification by column chromatography (4 g cartridge, 0-15% MeOH (containing 0.7 M $NH_3$)/DCM) gave the title compound (33 mg, 0.070 mmol, 67% yield, 95% purity) as an off-white solid after drying under vacuum at 50° C. overnight.

UPLC/MS (Method 4): m/z 449 (M+H)+, $R_T$ 1.07 min.

$^1$H NMR (500 MHz, DMSO-$d_6$) δ 8.36 (d, J=6.9 Hz, 1H), 7.68 (s, 1H), 7.67-7.65 (m, 1H), 7.64 (s, 1H), 7.30-7.25 (m, 1H), 6.82-6.76 (m, 1H), 6.70 (dd, J=7.0, 1.7 Hz, 1H), 5.61-5.55 (m, 1H), 5.27 (s, 1H), 4.53 (d, J=5.9 Hz, 2H), 3.62-3.51 (m, 1H), 3.25-3.20 (m, 1H), 3.19-3.12 (m, 1H), 3.01 (dd, J=11.6, 4.4 Hz, 1H), 2.99-2.93 (m, 1H), 2.92-2.87 (m, 1H), 2.47-2.42 (m, 1H), 2.33 (s, 3H), 2.32-2.26 (m, 1H), 1.67-1.61 (m, 1H), 1.46-1.38 (m, 1H), 1.30-1.26 (m, 1H), 1.24 (t, J=6.6 Hz, 6H). 1H under water.

Synthesis 10

(3R,4R)-4-(((3-isopropyl-7-(((5-methylimidazo[1,2-a]pyridin-2-yl)methyl)amino)pyrazolo[1,5-a]pyrimidin-5-yl)amino)methyl)piperidin-3-ol (H-APPAMP-010)

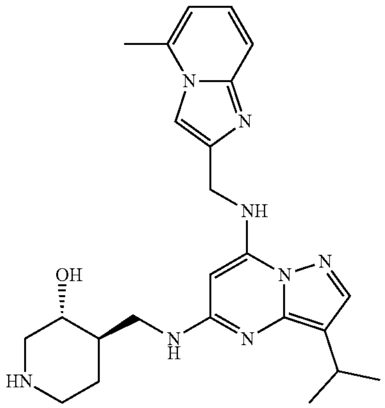 [SMILES: Cc1cccc2nc(CNc3cc(NC[C@H]4CCNC[C@@H]4O)nc4c(C(C)C)cnn34)cn12]

Step 4: tert-butyl (3R,4R)-3-hydroxy-4-(((3-isopropyl-7-(((5-methylimidazo[1,2-a]pyridin-2-yl)methyl)amino)pyrazolo[1,5-a]pyrimidin-5-yl)amino)methyl)piperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (80 mg, 0.145 mmol) was added to a solution of (5-methylimidazo[1,2-a]pyridin-2-yl)methanamine, 2HCl (102 mg, 0.435 mmol) and DIPEA (0.228 ml, 1.305 mmol) in EtOH (2.0 mL). The resultant mixture was heated at 140° C. under microwave irradiation for 4 h. The reaction mixture was cooled to RT and concentrated in vacuo. Purification by column chromatography (4 g cartridge, 0-10% MeOH (containing 0.7 M $NH_3$)/DCM) gave the title compound (85 mg, 0.116 mmol, 80% yield, 75% purity) as a brown oil.

UPLC/MS (Method 4): m/z 549 (M+H)+, $R_T$ 1.50 min.

Step 5: (3R,4R)-4-(((3-isopropyl-7-(((5-methylimidazo[1,2-a]pyridin-2-yl)methyl)amino)pyrazolo[1,5-a]pyrimidin-5-yl)amino)methyl)piperidin-3-ol A solution of tert-butyl (3R,4R)-3-hydroxy-4-(((3-isopropyl-7-(((5-methylimidazo[1,2-a]pyridin-2-yl)methyl)amino)pyrazolo[1,5-a]pyrimidin-5-yl)amino)methyl)piperidine-1-carboxylate (85 mg, 0.116 mmol) in 1,4-dioxane (2.0 mL) was treated with HCl (4M in 1,4-dioxane) (0.436 mL, 1.743 mmol). The reaction mixture was stirred at RT overnight and concentrated to dryness. Purification by column chromatography on RP Flash C18 (4 g cartridge, 15-50% MeCN/10 mM ammonium bicarbonate) gave the title compound (12 mg, 0.025 mmol, 21% yield, 93% purity) as an off-white solid after drying under vacuum at 50° C. overnight.

UPLC/MS (Method 4): m/z 449 (M+H)+, $R_T$ 1.07 min.

$^1$H NMR (500 MHz, DMSO-$d_6$) δ 7.67 (s, 1H), 7.63 (s, 1H), 7.58 (t, J=6.1 Hz, 1H), 7.43 (dd, J=8.9, 1.2 Hz, 1H), 7.21 (dd, J=9.0, 6.8 Hz, 1H), 6.79-6.75 (m, 2H), 5.44-5.37 (m, 1H), 5.33 (s, 1H), 4.59 (d, J=5.9 Hz, 2H), 3.61-3.49 (m, 1H), 3.25-3.19 (m, 1H), 3.11-3.05 (m, 1H), 2.99-2.92 (m, 2H), 2.87-2.81 (m, 1H), 2.56 (s, 3H), 2.40-2.33 (m, 1H), 2.26-2.20 (m, 1H), 1.64-1.57 (m, 1H), 1.42-1.34 (m, 1H), 1.24 (dd, J=6.9, 6.0 Hz, 6H), 1.21-1.15 (m, 1H). 1H under water.

Synthesis 11

(3R,4R)-4-(((7-(((6-fluoroimidazo[1,2-a]pyridin-2-yl)methyl)amino)-3-isopropylpyrazolo[1,5-a]pyrimidin-5-yl)amino)methyl)piperidin-3-ol (H-APPAMP-011)

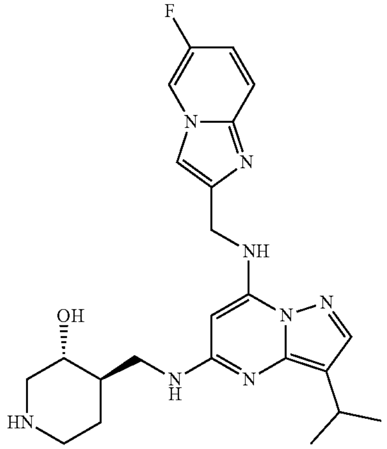 [SMILES: CC(C)c1cnn2c(NCc3cn4cc(F)ccc4n3)cc(NC[C@H]3CCNC[C@@H]3O)nc12]

Step 4: (3R,4R)-4-(((7-(((6-fluoroimidazo[1,2-a]pyridin-2-yl)methyl)amino)-3-isopropylpyrazolo[1,5-a]pyrimidin-5-yl)amino)methyl)piperidin-3-ol tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (60 mg, 0.109 mmol) was added to a solution of (6-fluoroimidazo[1,2-a]pyridin-2-yl)methanamine (53.9 mg, 0.326 mmol) and DIPEA (0.171 mL, 0.979 mmol) in EtOH (4.0 mL). The resultant mixture was heated at 140° C. under microwave irradiation for 4 h, concentrated to dryness and redissolved in NMP (3.0 mL). The resultant mixture was heated at 160° C. under microwave irradiation for 4 h. The crude oil was filtered through SCX (2 g—wash with MeOH (15 mL), elution with MeOH containing 0.7 M $NH_3$ (15 mL)) gave a brown oil. Purification by column (4 g cartridge (dry load), 0-10% MeOH (containing 0.7 M $NH_3$)/DCM then 100% MeOH (containing 0.7 M $NH_3$)) followed by purification by column chromatography on RP Flash C18 (4 g cartridge, 15-75% MeCN/10 mM ammonium bicarbonate) gave the title compound (5 mg, 9.94 μmol, 9% yield, 90% purity) as a tan solid after precipitation from $Et_2O$.

UPLC/MS (Method 4): m/z 453 (M+H)+, $R_T$ 1.01 min.

$^1$H NMR (500 MHz, DMSO-$d_6$) δ 8.69 (dd, J=4.7, 2.5 Hz, 1H), 7.79 (s, 1H), 7.68 (t, J=6.2 Hz, 1H), 7.63 (s, 1H), 7.57 (dd, J=10.0, 5.3 Hz, 1H), 7.30 (ddd, J=10.2, 8.4, 2.5 Hz, 1H), 6.75-6.68 (m, 1H), 5.30-5.27 (m, 1H), 5.26 (s, 1H), 4.56 (d, J=6.1 Hz, 2H), 3.60-3.47 (m, 1H), 3.23-3.15 (m, 1H), 3.07-2.99 (m, 1H), 2.98-2.92 (m, 1H), 2.89 (dd, J=11.4, 4.5 Hz, 1H), 2.82-2.73 (m, 1H), 2.33-2.23 (m, 1H), 2.14 (dd, J=11.7, 9.9 Hz, 1H), 1.58-1.51 (m, 1H), 1.37-1.27 (m, 1H), 1.23 (t, J=6.5 Hz, 6H), 1.19-1.11 (m, 1H). 1H under water.

Synthesis 12

(3R,4R)-4-(((7-(((6-chloroimidazo[1,2-a]pyridin-2-yl)methyl)amino)-3-isopropylpyrazolo[1,5-a]pyrimidin-5-yl)amino)methyl)piperidin-3-ol (H-APPAMP-012)

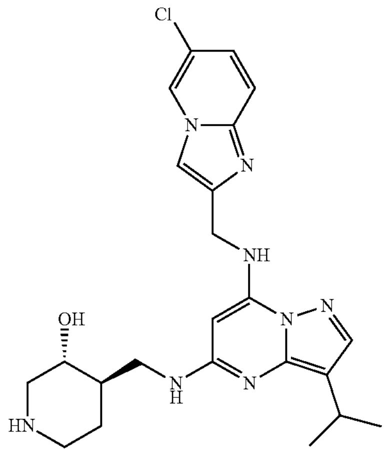

Step 4: tert-butyl (3R,4R)-4-(((7-(((6-chloroimidazo[1,2-a]pyridin-2-yl)methyl)amino)-3-isopropylpyrazolo[1,5-a]pyrimidin-5-yl)amino)methyl)-3-hydroxypiperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (60 mg, 0.109 mmol) was added to a solution of (6-chloroimidazo[1,2-a]pyridin-2-yl)methanamine (59.3 mg, 0.326 mmol) and DIPEA (0.171 mL, 0.979 mmol) in EtOH (4 mL). The resultant mixture was heated at 140° C. under microwave irradiation for 4 h, concentrated to dryness and redissolved in NMP (3 mL). The resultant mixture was heated at 160° C. under microwave irradiation for 4 h. The crude oil was filtered through SCX (2 g—wash with MeOH (15 mL), elution with MeOH containing 0.7 M $NH_3$ (15 mL)) gave a brown oil. Purification by column chromatography on RP Flash C18 (4 g cartridge, 35-100% MeCN/10 mM ammonium bicarbonate) gave the title compound (32 mg, 42 μmol, 38% yield, 75% purity) as a brown oil.

UPLC/MS (Method 4): m/z 569 (M+H)+, $R_T$ 1.55 min.

Step 5: (3R,4R)-4-(((7-(((6-chloroimidazo[1,2-a]pyridin-2-yl)methyl)amino)-3-isopropylpyrazolo[1,5-a]pyrimidin-5-yl)amino)methyl)piperidin-3-ol A solution of tert-butyl (3R,4R)-4-(((7-(((6-chloroimidazo[1,2-a]pyridin-2-yl)methyl)amino)-3-isopropylpyrazolo[1,5-a]pyrimidin-5-yl)amino)methyl)-3-hydroxypiperidine-1-carboxylate (32 mg, 0.045 mmol) in 1,4-dioxane (2 mL) was treated with HCl (4M in 1,4-dioxane) (0.169 mL, 0.675 mmol). The reaction mixture was stirred at RT overnight and concentrated to dryness. The crude oil was filtered through SCX (2 g—wash with MeOH (15 mL), elution with MeOH containing 0.7 M $NH_3$ (15 mL) to give a brown oil. Purification by column (4 g cartridge (dry load), 0-20% MeOH (containing 0.7 M $NH_3$)/DCM) followed by purification by column chromatography on RP Flash C18 (4 g cartridge, 35-100% MeCN/10 mM ammonium bicarbonate) gave the title compound (10 mg, 0.020 mmol, 44% yield, 92% purity) as a tan solid after precipitation from $Et_2O$ then drying under vacuum at 50° C. overnight.

UPLC/MS (Method 4): m/z 469 (M+H)+, $R_T$ 1.08 min.

$^1$H NMR (500 MHz, DMSO-$d_6$) δ 8.76 (d, J=2.1 Hz, 1H), 7.77 (s, 1H), 7.69 (t, J=6.3 Hz, 1H), 7.63 (s, 1H), 7.55 (d, J=9.6 Hz, 1H), 7.26 (dd, J=9.6, 2.1 Hz, 1H), 6.76-6.68 (m, 1H), 5.32-5.27 (m, 1H), 5.25 (s, 1H), 4.56 (d, J=6.1 Hz, 2H), 3.60-3.47 (m, 1H), 3.24-3.16 (m, 1H), 3.05-2.98 (m, 1H), 2.98-2.91 (m, 1H), 2.91-2.87 (m, 1H), 2.80-2.73 (m, 1H), 2.33-2.24 (m, 1H), 2.18-2.11 (m, 1H), 1.58-1.50 (m, 1H), 1.39-1.27 (m, 1H), 1.26-1.21 (m, 6H), 1.18-1.09 (m, 1H). 1H under water.

Synthesis 13

(3R,4R)-4-(((7-(((8-cyclopropylimidazo[1,2-a]pyridin-2-yl)methyl)amino)-3-isopropylpyrazolo[1,5-a]pyrimidin-5-yl)amino)methyl)piperidin-3-ol (H-AP-PAMP-013)

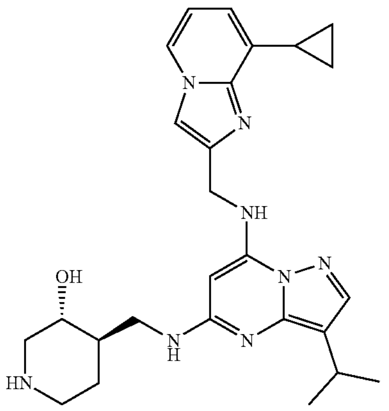 [SMILES: CC(C)c1cnn2c(NCc3cn4cccc(C5CC5)c4n3)cc(NC[C@H]3CCNC[C@@H]3O)nc12]

Step 4: tert-butyl (3R,4R)-4-(((7-(((8-cyclopropylimidazo[1,2-a]pyridin-2-yl)methyl)amino)-3-isopropylpyrazolo[1,5-a]pyrimidin-5-yl)amino)methyl)-3-hydroxypiperidine-1-carboxylate tert-Butyl (3R,4R)-3-hydroxy-4-(((3-isopropyl-7-(methylsulfinyl)pyrazolo[1,5-a]pyrimidin-5-yl)amino)methyl)piperidine-1-carboxylate (120 mg, 99% Wt, 0.22 mmol) was added to a solution of (8-cyclopropylimidazo[1,2-a]pyridin-2-yl)methanamine, Acetic acid (0.11 g, 0.43 mmol) and DIPEA (0.19 mL, 1.1 mmol) in NMP (2 mL).). The resultant mixture was heated at 140° C. under microwave irradiation for 4 h then at 160° C. for 4 h. The crude oil was filtered through SCX (4 g—wash with MeOH (30 mL), elution with MeOH containing 0.7 M $NH_3$ (30 mL)) gave a brown oil. Purification by column (4 g cartridge (dry load), 0-15% MeOH (containing 0.7 M $NH_3$)/DCM) gave the title compound (42 mg, 67 μmol, 31% yield, 92% Purity) as a brown oil.

UPLC/MS (Method 4): m/z 575 (M+H)+, $R_T$ 1.58 min.

Step 5: (3R,4R)-4-(((7-(((8-cyclopropylimidazo[1,2-a]pyridin-2-yl)methyl)amino)-3-isopropylpyrazolo[1,5-a]pyrimidin-5-yl)amino)methyl)piperidin-3-ol tert-Butyl (3R,4R)-4-(((7-(((8-cyclopropylimidazo[1,2-a]pyridin-2-yl)methyl)amino)-3-isopropylpyrazolo[1,5-a]pyrimidin-5-yl)amino)methyl)-3-hydroxypiperidine-1-carboxylate (23 mg, 37 μmol) in 1,4-dioxane (0.25 mL) was treated with HCl (4M in 1,4-dioxane) (0.14 mL, 0.55 mmol). The reaction mixture was stirred at 35° C. for 1 hour and concentrated to dryness. The crude oil was purified through SCX (4 g—wash with MeOH (30 mL), elution with MeOH containing 0.7 M $NH_3$ (30 mL)) gave the title compound (17 mg, 34 μmol, 92% yield, 95% Purity) as a brown solid after precipitation from $Et_2O$ then drying under vacuum at 50° C. overnight.

UPLC/MS (Method 4): m/z 475 (M+H)+, $R_T$ 1.14 min.

$^1H$ NMR (500 MHz, DMSO-$d_6$) δ 8.30-8.23 (m, 1H), 7.74 (s, 1H), 7.67 (t, J=6.2 Hz, 1H), 7.64 (s, 1H), 6.74-6.69 (m, 3H), 5.36-5.30 (m, 1H), 5.28 (s, 1H), 4.58 (d, J=5.9 Hz, 2H), 3.59-3.49 (m, 1H), 3.23-3.16 (m, 1H), 3.08-3.00 (m, 1H), 2.99-2.92 (m, 1H), 2.91 (dd, J=11.8, 4.9 Hz, 1H), 2.81-2.75 (m, 1H), 2.48-2.43 (m, 1H), 2.35-2.26 (m, 1H), 2.16 (dd, J=11.7, 9.9 Hz, 1H), 1.59-1.52 (m, 1H), 1.39-1.29 (m, 1H), 1.24 (dd, J=6.9, 5.9 Hz, 6H), 1.20-1.11 (m, 1H), 1.04-0.98 (m, 2H), 0.98-0.92 (m, 2H). 1H under water.

Intermediate Synthesis A1

(8-cyclopropylimidazo[1,2-a]pyridin-2-yl)methanamine, AcOH

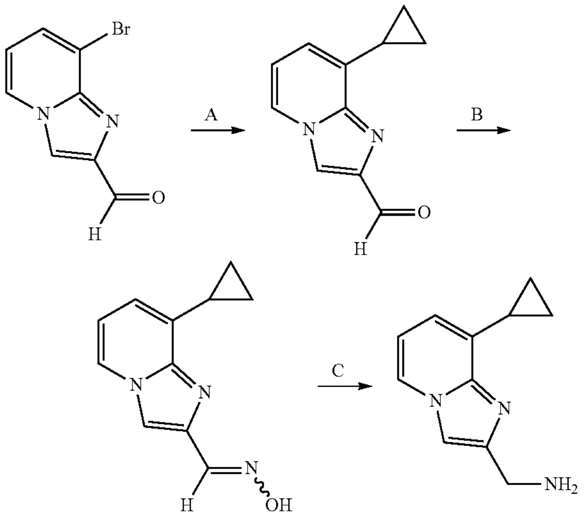

Step A: 8-cyclopropylimidazo[1,2-a]pyridine-2-carbaldehyde

A solution of tripotassium phosphate (755 mg, 3.55 mmol) in water (2.5 mL) was added to a solution of 8-bromoimidazo[1,2-a]pyridine-2-carbaldehyde (200 mg, 0.889 mmol) and cyclopropylboronic acid (229 mg, 2.67 mmol) in 1,4-dioxane (10 mL). $N_2$ was bubbled through the reaction mixture for 10 minutes then PdC12(dppf) (65.0 mg, 0.089 mmol) was added. $N_2$ was bubbled through the reaction mixture for another 5 minutes before being heated at 100° C. for 3 h. At RT, water (20 mL) and EtOAc (40 mL) were added. The layers were separated, and the aqueous layer was extracted with EtOAc (3×15 mL). The combined organic layers were filtered through a phase separator and concentrated. Purification by column (12 g cartridge (dry load), 0-100% EtOAc/isohexane) gave the title compound (141 mg, 0.750 mmol, 71% yield, 99% purity) as a yellow solid.

Step B/C: 8-cyclopropylimidazo[1,2-a]pyridine-2-carbaldehyde oxime/(8-cyclopropylimidazo[1,2-a]pyridin-2-yl)methanamine, AcOH A solution of 8-cyclopropylimidazo[1,2-a]pyridine-2-carbaldehyde (130 mg, 698 μmol), hydroxylamine hydrochloride (121 mg, 1.75 mmol) and pyridine (0.14 mL, 1.75 mmol) in EtOH (3.5 mL) was stirred at 80° C. for 2 h. At RT, the precipitate was collected by filtration, rinsing with EtOH (2×2 mL). The solid was further dried under vacuum to afford 8-cyclopropylimidazo[1,2-a]pyridine-2-carbaldehyde oxime (135 mg) as a tan solid which was dissolved in AcOH (3 mL). The solution was cooled at 0° C. then sodium acetate (11.0 mg, 134 μmol) and zinc dust (658 mg, 10.1 mmol) were added. The reaction mixture was stirred at RT overnight before being filtered through celite, rinsing with DCM (20 mL) and MeOH (20 mL). The filtrate was concentrated to dryness to afford an oil. Filtration through SCX (10 g—wash with MeOH (50 mL), elution with MeOH containing 0.7 M $NH_3$ (50 mL)) gave the title compound (164 mg, 663 μmol, 99% yield, 95% purity) as a slightly yellow oil.

$^1$H NMR (500 MHz, DMSO-$d_6$) was consistent with product structure.

Synthesis 14

(3R,4R)-4-(((3-isopropyl-7-((quinolin-2-ylmethyl)amino)pyrazolo[1,5-a]pyrimidin-5-yl)amino)methyl)piperidin-3-ol (H-APPAMP-014)

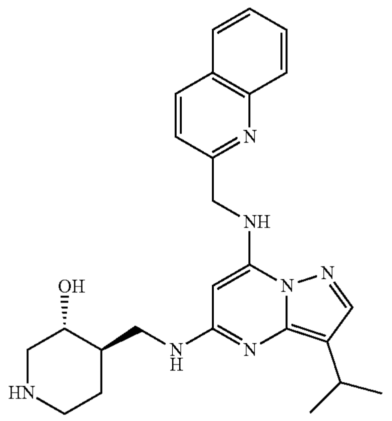 [SMILES: CC(C)c1cnn2c(NCc3ccc4ccccc4n3)cc(NC[C@H]3CCNC[C@@H]3O)nc12]

Step 1: 5-chloro-3-isopropyl-N-(quinolin-2-ylmethyl)pyrazolo[1,5-a]pyrimidin-7-amine Quinolin-2-ylmethanamine (165 mg, 1.04 mmol) was added to a solution of 5,7-dichloro-3-isopropylpyrazolo[1,5-a]pyrimidine (200 mg, 0.869 mmol) and DIPEA (908 μL, 5.21 mmol) in EtOH (3.3 mL). The reaction mixture was heated to reflux overnight. The reaction mixture was concentrated in vacuo to give an orange solid Purification by column (12 g cartridge, DCM) gave the title compound (240 mg, 0.67 mmol, 78% yield, 99% purity) as an orange solid.

$^1$H NMR (500 MHz, DMSO-$d_6$) was consistent with product structure.

Step 2: tert-butyl (5-chloro-3-isopropylpyrazolo[1,5-a]pyrimidin-7-yl)(quinolin-2-ylmethyl)carbamate BOC-Anhydride (193 mg, 886.1 μmol) was added to a solution of 5-chloro-3-isopropyl-N-(quinolin-2-ylmethyl)pyrazolo[1,5-a]pyrimidin-7-amine (240 mg, 681.6 μmol) and DMAP (17 mg, 136.3 μmol) in THE (13.6 mL). The reaction mixture was stirred at 60° C. for 1.5 h. The reaction mixture was concentrated under reduced pressure then diluted in DCM (15 mL) and washed with brine (3×10 mL). The combined organic layers were filtered through a phase separator and concentrated under reduced pressure. Purification by column chromatography (12 g cartridge, 0-2.5% MeOH/DCM) gave the title compound (317 mg, 0.67 mmol, 98% yield, 95% purity) as an orange oil.

UPLC/MS (Method 6): m/z 453 (M+H)+, $R_T$ 0.92 min.

Step 3: tert-butyl (3R,4R)-4-(((7-((tert-butoxycarbonyl)(quinolin-2-ylmethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(quinolin-2-ylmethyl)carbamate (115 mg, 0.25 mmol), (3R,4R)-tert-butyl 4-(aminomethyl)-3-hydroxypiperidine-1-carboxylate (63 mg, 0.27 mmol) and $^t$Bu-BrettPhos Pd G3 (21 mg, 25 μmol) in THE (2.1 mL) was degassed with N2 for 10 min. LiHMDS (1M in THF) (0.37 mL, 0.37 mmol) was added in one portion under bubbling N2. Bubbling was ceased and the reaction mixture heated to 60° C. for 1 h. The reaction was quenched with water (5 mL) and extracted with EtOAc (3×5 mL). The combined organic layers were dried over Na2SO4 and concentrated under reduced pressure. Purification by column chromatography (12 g cartridge, 0-100% EtOAc/isohexane) gave the title compound (130 mg, 0.19 mmol, 77% yield, 95% purity) as a yellow oil.

UPLC/MS (Method 4): m/z 646 (M+H)+, $R_T$ 1.85 min.

Step 4: (3R,4R)-4-(((3-isopropyl-7-((quinolin-2-ylmethyl)amino)pyrazolo[1,5-a]pyrimidin-5-yl)amino)methyl)piperidin-3-ol Hydrogen chloride (4 M in 1,4-dioxane) (0.88 mL, 3.5 mmol) was added to a suspension of tert-butyl (3R,4R)-4-(((7-((tert-butoxycarbonyl)(quinolin-2-ylmethyl)amino)-3-isopropylpyrazolo[1,5-a]pyrimidin-5-yl)amino)methyl)-3-hydroxypiperidine-1-carboxylate (120 mg, 0.18 mmol) in 1,4-dioxane (1 mL). The reaction mixture was stirred at 35° C. for 1 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (66 mg, 0.14 mmol, 81% yield, 97% purity) as an off-white solid after precipitation from $Et_2O$ and drying overnight at 40° C. under vacuum.

UPLC/MS (Method 4): m/z 446 (M+H)+, $R_T$ 1.18 min.

$^1$H NMR (500 MHz, DMSO-$d_6$) δ 8.35 (d, J=8.5 Hz, 1H), 8.04-7.99 (m, 2H), 7.97 (dd, J=8.2, 1.4 Hz, 1H), 7.81-7.74 (m, 1H), 7.68 (s, 1H), 7.62-7.57 (m, 1H), 7.53 (d, J=8.5 Hz, 1H), 6.75-6.68 (m, 1H), 5.29-5.23 (m, 1H), 5.19 (s, 1H), 4.73 (d, J=6.0 Hz, 2H), 3.56-3.44 (m, 1H), 3.21-3.14 (m, 1H), 3.05-2.98 (m, 1H), 2.99-2.92 (m, 1H), 2.88 (dd, J=11.5, 4.5 Hz, 1H), 2.78-2.72 (m, 1H), 2.31-2.23 (m, 1H), 2.17-2.11 (m, 1H), 1.55-1.49 (m, 1H), 1.36-1.27 (m, 1H), 1.27-1.22 (m, 6H), 1.16-1.11 (m, 1H). 1H underwater.

Synthesis 15

(3R,4R)-4-(((7-(((2,7-dimethylimidazo[1,2-a]pyridin-3-yl)methyl)amino)-3-isopropylpyrazolo[1,5-a]pyrimidin-5-yl)amino)methyl)piperidin-3-ol (H-AP-PAMP-015)

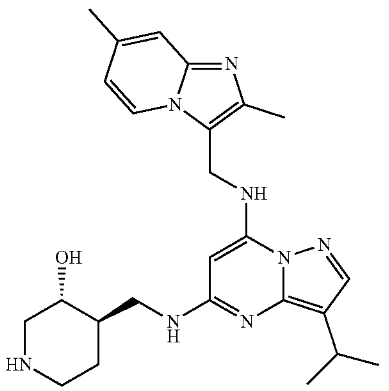 [SMILES: Cc1ccn2c(CNc3cc(NC[C@H]4CCNC[C@@H]4O)nc4c(C(C)C)cnn34)c(C)nc2c1]

Step 1: 5-chloro-N-((2,7-dimethylimidazo[1,2-a]pyridin-3-yl)methyl)-3-isopropylpyrazolo[1,5-a]pyrimidin-7-amine (2,7-Dimethylimidazo[1,2-a]pyridin-3-yl)methanamine (171 mg, 0.976 mmol) was added to a solution of 5,7-dichloro-3-isopropylpyrazolo[1.5-a]pyrimidine (187 mg, 0.813 mmol) and DIPEA (0.85 mL, 4.874 mmol) in EtOH (3.2 mL). The reaction mixture was heated to reflux overnight. The reaction mixture was concentrated in vacuo. Purification by column chromatography (12 g cartridge, 0-100% EtOAc in isohexane) gave the title compound (233 mg, 0.57 mmol, 70% yield, 90% purity) as an off-white solid.

UPLC/MS (Method 6): m/z 369 (M+H)+, $R_T$ 0.73 min

Step 2: tert-butyl (5-chloro-3-isopropylpyrazolo[1,5-a]pyrimidin-7-yl)((2,7-dimethylimidazo[1,2-a]pyridin-3-yl)methyl)carbamate BOC-Anhydride (179 mg, 819 μmol) was added to a solution of 5-chloro-N-((2,7-dimethylimidazo[1,2-a]pyridin-3-yl)methyl)-3-isopropylpyrazolo[1,5-a]pyrimidin-7-amine (233 mg, 0.63 mmol) and DMAP (15.4 mg, 126 μmol) in THE (12.6 mL). The reaction mixture was stirred at 60° C. for 16 min. The reaction mixture was concentrated under reduced pressure and the residue partitioned between DCM (15 mL) and water (10 mL). The organic layer was washed with brine (2×10 mL), filtered through a phase separator, and concentrated under reduced pressure. Purification by column chromatography (12 g cartridge, 0-4% MeOH/DCM) gave the title compound (249 mg, 0.50 mmol, 79% yield, 94% purity) as a pale yellow solid.

UPLC/MS (Method 6): m/z 469 (M+H)+, $R_T$ 0.84 min.

Step 3: tert-butyl (3R,4R)-4-(((7-((tert-butoxycarbonyl)((2,7-dimethylimidazo[1,2-a]pyridin-3-yl)methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)((2,7-dimethylimidazo[1,2-a]pyridin-3-yl)methyl)carbamate (120 mg, 0.256 mmol), (3R,4R)-tert-butyl 4-(aminomethyl)-3-hydroxypiperidine-1-carboxylate (64.9 mg, 0.282 mmol) and $^{t}$BuBrettPhos Pd G3 (21.9 mg, 0.0256 mmol) in THE (2.5 mL) was degassed with N2 for 10 min. LiHMDS (1 M in THF) (0.33 mL, 333 μmol) was added in one portion under bubbling N2. Bubbling was ceased and the reaction mixture heated to 60° C. for 4.5 h. At RT, the reaction mixture was filtered through celite, rinsing with EtOAc (15 mL). The filtrate was diluted with water and the aqueous was extracted with EtOAc (3×20 mL). The combined organic layers were dried over Na2SO4, filtered and concentrated under reduced pressure. Purification by column chromatography (12 g cartridge, 0-80% (1:3 EtOH/EtOAc)/isohexane) gave the title compound (89 mg, 0.10 mmol, 39% yield, 75% purity) as a brown oil.

UPLC/MS (Method 4): m/z 663 (M+H)+, $R_T$ 1.75 min.

Step 4: (3R,4R)-4-(((7-((imidazo[1,2-a]pyrimidin-2-ylmethyl)amino)-3-isopropylpyrazolo[1,5-a]pyrimidin-5-yl)amino)methyl)piperidin-3-ol Hydrogen chloride (4 M in 1,4-dioxane) (0.66 mL, 2.62 mmol) was added to a suspension of tert-butyl (3R,4R)-4-(((7-((tert-butoxycarbonyl)((2,7-dimethylimidazo[1,2-a]pyridin-3-yl)methyl)amino)-3-isopropylpyrazolo[1,5-a]pyrimidin-5-yl)amino)methyl)-3-hydroxypiperidine-1-carboxylate (87 mg, 0.131 mmol) in 1,4-dioxane (1.0 mL). The reaction mixture was stirred at 35° C. for 2.5 h and concentrated in vacuo. The residue was loaded onto a column of SCX. The column was washed with MeOH (30 mL) and the product eluted with 0.7 M $NH_3$ in MeOH (60 mL). The ammoniacal methanol solution was concentrated in vacuo to give the title compound (40 mg, 83 mmol, 63% yield, 95% purity) as a pale yellow solid after precipitation from $Et_2O$ and drying overnight at 40° C. under vacuum.

UPLC/MS (Method 4): m/z 463 (M+H)+, $R_T$ 1.05 min.

$^1$H NMR (500 MHz, DMSO-$d_6$) δ 8.51 (d, J=7.0 Hz, 1H), 7.80 (t, J=5.4 Hz, 1H), 7.59 (s, 1H), 7.21 (s, 1H), 6.85-6.79 (m, 1H), 6.75 (dd, J=7.0, 1.7 Hz, 1H), 5.33-5.28 (m, 1H), 5.17 (s, 1H), 4.73 (d, J=5.1 Hz, 2H), 3.61-3.48 (m, 1H), 3.23-3.16 (m, 1H), 3.06-2.98 (m, 1H), 2.95-2.86 (m, 2H), 2.84-2.76 (m, 1H), 2.48 (s, 3H), 2.33-2.30 (m, 4H), 2.19-2.12 (m, 1H), 1.61-1.53 (m, 1H), 1.39-1.32 (m, 1H), 1.22-1.18 (m, 6H), 1.19-1.12 (m, 1H). 1H under water.

Intermediate Synthesis A2

(2,7-dimethylimidazo[1,2-a]pyridin-3-yl)methanamine

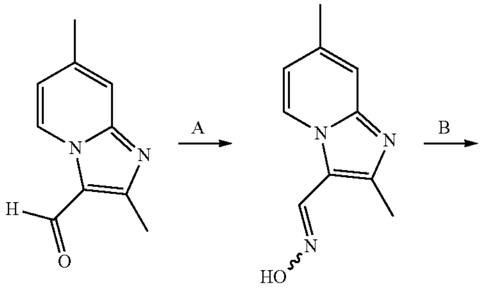

-continued

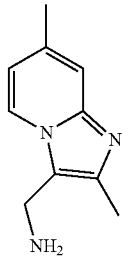

Step A/B: 2,7-dimethylimidazo[1,2-a]pyridine-3-carbaldehyde oxime/(2,7-dimethylimidazo[1,2-a]pyridin-3-yl)methanamine A solution of 2,7-dimethylimidazo[1,2-a]pyridine-3-carbaldehyde (0.525 g, 3.01 mmol), hydroxylamine hydrochloride (0.524 g, 7.54 mmol) and pyridine (0.61 mL, 7.54 mmol) in EtOH (14.8 mL) was stirred at 80° C. for 2 h. The reaction mixture was concentrated under reduced pressure then redissolved in AcOH (10.5 mL). The solution was cooled at 0° C. then sodium acetate (50 mg, 604 μmol) and zinc dust (2.96 g, 45.3 mmol) were added. The reaction mixture was stirred at RT overnight before being filtered through celite, rinsing with DCM (100 mL). The filtrate was concentrated to dryness to afford an oil. Filtration through SCX (14 g—wash with MeOH (100 mL), elution with MeOH containing 0.7 M $NH_3$ (100 mL)) gave the title compound (2,7-dimethylimidazo[1,2-a]pyridin-3-yl)methanamine (0.259 g, 1.33 mmol, 44% yield, 90% purity) as a white solid.

UPLC/MS (Method 6): m/z 176 (M+H)+, $R_T$ 0.42 min.

Synthesis 16

(3R,4R)-4-(((7-((imidazo[1,2-a]pyridin-3-ylmethyl)amino)-3-isopropylpyrazolo[1,5-a]pyrimidin-5-yl)amino)methyl)piperidin-3-ol (H-APPAMP-016)

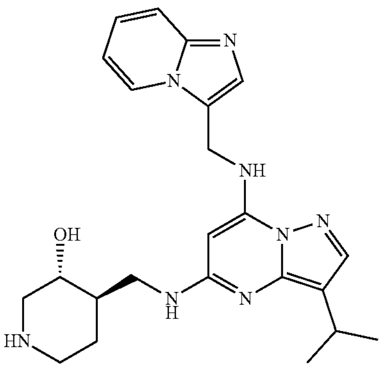 [SMILES: CC(C)c1cnn2c(NCc3cnc4ccccn34)cc(NC[C@H]3CCNC[C@@H]3O)nc12]

Step 1: 5-chloro-N-(imidazo[1,2-a]pyridin-3-ylmethyl)-3-isopropylpyrazolo[1,5-a]pyrimidin-7-amine Imidazo[1,2-a]pyridin-3-ylmethanamine, 2HCl (115 mg, 522 μmol) was added to a solution of 5,7-dichloro-3-isopropylpyrazolo[1,5-a]pyrimidine (100 mg, 435 μmol) and DIPEA (0.38 mL, 2.17 mmol) in EtOH (1.5 mL). The reaction mixture was heated at reflux overnight. The reaction mixture was concentrated in vacuo Purification by column chromatography (24 g cartridge, 0-100% EtOAc/isohexane) gave the title compound 5-chloro-N-(imidazo[1,2-a]pyridin-3-ylmethyl)-3-isopropylpyrazolo[1,5-a]pyrimidin-7-amine (137 mg, 0.38 mmol, 88% yield, 95% purity) as a white solid.

$^1H$ NMR (500 MHz, DMSO-$d_6$) was consistent with product structure.

Step 2: tert-butyl (5-chloro-3-isopropylpyrazolo[1,5-a]pyrimidin-7-yl)(imidazo[1,2-a]pyridin-3-ylmethyl)carbamate BOC-Anhydride (97 mg, 442 μmol) was added to a solution of 5-chloro-N-(imidazo[1,2-a]pyridin-3-ylmethyl)-3-isopropylpyrazolo[1,5-a]pyrimidin-7-amine (137 mg, 402 μmol) and DMAP (5 mg, 40.2 μmol) in THE (2 mL). The reaction mixture was stirred at RT for 3 h. The reaction mixture was concentrated under reduced pressure Purification by column chromatography (24 g cartridge, 0-100% EtOAc/isohexane) gave the title compound tert-butyl (5-chloro-3-isopropylpyrazolo[1,5-a]pyrimidin-7-yl)(imidazo[1,2-a]pyridin-3-ylmethyl)carbamate (169 mg, 0.36 mmol, 91% yield, 95% purity) as a white solid.

UPLC/MS (Method 4): m/z 441 (M+H)+, $R_T$ 1.71 min.

Step 3: tert-Butyl (3R,4R)-4-(((7-((tert-butoxycarbonyl)(imidazo[1,2-a]pyridin-3-ylmethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(imidazo[1,2-a]pyridin-3-ylmethyl)carbamate (167 mg, 379 μmol), (3R,4R)-tert-butyl 4-(aminomethyl)-3-hydroxypiperidine-1-carboxylate (96.0 mg, 417 μmol) and $^t$BuBrettPhos Pd G3 (32.4 mg, 37.9 μmol) in THE (3.3 mL) was degassed with N2 for 10 min. LiHMDS (1M in THF) (492 μl, 492 μmol) was added in one portion under bubbling N2. Bubbling was ceased and the reaction mixture heated to 60° C. for 2 h. The reaction was quenched with water (15 mL) and extracted with EtOAc (3×15 mL). The combined organic layers were filtered through a phase separator and concentrated under reduced pressure.

Purification by column chromatography (12 g cartridge, 0-100% EtOAc/isohexane then 0-5% (MeOH containing 0.7 M $NH_3$)/DCM) gave an oil. Further purification by column chromatography (12 g cartridge, 0-10% (MeOH containing 0.7 M $NH_3$)/DCM) gave the title compound (112 mg, 0.17 mmol, 46% yield, 98% purity) as a yellow oil.

UPLC/MS (Method 4): m/z 635 (M+H)+, $R_T$ 1.64 min.

Step 4: (3R,4R)-4-(((7-((imidazo[1,2-a]pyridin-3-ylmethyl)amino)-3-isopropylpyrazolo[1,5-a]pyrimidin-5-yl)amino)methyl)piperidin-3-ol Hydrogen chloride (4 M in 1,4-dioxane) (0.88 mL, 3.53 mmol) was added to a solution of tert-butyl (3R,4R)-4-(((7-((tert-butoxycarbonyl)(imidazo[1,2-a]pyridin-3-ylmethyl)amino)-3-isopropylpyrazolo[1,5-a]pyrimidin-5-yl)amino)methyl)-3-hydroxypiperidine-1-carboxylate (112 mg, 176 μmol) in 1,4-dioxane (0.5 mL). The reaction mixture was stirred at 35 for 1 h and concentrated in vacuo. The residue was loaded onto a column of SCX. The column was washed with MeOH (40 mL) and the product eluted with MeOH containing 0.7 M $NH_3$ (40 mL). The ammoniacal methanol solution was concentrated in vacuo to give the title compound (57 mg, 0.13 mmol, 73% yield, 98% purity) as a white solid after precipitation from $Et_2O$.

UPLC/MS (Method 4): m/z 435 (M+H)+, $R_T$ 0.97 min.

$^1H$ NMR (500 MHz, DMSO-$d_6$) δ 8.48 (dd, J=6.8, 1.2 Hz, 1H), 7.78 (s, 1H), 7.65 (t, J=6.1 Hz, 1H), 7.63 (s, 1H), 7.50 (d, J=9.1 Hz, 1H), 7.24-7.18 (m, 1H), 6.85 (td, J=6.7, 1.2 Hz, 1H), 6.75-6.69 (m, 1H), 5.33-5.29 (m, 1H), 5.28 (s, 1H), 4.56 (d, J=6.0 Hz, 2H), 3.60-3.47 (m, 1H), 3.22-3.15 (m, 1H), 3.06-2.99 (m, 1H), 2.99-2.92 (m, 1H), 2.90 (dd, J=11.6, 4.5 Hz, 1H), 2.81-2.74 (m, 1H), 2.33-2.25 (m, 1H), 2.15 (dd, J=11.6, 9.9 Hz, 1H), 1.57-1.51 (m, 1H), 1.38-1.28 (m, 1H), 1.23 (t, J=6.5 Hz, 6H), 1.19-1.10 (m, 1H). 1H under water.

Synthesis 17

(3R,4R)-4-(((3-isopropyl-7-(((3-methylimidazo[1,2-a]pyridin-2-yl)methyl)amino)pyrazolo[1,5-a]pyrimidin-5-yl)amino)methyl)piperidin-3-ol (H-APPAMP-017)

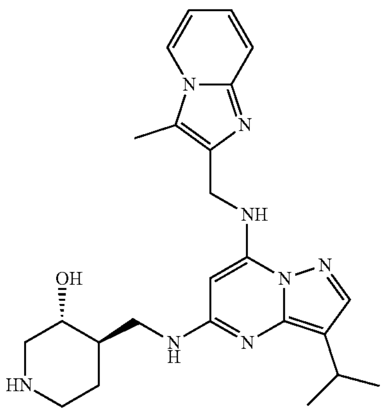

Step 1: 5-chloro-3-isopropyl-N-((3-methylimidazo[1,2-a]pyridin-2-yl)methyl)pyrazolo[1,5-a]pyrimidin-7-amine (3-Methylimidazo[1,2-a]pyridin-2-yl)methanamine (105 mg, 652 μmol) was added to a solution of 5,7-dichloro-3-isopropylpyrazolo[1,5-a]pyrimidine (150 mg, 652 μmol) and DIPEA (0.85 mL, 4.89) in EtOH (3.2 mL). The reaction mixture was heated at 80° C. overnight. The reaction mixture was concentrated in vacuo. Purification by column chromatography (12 g cartridge, 0-100% EtOAc/isohexane) gave the title compound (130 mg, 0.31 mmol, 48% yield, 85% purity) as a yellow solid.

UPLC/MS (Method 4): m/z 355 (M+H)+, $R_T$ 1.48 min

Step 2: tert-butyl (5-chloro-3-isopropylpyrazolo[1,5-a]pyrimidin-7-yl)((3-methylimidazo[1,2-a]pyridin-2-yl)methyl)carbamate BOC-Anhydride (32 mg, 0.15 mmol) was added to a solution of 5-chloro-3-isopropyl-N-((3-methylimidazo[1,2-a]pyridin-2-yl)methyl)pyrazolo[1,5-a]pyrimidin-7-amine (44 mg, 0.12 mmol) and DMAP (3 mg, 25 μmol) in THE (1.2 mL). The reaction mixture was stirred at RT for 2 h. The reaction mixture was concentrated under reduced pressure. Purification $N_2$ by column chromatography (4 g cartridge, 0-100% EtOAc/isohexane) gave the title compound (51 mg, 0.11 mmol, 89% yield, 99% purity) as a white solid.

UPLC/MS (Method 4): m/z 455 (M+H)+, $R_T$ 1.80 min.

Step 3: tert-butyl (3R,4R)-4-(((7-((tert-butoxycarbonyl)((3-methylimidazo[1,2-a]pyridin-2-yl)methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)((3-methylimidazo[1,2-a]pyridin-2-yl)methyl)carbamate (88 mg, 0.19 mmol), (3R,4R)-tert-butyl 4-(aminomethyl)-3-hydroxypiperidine-1-carboxylate (49 mg, 0.21 mmol) and $^t$BuBrettPhos Pd G3 (17 mg, 19 μmol) in THE (1.9 mL) was degassed with $N_2$ for 10 min. LiHMDS (1 M in THF) (0.25 mL, 0.25 mmol) was added in one portion under bubbling $N_2$. Bubbling was ceased and the reaction mixture heated to 60° C. for 1.5 h. The reaction mixture was concentrated under reduced pressure. Purification by column chromatography (12 g cartridge, 0-100% EtOAc/isohexane then 0-100% (1:3 EtOH/EtOAc)/isohexane) gave the title compound (140 mg, 0.18 mmol, 95% yield, 85% purity) as a brown oil.

UPLC/MS (Method 4): m/z 649 (M+H)+, $R_T$ 1.69 min.

Step 4: ((3R,4R)-4-(((3-isopropyl-7-(((3-methylimidazo[1,2-a]pyridin-2-yl)methyl)amino)pyrazolo[1,5-a]pyrimidin-5-yl)amino)methyl)piperidin-3-ol Hydrogen chloride (4 M in dioxane) (1.02 mL, 4.10 mmol) was added to a suspension of tert-butyl (3R,4R)-4-(((7-((tert-butoxycarbonyl)((3-methylimidazo[1,2-a]pyridin-2-yl)methyl)amino)-3-isopropylpyrazolo[1,5-a]pyrimidin-5-yl)amino)methyl)-3-hydroxypiperidine-1-carboxylate (140 mg, 205 μmol) in dioxane (1.0 mL). The reaction mixture was stirred at 35° C. for 1.5 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (30 mg, 60 μmol, 32%, 95% purity) as a cream solid after precipitation from $Et_2O$ and drying overnight at 40° C. under vacuum.

UPLC/MS (Method 4): m/z 449 (M+H)+, $R_T$ 1.02 min.

$^1H$ NMR (400 MHz, DMSO-$d_6$) δ 8.23 (d, J=6.9 Hz, 1H), 7.61 (s, 1H), 7.53-7.49 (m, 1H), 7.44 (t, J=5.8 Hz, 1H), 7.26-7.17 (m, 1H), 6.93 (td, J=6.8, 1.2 Hz, 1H), 6.80-6.74 (m, 1H), 5.39 (s, 1H), 5.35-5.31 (m, 1H), 4.55 (d, J=5.7 Hz, 2H), 3.61-3.47 (m, 1H), 3.24-3.15 (m, 1H), 3.08-2.99 (m, 1H), 2.99-2.86 (m, 2H), 2.82-2.74 (m, 1H), 2.35-2.24 (m, 1H), 2.16 (dd, J=11.6, 9.9 Hz, 1H), 1.61-1.52 (m, 1H), 1.40-1.29 (m, 1H), 1.22 (dd, J=6.9, 5.0 Hz, 6H), 1.19-1.13 (m, 1H). 4H not visible.

Intermediate Synthesis A3

3-methylimidazo[1,2-a]pyridin-2-yl)methanamine

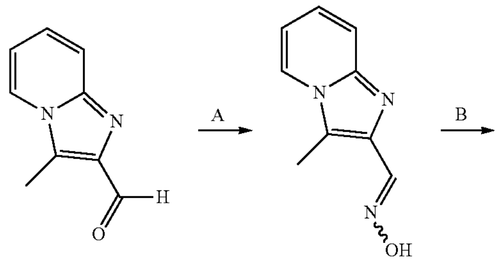

-continued

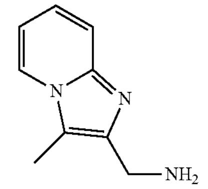

Step A/B: 3-methylimidazo[1,2-a]pyridine-2-carbaldehyde oxime/(3-methylimidazo[1,2-a]pyridin-2-yl) methanamine A suspension of 3-methylimidazo[1,2-a]pyridine-2-carbaldehyde (500 mg, 3.12 mmol), hydroxylamine hydrochloride (542 mg, 7.80 mmol) and pyridine (0.63 mL, 7.80 mmol) in EtOH (5.0 mL) was stirred at 80° C. for 2 h. The reaction mixture was concentrated under reduced pressure then redissolved in AcOH (5.0 mL). The solution was cooled at 0° C. then sodium acetate (51 mg, 616 μmol) and zinc dust (2.02 g, 30.8 mmol) were added. The reaction mixture was stirred at RT overnight before being filtered through celite, rinsing with DCM (50 mL) and MeOH (50 mL). The filtrate was concentrated to dryness to afford an oil. Filtration through SCX (14 g—wash with MeOH (50 mL), elution with MeOH containing 0.7M $NH_3$ (50 mL)) gave the title compound (371 mg, 2.2 mmol, 71% yield, 95% purity) as a white solid.

$^1$H NMR in DMSO-d6 was consistent with product structure.

Synthesis 18

(3R,4R)-4-(((7-((imidazo[1,2-a]pyridin-2-ylmethyl-d2)amino)-3-isopropylpyrazolo[1,5-a]pyrimidin-5-yl)amino)methyl)piperidin-3-ol (H-APPAMP-018)

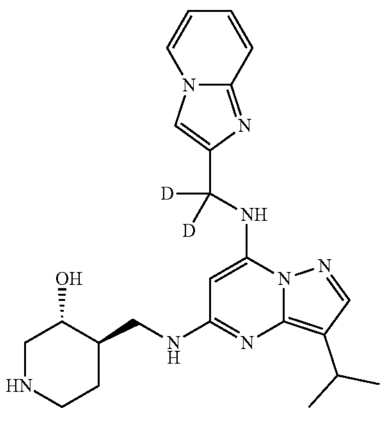 [SMILES: [2H]C([2H])(Nc1cc(NC[C@H]2CCNC[C@@H]2O)nc2c(C(C)C)cnn12)c1cn2ccccc2n1]

Step 1: 5-chloro-N-(imidazo[1,2-a]pyridin-2-ylmethyl-d2)-3-isopropylpyrazolo[1,5-a]pyrimidin-7-amine Imidazo[1,2-a]pyridin-2-ylmethan-d2-amine (102 mg, 684 μmol) was added to a solution of 5,7-dichloro-3-isopropylpyrazolo[1,5-a]pyrimidine (157 mg, 684 μmol) and DIPEA (0.89 mL, 893 μmol) in EtOH (7.0 mL). The reaction mixture was heated at 80° C. overnight. The reaction mixture was concentrated in vacuo. Purification by column chromatography (4 g cartridge, 0-100% EtOAc/isohexane) gave the title compound (180 mg, 0.50 mmol, 73% yield, 95% purity) as a white solid.

UPLC/MS (Method 4): m/z 345 (M+H)+, $R_T$ 1.36 min.

Step 2: tert-butyl (5-chloro-3-isopropylpyrazolo[1,5-a]pyrimidin-7-yl)(imidazo[1,2-a]pyridin-2-ylmethyl-d2)carbamate BOC-Anhydride (131 mg, 599 μmol) was added to a solution of 5-chloro-N-(imidazo[1,2-a]pyridin-2-ylmethyl-d2)-3-isopropylpyrazolo[1,5-a]pyrimidin-7-amine (180 mg, 499 μmol) and DMAP (12 mg, 99.8 μmol) in THE (5.0 mL). The reaction mixture was stirred at RT for 2 h. The reaction mixture was concentrated under reduced pressure. Purification by column chromatography (12 g cartridge, 0-100% EtOAc/isohexane) gave the title compound (184 mg, 0.36 mmol, 72% yield, 87% purity) as a white solid.

UPLC/MS (Method 4): m/z 445 (M+H)+, $R_T$ 1.72 min.

Step 3: tert-butyl (3R,4R)-4-(((7-((tert-butoxycarbonyl)(imidazo[1,2-a]pyridin-2-ylmethyl-d2)amino)-3-isopropylpyrazolo[1,5-a]pyrimidin-5-yl)amino) methyl)-3-hydroxypiperidine-1-carboxylate A solution of tert-butyl (5-chloro-3-isopropylpyrazolo[1,5-a]pyrimidin-7-yl)(imidazo[1,2-a]pyridin-2-ylmethyl-d2) carbamate (184 mg, 415 μmol), (3R,4R)-tert-butyl 4-(aminomethyl)-3-hydroxypiperidine-1-carboxylate (105 mg, 457 μmol) and $^t$BuBrettPhos Pd G3 (35.5 mg, 41.5 μmol) in THE (1.9 mL) was degassed with $N_2$ for 10 min. LiHMDS (1 M in THF) (540 μL, 540 μmol) was added in one portion under bubbling $N_2$. Bubbling was ceased and the reaction mixture heated to 60° C. for 1.5 h. Purification by column chromatography (12 g cartridge, 0-100% EtOAc/isohexane) gave the title compound (236 mg, 0.33 mmol, 80% yield, 90% purity) as a white solid.

UPLC/MS (Method 4): m/z 637 (M+H)+, $R_T$ 1.64 min.

Step 4: (3R,4R)-4-(((7-((imidazo[1,2-a]pyridin-2-ylmethyl-d2)amino)-3-isopropylpyrazolo[1,5-a]pyrimidin-5-yl)amino)methyl)piperidin-3-ol Hydrogen chloride (4 M in dioxane) (0.79 mL, 3.14 mmol) was added to a suspension of tert-butyl (3R,4R)-4-(((7-((tert-butoxycarbonyl)(imidazo[1,2-a]pyridin-2-ylmethyl-d2)amino)-3-isopropylpyrazolo[1,5-a]pyrimidin-5-yl) amino)methyl)-3-hydroxypiperidine-1-carboxylate (100 mg, 157 μmol) in dioxane (1.0 mL). The reaction mixture was stirred at 35° C. for 4 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (61 mg, 0.13 mmol, 85% yield, 95% purity) as a white solid after precipitation from $Et_2O$ and drying overnight at 40° C. under vacuum.

UPLC/MS (Method 4): m/z 437 (M+H)+, $R_T$ 1.03 min.

$^1$H NMR (400 MHz, DMSO-$d_6$) δ 8.48 (dt, J=6.8, 1.3 Hz, 1H), 7.78 (s, 1H), 7.63 (s, 2H), 7.50 (d, J=9.1 Hz, 1H), 7.20 (m, 1H), 6.85 (td, J=6.8, 1.2 Hz, 1H), 6.76-6.68 (m, 1H), 5.29 (m, 2H), 3.60-3.48 (m, 1H), 3.23-3.13 (m, 1H), 3.07-2.85 (m, 3H), 2.80-2.72 (m, 1H), 2.34-2.23 (m, 1H), 2.14 (dd, J=11.5, 10.0 Hz, 1H), 1.58-1.49 (m, 1H), 1.37-1.27 (m, 1H), 1.23 (dd, J=6.9, 4.9 Hz, 6H), 1.19-1.11 (m, 1H). 1H under water.

Intermediate Synthesis A4

Imidazo[1,2-a]pyridin-2-ylmethan-d2-amine

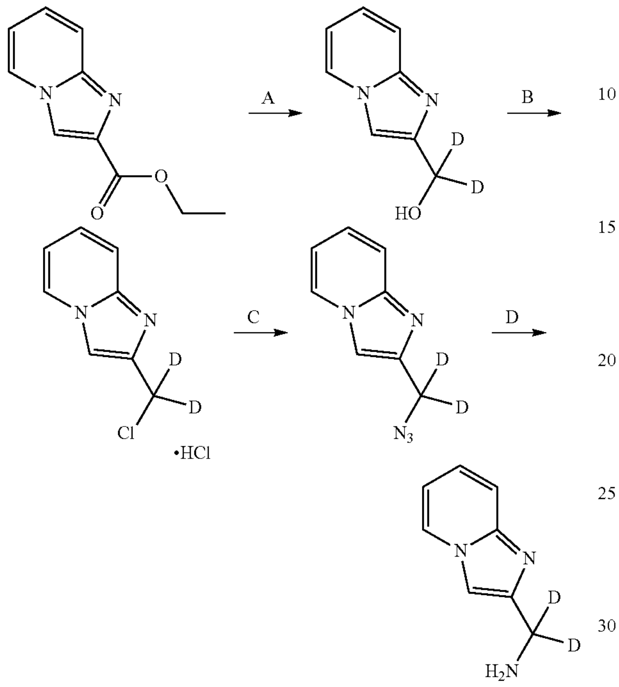

Step A: imidazo[1,2-a]pyridin-2-ylmethan-d2-ol

Lithium aluminium deuteride (88 mg, 2.10 mmol) was added to a solution of ethyl imidazo[1,2-a]pyridine-2-carboxylate (400 mg, 2.10 mmol) in THE (21 mL) at 0° C. The mixture was stirred for 15 min at 0° C. then water (0.1 mL) was added followed by 2M aq. NaOH solution (0.1 mL) then water (0.3 mL). The solution was warmed to RT, stirred for 15 min then anhydrous $MgSO_4$ was added and the mixture was stirred for a further 15 min. The mixture was concentrated under reduced pressure.

Purification by chromatography (12 g cartridge, 0-100% (3:1 EtOAc/EtOH)/isohexane) gave the title compound (211 mg, 1.4 mmol, 65% yield, 98% purity) as a white solid.

UPLC/MS (Method 4): m/z 151 (M+H)+, $R_T$ 0.47 min.

Step B: 2-(chloromethyl-d2)imidazo[1,2-a]pyridine, HCl

Thionyl chloride (205 μL, 2.81 mmol) was added dropwise to a solution of imidazo[1,2-a]pyridin-2-ylmethan-d2-ol (211 mg, 1.40 mmol) in DCM (14 mL) at 0° C. The mixture was stirred at 0° C. for 2 h then concentrated to dryness under reduced pressure to give the title compound (278 mg, 1.3 mmol, 92% yield, 95% purity) as a cream solid.

UPLC/MS (Method 3): m/z 169 (M+H)+, $R_T$ 0.16 min.

Step C: 2-(azidomethyl-d2)imidazo[1,2-a]pyridine

A solution of 2-(chloromethyl-d2)imidazo[1,2-a]pyridine, HCl (278 mg, 1.36 mmol) and DIPEA (708 μL, 4.07 mmol) in DMF (14 mL) was treated with sodium azide (132 mg, 2.03 mmol). The mixture was heated to 60° C. and stirred for 2 h. The mixture was cooled to RT, diluted with water (100 mL). Extraction with TBME (3×25 mL). The combined organic layers were dried over $MgSO_4$ and concentrated under reduced pressure. Purification by chromatography (12 g cartridge, 0-100% (3:1 EtOAc/EtOH)/isohexane) gave the title compound (150 mg, 0.66 mmol, 49% yield, 77% purity) as a yellow oil.

UPLC/MS (Method 4): m/z 176 (M+H)+, $R_T$ 0.77 min.

Step D: imidazo[1,2-a]pyridin-2-ylmethan-d2-amine 2-(Azidomethyl-d2)imidazo[1,2-a]pyridine (150 mg, 659 μmol) and triphenylphosphine (208 mg, 791 μmol) were dissolved in THE (8.0 mL) and water (0.8 mL). The mixture was heated to 50° C. and stirred for 1 h before removal of the solvent in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (102 mg, 0.65 mmol, 99% yield, 95% purity) as a white solid.

$^1H$ NMR in DMSO-$d_6$ was consistent with product structure.

Synthesis 19

(3R,4R)-4-(((7-((1-(imidazo[1,2-a]pyridin-2-yl)ethyl)amino)-3-isopropylpyrazolo[1,5-a]pyrimidin-5-yl)amino)methyl)piperidin-3-ol (H-APPAMP-019)

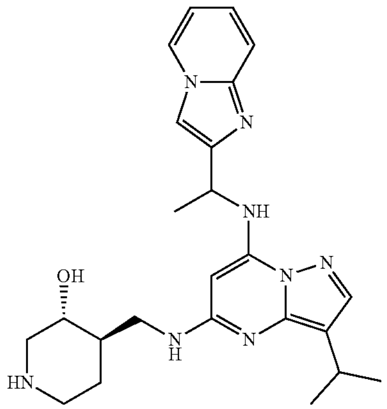 [SMILES: CC(C)c1cnn2c(NC(C)c3cn4ccccc4n3)cc(NC[C@H]3CCNC[C@@H]3O)nc12]

Step 1: 5-chloro-N-(1-(imidazo[1,2-a]pyridin-2-yl)ethyl)-3-isopropylpyrazolo[1,5-a]pyrimidin-7-amine 1-(Imidazo[1,2-a]pyridin-2-yl)ethan-1-amine (133 mg, 782 μmol) was added to a solution of 5,7-dichloro-3-isopropylpyrazolo[1,5-a]pyrimidine (100 mg, 435 μmol) and DIPEA (0.38 mL, 2.17 mmol) in EtOH (3.0 mL). The reaction mixture was heated at 90° C. for 1 h. The reaction mixture was concentrated in vacuo.

Purification by chromatography (12 g cartridge, 0-100% EtOAc/isohexane) gave the title compound (158 mg, 0.42 mmol, 97% yield, 95% purity) as a white solid.

UPLC/MS (Method 4): m/z 355 (M+H)+, $R_T$ 1.47 min.

Step 2: tert-butyl (5-chloro-3-isopropylpyrazolo[1,5-a]pyrimidin-7-yl)(1-(imidazo[1,2-a]pyridin-2-yl)ethyl)carbamate BOC-Anhydride (136 mg, 623 μmol) was added to a solution of 5-chloro-N-(1-(imidazo[1,2-a]pyridin-2-yl)

ethyl)-3-isopropylpyrazolo[1,5-a]pyrimidin-7-amine (158 mg, 445 μmol) and DMAP (5.4 mg, 44.5 μmol) in THE (2.5 mL). The reaction mixture was stirred at 50° C. overnight. More BOC-Anhydride (136 mg, 623 μmol) was added and the reaction mixture was stirred at 50° C. for 3 h. The reaction mixture was concentrated in vacuo. Purification by column chromatography (12 g cartridge, 0-100% EtOAc/isohexane) gave the title compound (171 mg, 0.36 mmol, 80% yield, 95% purity) as a yellow oil.

UPLC/MS (Method 3): m/z 455 (M+H)+, $R_T$ 1.79 min.

Step 3: tert-butyl (3R,4R)-4-(((7-((tert-butoxycarbonyl)(1-(imidazo[1,2-a]pyridin-2-yl)ethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(1-(imidazo[1,2-a]pyridin-2-yl)ethyl) carbamate (171 mg, 376 μmol), (3R,4R)-tert-butyl 4-(aminomethyl)-3-hydroxypiperidine-1-carboxylate (95 mg, 413 μmol) and $^{t}$BuBrettPhos Pd G3 (32 mg, 37.6 μmol) in THE (3.2 mL) was degassed with $N_2$ for 10 min. LiHMDS (1 M in THF) (0.49 mL, 489 μmol) was added in one portion under bubbling $N_2$. Bubbling was ceased and the reaction mixture heated to 60° C. for 2 h. At RT, water (15 mL) and EtOAc (25 mL) were added. The layers were separated, and the aq. layer extracted with EtOAc (2×15 mL). The combined organic layers were filtered through a phase separator and concentrated. Purification by column chromatography (12 g cartridge, 0-10% MeOH/DCM) gave the title compound (168 mg, 0.24 mmol, 64% yield, 93% purity) as a yellow oil.

UPLC/MS (Method 4): m/z 649 (M+H)+, $R_T$ 1.68 min.

Step 4: (3R,4R)-4-(((7-((1-(imidazo[1,2-a]pyridin-2-yl)ethyl)amino)-3-isopropylpyrazolo[1,5-a]pyrimidin-5-yl)amino)methyl)piperidin-3-ol Hydrogen chloride (4 M in dioxane) (1.17 mL, 4.69 mmol) was added to a solution of tert-butyl (3R,4R)-4-(((7-((tert-butoxycarbonyl)(1-(imidazo[1,2-a]pyridin-2-yl)ethyl) amino)-3-isopropylpyrazolo[1,5-a]pyrimidin-5-yl)amino) methyl)-3-hydroxypiperidine-1-carboxylate (160 mg, 234 μmol) in dioxane (1.2 mL). The reaction mixture was stirred at 35° C. for 1 h and concentrated in vacuo. The residue was loaded onto a column of SCX. The column was washed with MeOH (40 mL) and the product eluted with 0.7 M $NH_3$ in MeOH (40 mL). The ammoniacal methanol solution was concentrated in vacuo to give the title compound (70 mg, 0.15 mmol, 63% yield, 95% purity) as an off-white solid after trituration from $Et_2O$ and drying overnight at 40° C. under vacuum.

UPLC/MS (Method 4): m/z 449 (M+H)+, $R_T$ 1.02 min.

$^{1}$H NMR (400 MHz, DMSO-$d_6$) δ 8.49 (d, J=6.8 Hz, 1H), 7.80 (d, J=4.9 Hz, 1H), 7.62 (s, 1H), 7.52 (d, J=9.1 Hz, 1H), 7.26-7.18 (m, 1H), 7.13 (d, J=7.8 Hz, 1H), 6.85 (t, J=6.7 Hz, 1H), 6.76-6.68 (m, 1H), 5.32 (d, J=2.0 Hz, 1H), 5.31-5.23 (m, 1H), 4.87-4.81 (m, 1H), 3.60-3.43 (m, 1H), 3.27-3.17 (m, 1H), 3.08-2.98 (m, 1H), 2.99-2.86 (m, 2H), 2.82-2.73 (m, 1H), 2.35-2.25 (m, 1H), 2.16 (td, J=10.8, 4.3 Hz, 1H), 1.66 (d, J=6.6 Hz, 3H), 1.60-1.51 (m, 1H), 1.40-1.28 (m, 1H), 1.26-1.20 (m, 6H), 1.18-1.12 (m, 1H). 1H underwater.

Intermediate Synthesis A5

1-(imidazo[1,2-a]pyridin-2-yl)ethan-1-amine

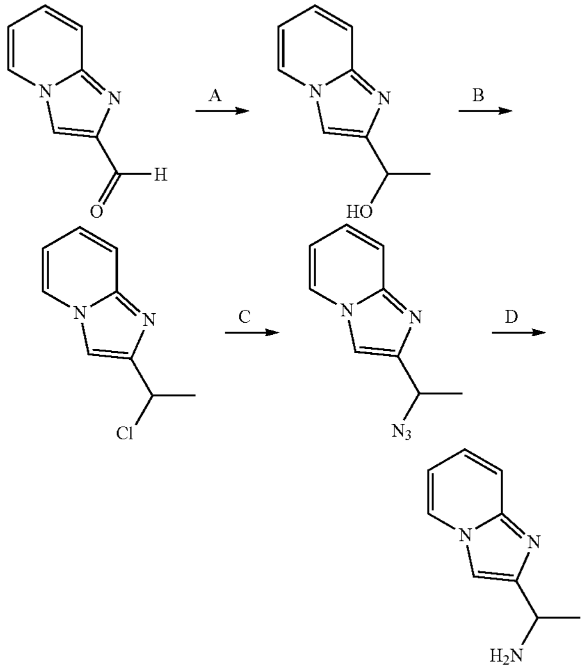

Step A: 1-(imidazo[1,2-a]pyridin-2-yl)ethan-1-ol

Methylmagnesium bromide (3M in $Et_2O$) (1.71 mL, 5.13 mmol) was added to a solution of imidazo[1,2-a]pyridine-2-carbaldehyde (0.500 g, 3.42 mmol) in THE (10 mL) at −10° C. The mixture was slowly warmed to RT and stirred overnight. Water (50 mL) was added and the aq. layer was extracted with EtOAc (3×50 mL). The combined organic layer was collected, dried over sodium sulfate, filtered and concentrated in vacuo to give the title (350 mg, 2.1 mmol, 61% yield, 96% purity) as a white solid.

UPLC/MS (Method 3): m/z 163 (M+H)+, $R_T$ 0.15 min.

Step B: 2-(1-chloroethyl)imidazo[1,2-a]pyridine, HCl

Thionyl chloride (675 μL, 9.25 mmol) was added dropwise to a solution of 1-(imidazo[1,2-a]pyridin-2-yl)ethan-1-ol (300 mg, 1.85 mmol) in DCE (5.0 mL) at RT. The mixture was stirred at 45° C. for 3 h then concentrated to dryness under reduced pressure to give the title compound (300 mg, 1.4 mmol, 74% yield, 82% purity) as a colourless oil.

UPLC/MS (Method 3): m/z 181 (M+H)+, $R_T$ 0.15 min.

Step C: 2-(1-azidoethyl)imidazo[1,2-a]pyridine

A solution of 2-(1-chloroethyl)imidazo[1,2-a]pyridine, HCl (200 mg, 921 μmol) and DIPEA (390 μL, 2.76 mmol) in DMF (14 mL) was treated with sodium azide (90 mg, 1.38 mmol). The mixture was heated to 60° C. and stirred for 6 h. The mixture was cooled to RT, diluted with water (40 mL) and brine (60 mL). Extraction with TBME (3×50 mL) and EtOAc (50 mL). The combined organic layers were dried over $Na_2SO_4$ and concentrated under reduced pressure. Purification by chromatography (12 g cartridge, 0-100% EtOAc/isohexane) gave the title compound (190 mg, 0.81 mmol, 88% yield, 80% purity) as a brown oil.

UPLC/MS (Method 4): m/z 188 (M+H)+, $R_T$ 0.90 min.

Step D: 1-(imidazo[1,2-a]pyridin-2-yl)ethan-1-amine 2-(1-Azidoethyl)imidazo[1,2-a]pyridine (190 mg, 913 μmol) and triphenylphosphine (287 mg, 1.10 mmol) were dissolved in THF (4.5 mL) and water (0.5 mL). The mixture was stirred at RT for 1 h then at 50° C. and stirred for 1 h before removal of the solvent in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (144 mg, 0.85 mmol, 93% yield, 95% purity) as a yellow oil.

UPLC/MS (Method 4): m/z 162 (M+H)+, $R_T$ 0.48 min.

Synthesis 20

(3R,4R)-4-(((7-((benzofuran-2-ylmethyl)amino)-3-isopropylpyrazolo[1,5-a]pyrimidin-5-yl)amino)methyl)piperidin-3-ol (H-APPAMP-020)

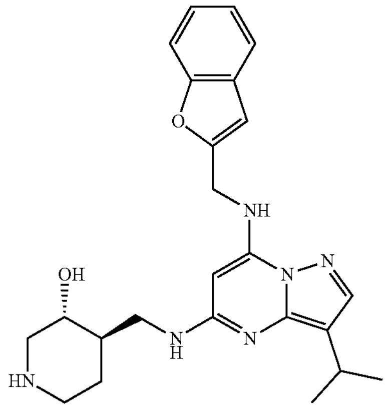 [SMILES: CC(C)c1cnn2c(NCc3cc4ccccc4o3)cc(NC[C@H]3CCNC[C@@H]3O)nc12]

Step 1: N-(benzofuran-2-ylmethyl)-5-chloro-3-isopropylpyrazolo[1,5-a]pyrimidin-7-amine Benzofuran-2-ylmethanamine hydrochloride (100 mg, 0.547 mmol) was added to a solution of 5,7-dichloro-3-isopropylpyrazolo[1,5-a]pyrimidine (105 mg, 0.456 mmol) and DIPEA (0.48 mL, 2.74 mmol) in EtOH (1.9 mL). The reaction mixture was heated at 90° C. overnight. The reaction mixture was concentrated in vacuo. Purification by column chromatography (12 g cartridge, 0-30% EtOAc/heptane) gave the title compound (157 mg, 0.42 mmol, 91% yield, 90% purity) as a yellow oil.

UPLC/MS (Method 4): m/z 341 (M+H)+, $R_T$ 1.82 min

Step 2: tert-butyl (benzofuran-2-ylmethyl)(5-chloro-3-isopropylpyrazolo[1,5-a]pyrimidin-7-yl)carbamate BOC-Anhydride (109 mg, 0.498 mmol) was added to a solution of N-(benzofuran-2-ylmethyl)-5-chloro-3-isopropylpyrazolo[1,5-a]pyrimidin-7-amine (157 g, 0.415 mmol) and DMAP (10 mg, 83 μmol) in THF (8.0 mL). The reaction mixture was stirred at 65° C. for 2 h. The reaction mixture was concentrated under reduced pressure and the residue partitioned between DCM (15 mL) and water (30 mL). The aq. layer was extracted with DCM (2×30 mL) and the combined organic layers were washed with brine (30 mL), filtered through a phase separator and concentrated under reduced pressure. Purification by column chromatography (12 g cartridge, 0-20% EtOAc/isohexane) gave the title compound (164 mg, 0.37 mmol, 89% yield, 99% purity) as a cream solid.

UPLC/MS (Method 4): m/z 385 (M+H-tBu)+, $R_T$ 2.10 min.

Step 3: tert-butyl (3R,4R)-4-(((7-((benzofuran-2-ylmethyl)(tert-butoxycarbonyl)amino)-3-isopropylpyrazolo[1,5-a]pyrimidin-5-yl)amino)methyl)-3-hydroxypiperidine-1-carboxylate A solution of tert-butyl (benzofuran-2-ylmethyl)(5-chloro-3-isopropylpyrazolo[1,5-a]pyrimidin-7-yl)carbamate (164 mg, 0.372 mmol), (3R,4R)-tert-butyl 4-(aminomethyl)-3-hydroxypiperidine-1-carboxylate (94 mg, 0.409 mmol) and $^t$BuBrettPhos Pd G3 (31.8 mg, 37.2 μmol) in THF (3.6 mL) was degassed with $N_2$ for 10 min. LiHMDS (1M in THF) (0.48 mL, 0.48 mmol) was added in one portion under bubbling $N_2$. Bubbling was ceased and the reaction mixture heated to 60° C. for 2 h. At RT, the mixture was filtered through celite, rinsing with EtOAc (15 mL). The filtrate was washed with water (15 mL) and the aq. layer was extracted with EtOAc (3×20 mL). The combined organic layers were dried over $Na_2SO_4$ and concentrated under reduced pressure. Purification by column chromatography (12 g cartridge, 0-100% EtOAc/isohexane) gave the title compound (235 mg, 0.33 mmol, 89 yield, 90% purity) as an orange solid.

UPLC/MS (Method 4): m/z 635 (M+H)+, $R_T$ 1.96 min.

Step 4: (3R,4R)-4-(((7-((benzofuran-2-ylmethyl)amino)-3-isopropylpyrazolo[1,5-a]pyrimidin-5-yl)amino)methyl)piperidin-3-ol Hydrogen chloride (4 M in dioxane) (2.0 mL, 8.0 mmol) was added to a suspension of tert-butyl (3R,4R)-4-(((7-((benzofuran-2-ylmethyl)(tert-butoxycarbonyl)amino)-3-isopropylpyrazolo[1,5-a]pyrimidin-5-yl)amino)methyl)-3-hydroxypiperidine-1-carboxylate (233 mg, 0.367 mmol) in dioxane (2.5 mL). The reaction mixture was stirred at 35° C. for 2 h then more hydrogen chloride (4 M in dioxane) (0.92 mL, 3.67 mmol) was added. The reaction mixture was stirred at 35° C. for 2.5 h then concentrated in vacuo.

The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (88 mg, 0.20 mmol, 54% yield, 97% purity) as a beige solid after trituration from $Et_2O$ and drying overnight at 40° C. under vacuum.

UPLC/MS (Method 4): m/z 435 (M+H)+, $R_T$ 1.37 min.

$^1H$ NMR (400 MHz, DMSO-$d_6$) δ 7.81 (t, J=6.3 Hz, 1H), 7.63 (s, 1H), 7.58 (dd, J=7.5, 1.6 Hz, 1H), 7.53 (d, J=8.0 Hz, 1H), 7.30-7.17 (m, 2H), 6.78 (s, 1H), 6.74 (t, J=6.1 Hz, 1H), 5.37 (s, 1H), 5.28-5.20 (m, 1H), 4.62 (d, J=6.1 Hz, 2H), 3.56-3.45 (m, 1H), 3.27-3.17 (m, 1H), 3.08-2.98 (m, 1H), 2.98-2.87 (m, 2H), 2.82-2.72 (m, 1H), 2.36-2.23 (m, 1H), 2.15 (dd, J=11.5, 10.0 Hz, 1H), 1.62-1.52 (m, 1H), 1.39-1.29 (m, 1H), 1.23 (dd, J=6.9, 4.7 Hz, 6H), 1.18-1.09 (m, 1H). 1H under water Synthesis 21

(3R,4R)-4-(((3-isopropyl-7-((quinolin-3-ylmethyl)amino)pyrazolo[1,5-a]pyrimidin-5-yl)amino)methyl)piperidin-3-ol (H-APPAMP-021)

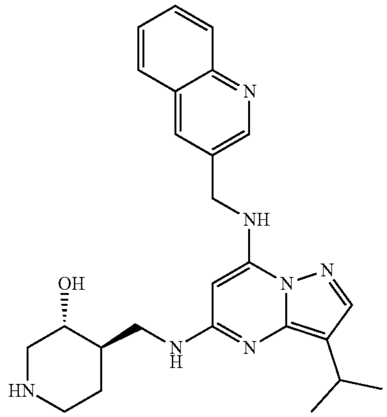 [SMILES: CC(C)c1cnn2c(NCc3cnc4ccccc4c3)cc(NC[C@H]3CCNC[C@@H]3O)nc12]

Step 1: 5-chloro-3-isopropyl-N-(quinolin-3-ylmethyl)pyrazolo[1,5-a]pyrimidin-7-amine Quinolin-3-ylmethanamine dihydrochloride (121 mg, 0.522 mmol) was added to a solution of 5,7-dichloro-3-isopropylpyrazolo[1,5-a]pyrimidine (100 mg, 0.435 mmol) and DIPEA (0.68 mL, 3.92 mmol) in EtOH (2.0 mL). The reaction mixture was heated at 90° C. overnight. The reaction mixture was concentrated in vacuo and the residue was partitioned between DCM (20 mL) and aq. sat. $NaHCO_3$ (10 mL). The organic layer was washed with aq. sat. $NaHCO_3$ (3×10 mL), filtered through a phase separator and concentrated under reduced pressure. Purification by column chromatography (80 g cartridge, 0-30% EtOAc/isohexane) gave the title compound (109 mg, 0.29 mmol, 66% yield, 93% purity) as a yellow solid.

UPLC/MS (Method 3): m/z 352 (M+H)+, $R_T$ 1.56 min

Step 2: tert-butyl (5-chloro-3-isopropylpyrazolo[1,5-a]pyrimidin-7-yl)(quinolin-3-ylmethyl)carbamate BOC-Anhydride (80 mg, 0.368 mmol) was added to a solution of 5-chloro-3-isopropyl-N-(quinolin-3-ylmethyl)pyrazolo[1,5-a]pyrimidin-7-amine (108 mg, 0.307 mmol) and DMAP (7.5 mg, 61.4 μmol) in THE (6.0 mL). The reaction mixture was stirred at 65° C. for 2.5 h. More BOC-Anhydride (34 mg, 0.154 mmol) was added and the reaction mixture was stirred at 65° C. for 1.5 h. The reaction mixture was concentrated under reduced pressure and the residue partitioned between DCM (15 mL) and water (30 mL). The aq. layer was extracted with DCM (2×30 mL) and the combined organic layers were washed with brine (30 mL), filtered through a phase separator and concentrated under reduced pressure. Purification by column chromatography (12 g cartridge, 0-100% EtOAc/isohexane) gave the title compound (143 mg, 0.29 mmol, 94% yield, 91% purity) as a yellow oil.

UPLC/MS (Method 4): m/z 452 (M+H)+, $R_T$ 1.91 min.

Step 3: tert-butyl (3R,4R)-4-(((7-((tert-butoxycarbonyl)(quinolin-3-ylmethyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)(quinolin-3-ylmethyl)carbamate (139 mg, 0.308 mmol), (3R,4R)-tert-butyl 4-(aminomethyl)-3-hydroxypiperidine-1-carboxylate (78 mg, 0.339 mmol) and $^t$BuBrettPhos Pd G3 (26.3 mg, 30.8 μmol) in THE (3.0 mL) was degassed with $N_2$ for 10 min. LiHMDS (1 M in THF) (399 μl, 0.399 mmol) was added in one portion under bubbling $N_2$. Bubbling was ceased and the reaction mixture heated to 60° C. for 1.5 h.

At RT, the mixture was filtered through celite, rinsing with EtOAc (15 mL). The filtrate was washed with water (15 mL) and the aq. layer was extracted with EtOAc (3×20 mL). The combined organic layers were dried over $Na_2SO_4$ and concentrated under reduced pressure. Purification by column chromatography (12 g cartridge, 0-100% EtOAc/isohexane) gave the title compound (146 mg, 0.18 mmol, 67% yield, 80% purity) as a brown oil.

UPLC/MS (Method 4): m/z 646 (M+H)+, $R_T$ 1.80 min.

Step 4: (3R,4R)-4-(((3-isopropyl-7-((quinolin-3-ylmethyl)amino)pyrazolo[1,5-a]pyrimidin-5-yl)amino)methyl)piperidin-3-ol Hydrogen chloride (4 M in dioxane) (0.90 mL, 3.60 mmol) was added to a suspension of tert-butyl (3R,4R)-4-(((7-((tert-butoxycarbonyl)(quinolin-3-ylmethyl)amino)-3-isopropylpyrazolo[1,5-a]pyrimidin-5-yl)amino)methyl)-3-hydroxypiperidine-1-carboxylate (116 mg, 0.18 mmol) in dioxane (2.6 mL). The reaction mixture was stirred at 35° C. for 3 h. More hydrogen chloride (4 M in dioxane) (0.23 mL, 0.90 mmol) was added, and the reaction mixture was stirred at 35° C. for 1 h then concentrated in vacuo. The residue was loaded onto a column of SCX. The column was washed with MeOH (20 mL) and the product eluted with 0.7 M $NH_3$ in MeOH (60 mL). The ammoniacal methanol solution was concentrated in vacuo to give the title compound (51 mg, 0.11 mmol, 71% yield, 99% purity) as an off-white solid after trituration from $Et_2O$ and drying overnight at 40° C. under vacuum.

UPLC/MS (Method 3): m/z 446 (M+H)+, $R_T$ 0.67 min.

$^1$H NMR (400 MHz, DMSO-$d_6$) δ 8.96 (d, J=2.2 Hz, 1H), 8.24 (s, 1H), 8.07-7.99 (m, 2H), 7.99-7.95 (m, 1H), 7.80-7.71 (m, 1H), 7.66 (s, 1H), 7.60 (ddd, J=1.2, 6.8, 8.1 Hz, 1H), 6.66 (t, J=6.1 Hz, 1H), 5.23 (s, 2H), 4.68 (d, J=6.2 Hz, 2H), 3.59-3.41 (m, 1H), 3.22-3.13 (m, 1H), 3.05-2.84 (m, 3H), 2.79-2.70 (m, 1H), 2.30-2.21 (m, 1H), 2.18-2.05 (m, 1H), 1.59-1.46 (m, 1H), 1.37-1.26 (m, 1H), 1.23 (dd, J=5.3, 6.9 Hz, 6H), 1.17-1.04 (m, 1H). 1H underwater.

Synthesis 22

(3R,4R)-4-(((3-cyclopropyl-7-(((8-methylimidazo[1,2-a]pyridin-2-yl)methyl)amino)pyrazolo[1,5-a]pyrimidin-5-yl)amino)methyl)piperidin-3-ol (H-AP-PAMP-022)

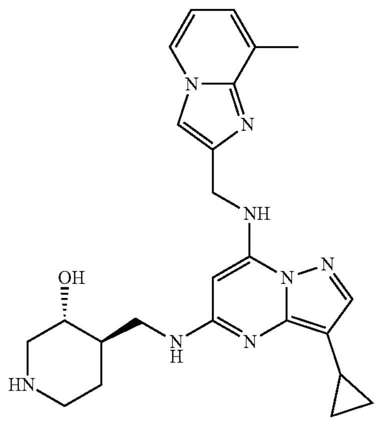 [SMILES: Cc1cccn2cc(CNc3cc(NC[C@H]4CCNC[C@@H]4O)nc4c(C5CC5)cnn34)nc12]

Step 1: 5-chloro-3-cyclopropyl-N-((8-methylimidazo[1,2-a]pyridin-2-yl)methyl)pyrazolo[1,5-a]pyrimidin-7-amine (8-Methylimidazo[1,2-a]pyridin-2-yl)methanamine, 2HCl (101 mg, 0.432 mmol) was added to a solution of 5,7-dichloro-3-cyclopropylpyrazolo[1,5-a]pyrimidine (83.0 mg, 0.364 mmol) and DIPEA (0.57 mL, 3.28 mmol) in EtOH (2.0 mL). The reaction mixture was heated at 65° C. for 1 h. The reaction mixture was concentrated in vacuo and the residue was diluted with DCM (20 mL) then the solution washed with aq. sat. $NaHCO_3$ (20 mL) then brine (20 mL). The organic layer was filtered through a phase separator and concentrated under reduced pressure to give the title compound (129 mg, 0.36 mmol, 99% yield, 99% purity) as an off-white solid.

UPLC/MS (Method 5): m/z 353 (M+H)+, $R_T$ 1.37 min

Step 2: tert-butyl (5-chloro-3-cyclopropylpyrazolo[1,5-a]pyrimidin-7-yl)((8-methylimidazo[1,2-a]pyridin-2-yl)methyl)carbamate BOC-Anhydride (94.50 mg, 0.433 mmol) was added to a solution of 5-chloro-3-cyclopropyl-N-((8-methylimidazo[1,2-a]pyridin-2-yl)methyl)pyrazolo[1,5-a]pyrimidin-7-amine (128.6 mg, 0.361 mmol) and DMAP (8.8 mg, 0.072 mmol) in THF (10 mL). The reaction mixture was stirred at 65° C. for 3 h then more BOC-Anhydride (94.50 mg, 0.433 mmol). The reaction mixture was stirred at 65° C. for 1 h. The reaction mixture was concentrated under reduced pressure and the residue diluted with DCM (20 mL). The solution was washed with water (15 mL) then brine (15 mL). The organic layer was filtered through a phase separator then concentrated under reduced pressure. Purification by column chromatography (12 g cartridge, 0-100% EtOAc/Heptane) gave the title compound (150 mg, 0.33 mmol, 91% yield, 99% purity) as a yellow solid.

UPLC/MS (Method 5): m/z 452 (M+H)+, $R_T$ 1.73 min.

Step 3: tert-butyl (3R,4R)-4-(((7-((tert-butoxycarbonyl)((8-methylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((8-methylimidazo[1,2-a]pyridin-2-yl)methyl)carbamate (150.2 mg, 0.332 mmol), (3R,4R)-tert-butyl 4-(aminomethyl)-3-hydroxypiperidine-1-carboxylate (84.02 mg, 0.3645 mmol) and $^{t}$BuBrettPhos Pd G3 (28.33 mg, 0.033 mmol) in THF (3.2 mL) was degassed with $N_2$ for 10 min. LiHMDS (1 M in THF) (0.37 g, 0.431 mL, 431.1 μmol) was added in one portion under bubbling $N_2$. Bubbling was ceased and the reaction mixture heated to 60° C. for 1.5 h. At RT, the reaction mixture was filtered through celite and washed with EtOAc (15 mL). The filtrate was diluted with water and the aq. layer was extracted with EtOAc (3×20 mL), dried over $Na_2SO_4$ and concentrated under reduced pressure. Purification by column chromatography (12 g cartridge, 0-100% (3:1 EtOAc/EtOH)/isohexane) gave the title compound (221 mg, 0.30 mmol, 92% yield, 89% purity) as a beige solid.

UPLC/MS (Method 5): m/z 647 (M+H)+, $R_T$ 1.62 min.

Step 4: (3R,4R)-4-(((3-cyclopropyl-7-(((8-methylimidazo[1,2-a]pyridin-2-yl)methyl)amino)pyrazolo[1,5-a]pyrimidin-5-yl)amino)methyl)piperidin-3-ol TFA (0.6 mL) was added to a suspension of tert-butyl (3R,4R)-4-(((7-((tert-butoxycarbonyl)((8-methylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (77 mg, 0.115 mmol) in DCM (2.4 mL). The reaction mixture was stirred at RT for 18 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (42 mg, 90 μmol, 78% yield, 95% purity) as a white solid after trituration from $Et_2O$ and drying overnight at 40° C. under vacuum.

UPLC/MS (Method 5): m/z 447 (M+H)+, $R_T$ 1.09 min.

$^1$H NMR (400 MHz, DMSO-$d_6$) δ 8.32 (d, J=6.7 Hz, 1H), 7.73 (s, 1H), 7.64 (t, J=6.1 Hz, 1H), 7.52 (s, 1H), 7.01 (dt, J=6.9, 1.3 Hz, 1H), 6.78-6.69 (m, 2H), 5.36-5.30 (m, 1H), 5.27 (s, 1H), 4.56 (d, J=5.8 Hz, 2H), 3.57-3.46 (m, 1H), 3.25-3.15 (m, 1H), 3.10-2.97 (m, 1H), 2.91 (dd, J=11.6, 4.5 Hz, 1H), 2.83-2.73 (m, 1H), 2.47 (s, 3H), 2.35-2.24 (m, 1H), 2.20-2.12 (m, 1H), 1.78-1.67 (m, 1H), 1.61-1.51 (m, 1H), 1.40-1.26 (m, 1H), 1.22-1.11 (m, 1H), 0.79-0.73 (m, 2H), 0.70-0.59 (m, 2H). 1H under water.

Synthesis 23

(3R,4R)-4-(((3-isopropyl-7-(((3-(trifluoromethyl) imidazo[1,2-a]pyridin-2-yl)methyl)amino)pyrazolo [1,5-a]pyrimidin-5-yl)amino)methyl)piperidin-3-ol (H-APPAMP-023)

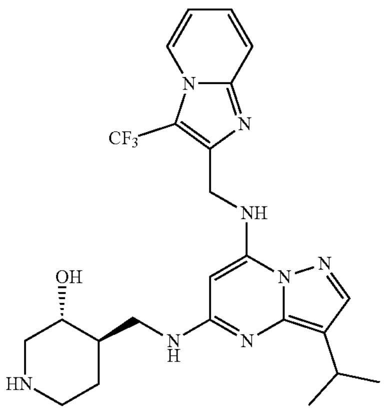 [SMILES: CC(C)c1cnn2c(NCc3nc4ccccn4c3C(F)(F)F)cc(NC[C@H]3CCNC[C@@H]3O)nc12]

Step 1: 5-chloro-3-isopropyl-N-((3-(trifluoromethyl) imidazo[1,2-a]pyridin-2-yl)methyl)pyrazolo[1,5-a] pyrimidin-7-amine (3-(Trifluoromethyl)imidazo[1,2-a]pyridin-2-yl)methanamine (139 mg, 646 µmol) was added to a solution of 5,7-dichloro-3-isopropylpyrazolo[1,5-a]pyrimidine (149 mg, 646 µmol) and DIPEA (0.84 mL, 4.84 mmol) in EtOH (6.0 mL). The reaction mixture was heated at 60° C. for 3 h. The reaction mixture was concentrated in vacuo. At RT, water (50 mL) was added and the mixture was extracted with DCM (3×25 mL). The combined organic layers were dried over $MgSO_4$ and concentrated under reduced pressure to give the title compound (246 mg, 487 µmol, 76% yield, 81% purity) as a white solid.

UPLC/MS (Method 4): m/z 409 (M+H)+, $R_T$ 0.83 min

Step 2: tert-butyl (5-chloro-3-isopropylpyrazolo[1, 5-a]pyrimidin-7-yl)((3-(trifluoromethyl)imidazo[1,2-a]pyridin-2-yl)methyl)carbamate BOC-Anhydride (158 mg, 166 µL, 722 µmol) was added to a solution of 5-chloro-3-isopropyl-N-((3-(trifluoromethyl)imidazo[1,2-a]pyridin-2-yl)methyl)pyrazolo[1,5-a] pyrimidin-7-amine (246 mg, 602 µmol) and DMAP (14.7 mg, 120 µmol) in THE (6.0 mL). The reaction mixture was stirred at RT for 3 h.

The mixture was diluted with water (100 mL), then extracted with DCM (3×30 mL). The combined organic layers were dried over $MgSO_4$ and concentrated in vacuo.

Purification by column chromatography (12 g cartridge, 0-70% EtOAc/cyclohexane) gave the title compound (226 mg, 400 µmol, 66% yield, 90% purity) as a yellow solid.

UPLC/MS (Method 4): m/z 509 (M+H)+, $R_T$ 1.99 min.

Step 3: tert-butyl (3R,4R)-4-(((7-((tert-butoxycarbonyl)((3-(trifluoromethyl)imidazo[1,2-a]pyridin-2-yl) methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1, 5-a]pyrimidin-7-yl)((3-(trifluoromethyl)imidazo[1,2-a]pyridin-2-yl)methyl)carbamate (100 mg, 196 µmol), (3R,4R)-tert-butyl 4-(aminomethyl)-3-hydroxypiperidine-1-carboxylate (45.3 mg, 196 µmol) and $^{t}$BuBrettPhos Pd G3 (16.8 mg, 19.6 µmol) in THE (2.0 mL) was degassed with $N_2$ for 10 min. LiHMDS (1M in THF) (255 µL, 255 µmol) was added in one portion under bubbling $N_2$. Bubbling was ceased and the reaction mixture heated to 60° C. for 3 h. The reaction mixture was concentrated under reduced pressure. Purification by column chromatography (12 g cartridge, 0-100% EtOAc/isohexane) then purification by column chromatography (12 g cartridge, 0-10% MeOH/DCM) then further purification on RP Flash C18 (12 g cartridge, 5-100% MeCN/10 mM ammonium bicarbonate) gave the title compound (68 mg, 92 µmol, 47% yield, 95% purity) as an white solid.

UPLC/MS (Method 5): m/z 704 (M+H)+, $R_T$ 0.85 min.

Step 4: (3R,4R)-4-(((3-isopropyl-7-(((3-(trifluoromethyl)imidazo[1,2-a]pyridin-2-yl)methyl)amino) pyrazolo[1,5-a]pyrimidin-5-yl)amino)methyl)piperidin-3-ol TFA (0.6 mL) was added to a solution of tert-butyl (3R,4R)-4-(((7-((tert-butoxycarbonyl)((3-(trifluoromethyl) imidazo[1,2-a]pyridin-2-yl)methyl)amino)-3-isopropylpyrazolo[1,5-a]pyrimidin-5-yl)amino)methyl)-3-hydroxypiperidine-1-carboxylate (68 mg, 96.8 µmol) in DCM (2.4 mL). The reaction mixture was stirred at RT for 6 h and concentrated in vacuo. The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (20 mg, 39 µmol, 40% yield, 98% purity) as a white solid after trituration from $Et_2O$ and drying overnight at 40° C. under vacuum.

UPLC/MS (Method 3): m/z 504 (M+H)+, $R_T$ 0.78 min.

$^1$H NMR (400 MHz, DMSO-$d_6$) δ 8.52 (d, J=6.9 Hz, 1H), 7.83-7.78 (m, 1H), 7.64 (s, 1H), 7.55 (m, 1H), 7.49 (t, J=5.7 Hz, 1H), 7.20 (m, 1H), 6.78-6.70 (m, 1H), 5.31 (s, 1H), 5.29-5.20 (m, 1H), 4.72 (d, J=5.3 Hz, 2H), 3.59-3.47 (m, 1H), 3.25-3.19 (m, 1H), 3.08-2.87 (m, 3H), 2.81-2.74 (m, 1H), 2.34-2.25 (m, 1H), 2.15 (dd, J=11.6, 9.9 Hz, 1H), 1.60-1.53 (m, 1H), 1.40-1.29 (m, 1H), 1.24 (dd, J=6.9, 4.3 Hz, 6H), 1.21-1.12 (m, 1H). 1H underwater.

Intermediate Synthesis A6

(3-(trifluoromethyl)imidazo[1,2-a]pyridin-2-yl) methanamine

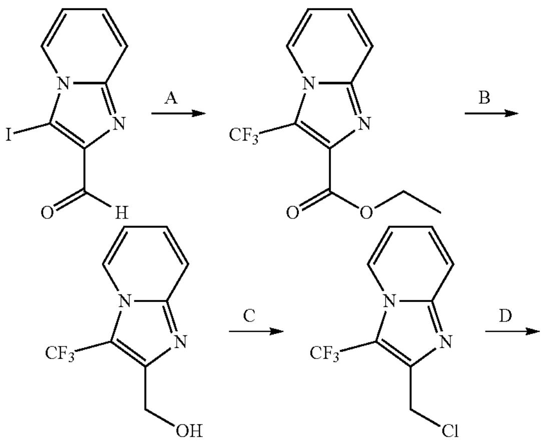

-continued

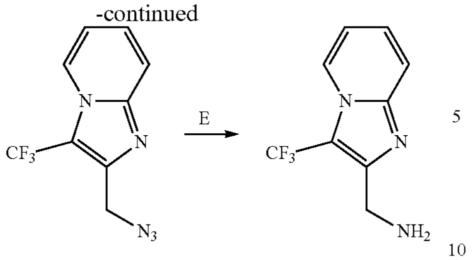

Step A: ethyl 3-(trifluoromethyl)imidazo[1,2-a]pyridine-2-carboxylate

Under $N_2$, trifluoromethyltrimethylsilane (1.50 g, 1.6 mL, 10.5 mmol) was added to a mixture of ethyl imidazo[1,2-a]pyridine-2-carboxylate (500 mg, 2.63 mmol), iodobenzene diacetate (1.69 g, 5.26 mmol) and cesium fluoride (1.60 g, 10.5 mmol) in MeCN (15 mL). The reaction mixture was heated to 30° C. for 3 h then concentrated to dryness under reduced pressure. Purification by column (12 g cartridge, 0-100% EtOAc/isohexane) gave the title compound (203 mg, 680 μmol, 26% yield, 87% purity) as a white solid.

UPLC/MS (Method 5): m/z 259 (M+H)+, $R_T$ 1.17 min.

Step B: (3-(trifluoromethyl)imidazo[1,2-a]pyridin-2-yl)methanol $LiAlH_4$ (2 M in THF) (0.393 mL, 786 μmol) was added to a solution of ethyl 3-(trifluoromethyl)imidazo[1,2-a]pyridine-2-carboxylate (203 mg, 786 μmol) in THE (8.0 mL) at 0° C. The reaction mixture was warmed to RT and stirred for 1 h. At 0° C. aq. sat. $NH_4Cl$ (10 mL) and water (10 mL) were added. The aq. layer was extracted with DCM (3×20 mL) and the combined organic layers were dried over $MgSO_4$, filtered and concentrated under reduced pressure. Purification by column (12 g cartridge, 0-100% (3:1 EtOAc/EtOH)/isohexane) gave the title compound (102 mg, 0.45 mmol, 58% yield, 96% purity) as a white solid.

UPLC/MS (Method 5): m/z 217 (M+H)+, $R_T$ 0.81 min.

Step C: 2-(chloromethyl)-3-(trifluoromethyl)imidazo[1,2-a]pyridine, HCl

Thionyl chloride (203 μL, 2.78 mmol) was added dropwise to a solution of (3-(trifluoromethyl)imidazo[1,2-a]pyridin-2-yl)methanol (250 mg, 1.11 mmol) in DCM (5.0 mL) at 0° C.

The mixture was stirred at 0° C. for 2 h. Concentration to dryness under reduced pressure gave the title compound (250 mg, 0.89 mmol, 80% yield, 96% purity) as a yellow solid.

UPLC/MS (Method 5): m/z 235 (M—OH)+, $R_T$ 1.19 min.

Step D: 2-(azidomethyl)-3-(trifluoromethyl)imidazo[1,2-a]pyridine

A solution 2-(chloromethyl)-3-(trifluoromethyl)imidazo[1,2-a]pyridin-1-ium chloride (250 mg, 922 μmol), and DIPEA (0.48 mL, 2.77 mmol) in DMF (4.0 mL) was treated with sodium azide (90 mg, 1.38 mmol). The mixture was heated to 50° C. and stirred for 2 h. The mixture was cooled to RT, diluted with water (10 mL) and brine (10 mL). Extraction with DCM (3×20 mL). The combined organic layers were dried over $MgSO_4$ and concentrated under reduced pressure. Purification by column (12 g cartridge, 0-100% EtOAc/cyclohexane) gave the title compound (209 mg, 0.75 mmol, 81% yield, 86% purity) as a colourless oil.

UPLC/MS (Method 3): m/z 242 (M+H)+, $R_T$ 1.20 min.

Step E: (3-(trifluoromethyl)imidazo[1,2-a]pyridin-2-yl)methanamine 2-(Azidomethyl)-3-(trifluoromethyl)imidazo[1,2-a]pyridine (209 mg, 780 μmol) and triphenylphosphine (245 mg, 936 μmol) were dissolved in dioxane (4.0 mL) and water (0.4 mL). The mixture was stirred at 50° C. overnight before removal of the solvent in vacuo.

The residue was loaded onto a column of SCX. The column was washed with MeOH (60 mL) and the product eluted with 0.7 M $NH_3$ in MeOH (40 mL). The ammoniacal methanol solution was concentrated in vacuo to give the title compound (139 mg, 588 μmol, 77% yield, 91% purity) as a white solid.

UPLC/MS (Method 5): m/z 216 (M+H)+, $R_T$ 0.82 min.

Synthesis 24

(3R,4R)-4-(((7-(((3-cyclopropylimidazo[1,2-a]pyridin-2-yl)methyl)amino)-3-isopropylpyrazolo[1,5-a]pyrimidin-5-yl)amino)methyl)piperidin-3-ol (H-AP-PAMP-024)

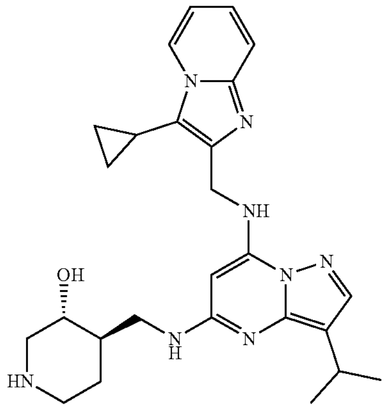 [SMILES: CC(C)c1cnn2c(NCc3nc4ccccn4c3C3CC3)cc(NC[C@H]3CCNC[C@@H]3O)nc12]

Step 1: 5-chloro-N-((3-cyclopropylimidazo[1,2-a]pyridin-2-yl)methyl)-3-isopropylpyrazolo[1,5-a]pyrimidin-7-amine (3-Cyclopropylimidazo[1,2-a]pyridin-2-yl)methanamine (52 mg, 0.22 mmol) was added to a solution of 5,7-dichloro-3-isopropylpyrazolo[1,5-a]pyrimidine (61 mg, 0.27 mmol) and DIPEA (0.29 mL, 1.70 mmol) in EtOH (2.2 mL). The reaction mixture was heated at 60° C. for 18 h. The reaction mixture was concentrated in vacuo. Purification by column chromatography (4 g cartridge, 0-50% (3:1 EtOAc/EtOH)/isohexane) gave the title compound (74 mg, 155 μmol, 70% yield, 80% purity) as a pink solid.

UPLC/MS (Method 5): m/z 381 (M+H)+, $R_T$ 1.63 min.

Step 2: tert-butyl (5-chloro-3-isopropylpyrazolo[1,5-a]pyrimidin-7-yl)((3-cyclopropylimidazo[1,2-a]pyridin-2-yl)methyl)carbamate BOC-Anhydride (51 mg, 0.23 mmol) was added to a solution of 5-chloro-N-((3-cyclopropylimidazo[1,2-a]pyridin-2-yl)methyl)-3-isopropylpyrazolo[1,5-a]pyrimidin-7-amine (74 mg, 155 μmol) and DMAP (5 mg, 40 μmol) in THE (1.9 mL). The reaction mixture was stirred at RT for 3 h. The reaction mixture was concentrated under reduced pressure. Purification by column chromatography (4 g cartridge, 0-100% EtOAc/isohexane) gave the title compound (74 mg, 154 μmol, 99% yield, 99% purity) as a white solid.

UPLC/MS (Method 5): m/z 783 (M+H)+, $R_T$ 1.89 min.

Step 3: tert-butyl (3R,4R)-4-(((7-((tert-butoxycarbonyl)((3-cyclopropylimidazo[1,2-a]pyridin-2-yl)methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)((3-cyclopropylimidazo[1,2-a]pyridin-2-yl)methyl)carbamate (74.0 mg, 0.154 mmol), (3R,4R)-tert-butyl 4-(aminomethyl)-3-hydroxypiperidine-1-carboxylate (40.0 mg, 0.170 mmol) and $^t$BuBrettPhos Pd G3 (13.9 mh, 0.015 mmol) in THE (3.0 mL) was degassed with $N_2$ for 10 min. LiHMDS (1M in THF) (0.200 mL, 0.200 mmol) was added in one portion under bubbling $N_2$. Bubbling was ceased and the reaction mixture heated to 60° C. for 16 h. The reaction mixture was concentrated under reduced pressure. Purification by column chromatography (4 g cartridge, 0-100% EtOAc/isohexane) followed by further purification on RP Flash C18 (4 g cartridge, 15-100% MeCN/10 mM ammonium bicarbonate) gave the title compound (60 mg, 89 μmol, 58% yield, 99% purity) as an white solid.

UPLC/MS (Method 5): m/z 675 (M+H)+, $R_T$ 1.77 min.

Step 4: (3R,4R)-4-(((7-(((3-cyclopropylimidazo[1,2-a]pyridin-2-yl)methyl)amino)-3-isopropylpyrazolo[1,5-a]pyrimidin-5-yl)amino)methyl)piperidin-3-ol TFA (0.3 mL) was added to a solution of tert-butyl (3R,4R)-4-(((7-((tert-butoxycarbonyl)((3-cyclopropylimidazo[1,2-a]pyridin-2-yl)methyl)amino)-3-isopropylpyrazolo[1,5-a]pyrimidin-5-yl)amino)methyl)-3-hydroxypiperidine-1-carboxylate (60 mg, 89 μmol) in DCM (1.0 mL). The reaction mixture was stirred at RT for 18 h and concentrated in vacuo.

The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (13 mg, 27 μmol, 30% yield, 99% purity).

UPLC/MS (Method 5): m/z 475 (M+H)+, $R_T$ 1.25 min.

$^1$H NMR (400 MHz, DMSO-$d_6$) δ 8.43 (d, J=6.8 Hz, 1H), 7.61 (s, 1H), 7.54 (d, J=9.1, 1H), 7.26 (m, 2H), 6.98 (td, J=6.8, 1.2 Hz, 1H), 6.85-6.76 (m, 1H), 5.43-5.36 (m, 2H), 4.58 (d, J=5.1 Hz, 2H), 3.61-3.51 (m, 1H), 3.27-3.20 (m, 1H), 3.14-3.06 (m, 1H), 3.00-2.90 (m, 2H), 2.88-2.79 (m, 1H), 2.41-2.31 (m, 1H), 2.26-2.17 (m, 1H), 1.96-1.87 (m, 1H), 1.65-1.57 (m, 1H), 1.44-1.34 (m, 1H), 1.28-1.17 (m, 7H), 1.15-1.08 (m, 2H), 0.74-0.67 (m, 2H). 1H under water.

Intermediate Synthesis A7

(3-cyclopropylimidazo[1,2-a]pyridin-2-yl)methanamine synthesis

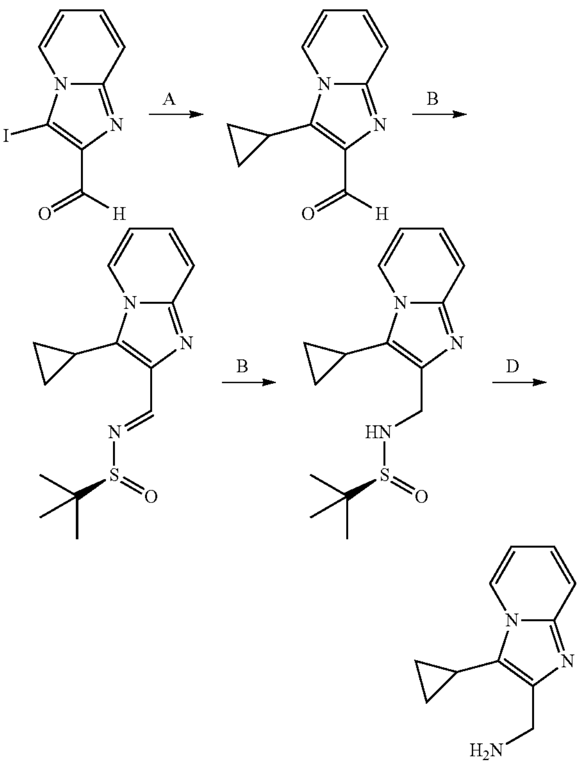

Step A: 3-cyclopropylimidazo[1,2-a]pyridine-2-carbaldehyde

A solution of tripotassium phosphate (1.56 g, 7.35 mmol) in water (4.0 mL) was added to a solution of 3-iodoimidazo[1,2-a]pyridine-2-carbaldehyde (500 mg, 1.84 mmol), cyclopropaneboronic acid (474 mg, 5.51 mmol) and $PdCl_2$(dppf)-$CH_2Cl_2$ adduct (300 mg, 368 μmol) in dioxane (20 mL). $N_2$ was bubbled through the reaction mixture for 10 min then the reaction mixture was heated at 80° C. for 20 h. At RT, the mixture was filtered through celite, rinsing with DCM (25 mL). Water (50 mL) was added to the filtrate, the layers were separated, and the aq. layer was extracted with DCM (2×25 mL). The combined organic fractions were dried over $MgSO_4$ and concentrated in vacuo. Purification by column (12 g cartridge, 0-100% EtOAc/isohexane) gave the title compound (111 mg, 513 μmol, 28% yield, 90% purity) as a white solid.

UPLC/MS (Method 5): m/z 187 (M+H)+, $R_T$ 0.80 min.

Step B: (S,E)-N-((3-cyclopropylimidazo[1,2-a]pyridin-2-yl)methylene)-2-methylpropane-2-sulfinamide (S)-2-Methylpropane-2-sulfinamide (86.7 mg, 715 μmol) then titanium(IV) propan-2-olate (0.53 mL, 1.79 mmol) were added to a solution of 3-cyclopropylimidazo[1,2-a]pyridine-2-carbaldehyde (111 mg, 596 μmol) in DCM (6.0 mL) at 0° C. The reaction mixture was stirred at 40° C. for 18 h. Brine (50 mL) and celite were added to the reaction mixture while stirring. The mixture was filled through a pad of celite and washed with DCM (100 mL). The organic layer was collected from the filtrate and the aq. layer further extracted with DCM (2×25 mL). The combined organic layers were dried over $MgSO_4$ then concentrated under reduced pressure. Purification by column (12 g cartridge, 0-100% (3:1 EtOAc/EtOH)/cyclohexane) gave the title compound (139 mg, 0.39 mmol, 65% yield, 81% purity) as a yellow oil.

UPLC/MS (Method 5): m/z 290 (M+H)+, $R_T$ 1.08 min.

Step C: (S)—N-((3-cyclopropylimidazo[1,2-a]pyridin-2-yl)methyl)-2-methylpropane-2-sulfinamide Sodium borohydride (18 mg, 476 μmol) was added to a solution of S,E)-N-((3-cyclopropylimidazo[1,2-a]pyridin-2-yl)methylene)-2-methylpropane-2-sulfinamide (139 mg, 389 μmol) in MeOH (2.4 mL) at 0° C. The reaction was warmed to RT and stirred for 1 h. Water (30 mL) and DCM (25 mL) were added. The layers were separated and the aq. layer further extracted with DCM (2×25 mL). The combined organic layers were filtered through a phase separator and concentrated under reduced pressure to give the title compound (139 mg, 382 μmol, 98% yield, 80% purity) as a pink solid.

UPLC/MS (Method 4): m/z 292 (M−OH)+, $R_T$ 1.05 min.

Step D: (3-cyclopropylimidazo[1,2-a]pyridin-2-yl) methanamine

Hydrogen chloride (1.25 M in MeOH) (0.9 mL, 1.14 mmol) was added to a solution of (S)—N-((3-cyclopropylimidazo[1,2-a]pyridin-2-yl)methyl)-2-methylpropane-2-sulfinamide (139 mg, 382 μmol) in MeOH (1.0 mL). The reaction was stirred at RT for 2 h then more hydrogen chloride (1.25 M in MeOH) (0.9 mL, 1.14 mmol) and the mixture was stirred for 1 h before being concentrated under reduced pressure. The residue was loaded onto a column of SCX. The column was washed with MeOH (50 mL) and the product eluted with 0.7 M $NH_3$ in MeOH (20 mL). The ammoniacal methanol solution was concentrated in vacuo to give the title compound (53 mg, 226 μmol, 59% yield, 80% purity) as a yellow oil.

$^1H$ NMR in DMSO-$d_6$ was consistent with product structure.

Synthesis 25

(3R,4R)-4-(((3-cyclopropyl-7-(((5-methylimidazo[1,2-a]pyridin-2-yl)methyl)amino)pyrazolo[1,5-a]pyrimidin-5-yl)amino)methyl)piperidin-3-ol (H-AP-PAMP-095)

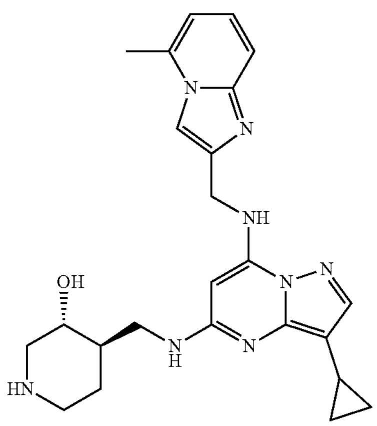 [SMILES: Cc1cccc2nc(CNc3cc(NC[C@H]4CCNC[C@@H]4O)nc4c(C5CC5)cnn34)cn12]

Step 1: 5-chloro-3-cyclopropyl-N-((5-methylimidazo[1,2-a]pyridin-2-yl)methyl)pyrazolo[1,5-a]pyrimidin-7-amine (5-Methylimidazo[1,2-a]pyridin-2-yl)methanamine, 2HCl (111 mg, 0.474 mmol) was added to a solution of 5,7-dichloro-3-cyclopropylpyrazolo[1,5-a]pyrimidine (90 mg, 0.395 mmol) and DIPEA (0.62 mL, 3.55 mmol) in EtOH (1.5 mL). The reaction mixture was heated at 65° C. for 1.5 h. The reaction mixture was concentrated in vacuo. The residue was diluted in DCM (15 mL) and washed with aq. sat. $NaHCO_3$ (15 mL) and brine (15 mL). The organic layer was filtered through a phase separator and concentrated under reduced pressure to give the title compound (118 mg, 0.33 mmol, 83% yield, 98% purity) as a grey solid.

UPLC/MS (Method 3): m/z 353 (M+H)+, $R_T$ 1.36 min

Step 2: tert-butyl (5-chloro-3-cyclopropylpyrazolo[1,5-a]pyrimidin-7-yl)((5-methylimidazo[1,2-a]pyridin-2-yl)methyl)carbamate BOC-Anhydride (87 mg, 0.398 mmol) was added to a solution of 5-chloro-3-cyclopropyl-N-((5-methylimidazo[1,2-a]pyridin-2-yl)methyl)pyrazolo[1,5-a]pyrimidin-7-amine (117.0 mg, 331.6 mmol) and DMAP (8.1 mg, 66 μmol) in THE (6.5 mL). The reaction mixture was stirred at 65° C. for 1 h then recharged with BOC-anhydride (87 mg, 0.398 mmol) and DMAP (8.1 mg, 66 μmol) and stirred at 65° C. for 1 h. The reaction mixture was concentrated under reduced pressure and the residue diluted in DCM (15 mL). The organic layer was washed with brine (3×10 mL), filtered through a phase separator and concentrated under reduced. Purification by column chromatography (12 g cartridge, 0-100% EtOAc/isohexane) gave the title compound (135 mg, 0.29 mmol, 87% yield, 97% purity) as a green solid.

UPLC/MS (Method 3): m/z 453 (M+H)+, $R_T$ 1.71 min.

Step 3: tert-butyl (3R,4R)-4-(((7-((tert-butoxycarbonyl)((5-methylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5-methylimidazo[1,2-a]pyridin-2-yl)methyl)carbamate (136 mg, 0.30 mmol), (3R,4R)-tert-butyl 4-(aminomethyl)-3-hydroxypiperidine-1-carboxylate (83 mg, 360 μmol) and $^{t}$BuBrettPhos Pd G3 (26 mg, 30 μmol) in THE (2.9 mL) was degassed with $N_2$ for 10 min. LiHMDS (1 M in THF) (0.39 mL, 390 μmol) was added in one portion under bubbling $N_2$. Bubbling was ceased and the reaction mixture heated to 60° C. for 2 h. At RT, the mixture was filtered through celite, washing with EtOAc (15 mL). The filtrate was partitioned with water (10 mL) and the aq. layer was re-extracted with EtOAc (3×20 mL). The combined organic layers were washed with brine (10 mL), dried over $Na_2SO_4$ and concentrated under reduced pressure. Purification by column chromatography (12 g cartridge, 0-100% EtOAc/isohexane) gave the title compound (163 mg, 0.22 mmol, 74% yield, 88% purity) as a brown oil.

UPLC/MS (Method 3): m/z 647 (M+H)+, $R_T$ 1.22 min.

Step 4: (3R,4R)-4-(((3-cyclopropyl-7-(((5-methylimidazo[1,2-a]pyridin-2-yl)methyl)amino)pyrazolo[1,5-a]pyrimidin-5-yl)amino)methyl)piperidin-3-ol TFA (0.5 mL) was added to a solution of tert-butyl (3R,4R)-4-(((7-((tert-butoxycarbonyl)((5-methylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (163 mg, 252 μmol) in DCM (2.0 mL). The reaction mixture was stirred at RT for 18 h and concentrated in vacuo. The residue was loaded onto a column of SCX. The column was washed with MeOH (50 mL) and the product eluted with 0.7 M $NH_3$ in MeOH (60 mL). The ammoniacal methanol solution was concentrated in vacuo to give the title compound (81 mg, 0.18 mmol, 71% yield, 98% purity) as a beige solid after trituration from $Et_2O$ and drying overnight at 40° C. under vacuum.

UPLC/MS (Method 5): m/z 447 (M+H)+, $R_T$ 1.42 min.

$^1$H NMR (400 MHz, DMSO-$d_6$) δ 7.66 (s, 1H), 7.56 (t, J=6.0 Hz, 1H), 7.51 (s, 1H), 7.42 (d, J=9.0 Hz, 1H), 7.21 (dd, J=9.1, 6.8 Hz, 1H), 6.79-6.73 (m, 2H), 5.44-5.37 (m, 1H), 5.32 (s, 1H), 4.57 (d, J=5.9 Hz, 2H), 3.58-3.46 (m, 1H), 3.26-3.17 (m, 1H), 3.12-3.03 (m, 1H), 2.94 (dd, J=11.5, 4.5 Hz, 1H), 2.87-2.78 (m, 1H), 2.55 (s, 3H), 2.40-2.31 (m, 1H), 2.27-2.16 (m, 1H), 1.76-1.67 (m, 1H), 1.63-1.55 (m, 1H), 1.42-1.32 (m, 1H), 1.25-1.11 (m, 1H), 0.80-0.71 (m, 2H), 0.69-0.58 (m, 2H). 1H under water.

Synthesis 26

(3R,4R)-4-(((3-ethyl-7-(((8-methylimidazo[1,2-a]pyridin-2-yl)methyl)amino)pyrazolo[1,5-a]pyrimidin-5-yl)amino)methyl)piperidin-3-ol (H-APPAMP-026)

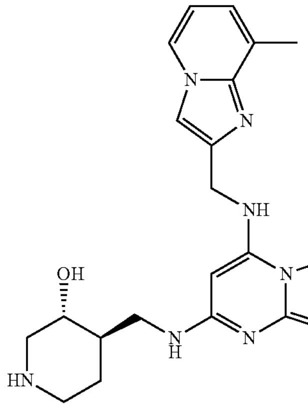

Step 1: 5-chloro-3-ethyl-N-((8-methylimidazo[1,2-a]pyridin-2-yl)methyl)pyrazolo[1,5-a]pyrimidin-7-amine (8-Methylimidazo[1,2-a]pyridin-2-yl)methanamine, HCl (96.1 mg, 486 μmol), was added to a solution of 5,7-dichloro-3-ethylpyrazolo[1,5-a]pyrimidine (100 mg, 463 μmol) and DIPEA (0.56 ml, 3.24 mmol) in EtOH (2.0 mL). The reaction mixture was heated at 50° C. for 18 h. The reaction mixture was concentrated in vacuo.

Purification by column chromatography (12 g cartridge, 0-100% EtOAc/isohexane) gave the title compound (128 mg, 0.36 mmol, 77% yield, 95% purity) as a white solid.

UPLC/MS (Method 5): m/z 341 (M+H)+, $R_T$ 1.22 min.

Step 2: tert-butyl (5-chloro-3-ethylpyrazolo[1,5-a]pyrimidin-7-yl)((8-methylimidazo[1,2-a]pyridin-2-yl)methyl)carbamate BOC-Anhydride (98 mg, 451 μmol) was added to a solution of 5-chloro-3-ethyl-N-((8-methylimidazo[1,2-a]pyridin-2-yl)methyl)pyrazolo[1,5-a]pyrimidin-7-amine (128 mg, 376 μmol) and DMAP (9 mg, 75 μmol) in THE (4.0 mL). The reaction mixture was stirred at RT for 18 h. The reaction mixture was concentrated under reduced pressure. Purification by column chromatography (12 g cartridge, 0-100% (3:1 EtOAc/EtOH)/isohexane) gave the title compound (138 mg, 0.30 mmol, 80% yield, 96% purity) as a tan solid.

UPLC/MS (Method 5): m/z 441 (M+H)+, $R_T$ 1.61 min.

Step 3: tert-butyl (3R,4R)-4-(((7-((tert-butoxycarbonyl)((8-methylimidazo[1,2-a]pyridin-2-yl)methyl)amino)-3-ethylpyrazolo[1,5-a]pyrimidin-5-yl)amino)methyl)-3-hydroxypiperidine-1-carboxylate A solution of tert-butyl (5-chloro-3-ethylpyrazolo[1,5-a]pyrimidin-7-yl)((8-methylimidazo[1,2-a]pyridin-2-yl)methyl)carbamate (138 mg, 300 μmol), (3R,4R)-tert-butyl 4-(aminomethyl)-3-hydroxypiperidine-1-carboxylate (83 mg, 361 μmol) and $^t$BuBrettPhos Pd G3 (0.62 g, 0.72 mmol) in THE (2.0 mL) was degassed with $N_2$ for 10 min. LiHMDS (1 M in THF) (391 μL, 391 μmol) was added in one portion under bubbling $N_2$. Bubbling was ceased and the reaction mixture heated to 60° C. for 18 h. The reaction mixture was concentrated under reduced pressure. Purification by column chromatography (24 g cartridge, 0-10% (0.7 M $NH_3$/MeOH)/DCM) gave the title compound (141 mg, 222 μmol, 74% yield, 98% purity) as a white solid.

UPLC/MS (Method 3): m/z 635 (M+H)+, $R_T$ 1.62 min.

Step 4: (3R,4R)-4-(((3-ethyl-7-(((8-methylimidazo[1,2-a]pyridin-2-yl)methyl)amino)pyrazolo[1,5-a]pyrimidin-5-yl)amino)methyl)piperidin-3-ol TFA (0.5 mL) was added to a solution of tert-butyl (3R,4R)-4-(((7-((tert-butoxycarbonyl)((8-methylimidazo[1,2-a]pyridin-2-yl)methyl)amino)-3-ethylpyrazolo[1,5-a]pyrimidin-5-yl)amino)methyl)-3-hydroxypiperidine-1-carboxylate (140 mg, 221 μmol) in dioxane (2.0 mL). The reaction mixture was stirred at RT for 18 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (71 mg, 160 μmol, 73% yield, 98% purity).

UPLC/MS (Method 5): m/z 435 (M+H)+, $R_T$ 1.02 min.

$^1$H NMR (400 MHz, DMSO-$d_6$) δ 8.32 (d, J=6.5 Hz, 1H), 7.74 (s, 1H), 7.69-7.63 (m, 2H), 7.01 (dt, J=6.9, 1.3 Hz, 1H), 6.71-6.79 (m, 2H), 5.46-5.37 (m, 1H), 5.27 (s, 1H), 4.57 (d, J=6.0 Hz, 2H), 3.49-3.60 (m, 1H), 3.11-3.20 (m, 1H), 3.06-2.95 (m, 1H), 2.89 (dd, J=11.5, 4.6 Hz, 1H), 2.81-2.73 (m, 1H), 2.47 (s, 3H), 2.24-2.34 (m, 1H), 2.19-2.10 (m, 1H), 1.57-1.48 (m, 1H), 1.36-1.25 (m, 1H), 1.11-1.20 (m, 4H). 1 $CH_2$ under DMSO. 1H under water.

Synthesis 27

(3R,4R)-4-(((3-cyclopropyl-7-(((5-methoxyimidazo[1,2-a]pyridin-2-yl)methyl)amino)pyrazolo[1,5-a]pyrimidin-5-yl)amino)methyl)piperidin-3-ol (H-AP-PAMP-027)

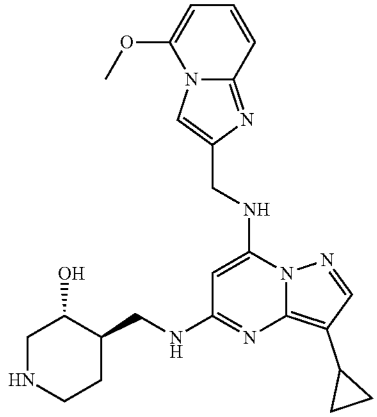 [SMILES: COc1cccc2nc(CNc3cc(NC[C@H]4CCNC[C@@H]4O)nc4c(C5CC5)cnn34)cn12]

Step 1: 5-chloro-3-cyclopropyl-N-((5-methoxyimidazo[1,2-a]pyridin-2-yl)methyl)pyrazolo[1,5-a]pyrimidin-7-amine (5-Methoxyimidazo[1,2-a]pyridin-2-yl)methanamine (64 mg, 0.34 mmol) was added to a solution of 5,7-dichloro-3-cyclopropylpyrazolo[1,5-a]pyrimidine (86 mg, 0.38 mmol) and DIPEA (0.42 mL, 2.4 mmol) in EtOH (3.0 mL). The reaction mixture was heated at 50° C. for 20 h. The reaction mixture was concentrated in vacuo. Purification by column chromatography (12 g cartridge, 0-10% MeOH/DCM) gave the title compound (105 mg, 0.27 mmol, 78% yield, 94% purity) as a tan solid.

UPLC/MS (Method 5): m/z 369 (M+H)+, $R_T$ 1.35 min.

Step 2: tert-butyl (5-chloro-3-cyclopropylpyrazolo[1,5-a]pyrimidin-7-yl)((5-methoxyimidazo[1,2-a]pyridin-2-yl)methyl)carbamate BOC-Anhydride (70 mg, 321 μmol) was added to a solution of 5-chloro-3-cyclopropyl-N-((5-methoxyimidazo[1,2-a]pyridin-2-yl)methyl)pyrazolo[1,5-a]pyrimidin-7-amine (105 mg, 268 μmol) and DMAP (6.5 mg, 54 μmol) in THE (3.0 mL). The reaction mixture was stirred at RT for 1 h. The reaction mixture was concentrated under reduced pressure. Purification by column chromatography (12 g cartridge, 0-10% MeOH/DCM) gave the title compound (120 mg, 256 μmol, 95% yield, 99% purity) as a white solid.

UPLC/MS (Method 5): m/z 469 (M+H)+, $R_T$ 0.81 min.

Step 3: tert-butyl (3R,4R)-4-(((7-((tert-butoxycarbonyl)((5-methoxyimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5-methoxyimidazo[1,2-a]pyridin-2-yl)methyl)carbamate (140 mg, 299 μmol), (3R,4R)-tert-butyl 4-(aminomethyl)-3-hydroxypiperidine-1-carboxylate (83 mg, 358 μmol) and $^t$BuBrettPhos Pd G3 (25 mg, 29.9 μmol) in THE (2.0 mL) was degassed with $N_2$ for 10 min. LiHMDS (1 M in THF) (388 μL, 388 μmol) was added in one portion under bubbling $N_2$. Bubbling was ceased and the reaction mixture heated to 60° C. for 18 h. The reaction mixture was concentrated under reduced pressure. Purification by column chromatography (12 g cartridge, 0-10% MeOH/DCM) gave the title compound (167 mg, 0.21 mmol, 69% yield, 82% purity) as a white solid.

UPLC/MS (Method 5): m/z 663 (M+H)+, $R_T$ 1.61 min.

Step 4: (3R,4R)-4-(((3-cyclopropyl-7-(((5-methoxyimidazo[1,2-a]pyridin-2-yl)methyl)amino)pyrazolo[1,5-a]pyrimidin-5-yl)amino)methyl)piperidin-3-ol Hydrogen chloride (4 M in dioxane) (1.04 mL, 4.16 mmol) was added to a solution of tert-butyl (3R,4R)-4-(((7-((tert-butoxycarbonyl)((5-methoxyimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (168 mg, 208 μmol) in dioxane (2.0 mL). The reaction mixture was stirred at 35° C. for 1 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (62 mg, 0.13 mmol, 61% yield, 95% purity).

UPLC/MS (Method 5): m/z 463 (M+H)+, $R_T$ 1.04 min.

$^1$H NMR (400 MHz, DMSO-$d_6$) δ 7.61 (t, J=6.1 Hz, 1H), 7.56 (s, 1H), 7.52 (s, 1H), 7.29 (dd, J=9.0, 7.5 Hz, 1H), 7.15 (d, J=9.0 Hz, 1H), 6.77-6.71 (m, 1H), 6.34 (d, J=7.4 Hz, 1H), 5.36-5.32 (m, 1H), 5.30 (s, 1H), 4.55 (d, J=5.9 Hz, 2H), 4.06 (s, 3H), 3.57-3.49 (m, 1H), 3.26-3.15 (m, 1H), 3.09-2.99 (m, 1H), 2.92 (dd, J=11.5, 4.6 Hz, 1H), 2.83-2.76 (m, 1H), 2.36-2.26 (m, 1H), 2.17 (dd, J=11.6, 9.9 Hz, 1H), 1.78-1.66 (m, 1H), 1.61-1.53 (m, 1H), 1.36-1.29 (m, 1H), 1.22-1.11 (m, 1H), 0.82-0.72 (m, 2H), 0.76-0.59 (m, 2H). 1H under water.

Intermediate Synthesis A8

(5-methoxyimidazo[1,2-a]pyridin-2-yl)methanamine

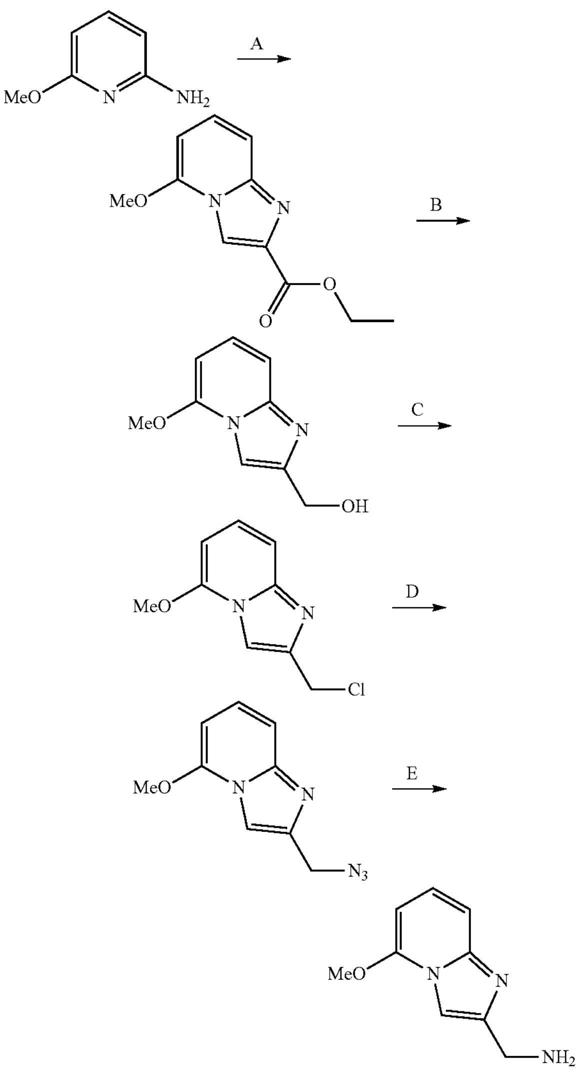

Step A: ethyl 5-methoxyimidazo[1,2-a]pyridine-2-carboxylate

6-Methoxypyridin-2-amine (400 mg, 3.22 mmol) and ethyl 3-bromo-2-oxopropanoate (0.81 mL, 6.44 mmol) in IPA (2.0 ml) and water (2.0 ml) were heated at 80° C. under microwave irradiation for 1 h. The reaction mixture was diluted with water (50 mL) and extracted with DCM (3×25 mL). The combined organic fractions were dried over $MgSO_4$, filtered, then concentrated under vacuum. Purification by column chromatography (40 g cartridge, 0-10% MeOH/DCM) gave the title compound (280 mg, 1.3 mmol, 39% yield, 99% purity) as a yellow solid.

UPLC/MS (Method 5): m/z 221 (M+H)+, $R_T$ 0.93 min.

Step B: (5-methoxyimidazo[1,2-a]pyridin-2-yl) methanol lithium borohydride (2M in THF) (0.63 mL, 1.26 mmol) was added to a solution of ethyl 5-methoxyimidazo[1,2-a]pyridine-2-carboxylate (280 mg, 1.26 mmol) in THE (6.0 mL) at 0° C. The reaction mixture was allowed to warm to RT overnight. At 0° C. water (5 mL) aq. sat. $NH_4Cl$ solution (10 mL) were added. The aqueous was extracted with DCM (3×20 mL) and the combined organic layers were dried over $MgSO_4$, filtered and concentrated under reduced pressure. Purification by column (24 g cartridge, 0-10% MeOH/DCM) gave the title compound (120 mg, 0.61 mmol, 49% yield, 91% purity) as a white solid.

UPLC/MS (Method 5): m/z 179 (M+H)+, $R_T$ 0.62 min.

Step C: 2-(chloromethyl)-5-methoxyimidazo[1,2-a]pyridine, HCl thionyl chloride (112 μL, 1.53 mmol) was added dropwise to a solution of (5-methoxyimidazo[1,2-a]pyridin-2-yl) methanol (120 mg, 613 μmol) in DCM (7.0 mL) at 0° C. The mixture was stirred at 0° C. for 2 h. Concentration to dryness under reduced pressure gave the title compound (142 mg, 0.60 mmol, 98% yield, 99% purity) as an off-white solid.

$^1$H NMR in DMSO-d6 was consistent with product structure.

Step D: 2-(azidomethyl)-5-methoxyimidazo[1,2-a]pyridine

A solution of 2-(chloromethyl)-5-methoxyimidazo[1,2-a]pyridine, HCl (142 mg, 597 μmol) and DIPEA (0.31 mL, 1.79 mmol) in DMF (3.0 mL) was treated with sodium azide (58 mg, 0.90 mmol). The mixture was heated to 50° C. and stirred for 2 h. The mixture was cooled to RT, diluted with water (10 mL) and brine (10 mL), before extraction with TBME (3×20 mL) then EtOAc (3×20 mL). The combined organic layers were washed with brine (4×20 mL), dried over $Na_2SO_4$ and concentrated under reduced pressure. Purification by column (12 g cartridge, 0-10% MeOH/DCM) gave the title compound (91 mg, 0.37 mmol, 62% yield, 83% purity) as a white solid.

UPLC/MS (Method 5): m/z 205 (M+H)+, $R_T$ 0.94 min.

Step E: (5-methoxyimidazo[1,2-a]pyridin-2-yl) methanamine 2-(azidomethyl)-5-methoxyimidazo[1,2-a]pyridine (91 mg, 0.45 mmol) and triphenylphosphine (0.14 g, 0.54 mmol), were dissolved in THE (1.8 mL) and water (0.2 mL). The mixture was stirred at RT overnight before removal of the solvent in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (64 mg, 0.34 mmol, 77% yield, 95% purity) as a white solid.

UPLC/MS (Method 5): m/z 178 (M+H)+, $R_T$ 0.64 min.

Synthesis 28

(3R,4R)-4-(((3-cyclopropyl-7-(((6-cyclopropylimidazo[1,2-b]pyridazin-2-yl)methyl)amino)pyrazolo[1,5-a]pyrimidin-5-yl)amino)methyl)piperidin-3-ol (H-APPAMP-028)

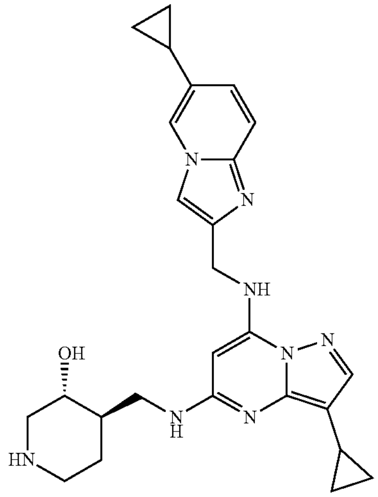

Step 1: 5-chloro-3-cyclopropyl-N-((6-cyclopropylimidazo[1,2-b]pyridazin-2-yl)methyl)pyrazolo[1,5-a]pyrimidin-7-amine (6-Cyclopropylimidazo[1,2-b]pyridazin-2-yl)methanamine (130 mg, 691 μmol) was added to a solution of 5,7-dichloro-3-cyclopropylpyrazolo[1,5-a]pyrimidine (158 mg, 691 μmol) and DIPEA (0.84 mL, 4.83 mmol) in EtOH (3.0 mL). The reaction mixture was heated at 50° C. for 2 h. The reaction mixture was concentrated in vacuo to give the title compound (449 mg, 0.69 mmol, 99% yield, 58% purity) as a brown solid.

UPLC/MS (Method 5): m/z 380 (M+H)+, $R_T$ 1.45 min

Step 2: tert-butyl (5-chloro-3-cyclopropylpyrazolo[1,5-a]pyrimidin-7-yl)((6-cyclopropylimidazo[1,2-b]pyridazin-2-yl)methyl)carbamate BOC-Anhydride (129 mg, 592 μmol) was added to a solution of 5-chloro-3-cyclopropyl-N-((6-cyclopropylimidazo[1,2-b]pyridazin-2-yl)methyl)pyrazolo[1,5-a]pyrimidin-7-amine (206 mg, 494 μmol) and DMAP (12.1 mg, 99 μmol) in THF (5.0 mL). The reaction mixture was stirred at RT for 3 h. The reaction mixture was concentrated under reduced pressure. Purification by column chromatography (24 g cartridge, 0-10% MeOH/DCM) gave the title compound (231 mg, 0.46 mmol, 93% yield, 95% purity) as a brown solid.

UPLC/MS (Method 5): m/z 480 (M+H)+, $R_T$ 1.83 min.

Step 3: tert-butyl (3R,4R)-4-(((7-((tert-butoxycarbonyl)((6-cyclopropylimidazo[1,2-b]pyridazin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((6-cyclopropylimidazo[1,2-b]pyridazin-2-yl)methyl)carbamate (254 mg, 529 μmol), (3R,4R)-tert-butyl 4-(aminomethyl)-3-hydroxypiperidine-1-carboxylate (146 mg, 635 μmol) and $^{t}$BuBrettPhos Pd G3 (45 mg, 52.9 μmol) in THF (5.0 mL) was degassed with $N_2$ for 10 min. LiHMDS (1M in THF) (688 μL, 688 μmol) was added in one portion under bubbling $N_2$. Bubbling was ceased and the reaction mixture heated to 60° C. for 72 h. The reaction was concentrated under reduced pressure. Purification by column chromatography (24 g cartridge, 0-10% MeOH/DCM) gave the title compound (230 mg, 0.32 mmol, 61% yield, 94% purity) as a brown solid.

UPLC/MS (Method 4): m/z 674 (M+H)+, $R_T$ 1.72 min.

Step 4: (3R,4R)-4-(((3-cyclopropyl-7-(((6-cyclopropylimidazo[1,2-b]pyridazin-2-yl)methyl)amino)pyrazolo[1,5-a]pyrimidin-5-yl)amino)methyl)piperidin-3-ol Hydrogen chloride (4 M in dioxane) (1.71 mL, 6.83 mmol) was added to a solution of tert-butyl (3R,4R)-4-(((7-((tert-butoxycarbonyl)((6-cyclopropylimidazo[1,2-b]pyridazin-2-yl)methyl)amino)-3-cyclopropylpyrazolo[1,5-a]pyrimidin-5-yl)amino)methyl)-3-hydroxypiperidine-1-carboxylate (230 mg, 341 μmol) in dioxane (2.0 mL). The reaction mixture was stirred at 35° C. for 4 h and concentrated in vacuo. The residue was loaded onto a column of SCX. The column was washed with MeOH (40 mL) and the product eluted with 0.7 M $NH_3$ in MeOH (10 mL). The ammoniacal methanol solution was concentrated in vacuo to give the title compound (145 mg, 0.30 mmol, 87% yield, 97% purity) after trituration from $Et_2O$ and drying overnight at 40° C. under vacuum.

UPLC/MS (Method 5): m/z 475 (M+H)+, $R_T$ 1.14 min.

$^1$H NMR (400 MHz, DMSO-$d_6$) δ 7.98 (s, 1H), 7.92 (d, J=9.4 Hz, 1H), 7.61 (t, J=6.1 Hz, 1H), 7.51 (s, 1H), 7.08 (d, J=9.4 Hz, 1H), 6.77 (t, J=6.0 Hz, 1H), 5.47-5.42 (m, 1H), 5.30 (s, 1H), 4.55 (d, J=5.9 Hz, 2H), 3.59-3.47 (m, 1H), 3.28-3.20 (m, 1H), 3.20-3.05 (m, 1H), 2.97 (dd, J=11.6, 4.5 Hz, 1H), 2.90-2.82 (m, 1H), 2.44-2.34 (m, 1H), 2.25 (dd, J=11.6, 10.0 Hz, 1H), 2.21-2.11 (m, 1H), 1.77-1.66 (m, 1H), 1.65-1.57 (m, 1H), 1.48-1.30 (m, 1H), 1.49-1.11 (m, 1H), 1.11-1.01 (m, 2H), 1.01-0.92 (m, 2H), 0.81-0.72 (m, 2H), 0.72-0.59 (m, 2H). 1H under water.

Intermediate Synthesis A9

(6-cyclopropylimidazo[1,2-b]pyridazin-2-yl)methanamine

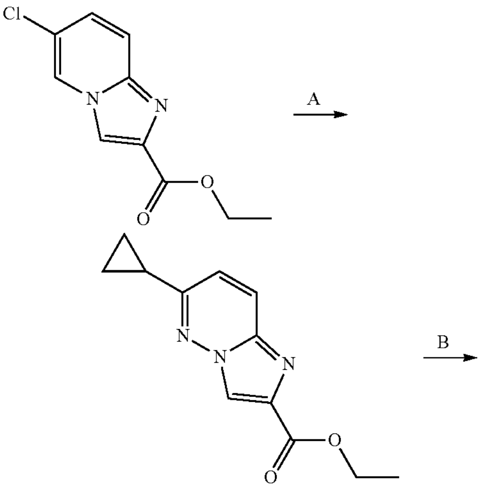

-continued

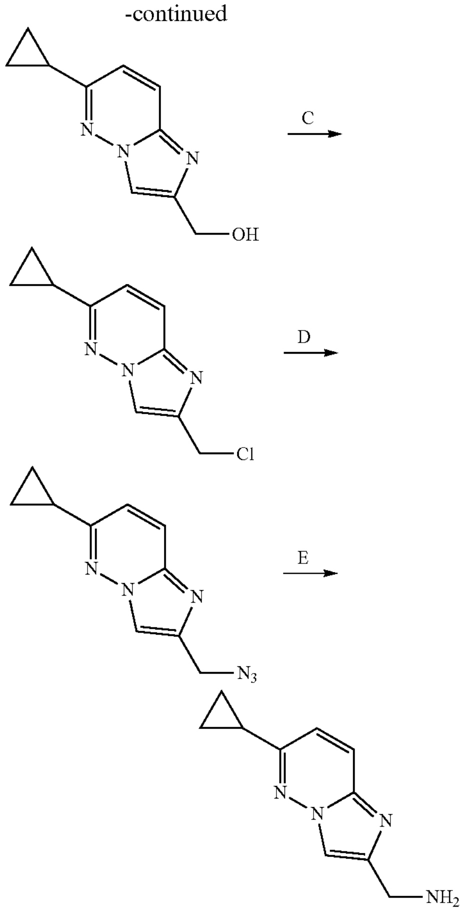

Step A: ethyl 6-cyclopropylimidazo[1,2-b]pyridazine-2-carboxylate

A mixture of ethyl 6-chloroimidazo[1,2-b]pyridazine-2-carboxylate (400 mg, 1.77 mmol), cesium fluoride (1.21 g, 7.98 mmol), $PdCl_2$ (dtbpf) (116 mg, 177 μmol), cyclopropylboronic acid (685 mg, 7.98 mmol) in dioxane (10 mL) was degassed with $N_2$ for 10 min. The mixture was then heated to 60° C. for 5.5 h before being concentrated to dryness under reduced pressure. Purification by column chromatography (24 g cartridge, 0-10% MeOH/DCM) gave the title compound (400 mg, 1.6 mmol, 93% yield, 95% purity) as a yellow solid.

UPLC/MS (Method 3): m/z 232 (M+H)+, $R_T$ 1.13 min.

Step B: (6-cyclopropylimidazo[1,2-b]pyridazin-2-yl)methanol

Diisobutylaluminum hydride (1M in DCM) (4.32 mL, 4.32 mmol) was added to a solution of ethyl 6-cyclopropylimidazo[1,2-b]pyridazine-2-carboxylate (400 mg, 1.73 mmol) in THF (20 mL) at −10° C. The reaction mixture was allowed to warm to RT and stirred for 2 h. At 0° C., MeOH (10 mL), followed by water (10 mL) and aq. 1M HCl (10 mL) were added. The mixture was stirred vigorously for 30 min and extracted with ethyl acetate (3×35 mL). The combined organic layers were washed with brine (20 mL), filtered through a phase separator and concentrated in vacuo. Purification by column chromatography (12 g cartridge, 0-10% MeOH/DCM) gave the title compound (220 mg, 1.10 mmol, 66% yield, 98% purity) as a brown oil.

UPLC/MS (Method 3): m/z 190 (M+H)+, $R_T$ 0.44 min.

Step C: 2-(chloromethyl)-6-cyclopropylimidazo[1,2-b]pyridazine, HCl

Thionyl chloride (434 μL, 5.95 mmol) was added to a solution of (6-cyclopropylimidazo[1,2-b]pyridazin-2-yl)methanol (225 mg, 1.19 mmol) in DCE (5.0 mL). The reaction mixture was stirred at 45° C. for 1 h. Concentration to dryness under reduced pressure gave the title compound (290 mg, 1.1 mmol, 95% yield, 95% purity) as a green solid.

UPLC/MS (Method 5): m/z 209 (M+H)+, $R_T$ 1.00 min.

Step D: 2-(azidomethyl)-6-cyclopropylimidazo[1,2-b]pyridazine

A solution 2-(chloromethyl)-6-cyclopropylimidazo[1,2-b]pyridazine, HCl (290 mg, 1.19 mmol) and DIPEA (0.62 mL, 3.56 mmol) in DMF (5.0 mL) was treated with sodium azide (116 mg, 1.78 mmol). The mixture was heated to 50° C. and stirred for 2 h. The mixture was cooled to RT and concentrated under reduced pressure. Purification by column chromatography (24 g cartridge, 0-10% MeOH/DCM) gave the title compound (155 mg, 0.67 mmol, 57% yield, 93% purity) as a colourless oil.

UPLC/MS (Method 5): m/z 216 (M+H)+, $R_T$ 1.10 min.

Step E: (6-cyclopropylimidazo[1,2-b]pyridazin-2-yl)methanamine 2-(azidomethyl)-6-cyclopropylimidazo[1,2-b]pyridazine (155 mg, 673 μmol) and triphenylphosphine (212 mg, 807 μmol) were dissolved in THF (3.6 mL) and water (0.4 mL). The mixture was stirred at RT overnight before removal of the solvent in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (130 mg, 0.66 mmol, 98% yield, 95% purity) as a white solid.

UPLC/MS (Method 5): m/z 189 (M+H)+, $R_T$ 0.76 min.

Synthesis 29

(3R,4R)-4-(((3-cyclobutyl-7-(((8-methylimidazo[1,2-a]pyridin-2-yl)methyl)amino)pyrazolo[1,5-a]pyrimidin-5-yl)amino)methyl)piperidin-3-ol (H-AP-PAMP-029)

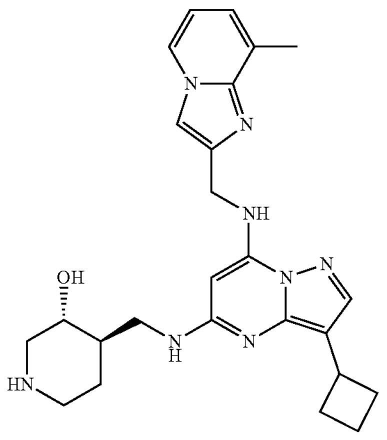 [SMILES: Cc1cccn2cc(CNc3cc(NC[C@H]4CCNC[C@@H]4O)nc4c(C5CCC5)cnn34)nc12]

Step 1: 5-chloro-3-iodo-N-((8-methylimidazo[1,2-a]pyridin-2-yl)methyl)pyrazolo[1,5-a]pyrimidin-7-amine (8-Methylimidazo[1,2-a]pyridin-2-yl)methanamine, 2HCl (1.98 g, 8.47 mmol) was added to a solution of 5,7-dichloro-3-iodopyrazolo[1,5-a]pyrimidine (2.80 g, 8.47 mmol) and DIPEA (4.4 mL, 25.4 mmol) in EtOH (38 mL). The reaction mixture was heated at 85° C. overnight. At RT, the precipitated solid was collected by filtration and rinsed with EtOH (100 mL) to give the title compound (3.57 g, 8.03 mmol, 94% yield, 98% purity) as a beige solid.

UPLC/MS (Method 5): m/z 439 (M+H)+, $R_T$ 1.77 min

Step 2: tert-butyl (5-chloro-3-iodopyrazolo[1,5-a]pyrimidin-7-yl)((8-methylimidazo[1,2-a]pyridin-2-yl)methyl)carbamate BOC-Anhydride (1.74 g, 7.99 mmol) was added to a solution of 5-chloro-3-iodo-N-((8-methylimidazo[1,2-a]pyridin-2-yl)methyl)pyrazolo[1,5-a]pyrimidin-7-amine (2.92 g, 6.66 mmol) and DMAP (81 mg, 0.66 mmol) in THE (23 mL) and DMF (23 mL). The reaction mixture was stirred at 50° C. for 1.5 h. At RT, water (20 mL) was added and the resulting solid was collected by filtration, before rinsing with water (25 mL) and TBME (25 mL) to afford the title compound (3.1 g, 5.68 mmol, 85% yield, 99% purity) as an off-white solid after drying at 40° C. overnight under vacuum.

UPLC/MS (Method 5): m/z 539 (M+H)+, $R_T$ 2.24 min.

Step 3: tert-butyl (3R,4R)-4-(((7-((tert-butoxycarbonyl)((8-methylimidazo[1,2-a]pyridin-2-yl)methyl)amino)-3-iodopyrazolo[1,5-a]pyrimidin-5-yl)amino)methyl)-3-hydroxypiperidine-1-carboxylate A solution of tert-butyl (5-chloro-3-iodopyrazolo[1,5-a]pyrimidin-7-yl)((8-methylimidazo[1,2-a]pyridin-2-yl)methyl)carbamate (1.00 g, 1.86 mmol), (3R,4R)-tert-butyl 4-(aminomethyl)-3-hydroxypiperidine-1-carboxylate (1.71 g, 7.42 mmol) and DIPEA (1.29 mL, 7.42 mmol)) in anhydrous NMP (11 mL) was degassed with $N_2$ then heated at 110° C. for 2 h. The reaction mixture was cooled at 0° C. water (30 mL) was added. The solid was collected by filtration, rinsing with more water (10 mL) then dried at 40° C. under reduced pressure to give the title compound (1.28 g, 1.6 mmol, 87% yield, 92% purity) as a pale solid.

UPLC/MS (Method 5): m/z 733 (M+H)+, $R_T$ 2.06 min.

Step 4: tert-butyl (3R,4R)-4-(((7-((tert-butoxycarbonyl)((8-methylimidazo[1,2-a]pyridin-2-yl)methyl)amino)-3-cyclobutylpyrazolo[1,5-a]pyrimidin-5-yl)amino)methyl)-3-hydroxypiperidine-1-carboxylate Under $N_2$, Cyclobutylzinc(II) bromide (0.38M in THF) (prepared according literature procedure) (3.59 mL, 1.37 mmol) was added dropwise to a solution of tert-butyl (3R,4R)-4-(((7-((tert-butoxycarbonyl)((8-methylimidazo[1,2-a]pyridin-2-yl)methyl)amino)-3-iodopyrazolo[1,5-a]pyrimidin-5-yl)amino)methyl)-3-hydroxypiperidine-1-carboxylate (200 mg, 273 μmol), XPhos Pd G3 (8 mg, 9.28 μmol) in THE (2.0 mL). The reaction mixture was stirred at RT for 18 h then quenched with water (10 mL) and extracted with DCM (3×10 mL). The combined organic layers were dried over $MgSO_4$, filtered then concentrated under reduced pressure. Purification by column chromatography (12 g cartridge, 0-10% MeOH/DCM) followed by further purification by RP preparative HPLC (25-100% MeCN/0.1% $NH_3$ in water) gave the title compound (19 mg, 29 μmol, 11% yield, 99% purity) as a white solid.

UPLC/MS (Method 3): m/z 662 (M+H)+, $R_T$ 1.34 min.

Step 5: (3R,4R)-4-(((3-cyclobutyl-7-(((8-methylimidazo[1,2-a]pyridin-2-yl)methyl)amino)pyrazolo[1,5-a]pyrimidin-5-yl)amino)methyl)piperidin-3-ol TFA (0.10 mL) was added to a solution of tert-butyl (3R,4R)-4-(((7-((tert-butoxycarbonyl)((8-methylimidazo[1,2-a]pyridin-2-yl)methyl)amino)-3-cyclobutylpyrazolo[1,5-a]pyrimidin-5-yl)amino)methyl)-3-hydroxypiperidine-1-carboxylate (19 mg, 29 μmol) in DCM (0.4 mL). The reaction mixture was stirred at RT for 16 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (10 mg, 21 μmol, 72% yield, 95% purity).

UPLC/MS (Method 5): m/z 461 (M+H)+, $R_T$ 1.82 min.

$^1H$ NMR (400 MHz, DMSO-$d_6$) δ 8.32 (d, J=6.7 Hz, 1H), 7.75 (d, J=4.9 Hz, 2H), 7.66 (t, J=6.2 Hz, 1H), 7.02 (dt, J=6.8, 1.2 Hz, 1H), 6.78-6.69 (m, 2H), 5.32-5.25 (m, 2H), 4.58 (d, J=6.0 Hz, 2H), 3.59-3.42 (m, 2H), 3.24-3.14 (m, 1H), 3.07-2.96 (m, 1H), 2.90 (dd, J=11.5, 4.5 Hz, 1H), 2.82-2.72 (m, 1H), 2.48 (s, 3H), 2.34-2.11 (m, 6H), 1.97-1.78 (m, 2H), 1.59-1.50 (m, 1H), 1.38-1.28 (m, 1H), 1.21-1.07 (m, 1H). 1H under water.

Synthesis 30

(3R,4R)-4-(((3-cyclopropyl-7-(((5-cyclopropylimidazo[1,2-a]pyridin-2-yl)methyl)amino)pyrazolo[1,5-a]pyrimidin-5-yl)amino)methyl)piperidin-3-ol (H-APPAMP-030)

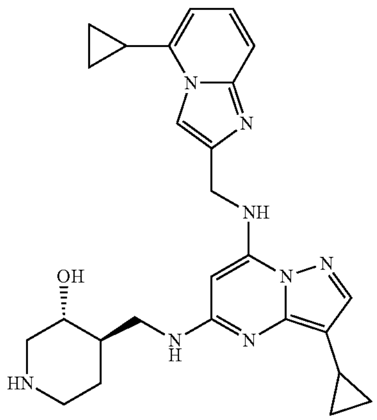 [SMILES: O[C@H]1CNCC[C@@H]1CNc1cc(NCc2cn3c(C4CC4)cccc3n2)n2ncc(C3CC3)c2n1]

Step 1: 5-chloro-3-cyclopropyl-N-((5-cyclopropylimidazo[1,2-a]pyridin-2-yl)methyl)pyrazolo[1,5-a]pyrimidin-7-amine (5-Cyclopropylimidazo[1,2-a]pyridin-2-yl)methanamine (90 mg, 481 μmol) was added to a solution of 5,7-dichloro-3-cyclopropylpyrazolo[1,5-a]pyrimidine (110 mg, 481 μmol) and DIPEA (0.59 ml, 3.36 mmol) in EtOH (3.0 mL). The reaction mixture was heated at 50° C. for 5 h. The reaction mixture was concentrated in vacuo to give the title compound (325 mg, 0.48 mmol, 99% yield, 56% purity) as a yellow liquid.

UPLC/MS (Method 5): m/z 379 (M+H)+, $R_T$ 1.48 min

Step 2: tert-butyl (5-chloro-3-cyclopropylpyrazolo[1,5-a]pyrimidin-7-yl)((5-cyclopropylimidazo[1,2-a]pyridin-2-yl)methyl)carbamate BOC-Anhydride (126 mg, 0.58 mmol) was added to a solution of 5-chloro-3-cyclopropyl-N-((5-cyclopropylimidazo[1,2-a]pyridin-2-yl)methyl)pyrazolo[1,5-a]pyrimidin-7-amine (325 mg, 0.48 mmol) and DMAP (12 mg, 96 μmol) in THE (5.0 mL). The reaction mixture was stirred at RT for 72 h. The reaction mixture was concentrated under reduced pressure. Purification by column chromatography (24 g cartridge, 0-10% MeOH/DCM) gave the title compound (145 mg, 0.29 mmol, 60% yield, 96% purity) as a brown solid.

UPLC/MS (Method 5): m/z 479 (M+H)+, $R_T$ 1.80 min.

Step 3: tert-butyl (3R,4R)-4-(((7-((tert-butoxycarbonyl)((5-cyclopropylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate, 0.3 formate A solution tert-butyl (5-chloro-3-cyclopropylpyrazolo[1,5-a]pyrimidin-7-yl)((5-cyclopropylimidazo[1,2-a]pyridin-2-yl)methyl)carbamate (145 mg, 303 μmol), (3R,4R)-tert-butyl 4-(aminomethyl)-3-hydroxypiperidine-1-carboxylate (83.7 mg, 363 μmol) and $^t$BuBrettPhos Pd G3 (25.9 mg, 30.3 μmol) in THE (2.0 mL) was degassed with $N_2$ for 10 min. LiHMDS (1M in THF) (0.39 ml, 394 μmol) was added in one portion under bubbling $N_2$. Bubbling was ceased and the reaction mixture heated to 60° C. for 18 h. The reaction mixture was concentrated under reduced pressure. Purification by column chromatography (12 g cartridge, 0-10% MeOH/DCM) follow by further purification on RP Flash C18 (24 g cartridge, 10-100% (0.1% Formic acid in MeCN)/(0.1% formic acid in water)) gave the title compound (83 mg, 0.12 mmol, 39% yield, 97% purity) as a white solid.

UPLC/MS (Method 5): m/z 673 (M+H)+, $R^T$ 1.70 min.

Step 4: (3R,4R)-4-(((3-cyclopropyl-7-(((5-cyclopropylimidazo[1,2-a]pyridin-2-yl)methyl)amino)pyrazolo[1,5-a]pyrimidin-5-yl)amino)methyl)piperidin-3-ol TFA (0.5 mL) was added to a solution of tert-butyl (3R,4R)-4-(((7-((tert-butoxycarbonyl)((5-cyclopropylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (83 mg, 0.12 mmol) in DCM (2.0 mL). The reaction mixture was stirred at RT for 18 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (49 mg, 0.10 mmol, 81% yield, 96% purity).

UPLC/MS (Method 5): m/z 473 (M+H)+, $R_T$ 1.16 min.

$^1$H NMR (400 MHz, DMSO-$d_6$) δ 7.91 (s, 1H), 7.57 (t, J=6.0 Hz, 1H), 7.52 (s, 1H), 7.43 (d, J=9.0 Hz, 1H), 7.20 (dd, J=9.0, 7.0 Hz, 1H), 6.79-6.74 (m, 1H), 6.69-6.64 (m, 1H), 5.36 (s, 1H), 5.34-5.29 (m, 1H), 4.60 (d, J=5.8 Hz, 2H), 3.59-3.47 (m, 1H), 3.26-3.19 (m, 1H), 3.10-3.00 (m, 1H), 2.91 (dd, J=11.5, 4.5 Hz, 1H), 2.84-2.75 (m, 1H), 2.36-2.26 (m, 1H), 2.22-2.12 (m, 2H), 1.77-1.68 (m, 1H), 1.63-1.53 (m, 1H), 1.40-1.29 (m, 1H), 1.22-1.10 (m, 1H), 1.10-1.03 (m, 2H), 0.82-0.73 (m, 4H), 0.71-0.61 (m, 2H). 1H under-water.

Intermediate Synthesis A10

(5-cyclopropylimidazo[1,2-a]pyridin-2-yl)methanamine

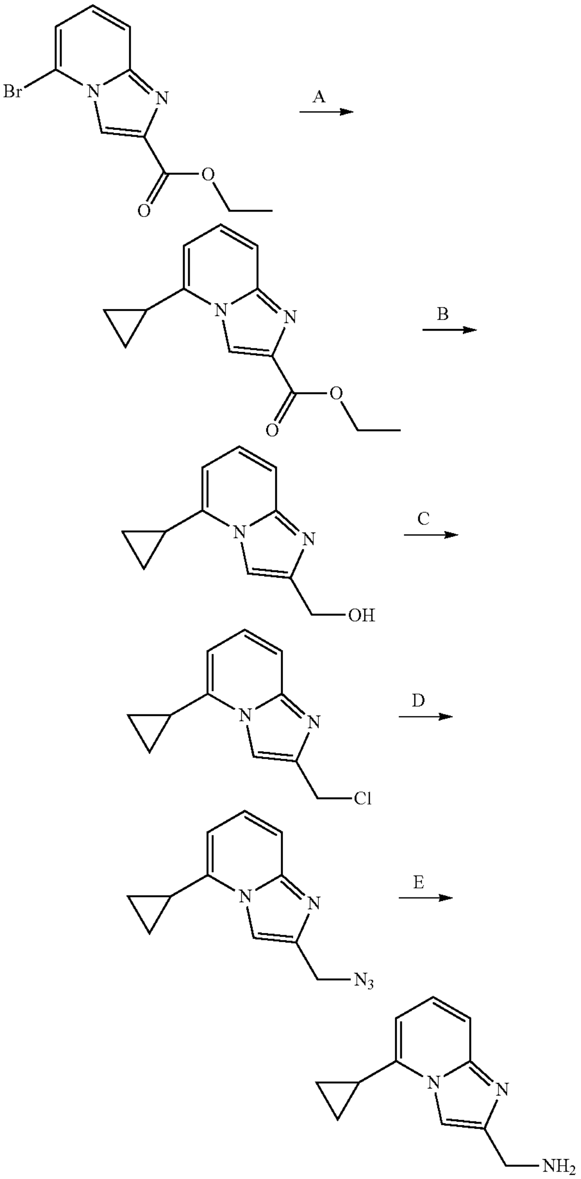

Step A: ethyl 5-cyclopropylimidazo[1,2-a]pyridine-2-carboxylate

A mixture of ethyl 5-bromoimidazo[1,2-a]pyridine-2-carboxylate (500 mg, 1.86 mmol), cesium fluoride (564 mg, 3.72 mmol), $PdCl_2$ (dtbpf) (121 mg, 186 μmol), cyclopropylboronic acid (319 mg, 3.72 mmol) in dioxane (10.0 mL)

was degassed with $N_2$ for 10 min. The mixture was then heated to 90° C. overnight. At RT, the reaction mixture was filtered through a short pad of celite, rinsing with 20% MeOH/DCM (20 mL) and the filtrate was concentrated under reduced pressure. Purification by column chromatography (24 g cartridge, 0-10% (0.7 M NH3/MeOH)/DCM) gave the title compound (440 mg, 1.7 mmol, 93% yield, 90% purity) as a brown oil.

UPLC/MS (Method 3): m/z 231 (M+H)+, $R_T$ 0.86 min.

Step B/C: (5-cyclopropylimidazo[1,2-a]pyridin-2-yl)methanol/2-(chloromethyl)-5-cyclopropylimidazo[1,2-a]pyridine, HCl Lithium borohydride (2M in THF) (860 μL, 1.72 mmol) was added to a solution of ethyl 5-cyclopropylimidazo[1,2-a]pyridine-2-carboxylate (440 mg, 1.72 mmol) in THE (8.0 mL) at 0° C. The reaction mixture was allowed to warm to RT then stirred for 20 h. At 0° C., MeOH (5 mL), followed by water (5 mL) and aq. 1M HCl (5 mL) were added. The mixture was stirred vigorously for 30 min and extracted with ethyl acetate (3×15 mL). The combined organic layers were washed with brine (15 mL), dried over MgSO4, and concentrated in vacuo to give the crude alcohol intermediate (5-cyclopropylimidazo[1,2-a]pyridin-2-yl)methanol (235 mg, 1.25 mmol) which was re-dissolved in dry DCE (5.0 mL). Thionyl chloride (455 μL, 6.24 mmol) was added and the reaction mixture was stirred at 45° C. for 1 h. Concentration to dryness under reduced pressure gave the title compound (260 mg, 1.00 mmol, 55% yield, 96% purity) as a yellow liquid.

UPLC/MS (Method 3): m/z 207 (M+H)+, $R_T$ 0.52 min.

Step D: 2-(azidomethyl)-5-cyclopropylimidazo[1,2-a]pyridine

A solution 2-(chloromethyl)-5-cyclopropylimidazo[1,2-a]pyridine, HCl (260 mg, 1.21 mmol) and DIPEA (0.63 mL, 3.62 mmol) in DMF (6.0 mL) was treated with sodium azide (118 mg, 1.81 mmol). The mixture was heated to 50° C. and stirred for 3 h. The mixture was cooled to RT and concentrated under reduced pressure. Purification by column chromatography (24 g cartridge, 0-10% MeOH/DCM) gave the title compound (218 mg, 0.97 mmol, 80% yield, 95% purity) as a colourless oil.

UPLC/MS (Method 6): m/z 214 (M+H)+, $R_T$ 0.63 min.

Step E: (5-cyclopropylimidazo[1,2-a]pyridin-2-yl)methanamine 2-(azidomethyl)-5-cyclopropylimidazo[1,2-a]pyridine (218 mg, 971 μmol) and triphenylphosphine (255 mg, 971 μmol) were dissolved in THE (3.6 mL) and Water (0.4 mL). The mixture was stirred at RT overnight before removal of the solvent in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (90 mg, 0.46 mmol, 48% yield, 96% purity) as a white solid.

UPLC/MS (Method 5): m/z 188 (M+H)+, $R_T$ 0.83 min.

Synthesis 31

(3R,4R)-4-(((3-ethyl-7-(((5-methylimidazo[1,2-a]pyridin-2-yl)methyl)amino)pyrazolo[1,5-a]pyrimidin-5-yl)amino)methyl)piperidin-3-ol (H-APPAMP-031)

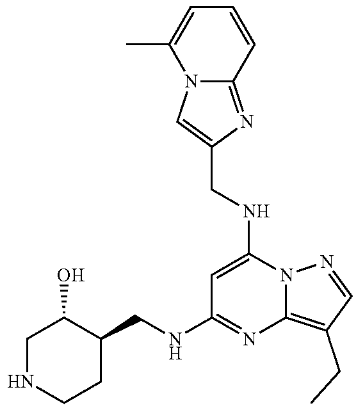 [SMILES: CCc1cnn2c(NCc3cn4c(C)cccc4n3)cc(NC[C@H]3CCNC[C@@H]3O)nc12]

Step 1: 5-chloro-3-ethyl-N-((5-methylimidazo[1,2-a]pyridin-2-yl)methyl)pyrazolo[1,5-a]pyrimidin-7-amine (5-Methylimidazo[1,2-a]pyridin-2-yl)methanamine (100 mg, 620 μmol) was added to a solution of 5,7-dichloro-3-ethylpyrazolo[1,5-a]pyrimidine (122 mg, 564 μmol) and DIPEA (0.69 ml, 3.95 mmol) in EtOH (3.0 mL). The reaction mixture was heated at 50° C. for 2.5 h. The reaction mixture was concentrated in vacuo. Purification by column chromatography (12 g cartridge, 0-10% MeOH/DCM) gave the title compound (70 mg, 0.20 mmol, 35% yield, 97% purity) as a white solid.

UPLC/MS (Method 5): m/z 341 (M+H)+, $R_T$ 1.33 min.

Step 2: tert-butyl (5-chloro-3-ethylpyrazolo[1,5-a]pyrimidin-7-yl)((5-methylimidazo[1,2-a]pyridin-2-yl)methyl)carbamate BOC-Anhydride (52 mg, 0.24 mmol) was added to a solution of 5-chloro-3-ethyl-N-((5-methylimidazo[1,2-a]pyridin-2-yl)methyl)pyrazolo[1,5-a]pyrimidin-7-amine (70 mg, 0.20 mmol) and DMAP (4.9 mg, 40 μmol) in THE (2.0 mL). The reaction mixture was stirred at RT for 18 h. The reaction mixture was concentrated under reduced pressure. Purification by column chromatography (12 g cartridge, 0-10% MeOH/DCM) gave the title compound (83 mg, 0.16 mmol, 82% yield, 87% purity) as a tan solid.

UPLC/MS (Method 5): m/z 441 (M+H)+, $R_T$ 1.69 min.

Step 3: tert-butyl (3R,4R)-4-(((7-((tert-butoxycarbonyl)((5-methylimidazo[1,2-a]pyridin-2-yl)methyl)amino)-3-ethylpyrazolo[1,5-a]pyrimidin-5-yl)amino)methyl)-3-hydroxypiperidine-1-carboxylate A solution of tert-butyl (5-chloro-3-ethylpyrazolo[1,5-a]pyrimidin-7-yl)((5-methylimidazo[1,2-a]pyridin-2-yl)methyl)carbamate (166 mg, 376 μmol), (3R,4R)-tert-butyl 4-(aminomethyl)-3-hydroxypiperidine-1-carboxylate (83.0 mg, 314 μmol) and $^t$BuBrettPhos Pd G3 (26.8 mg, 31.4

μmol) in THE (3.0 mL) was degassed with $N_2$ for 10 min. LiHMDS (1M in THF) (408 μl, 408 μmol) was added in one portion under bubbling $N_2$. Bubbling was ceased and the reaction mixture heated to 60° C. for 2.5 h. The reaction mixture was concentrated under reduced pressure. Purification by column chromatography (12 g cartridge, 0-10% MeOH/DCM) gave the title compound (61 mg, 91 μmol, 29% yield, 95% purity) as a yellow solid.

UPLC/MS (Method 5): m/z 635 (M+H)+, $R_T$ 1.63 min.

Step 4: (3R,4R)-4-(((3-ethyl-7-(((5-methylimidazo[1,2-a]pyridin-2-yl)methyl)amino)pyrazolo[1,5-a]pyrimidin-5-yl)amino)methyl)piperidin-3-ol TFA (0.4 mL) was added to a suspension of tert-butyl (3R,4R)-4-(((7-((tert-butoxycarbonyl)((5-methylimidazo[1,2-a]pyridin-2-yl)methyl)amino)-3-ethylpyrazolo[1,5-a]pyrimidin-5-yl)amino)methyl)-3-hydroxypiperidine-1-carboxylate (61 mg, 91 μmol) in DCM (1.6 mL). The reaction mixture was stirred at RT for 18 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (26 mg, 57 μmol, 62% yield, 95% purity) as an off-white solid.

UPLC/MS (Method 5): m/z 435 (M+H)+, $R_T$ 1.03 min.

$^1$H NMR (400 MHz, DMSO-$d_6$) δ 7.67 (s, 1H), 7.64 (s, 1H), 7.58 (t, J=6.0 Hz, 1H), 7.43 (d, J=9.1 Hz, 1H), 7.21 (dd, J=9.1, 6.8 Hz, 1H), 6.80-6.73 (m, 2H), 5.49-5.42 (m, 1H), 5.34 (s, 1H), 4.59 (d, J=5.7 Hz, 2H), 3.62-3.50 (m, 1H), 3.22-3.13 (m, 1H), 3.08-2.98 (m, 1H), 2.91 (dd, J=11.7, 4.5 Hz, 1H), 2.84-2.75 (m, 1H), 2.56 (s, 3H), 2.51-2.44 (m, 2H), 2.36-2.26 (m, 1H), 2.17 (dd, J=11.6, 9.9 Hz, 1H), 1.61-1.52 (m, 1H), 1.38-1.28 (m, 1H), 1.21-1.13 (m, 4H). 1H under water.

Synthesis 32

(3R,4R)-4-(((3-cyclopropyl-7-(((5,7-dimethylimidazo[1,2-a]pyridin-2-yl)methyl)amino)pyrazolo[1,5-a]pyrimidin-5-yl)amino)methyl)piperidin-3-ol (H-APPAMP-032)

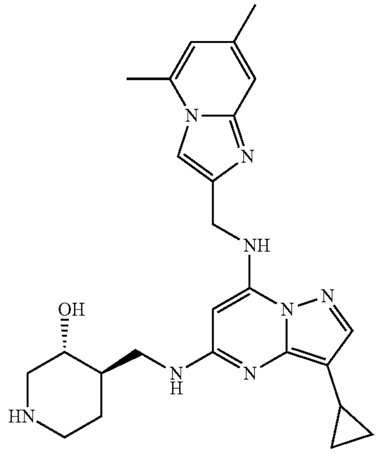 [SMILES: Cc1cc(C)n2cc(CNc3cc(NC[C@H]4CCNC[C@@H]4O)nc4c(C5CC5)cnn34)nc2c1]

Step 1: 5-chloro-3-cyclopropyl-N-((5,7-dimethylimidazo[1,2-a]pyridin-2-yl)methyl)pyrazolo[1,5-a]pyrimidin-7-amine (5,7-dimethylimidazo[1,2-a]pyridin-2-yl)methanamine (66 mg, 0.38 mmol) was added to a solution of 5,7-dichloro-3-cyclopropylpyrazolo[1,5-a]pyrimidine (86 mg, 0.38 mmol) and DIPEA (0.46 mL, 2.6 mmol) in EtOH (2.0 mL). The reaction mixture was heated at 50° C. for 16 h. The reaction mixture was concentrated in vacuo. Purification by column chromatography (12 g cartridge, 0-10% MeOH/DCM) gave the title compound (108 mg, 0.28 mmol, 74% yield, 95% purity) as a yellow oil.

UPLC/MS (Method 5): m/z 367 (M+H)+, $R_T$ 1.44 min.

Step 2: tert-butyl (5-chloro-3-cyclopropylpyrazolo[1,5-a]pyrimidin-7-yl)((5,7-dimethylimidazo[1,2-a]pyridin-2-yl)methyl)carbamate BOC-Anhydride (82.0 mg, 376 μmol) was added to a solution of 5-chloro-3-cyclopropyl-N-((5,7-dimethylimidazo[1,2-a]pyridin-2-yl)methyl)pyrazolo[1,5-a]pyrimidin-7-amine (106 mg, 289 μmol) and DMAP (1.9 mg, 57.8 μmol) in THE (2.0 mL). The reaction mixture was stirred at RT for 3 h. The reaction mixture was concentrated under reduced pressure. Purification by column chromatography (12 g cartridge, 0-10% MeOH/DCM) gave the title compound (148 mg, 0.29 mmol, 99% yield, 90% purity) as a white solid.

UPLC/MS (Method 5): m/z 467 (M+H)+, $R_T$ 1.78 min.

Step 3: tert-butyl (3R,4R)-4-(((7-((tert-butoxycarbonyl)((5,7-dimethylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5,7-dimethylimidazo[1,2-a]pyridin-2-yl)methyl)carbamate (130 mg, 278 μmol), (3R,4R)-tert-butyl 4-(aminomethyl)-3-hydroxypiperidine-1-carboxylate (76.9 mg, 334 μmol) and $^t$BuBrettPhos Pd G3 (35.7 mg, 41.8 μmol) in THE (2.3 mL) was degassed with $N_2$ for 10 min. LiHMDS (1M in THF) (418 μL, 418 μmol) was added in one portion under bubbling $N_2$. Bubbling was ceased and the reaction mixture heated to 60° C. for 2 h. The reaction mixture was concentrated under reduced pressure. Purification by column chromatography (4 g cartridge, 0-10% (0.7 M $NH_3$/MeOH)/DCM) followed by further Purification by column chromatography (4 g cartridge, 0-100% EtOAc/isohexane then 0-5% (0.7 M $NH_3$/MeOH)/DCM) gave the title compound (140 mg, 0.19 mmol, 68% yield, 90% purity) as a brown solid.

UPLC/MS (Method 4): m/z 661 (M+H)+, $R_T$ 1.68 min.

Step 4: (3R,4R)-4-(((3-cyclopropyl-7-(((5,7-dimethylimidazo[1,2-a]pyridin-2-yl)methyl)amino)pyrazolo[1,5-a]pyrimidin-5-yl)amino)methyl)piperidin-3-ol Hydrogen chloride (4 M in dioxane) (953 μL, 3.81 mmol) was added to a suspension tert-butyl (3R,4R)-4-(((7-((tert-butoxycarbonyl)((5,7-dimethylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (140 mg, 191 μmol) in dioxane (1.0 mL). The reaction mixture was stirred at 35° C. for 1 h and concentrated in vacuo. The residue was loaded onto a column of SCX. The column was washed with MeOH (40 mL) and the product eluted with 0.7 M $NH_3$ in MeOH (40 mL). The ammoniacal methanol solution was concentrated in vacuo to give the title compound (67 mg, 0.14 mmol, 72% yield, 95% purity) as a beige solid after drying under vacuum at 50° C. overnight.

UPLC/MS (Method 4): m/z 461 (M+H)+, $R_T$ 1.17 min.

$^1$H NMR (400 MHz, DMSO-$d_6$) δ 7.56 (s, 1H), 7.53-7.47 (m, 2H), 7.19 (s, 1H), 6.74 (t, J=6.1 Hz, 1H), 6.61 (s, 1H), 5.35-5.29 (m, 2H), 4.54 (d, J=5.8 Hz, 2H), 3.61-3.46 (m, 1H), 3.25-3.17 (m, 1H), 3.08-2.99 (m, 1H), 2.90 (dd, J=11.7, 4.5 Hz, 1H), 2.81-2.74 (m, 1H), 2.36-2.31 (m, 3H), 2.30-2.25 (m, 1H), 2.15 (dd, J=11.6, 9.9 Hz, 1H), 1.79-1.66 (m, 1H), 1.60-1.53 (m, 1H), 1.32 (s, 1H), 1.11-1.15 (m, 1H), 0.80-0.71 (m, 2H), 0.69-0.58 (m, 2H). 3H under DMSO. 1H under water.

Intermediate Synthesis A11

(5,7-dimethylimidazo[1,2-a]pyridin-2-yl)methanamine

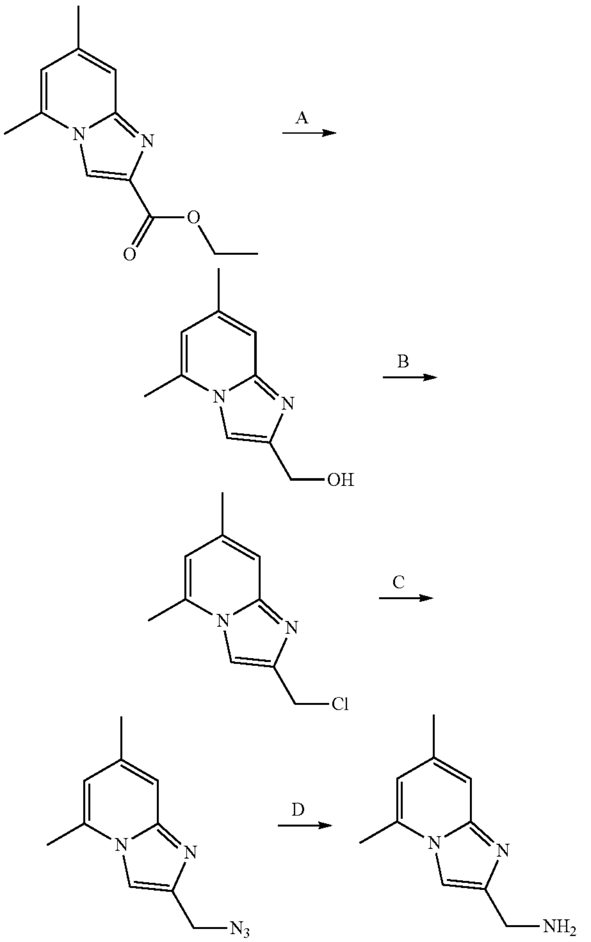

Step A: (5,7-dimethylimidazo[1,2-a]pyridin-2-yl) methanol

Diisobutylaluminum hydride (1 M in hexane) (3.44 mL, 3.44 mmol) was added to a solution of ethyl 5,7-dimethylimidazo[1,2-a]pyridine-2-carboxylate (300 mg, 1.37 mmol) in THF (8.0 mL) at 0° C. The reaction mixture was allowed to warm to RT and stirred for 18 h then MeOH (10 mL), followed by water (10 mL) and aq. 1 M HCl (10 mL) were added. The mixture was stirred vigorously for 30 min and extracted with ethyl acetate (3×25 mL). The combined organic layers were washed with brine (15 mL), dried over MgSO4, and concentrated in vacuo. Purification by column chromatography (12 g cartridge, 0-10% MeOH/DCM) gave the title compound (93 mg, 0.51 mmol, 37% yield, 98% purity) as a brown solid.

UPLC/MS (Method 5): m/z 177 (M+H)+, $R_T$ 0.77 min.

Step B: 2-(chloromethyl)-5,7-dimethylimidazo[1,2-a]pyridine, HCl

Thionyl chloride (96 μL, 1.32 mmol) was added dropwise to a solution of (5,7-dimethylimidazo[1,2-a]pyridin-2-yl) methanol (93.0 mg, 528 μmol) in DCM (2.5 mL) at 0° C. The mixture was stirred at RT for 1 h. Concentration to dryness under reduced pressure gave the title compound (132 mg, 0.52 mmol, 98% yield, 91% purity) as a yellow solid.

$^1$H NMR in DMSO-$d_6$ was consistent with product structure.

Step C: 2-(azidomethyl)-5,7-dimethylimidazo[1,2-a] pyridine

A solution of 2-(chloromethyl)-5,7-dimethylimidazo[1,2-a]pyridine (132 mg, 617 μmol) and DIPEA (322 μL, 1.85 mmol) in DMF (3.0 mL) was treated with sodium azide (40 mg, 617 μmol). The mixture was heated to 50° C. and stirred for 3 h. The mixture was concentrated under reduced pressure. Purification by column chromatography (12 g cartridge, 0-10% MeOH/DCM) gave the title compound 117 mg, 0.38 mmol, 61% yield, 65% purity) as a colourless oil.

UPLC/MS (Method 5): m/z 202 (M+H)+, $R_T$ 0.46 min.

Step D: (5,7-dimethylimidazo[1,2-a]pyridin-2-yl) methanamine 2-(Azidomethyl)-5,7-dimethylimidazo[1,2-a]pyridine (117 mg, 378 μmol) and triphenylphosphine (119 mg, 454 μmol) were dissolved in THF (1.8 mL) and Water (0.2 mL). The mixture was stirred at 50° C. for 16 h before removal of the solvent in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (66 mg, 377 μmol, 99% yield, 99% purity) as a tan solid.

UPLC/MS (Method 5): m/z 176 (M+H)+, $R_T$ 0.79 min.

Synthesis 33

(3R,4R)-4-(((7-(((8-chloro-6-(trifluoromethyl)imidazo[1,2-a]pyridin-2-yl)methyl)amino)-3-cyclopropylpyrazolo[1,5-a]pyrimidin-5-yl)amino)methyl)piperidin-3-ol (H-APPAMP-033)

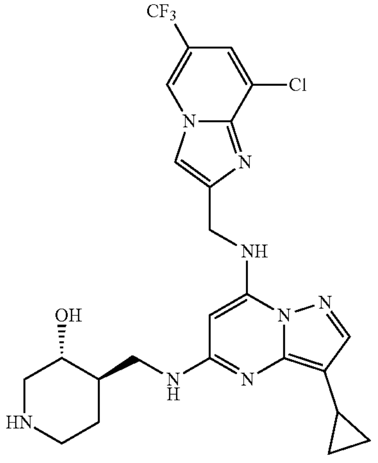 [SMILES: O[C@H]1CNCC[C@@H]1CNc1cc(NCc2cn3cc(C(F)(F)F)cc(Cl)c3n2)n2ncc(C3CC3)c2n1]

Step 1: 5-chloro-N-((8-chloro-6-(trifluoromethyl)imidazo[1,2-a]pyridin-2-yl)methyl)-3-cyclopropylpyrazolo[1,5-a]pyrimidin-7-amine (8-Chloro-6-(trifluoromethyl)imidazo[1,2-a]pyridin-2-yl)methanamine (175 mg, 701 μmol) was added to a solution of 5,7-dichloro-3-cyclopropylpyrazolo[1,5-a]pyrimidine (145 mg, 637 μmol) and DIPEA (666 μl, 3.82 mmol) in EtOH (10 mL). The reaction mixture was heated at 50° C. for 5 h. The reaction mixture was concentrated in vacuo to give the title compound (290 mg, 0.58 mmol, 91% yield, 88% purity) as a yellow solid.

UPLC/MS (Method 5): m/z 441 (M+H)+, $R_T$ 1.61 min

Step 2: tert-butyl (3R,4R)-4-(((7-((tert-butoxycarbonyl)((8-chloro-6-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of 5-chloro-N-((8-chloro-6-(trifluoromethyl)imidazo[1,2-a]pyridin-2-yl)methyl)-3-cyclopropylpyrazolo[1,5-a]pyrimidin-7-amine (130 mg, 295 μmol), tert-butyl (3R,4R)-4-(aminomethyl)-3-hydroxypiperidine-1-carboxylate (271 mg, 1.18 mmol) and DIPEA (232 μL, 1.33 mmol) in NMP (1.5 mL) was heated under microwave irradiation at 150° C. for 5 h. At RT, water was added. The resultant solid was collected by filtration to give the title compound (175 mg, 0.19 mmol, 65%, 69% Purity) as a yellow solid.

UPLC/MS (Method 3): m/z 535 (M-Boc)+, $R_T$ 1.09 min.

Step 3: (3R,4R)-4-(((7-(((8-chloro-6-(trifluoromethyl)imidazo[1,2-a]pyridin-2-yl)methyl)amino)-3-cyclopropylpyrazolo[1,5-a]pyrimidin-5-yl)amino)methyl)piperidin-3-ol Hydrogen chloride (4 M in dioxane) (1.29 mL, 5.16 mmol) was added to a suspension of tert-butyl (3R,4R)-4-(((7-((tert-butoxycarbonyl)((8-chloro-6-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (164 mg, 258 μmol) in dioxane (2.0 mL). The reaction mixture was stirred at 35° C. for 1 h and concentrated in vacuo. The residue was loaded onto a column of SCX. The column was washed with MeOH (40 mL) and the product eluted with 0.7 M $NH_3$ in MeOH (10 mL). The ammoniacal methanol solution was concentrated in vacuo. Further purification by RP preparative HPLC (25-100% MeCN/0.1% Formic acid in water) gave the title compound (84 mg, 0.15 mmol, 60% yield, 98% purity) as an off-white solid.

UPLC/MS (Method 5): m/z 535 (M+H)+, $R_T$ 1.27 min.

$^1$H NMR (400 MHz, DMSO-$d_6$) δ 9.18 (t, J=1.5 Hz, 1H), 8.00 (s, 1H), 7.85-7.77 (m, 2H), 7.54 (s, 1H), 6.72 (t, J=5.9 Hz, 1H), 5.34-5.28 (m, 1H), 5.25 (s, 1H), 4.63 (d, J=6.1 Hz, 2H), 3.59-3.47 (m, 1H), 3.27-3.18 (m, 1H), 3.11-3.01 (m, 1H), 2.93 (dd, J=11.6, 4.5 Hz, 1H), 2.84-2.77 (m, 1H), 2.36-2.26 (m, 1H), 2.18 (dd, J=11.6, 9.9 Hz, 1H), 1.79-1.67 (m, 1H), 1.62-1.53 (m, 1H), 1.38-1.29 (m, 1H), 1.26-1.07 (m, 1H), 0.83-0.73 (m, 2H), 0.77-0.60 (m, 2H). 1H under water.

Intermediate Synthesis A12

(8-chloro-6-(trifluoromethyl)imidazo[1,2-a]pyridin-2-yl)methanamine

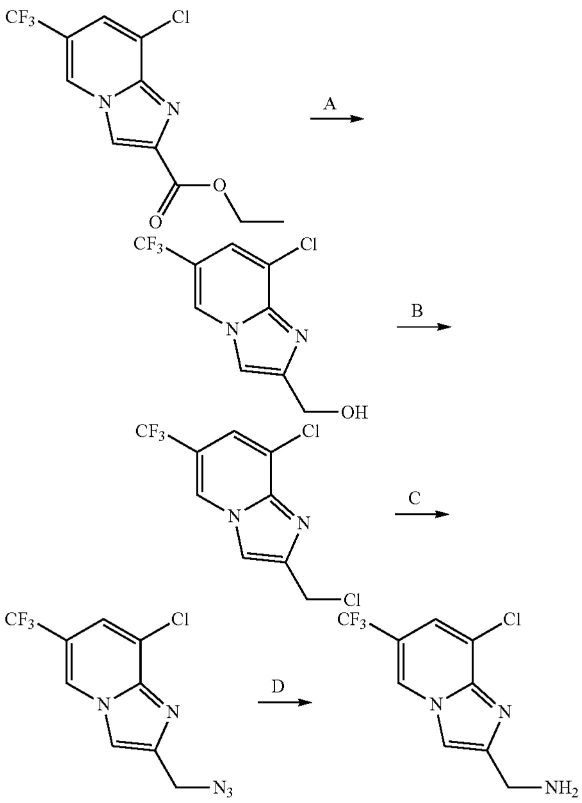

Step A: (8-chloro-6-(trifluoromethyl)imidazo[1,2-a]pyridin-2-yl)methanol

Diisobutylaluminum hydride (1M in hexane) (18.8 mL, 18.8 mmol) was added to a solution of ethyl 8-chloro-6-

(trifluoromethyl)imidazo[1,2-a]pyridine-2-carboxylate (2.20 g, 7.52 mmol) in THE (40 mL) at −40° C. The reaction mixture was allowed to warm to 0° C. and stirred at 0° C. for 2 h then MeOH (10 mL), followed by water (10 mL) and aq. 1 M HCl (10 mL) were added. The mixture was stirred vigorously for 30 min and extracted with ethyl acetate (3×25 mL). The combined organic layers were washed with brine (15 mL), dried over $MgSO_4$, and concentrated in vacuo to give the title compound (1.80 g, 6.9 mmol, 92% yield, 96% purity) as a white solid.

UPLC/MS (Method 5): m/z 251 (M+H)+, $R_T$ 0.94 min.

Step B: 8-chloro-2-(chloromethyl)-6-(trifluoromethyl)imidazo[1,2-a]pyridine

Thionyl chloride (2.6 mL, 36 mmol) was added dropwise to a solution of (8-chloro-6-(trifluoromethyl)imidazo[1,2-a]pyridin-2-yl)methanol (1.8 g, 7.2 mmol) in DCE (20 mL). The mixture was stirred at 45° C. for 3 h. Concentration to dryness under reduced pressure gave the title compound (2.0 g, 6.7 mmol, 93% yield, 90% purity) as a yellow solid.

UPLC/MS (Method 5): m/z 269 (M+H)+, $R_T$ 1.25 min.

Step C: 2-(azidomethyl)-8-chloro-6-(trifluoromethyl)imidazo[1,2-a]pyridine

A solution of 8-chloro-2-(chloromethyl)-6-(trifluoromethyl)imidazo[1,2-a]pyridine (2.00 g, 6.69 mmol) and DIPEA (3.5 mL, 20.1 mmol) in DMF (30 mL) was treated with sodium azide (652 mg, 10.0 mmol). The mixture was heated to 60° C. and stirred for 6 h. The mixture was cooled to RT, diluted with water (40 mL) and brine (60 mL) before extraction with TBME (4×50 mL) then EtOAc (50 mL). The combined organic layers were washed with brine (4×20 mL), dried over $Na_2SO_4$ and concentrated under reduced pressure. Purification by column chromatography (12 g cartridge, 0-100% TBME/isohexane) gave the title compound 1.80 g, 6.2 mmol, 93% yield, 95% purity) as a brown oil.

UPLC/MS (Method 5): m/z 276 (M+H)+, $R_T$ 1.27 min.

Step D: (8-chloro-6-(trifluoromethyl)imidazo[1,2-a]pyridin-2-yl)methanamine 2-(azidomethyl)-8-chloro-6-(trifluoromethyl)imidazo[1,2-a]pyridine (1.8 g, 6.5 mmol), triphenylphosphine (2.1 g, 7.8 mmol) were dissolved in THE (36 mL) and water (4.0 mL). The mixture was stirred at RT overnight before removal of the solvent in vacuo. The residue was loaded onto a column of SCX. The column was washed with MeOH (150 mL) and the product eluted with 0.7 M $NH_3$ in MeOH (100 mL). The ammoniacal methanol solution was concentrated in vacuo to give the title compound (1.32 g, 5.0 mmol, 77% yield, 95% purity) as a white solid.

UPLC/MS (Method 5): m/z 250 (M+H)+, $R_T$ 0.92 min.

Synthesis 34

(3R,4R)-4-(((3-ethyl-7-(((5-(trifluoromethyl)imidazo[1,2-a]pyridin-2-yl)methyl)amino)pyrazolo[1,5-a]pyrimidin-5-yl)amino)methyl)piperidin-3-ol (H-AP-PAMP-034)

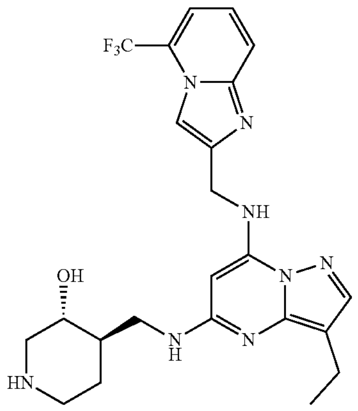 [SMILES: CCc1cnn2c(NCc3cn4c(C(F)(F)F)cccc4n3)cc(NC[C@H]3CCNC[C@@H]3O)nc12]

Step 1: 5-chloro-3-ethyl-N-((5-(trifluoromethyl)imidazo[1,2-a]pyridin-2-yl)methyl)pyrazolo[1,5-a]pyrimidin-7-amine (5-(Trifluoromethyl)imidazo[1,2-a]pyridin-2-yl)methanamine (106 mg, 444 μmol) was added to a solution of 5,7-dichloro-3-ethylpyrazolo[1,5-a]pyrimidine (80 mg, 370 μmol) and DIPEA (387 μL, 2.22 mmol) in EtOH (1.6 mL). The reaction mixture was heated at 65° C. for 5 h. The reaction mixture was concentrated in vacuo. Purification by column chromatography (12 g cartridge, 0-10% MeOH/DCM) gave the title compound (136 mg, 0.34 mmol, 91% yield, 98% purity) as an orange solid.

UPLC/MS (Method 3): m/z 395 (M+H)+, $R_T$ 1.51 min.

Step 2: tert-butyl (5-chloro-3-ethylpyrazolo[1,5-a]pyrimidin-7-yl)((5-(trifluoromethyl)imidazo[1,2-a]pyridin-2-yl)methyl)carbamate BOC-Anhydride (36.8 mg, 169 μmol) was added to a solution of 5-chloro-3-ethyl-N-((5-(trifluoromethyl)imidazo[1,2-a]pyridin-2-yl)methyl)pyrazolo[1,5-a]pyrimidin-7-amine (136 mg, 338 μmol) and DMAP (8.3 mg, 67.5 μmol) in THE (6.8 mL). The reaction mixture was stirred at 65° C. for 2 h. The reaction mixture was concentrated under reduced pressure and the residue partitioned between DCM (20 mL) and water (10 mL). The aq. layer was extracted with DCM (2×10 mL) and the combined organic layers were washed with brine (30 mL), dried over $Na_2SO_4$ and concentrated under reduced pressure. Purification by column chromatography (12 g cartridge, 0-10% MeOH/DCM) gave the title compound (159 mg, 0.29 mmol, 86% yield, 90% purity) as a yellow oil.

UPLC/MS (Method 5): m/z 495 (M+H)+, $R_T$ 1.88 min.

Step 3: tert-butyl (3R,4R)-4-(((7-((tert-butoxycarbonyl)((5-(trifluoromethyl)imidazo[1,2-a]pyridin-2-yl)methyl)amino)-3-ethylpyrazolo[1,5-a]pyrimidin-5-yl)amino)methyl)-3-hydroxypiperidine-1-carboxylate A solution of tert-butyl (5-chloro-3-ethylpyrazolo[1,5-a]pyrimidin-7-yl)((5-(trifluoromethyl)imidazo[1,2-a]pyridin-2-yl)methyl)carbamate (159 mg, 0.321 mmol), (3R,4R)-tert-butyl 4-(aminomethyl)-3-hydroxypiperidine-1-carboxylate (91.0 mg, 0.395 mmol) and $^t$BuBrettPhos Pd G3 (28 mg, 32.9 μmol) in THE (3.2 mL) was degassed with $N_2$ for 10 min. LiHMDS (1M in THF) (395 μl, 395 μmol) was added in one portion under bubbling $N_2$. Bubbling was ceased and the reaction mixture heated to 60° C. for 2 h. The reaction was quenched with water (20 mL) and extracted with EtOAc (3×20 mL). The combined organic layers were dried over $Na_2SO_4$ and concentrated under reduced pressure. Purification by column chromatography (12 g cartridge, 0-5% MeOH/DCM) followed by further purification on RP Flash C18 (24 g cartridge, 30-100% MeCN/10 mM ammonium bicarbonate) gave the title compound (153 mg, 0.18 mmol, 55% yield, 80% purity) as a yellow solid.

UPLC/MS (Method 5): m/z 689 (M+H)+, $R_T$ 1.77 min.

Step 4: (3R,4R)-4-(((3-ethyl-7-(((5-(trifluoromethyl)imidazo[1,2-a]pyridin-2-yl)methyl)amino)pyrazolo[1,5-a]pyrimidin-5-yl)amino)methyl)piperidin-3-ol Hydrogen chloride (4 M in dioxane) (900 μL, 3.6 mmol) was added to a suspension of tert-butyl (3R,4R)-4-(((7-((tert-butoxycarbonyl)((5-(trifluoromethyl)imidazo[1,2-a]pyridin-2-yl)methyl)amino)-3-ethylpyrazolo[1,5-a]pyrimidin-5-yl)amino)methyl)-3-hydroxypiperidine-1-carboxylate (155 mg, 0.180 mmol) in dioxane (2.3 mL). The reaction mixture was stirred at 40° C. RT for 2 h and concentrated in vacuo. The residue was loaded onto a column of SCX. The column was washed with MeOH (80 mL) and the product eluted with 0.7 M $NH_3$ in MeOH (100 mL). The ammoniacal methanol solution was concentrated in vacuo to give the title compound (89 mg, 0.18 mmol, 99% yield, 98% purity).

UPLC/MS (Method 3): m/z 489 (M+H)+, $R_T$ 0.70 min.

$^1$H NMR (400 MHz, DMSO-$d_6$) δ 7.95-7.87 (m, 2H), 7.68-7.60 (m, 2H), 7.57 (d, J=7.1 Hz, 1H), 7.41 (dd, J=7.1, 9.2 Hz, 1H), 6.77 (t, J=5.9 Hz, 1H), 5.41-5.36 (m, 1H), 5.35 (s, 1H), 4.62 (d, J=6.3 Hz, 2H), 3.60-3.47 (m, 1H), 3.23-3.14 (m, 1H), 3.06-2.96 (m, 1H), 2.90 (dd, J=4.5, 11.4 Hz, 1H), 2.82-2.73 (m, 1H), 2.48-2.44 (m, 2H), 2.36-2.26 (m, 1H), 2.15 (dd, J=9.9, 11.6 Hz, 1H), 1.60-1.50 (m, 1H), 1.42-1.27 (m, 1H), 1.17 (t, J=7.5 Hz, 3H), 1.16-1.09 (m, 1H). 1H under water.

Synthesis 35

(3R,4R)-4-(((3-cyclopropyl-7-(((7-(trifluoromethyl)imidazo[1,2-a]pyridin-2-yl)methyl)amino)pyrazolo[1,5-a]pyrimidin-5-yl)amino)methyl)piperidin-3-ol (H-APPAMP-035)

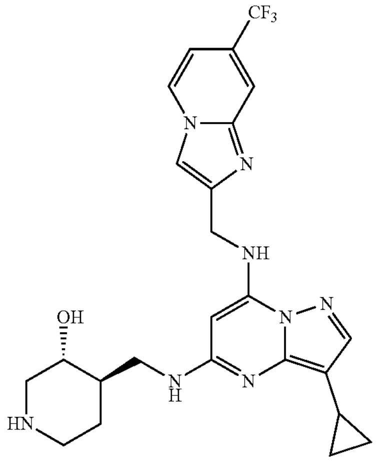 [SMILES: O[C@H]1CNCC[C@@H]1CNc1cc(NCc2cn3ccc(C(F)(F)F)cc3n2)n2ncc(C3CC3)c2n1]

Step 1: 5-chloro-3-cyclopropyl-N-((7-(trifluoromethyl)imidazo[1,2-a]pyridin-2-yl)methyl)pyrazolo[1,5-a]pyrimidin-7-amine (7-(Trifluoromethyl)imidazo[1,2-a]pyridin-2-yl)methanamine (90 mg, 0.30 mmol) was added to a solution of 5,7-dichloro-3-cyclopropylpyrazolo[1,5-a]pyrimidine (95 mg, 0.42 mmol) and DIPEA (0.69 mL, 3.9 mmol) in EtOH (2.0 mL). The reaction mixture was heated at 50° C. for 2 h. The reaction mixture was concentrated in vacuo. Purification by column chromatography (12 g cartridge, 10% MeOH/DCM) gave the title compound (79 mg, 0.16 mmol, 54% yield, 84% purity) as a beige solid.

UPLC/MS (Method 5): m/z 407 (M+H)+, $R_T$ 1.51 min.

Step 2: tert-butyl (5-chloro-3-cyclopropylpyrazolo[1,5-a]pyrimidin-7-yl)((7-(trifluoromethyl)imidazo[1,2-a]pyridin-2-yl)methyl)carbamate BOC-Anhydride (35 mg, 0.16 mmol) was added to a solution of 5-chloro-3-cyclopropyl-N-((7-(trifluoromethyl)imidazo[1,2-a]pyridin-2-yl)methyl)pyrazolo[1,5-a]pyrimidin-7-amine (55 mg, 0.14 mmol) and DMAP (3.3 mg, 27 μmol) in THE (2.0 mL). The reaction mixture was stirred at RT for 16 h. The reaction mixture was concentrated under reduced pressure. Purification by column chromatography (12 g cartridge, 0-100% EtOAc/isohexane) gave the title compound (57 mg, 0.10 mmol, 74% yield, 89% purity) as a yellow gum.

UPLC/MS (Method 5): m/z 507 (M+H)+, $R_T$ 1.84 min.

Step 3: tert-butyl (3R,4R)-4-(((7-((tert-butoxycarbonyl)((7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((7-(trifluoromethyl)imidazo[1,2-a]pyridin-2-yl)methyl)carbamate pyridin-2-yl)methyl)carbamate (55 mg, 0.11 mmol), (3R,4R)-tert-butyl 4-(aminomethyl)-3-hydroxypiperidine-1-carboxylate (27 mg, 0.12 mmol) and $^{t}$BuBrettPhos Pd G3 (9.3 mg, 11.3 μmol) in THE (1.0 mL) was degassed with $N_2$ for 10 min. LiHMDS (1M in THF) (0.14 mL, 0.14 mmol) was added in one portion under bubbling $N_2$. Bubbling was ceased and the reaction mixture heated to 60° C. for 3 h. The reaction mixture was concentrated under reduced pressure. Purification by column chromatography (4 g cartridge, 0-10% MeOH/DCM) gave the title compound (53 mg, 73 μmol, 67% yield, 96% purity) as a white solid.

UPLC/MS (Method 5): m/z 701 (M+H)+, $R_T$ 1.72 min.

Step 4: (3R,4R)-4-(((3-cyclopropyl-7-(((7-(trifluoromethyl)imidazo[1,2-a]pyridin-2-yl)methyl)amino)pyrazolo[1,5-a]pyrimidin-5-yl)amino)methyl)piperidin-3-ol TFA (0.20 mL) was added to a solution of tert-butyl (3R,4R)-4-(((7-((tert-butoxycarbonyl)((7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (50 mg, 71 μmol) in DCM (0.80 mL). The reaction mixture was stirred at RT for 18 h and concentrated in vacuo. The residue was loaded onto a column of SCX. The column was washed with MeOH (20 mL) and the product eluted with 0.7 M $NH_3$ in MeOH (20 mL). The ammoniacal methanol solution was concentrated in vacuo to the title compound (23 mg, 44 μmol, 61% yield, 95% purity) as an off-white solid after trituration from $Et_2O$ and drying overnight at 40° C. under vacuum.

UPLC/MS (Method 5): m/z 501 (M+H)+, $R_T$ 1.21 min.

$^1$H NMR (400 MHz, DMSO-$d_6$) δ 8.70 (d, J=7.1 Hz, 1H), 7.99 (s, 2H), 7.73 (t, J=6.2 Hz, 1H), 7.52 (s, 1H), 7.15 (dd, J=7.2, 1.9 Hz, 1H), 6.73-6.68 (m, 1H), 5.33-5.27 (m, 1H), 5.25 (s, 1H), 4.62 (d, J=6.1 Hz, 2H), 3.56-3.44 (m, 1H), 3.25-3.15 (m, 1H), 3.08-2.97 (m, 1H), 2.90 (dd, J=11.7, 4.5 Hz, 1H), 2.82-2.73 (m, 1H), 2 2.34-2.25 (m, 1H), 2.21-2.09 (m, 1H), 1.78-1.66 (m, 1H), 1.59-1.51 (m, 1H), 1.37-1.27 (m, 1H), 1.19-1.05 (m, 1H), 0.79-0.74 (m, 2H), 0.70-0.60 (m, 2H). 1H under water.

Intermediate Synthesis A13

(7-(trifluoromethyl)imidazo[1,2-a]pyridin-2-yl)methanamine

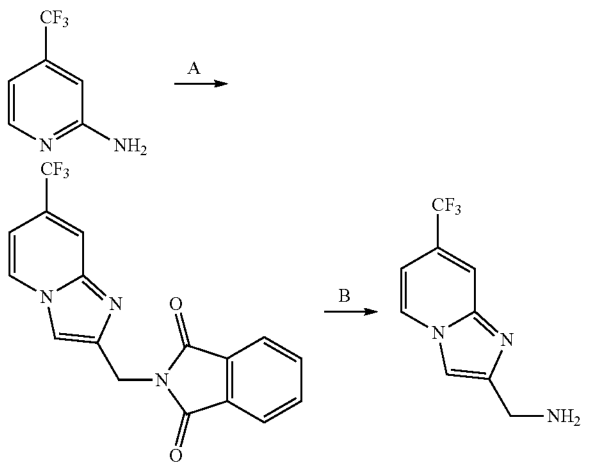

Step A: 2-((7-(trifluoromethyl)imidazo[1,2-a]pyridin-2-yl)methyl)isoindoline-1,3-dione 4-(Trifluoromethyl)pyridin-2-amine (200 mg, 1.23 mmol), 2-(3-bromo-2-oxopropyl)isoindoline-1,3-dione (366 mg, 1.23 mmol) and sodium bicarbonate (104 mg, 1.23 mmol) in Ethanol (0.60 mL) and heated to 80° C. under microwave irradiation for 1 h. The mixture was then concentrated under reduced pressure. Purification by column chromatography (24 g cartridge, 0-10% MeOH/DCM) gave the title compound (348 mg, 0.80 mmol, 65% yield, 79% purity) as a yellow solid.

UPLC/MS (Method 5): m/z 364 (M+H)+, $R_T$ 1.02 min.

Step B: (7-(trifluoromethyl)imidazo[1,2-a]pyridin-2-yl)methanamine

Hydrazine (35 wt % in water) (250 μL, 2.79 mmol) was added to a suspension of 2-(((7-(trifluoromethyl)imidazo[1,2-a]pyridin-2-yl)methyl)carbamoyl)benzoic acid (348 mg, 105 μmol) in EtOH (4.0 mL). The suspension was stirred at 65° C. for 3 h. The mixture was concentrated in vacuo then diluted with aq. 1 M HCl (20 mL), the white solid was filtered off and washed with aq. 1 M HCl (2×20 mL) then the combined aq. layers were basified with solid $NaHCO_3$ and extracted with EtOAc (3×20 mL). The combined organic layers were dried over $MgSO_4$, filtered then concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to the title compound (90 mg, 0.31 mmol, 38% yield, 73% purity) as a brown oil.

UPLC/MS (Method 5): m/z 216 (M+H)+, $R_T$ 0.82 min

Synthesis 36

(3R,4R)-4-(((3-cyclopropyl-7-(((5,6-difluoro-1-methyl-1H-benzo[d]imidazol-2-yl)methyl)amino)pyrazolo[1,5-a]pyrimidin-5-yl)amino)methyl)piperidin-3-ol (H-APPAMP-036)

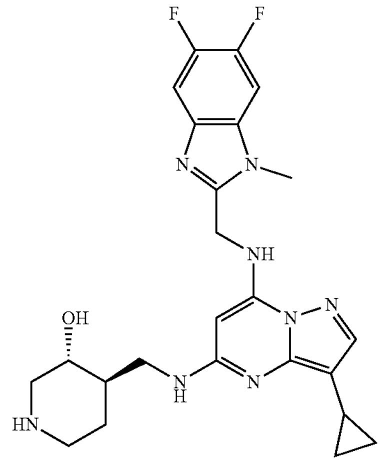 [SMILES: Cn1c(CNc2cc(NC[C@H]3CCNC[C@@H]3O)nc3c(C4CC4)cnn23)nc2cc(F)c(F)cc21]

Step 1: 5-chloro-3-cyclopropyl-N-((5,6-difluoro-1-methyl-1H-benzo[d]imidazol-2-yl)methyl)pyrazolo[1,5-a]pyrimidin-7-amine (5,6-Difluoro-1-methyl-1H-benzo[d]imidazol-2-yl)methanamine (155 mg, 786 μmol) was added to a solution 5,7-dichloro-3-cyclopropylpyrazolo[1,5-a]pyrimidine (163 mg, 715 μmol) and DIPEA (0.12 mL, 715 μmol) in EtOH (10 mL). The reaction mixture was heated at 90° C. for 3 h. The reaction mixture was concentrated in vacuo and the residue was triturated in MeCN to give the title compound (170 mg, 0.43 mmol, 61% yield, 99% purity) as a white solid.

UPLC/MS (Method 3): m/z 389 (M+H)+, $R_T$ 1.52 min

Step 2: tert-butyl (5-chloro-3-cyclopropylpyrazolo[1,5-a]pyrimidin-7-yl)((5,6-difluoro-1-methyl-1H-benzo[d]imidazol-2-yl)methyl)carbamate BOC-Anhydride (180 mg, 823 μmol) was added to a solution of 5-chloro-3-cyclopropyl-N-((5,6-difluoro-1-methyl-1H-benzo[d]imidazol-2-yl)methyl)pyrazolo[1,5-a]pyrimidin-7-amine (160 mg, 412 μmol) and DMAP (10.1 mg, 82.3 μmol) in DMF (5.0 mL). The reaction mixture was stirred at 60° C. for 2 h. The reaction mixture was partitioned between EtOAc (20 mL) and water (20 mL). The aq layer was extracted with EtOAc (2×20 mL) and the combined organic layers were washed with brine (2×20 mL), dried over $Na_2SO_4$ and concentrated under reduced pressure. Purification by column chromatography (24 g cartridge, 0-10% (0.7 M $NH_3$/MeOH)/DCM) gave the title compound (190 mg, 0.25 mmol, 60% yield, 64% purity) as a yellow solid.

UPLC/MS (Method 5): m/z 488 (M+H)+, $R_T$ 1.83 min.

Step 3: tert-butyl (3R,4R)-4-(((7-((tert-butoxycarbonyl)((5,6-difluoro-1-methyl-1H-benzo[d]imidazol-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5,6-difluoro-1-methyl-1H-benzo[d]imidazol-2-yl)methyl)carbamate (190 mg, 249 μmol), (3R,4R)-tert-butyl 4-(aminomethyl)-3-hydroxypiperidine-1-carboxylate (68.7 mg, 298 μmol) and $^t$BuBrettPhos Pd G3 (21.3 mg, 24.9 μmol) in THE (2.0 mL) was degassed with $N_2$ for 10 min. LiHMDS (1M in THF) (323 μL, 323 μmol) was added in one portion under bubbling $N_2$. Bubbling was ceased and the reaction mixture heated to 60° C. for 18 h. The reaction mixture was concentrated under reduced pressure. Purification by column chromatography (12 g cartridge, 0-10% MeOH/DCM) gave the title compound (103 mg, 0.13 mmol, 50% yield, 83% purity) as a yellow solid.

UPLC/MS (Method 5): m/z 684 (M+H)+, $R_T$ 1.73 min.

Step 4: (3R,4R)-4-(((3-cyclopropyl-7-(((5,6-difluoro-1-methyl-1H-benzo[d]imidazol-2-yl)methyl)amino)pyrazolo[1,5-a]pyrimidin-5-yl)amino)methyl)piperidin-3-ol Hydrogen chloride (4 M in dioxane) (626 μL, 2.50 mmol) was added to a solution of tert-butyl (3R,4R)-4-(((7-((tert-butoxycarbonyl)((5,6-difluoro-1-methyl-1H-benzo[d]imidazol-2-yl)methyl)amino)-3-cyclopropylpyrazolo[1,5-a]pyrimidin-5-yl)amino)methyl)-3-hydroxypiperidine-1-carboxylate (103 mg, 125 μmol) in dioxane (2.0 mL). The reaction mixture was stirred at 35° C. for 4 h and concentrated in vacuo. The residue was loaded onto a column of SCX. The column was washed with MeOH (40 mL) and the product eluted with 0.7 M $NH_3$ in MeOH (10 mL). The ammoniacal methanol solution was concentrated in vacuo to give the title compound (28 mg, 54 μmol, 43% yield, 93% purity).

UPLC/MS (Method 3): m/z 484 (M+H)+, $R_T$ 0.72 min.

$^1$H NMR (400 MHz, DMSO-$d_6$) δ 7.79-7.70 (m, 2H), 7.66 (dd, J=11.1, 7.4 Hz, 1H), 7.53 (s, 1H), 6.84-6.73 (m, 1H), 5.38 (s, 1H), 5.28-5.20 (m, 1H), 4.73 (d, J=5.5 Hz, 2H), 3.83 (s, 3H), 3.55-3.44 (m, 1H), 3.27-3.16 (m, 1H), 3.08-3.00 (m, 1H), 2.95-2.86 (m, 1H), 2.81-2.74 (m, 1H), 2.33-2.23 (m, 1H), 2.19-2.09 (m, 1H), 2.03-1.83 (m, 1H), 1.77-1.66 (m, 1H), 1.61-1.53 (m, 1H), 1.20-1.10 (m, 1H), 0.79-0.73 (m, 2H), 0.67-0.63 (m, 2H). 1H under water.

Intermediate Synthesis A14

(5,6-difluoro-1-methyl-1H-benzo[d]imidazol-2-yl)methanamine

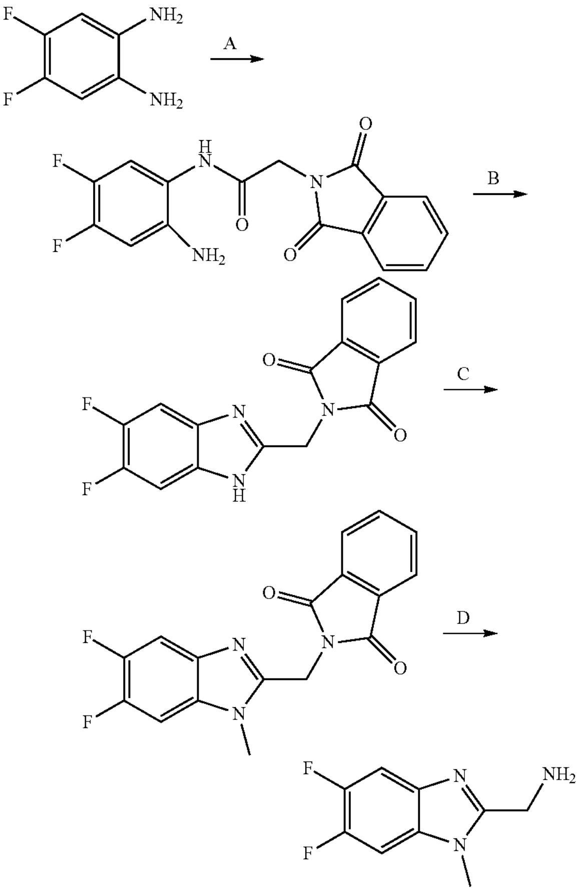

Step A: N-(2-amino-4,5-difluorophenyl)-2-(1,3-dioxoisoindolin-2-yl)acetamide

1-[Bis(dimethylamino)methylene]-1H-1,2,3-triazolo[4,5-b]pyridinium 3-oxid hexafluorophosphate (HATU) (3.96 g, 10.4 mmol) was added to a solution of 4,5-difluorobenzene-1,2-diamine (2.00 g, 13.9 mmol), 2-(1,3-dioxoisoindolin-2-yl)acetic acid (1.42 g, 6.94 mmol) and DIPEA (3.6 mL, 20.8 mmol) in THE (25 mL). The reaction mixture was stirred at 50° C. for 72 h. At RT, EtOAc (25 mL) and water (10 mL) were added. The resultant solid was collected by filtration then triturated in MeCN to give the title compound (1.81 g, 5.4 mmol, 78% yield, 99% purity) as an off white solid.

UPLC/MS (Method 5): m/z 332 (M+H)+, $R_T$ 1.46 min.

Step B: 2-((5,6-difluoro-1H-benzo[d]imidazol-2-yl) methyl)isoindoline-1,3-dione

A solution of N-(2-amino-4,5-difluorophenyl)-2-(1,3-dioxoisoindolin-2-yl)acetamide (1.81 g, 5.46 mmol) in AcOH (15 mL) was stirred at 60° C. for 3 h. The reaction mixture was concentrated to dryness and co-evaporated twice with toluene (2×10 mL) then triturated with MeCN to give the title compound (1.56 g, 4.9 mmol, 90% yield, 99% purity) as an off white solid.

UPLC/MS (Method 5): m/z 314 (M+H)+, $R_T$ 1.47 min.

Step C: 2-((5,6-difluoro-1-methyl-1H-benzo[d]imidazol-2-yl)methyl)isoindoline-1,3-dione 2-((5,6-Difluoro-1H-benzo[d]imidazol-2-yl)methyl) isoindoline-1,3-dione (600 mg, 1.92 mmol) was added to a solution of iodomethane (179 μL, 2.87 mmol) and K2CO3 (529 mg, 3.83 mmol) in DMF (15 mL) at 0° C. The reaction mixture was stirred at 0° C. for 5 min then at RT overnight before the resultant solid was collected by filtration, washing with water (2.0 mL) then MeCN (2.0 mL) to give the title compound (610 mg, 1.7 mmol, 88% yield, 90% purity) as a grey solid.

UPLC/MS (Method 5): m/z 328 (M+H)+, $R_T$ 1.21 min.

Step D: (5,6-difluoro-1-methyl-1H-benzo[d]imidazol-2-yl)methanamine

Hydrazine hydrate (259 μL, 5.33 mmol) was added to a solution of 2-((5,6-difluoro-1-methyl-1H-benzo[d]imidazol-2-yl)methyl)isoindoline-1,3-dione (600 mg, 1.52 mmol) in EtOH (10 mL). The suspension was stirred at 65° C. overnight. At RT, the suspension was filtered and the solid washed with IPA (5.0 mL). The filtrate was concentrated under reduced pressure. The residue was loaded onto a column of SCX. The column was washed with MeOH (40 mL) and the product eluted with 0.7 M $NH_3$ in MeOH (10 mL). The ammoniacal methanol solution was concentrated in vacuo to give the title compound (300 mg, 1.40 mmol, 89% yield, 89% purity) as a white solid.

UPLC/MS (Method 5): m/z 199 (M+H)+, $R_T$ 0.78 min.

Synthesis 37

(3R,4R)-4-(((3-cyclopropyl-7-(((5-(trifluoromethyl) imidazo[1,2-a]pyridin-2-yl)methyl)amino)pyrazolo [1,5-a]pyrimidin-5-yl)amino)methyl)piperidin-3-ol (H-APPAMP-037)

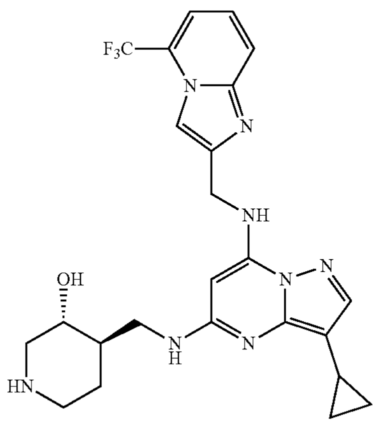 [SMILES: O[C@H]1CNCC[C@@H]1CNc1cc(NCc2cn3c(C(F)(F)F)cccc3n2)n2ncc(C3CC3)c2n1]

Step 1: 5-chloro-3-cyclopropyl-N-((5-(trifluoromethyl)imidazo[1,2-a]pyridin-2-yl)methyl)pyrazolo[1,5-a]pyrimidin-7-amine (5-(Trifluoromethyl)imidazo[1,2-a]pyridin-2-yl)methanamine (106 mg, 0.443 mmol) was added to a solution of 5,7-dichloro-3-cyclopropylpyrazolo[1,5-a]pyrimidine (86 mg, 0.377 mmol) and DIPEA (390 μL, 2.24 mmol) in EtOH (1.6 mL). The reaction mixture was heated at 65° C. for 2 h then was concentrated in vacuo.

Purification by column chromatography (12 g cartridge, 0-10% MeOH/DCM) gave the title compound (185 mg, 0.37 mmol, 99% yield, 82% purity) as a beige solid.

UPLC/MS (Method 3): m/z 407 (M+H)+, $R_T$ 1.54 min.

Step 2: tert-butyl (5-chloro-3-cyclopropylpyrazolo [1,5-a]pyrimidin-7-yl)((5-(trifluoromethyl)imidazo [1,2-a]pyridin-2-yl)methyl)carbamate BOC-Anhydride (97.8 mg, 0.448 mmol) was added to a solution of 5-chloro-3-cyclopropyl-N-((5-(trifluoromethyl) imidazo[1,2-a]pyridin-2-yl)methyl)pyrazolo[1,5-a]pyrimidin-7-amine (185 mg, 0.373 mmol) and DMAP (9.1 mg, 74.6 μmol) in THE (7.5 mL). The reaction mixture was stirred at 65° C. for 2 h. The reaction mixture was concentrated under reduced pressure and the residue partitioned between DCM (20 mL) and water (30 mL). The aq layer was extracted with DCM (2×30 mL) and the combined organic layers were washed with brine (30 mL), dried over $Na_2SO_4$ and concentrated under reduced pressure. Purification by column chromatography (12 g cartridge, 0-10% MeOH/DCM) gave the title compound (167 mg, 0.32 mmol, 87% yield, 98% purity) as an orange oil.

UPLC/MS (Method 3): m/z 507 (M+H)+, $R_T$ 1.87 min.

Step 3: tert-butyl (3R,4R)-4-(((7-((tert-butoxycarbonyl)((5-(trifluoromethyl)imidazo[1,2-a]pyridin-2-yl) methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo [1,5-a]pyrimidin-7-yl)((5-(trifluoromethyl)imidazo[1,2-a]

pyridin-2-yl)methyl)carbamate (167 mg, 0.329 mmol), (3R,4R)-tert-butyl 4-(aminomethyl)-3-hydroxypiperidine-1-carboxylate (91 mg, 0.395 mmol) and $^{t}$BuBrettPhos Pd G3 (28 mg, 0.0329 mmol) in THE (3.2 mL) was degassed with $N_2$ for 10 min. LiHMDS (1 M in THF) (395 μL, 0.395 mmol) was added in one portion under bubbling $N_2$. Bubbling was ceased and the reaction mixture heated to 60° C. for 2 h. The reaction was quenched with water (10 mL) and extracted with EtOAc (3×10 mL). The combined organic layers were dried over $Na_2SO_4$ and concentrated under reduced pressure. Purification by column chromatography (80 g cartridge, 0-10% MeOH/DCM) gave the title compound (177 mg, 0.16 mmol, 49% yield, 64% purity) as an orange solid.

UPLC/MS (Method 3): m/z 701 (M+H)+, $R_T$ 1.76 min.

Step 4: (3R,4R)-4-(((3-cyclopropyl-7-(((5-(trifluoromethyl)imidazo[1,2-a]pyridin-2-yl)methyl)amino) pyrazolo[1,5-a]pyrimidin-5-yl)amino)methyl)piperidin-3-ol Hydrogen chloride (4 M in dioxane) (0.80 mL, 3.20 mmol) was added to a suspension of tert-butyl (3R,4R)-4-(((7-((tert-butoxycarbonyl)((5-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (175 mg, 160 μmol) in dioxane (2.2 mL). The reaction mixture was stirred at 40° C. for 3 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give a yellow solid. Further purification by prepHPLC (20-100% MeCN/0.1% $NH_3$ in water) to give the title compound (41 mg, 79 μmol, 50% yield, 98% purity) as a white solid.

UPLC/MS (Method 5): m/z 501 (M+H)+, $R_T$ 1.20 min.

$^1$H NMR (400 MHz, DMSO-$d_6$) δ 7.91 (d, J=9.3 Hz, 2H), 7.61 (t, J=6.2 Hz, 1H), 7.57 (d, J=7.1 Hz, 1H), 7.51 (s, 1H), 7.44-7.35 (m, 1H), 6.74 (t, J=6.1 Hz, 1H), 5.35 (s, 1H), 5.26 (s, 1H), 4.61 (d, J=6.0 Hz, 2H), 3.50 (s, 1H), 3.27-3.18 (m, 1H), 3.10-2.95 (m, 1H), 2.90 (dd, J=11.6, 4.5 Hz, 1H), 2.82-2.74 (m, 2H), 2.36-2.23 (m, 1H), 2.20-2.10 (m, 1H), 1.77-1.65 (m, 1H), 1.60-1.51 (m, 1H), 1.40-1.24 (m, 1H), 1.19-1.07 (m, 1H), 0.80-0.71 (m, 2H), 0.71-0.53 (m, 2H).

Intermediate Synthesis A15

(5-(trifluoromethyl)imidazo[1,2-a]pyridin-2-yl) methanamine

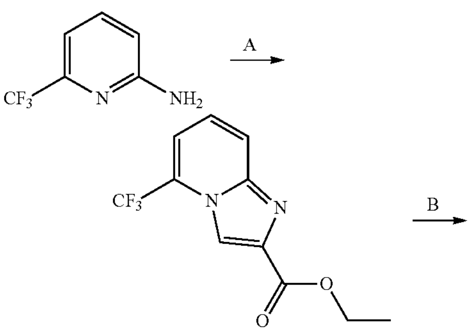

-continued

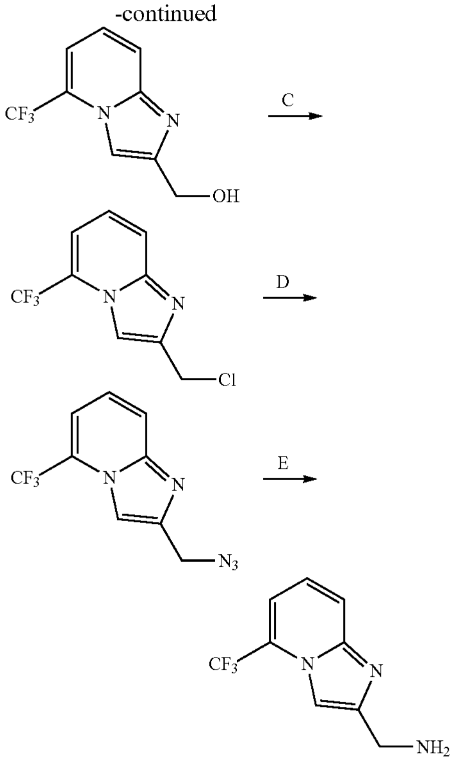

Step A: ethyl 5-(trifluoromethyl)imidazo[1,2-a]pyridine-2-carboxylate 6-(Trifluoromethyl)pyridin-2-amine (1.00 g, 6.17 mmol) and ethyl 3-bromo-2-oxopropanoate (1.6 mL, 12.3 mmol) in IPA (5.8 mL) and water (5.8 mL) were heated at 80° C. under microwave irradiation for 1 h. The reaction mixture was concentrated under vacuum. Purification by column (80 g cartridge, 0-5% (0.7 M $NH_3$/MeOH)/DCM) gave the title compound (1.24 g, 4.32 mmol, 67% yield, 90% purity) as a brown oil.

UPLC/MS (Method 5): m/z 259 (M+H)+, $R_T$ 1.13 min.

Step B: (5-(trifluoromethyl)imidazo[1,2-a]pyridin-2-yl)methanol

Diisobutylaluminum hydride (1M in hexane) (11 mL, 11.0 mmol) was added to a solution of ethyl 5-(trifluoromethyl)imidazo[1,2-a]pyridine-2-carboxylate (860 mg, 2.99 mmol) in THE (9.0 mL) at −40° C. The reaction mixture was allowed to warm to RT overnight. At 0° C., MeOH (5.0 mL), followed by water (5.0 mL) and aq. 1 M HCl (5.0 mL) were added. The mixture was stirred vigorously for 30 min and extracted with ethyl acetate (3×15 mL). The combined organic layers were washed with brine (15 mL), dried over $MgSO_4$, and concentrated in vacuo to give the title compound (453 mg, 2.0 mmol, 57% yield, 95% purity as a brown oil.

UPLC/MS (Method 5): m/z 217 (M+H)+, $R_T$ 0.82 min.

Step C: 2-(chloromethyl)-5-(trifluoromethyl)imidazo[1,2-a]pyridine, HCl

Thionyl chloride (363 μL, 4.98 mmol) was added dropwise to a solution of (5-(trifluoromethyl)imidazo[1,2-a]pyridin-2-yl)methanol (453 mg, 1.99 mmol) in DCM (8.5 mL) at 0° C.

The mixture was stirred at 0° C. for 2 h then at RT for 1 h. Concentration to dryness under reduced pressure gave the title compound (494 mg, 1.7 mmol, 87% yield, 95% purity) as a brown oil.

UPLC/MS (Method 3): m/z 271 (M+H)+, $R_T$ 1.14 min.

Step D: 2-(azidomethyl)-5-(trifluoromethyl)imidazo[1,2-a]pyridine

A solution of 2-(chloromethyl)-5-(trifluoromethyl)imidazo[1,2-a]pyridine, HCl (494 mg, 1.73 mmol) and DIPEA (1.9 mL, 11 mmol) in DMF (8.0 mL) was treated with sodium azide (176 mg, 2.71 mmol). The mixture was heated to 60° C. and stirred for 2.5 h. The mixture was cooled to RT, diluted with water (10 mL) and brine (10 mL). Extraction with TBME (3×20 mL) then EtOAc (3×20 mL). The combined organic layers were washed with brine (4×20 mL), dried over $Na_2SO_4$ and concentrated under reduced pressure to give the title compound (383 mg, 1.5 mmol, 89% yield, 97% purity) as a brown oil.

UPLC/MS (Method 5): m/z 242 (M+H)+, $R_T$ 1.12 min.

Step E: (5-(trifluoromethyl)imidazo[1,2-a]pyridin-2-yl)methanamine 2-(Azidomethyl)-5-(trifluoromethyl)imidazo[1,2-a]pyridine (383.5 mg, 1.54 mmol), triphenylphosphine (486 mg, 1.85 mmol) were dissolved in THE (8.0 mL) and Water (0.90 mL). The mixture was stirred at RT overnight before removal of the solvent in vacuo. The residue was loaded onto a column of SCX. The column was washed with MeOH (150 mL) and the product eluted with 0.7 M $NH_3$ in MeOH (100 mL). The ammoniacal methanol solution was concentrated in vacuo to give the title compound (336 mg, 1.4 mmol, 91% yield, 90% purity) as a brown oil.

UPLC/MS (Method 5): m/z 216 (M+H)+, $R_T$ 0.82 min.

Synthesis 38

(3R,4R)-4-(((7-(((6-cyclopropyl-8-(trifluoromethyl)imidazo[1,2-a]pyridin-2-yl)methyl)amino)-3-ethylpyrazolo[1,5-a]pyrimidin-5-yl)amino)methyl)piperidin-3-ol (H-APPAMP-038)

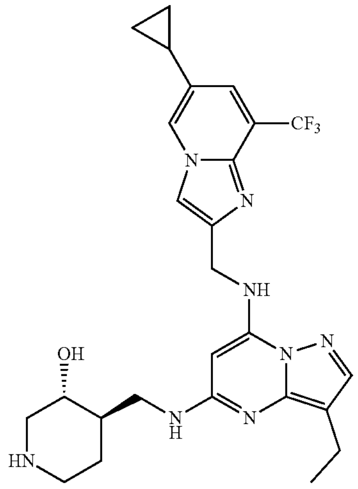 [SMILES: CCc1cnn2c(NCc3cn4cc(C5CC5)cc(C(F)(F)F)c4n3)cc(NC[C@H]3CCNC[C@@H]3O)nc12]

Step 1: 5-chloro-N-((6-cyclopropyl-8-(trifluoromethyl)imidazo[1,2-a]pyridin-2-yl)methyl)-3-ethylpyrazolo[1,5-a]pyrimidin-7-amine (6-Cyclopropyl-8-(trifluoromethyl)imidazo[1,2-a]pyridin-2-yl)methanamine (125 mg, 0.333 mmol) was added to a solution of 5,7-dichloro-3-ethylpyrazolo[1,5-a]pyrimidine (60.1 mg, 0.278 mmol) and DIPEA (291 μL, 1.67 mmol) in EtOH (1.1 mL). The reaction mixture was heated at 80° C. for 3 h then concentrated in vacuo. Purification by column chromatography (12 g cartridge, 0-10% MeOH/DCM) gave the title compound (103.6 mg, 0.23 mmol, 82% yield, 96% purity) as a pale beige solid.

UPLC/MS (Method 5): m/z 435 (M+H)+, $R_T$ 1.67 min

Step 2: tert-butyl (5-chloro-3-ethylpyrazolo[1,5-a]pyrimidin-7-yl)((6-cyclopropyl-8-(trifluoromethyl)imidazo[1,2-a]pyridin-2-yl)methyl)carbamate BOC-Anhydride (60.8 mg, 279 μmol) was added to a solution of 5-chloro-N-((6-cyclopropyl-8-(trifluoromethyl)imidazo[1,2-a]pyridin-2-yl)methyl)-3-ethylpyrazolo[1,5-a]pyrimidin-7-amine (103 mg, 232 μmol) and DMAP (5.6 mg, 46.4 μmol) in THE (4.6 mL). The reaction mixture was stirred at 65° C. for 2.5 h. The reaction mixture was concentrated under reduced pressure and the residue partitioned between DCM (20 mL) and water (30 mL). The aq. layer was extracted with DCM (2×30 mL) and the combined organic layers were washed with brine (30 mL), dried over $Na_2SO_4$ and concentrated under reduced pressure. Purification by column chromatography (12 g cartridge, 0-10% MeOH/DCM) gave the title compound (116 mg, 0.20 mmol, 88% yield, 94% purity) as an orange oil.

UPLC/MS (Method 3): m/z 535 (M+H)+, $R_T$ 2.01 min.

Step 3: tert-butyl (3R,4R)-4-(((7-((tert-butoxycarbonyl)((6-cyclopropyl-8-(trifluoromethyl)imidazo[1,2-a]pyridin-2-yl)methyl)amino)-3-ethylpyrazolo[1,5-a]pyrimidin-5-yl)amino)methyl)-3-hydroxypiperidine-1-carboxylate A solution of tert-butyl (5-chloro-3-ethylpyrazolo[1,5-a]pyrimidin-7-yl)((6-cyclopropyl-8-(trifluoromethyl)imidazo[1,2-a]pyridin-2-yl)methyl)carbamate (115 mg, 202 μmol), (3R,4R)-tert-butyl 4-(aminomethyl)-3-hydroxypiperidine-1-carboxylate (60.5 mg, 263 μmol) and $^t$BuBrettPhos Pd G3 ((25.9 mg, 30.3 μmol) in THE (2.0 mL) was degassed with $N_2$ for 10 min. LiHMDS (1 M in THF) (0.26 mL, 263 μmol) was added in one portion under bubbling $N_2$. Bubbling was ceased and the reaction mixture heated to 60° C. for 2 h. The reaction was quenched with water (50 mL) and extracted with EtOAc (3×30 mL). The combined organic layers were dried over $Na_2SO_4$ and concentrated under reduced pressure. Purification by column chromatography (12 g cartridge, 0-10% MeOH/DCM) gave the title compound (53 mg, 71 μmol, 35% yield, 98% purity) as a beige solid.

UPLC/MS (Method 5): m/z 729 (M+H)+, $R_T$ 1.84 min.

Step 4: (3R,4R)-4-(((7-(((6-cyclopropyl-8-(trifluoromethyl)imidazo[1,2-a]pyridin-2-yl)methyl)amino)-3-ethylpyrazolo[1,5-a]pyrimidin-5-yl)amino)methyl)piperidin-3-ol TFA (0.40 mL) was added to a solution of tert-butyl (3R,4R)-4-(((7-((tert-butoxycarbonyl)((6-cyclopropyl-8-(trifluoromethyl)imidazo[1,2-a]pyridin-2-yl)methyl)amino)-3-ethylpyrazolo[1,5-a]pyrimidin-5-yl)amino)

methyl)-3-hydroxypiperidine-1-carboxylate (53 mg, 73 μmol) in DCM (1.6 mL). The reaction mixture was stirred at RT overnight then concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (30 mg, 54 μmol, 75% yield, 96% purity) as a beige solid after trituration from $Et_2O$ and drying overnight at 40° C. under vacuum.

UPLC/MS (Method 5): m/z 529 (M+H)+, $R_T$ 1.34 min.

$^1$H NMR (400 MHz, DMSO-$d_6$) δ 8.55 (s, 1H), 7.78 (s, 1H), 7.76 (t, J=6.4 Hz, 1H), 7.66 (s, 1H), 7.46 (s, 1H), 6.74 (t, J=5.7 Hz, 1H), 5.53-5.40 (m, 1H), 5.24 (s, 1H), 4.59 (d, J=6.0 Hz, 2H), 3.60-3.48 (m, 1H), 3.22-3.12 (m, 1H), 3.10-2.97 (m, 1H), 2.92 (dd, J=4.5, 11.7 Hz, 1H), 2.84-2.76 (m, 1H), 2.48-2.44 (m, 2H), 2.39-2.28 (m, 1H), 2.24-2.13 (m, 1H), 2.04-1.96 (m, 1H), 1.62-1.50 (m, 1H), 1.38-1.28 (m, 1H), 1.18 (t, J=7.5 Hz, 3H), 1.25-1.12 (m, 1H), 0.98-0.89 (m, 2H), 0.78-0.67 (m, 2H). 1H under water.

Synthesis 39

(3R,4R)-4-(((3-cyclopropyl-7-(((5-methyl-7-(trifluoromethyl)imidazo[1,2-a]pyridin-2-yl)methyl)amino)pyrazolo[1,5-a]pyrimidin-5-yl)amino)methyl)piperidin-3-ol (H-APPAMP-039)

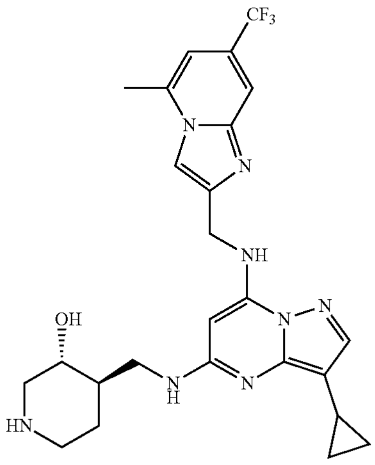

Step 1: 5-chloro-3-cyclopropyl-N-((5-methyl-7-(trifluoromethyl)imidazo[1,2-a]pyridin-2-yl)methyl)pyrazolo[1,5-a]pyrimidin-7-amine (5-Methyl-7-(trifluoromethyl)imidazo[1,2-a]pyridin-2-yl)methanamine (60 mg, 0.26 mmol) was added to a solution of 5,7-dichloro-3-cyclopropylpyrazolo[1,5-a]pyrimidine (50 mg, 0.22 mmol) and DIPEA (0.19 mL 1.1 mmol) in EtOH (1.0 mL). The reaction mixture was heated at 65° C. for 1 h. The reaction mixture was concentrated in vacuo. Purification by column chromatography (12 g cartridge, 0-10% (0.7 M $NH_3$/MeOH)/DCM) gave the title compound (90 mg, 0.20 mmol, 93% yield, 95% purity) as a beige solid.

UPLC/MS (Method 5): m/z 421 (M+H)+, $R_T$ 1.59 min.

Step 2: tert-butyl (5-chloro-3-cyclopropylpyrazolo[1,5-a]pyrimidin-7-yl)((5-methyl-7-(trifluoromethyl)imidazo[1,2-a]pyridin-2-yl)methyl)carbamate BOC-Anhydride (70 mg, 0.32 mmol) was added to a solution of 5-chloro-3-cyclopropyl-N-((5-methyl-7-(trifluoromethyl)imidazo[1,2-a]pyridin-2-yl)methyl)pyrazolo[1,5-a]pyrimidin-7-amine (90 mg, 0.21 mmol) and DMAP (1.4 mg, 43 μmol) in THE (2.0 mL). The reaction mixture was stirred at RT for 16 h then concentrated under reduced pressure. Purification by column chromatography (12 g cartridge, 0-10% (0.7 M $NH_3$/MeOH)/DCM) gave the title compound (105 mg, 0.19 mmol, 90% yield, 95% purity) as a yellow foam.

$^1$H NMR in DMSO-d6 was consistent with product structure.

Step 3: tert-butyl (3R,4R)-4-(((7-((tert-butoxycarbonyl)((5-methyl-7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5-methyl-7-(trifluoromethyl)imidazo[1,2-a]pyridin-2-yl)methyl)carbamate (100 mg, 192 μmol), (3R,4R)-tert-butyl 4-(aminomethyl)-3-hydroxypiperidine-1-carboxylate (53 mg, 230 μmol) and $^t$BuBrettPhos Pd G3 (24.6 mg, 28.8 μmol) in THE (1.0 mL) was degassed with $N_2$ for 10 min. LiHMDS (1M in THF) (230 μL, 230 μmol) was added in one portion under bubbling $N_2$. Bubbling was ceased and the reaction mixture heated to 60° C. for 2 h. The reaction mixture was concentrated under reduced pressure.

Purification by column chromatography (4 g cartridge, 0-10% (0.7 M $NH_3$/MeOH)/DCM) then further purification column chromatography (4 g cartridge, 0-100% EtOAc/isohexane then 0-5% (0.7 M $NH_3$/MeOH)/DCM) gave the title compound (140 mg, 0.18 mmol, 92% yield, 90% purity) as a brown solid.

UPLC/MS (Method 5): m/z 715 (M+H)+, $R_T$ 1.79 min.

Step 4: (3R,4R)-4-(((3-cyclopropyl-7-(((5-methyl-7-(trifluoromethyl)imidazo[1,2-a]pyridin-2-yl)methyl)amino)pyrazolo[1,5-a]pyrimidin-5-yl)amino)methyl)piperidin-3-ol TFA (0.2 mL) was added to a solution of tert-butyl (3R,4R)-4-(((7-((tert-butoxycarbonyl)((5-methyl-7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (77 mg, 0.11 mmol) in DCM (0.80 mL). The reaction mixture was stirred at RT for 16 h and concentrated in vacuo. The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (30 mg, 57 μmol, 52% yield, 97% purity) as an off-white solid after trituration from $Et_2O$ and drying overnight at 40° C. under vacuum.

UPLC/MS (Method 5): m/z 515 (M+H)+, $R_T$ 1.27 min.

$^1$H NMR (400 MHz, DMSO-$d_6$) δ 7.90 (s, 1H), 7.88 (s, 1H), 7.64 (t, J=6.0 Hz, 1H), 7.51 (s, 1H), 7.10 (s, 1H), 6.71 (t, J=5.8 Hz, 1H), 5.31-5.27 (m, 2H), 4.63 (d, J=5.9 Hz, 2H), 3.56-3.45 (m, 1H), 3.25-3.16 (m, 1H), 3.08-2.97 (m, 1H), 2.90 (dd, J=11.5, 4.5 Hz, 1H), 2.81-2.73 (m, 1H), 2.65 (s, 3H), 2.34-2.24 (m, 1H), 2.15 (dd, J=11.6, 9.9 Hz, 1H), 1.77-1.67 (m, 1H), 1.59-1.50 (m, 1H), 1.38-1.27 (m, 1H), 1.20-1.11 (m, 1H), 0.80-0.72 (m, 2H), 0.70-0.59 (m, 2H). 1H under water.

Intermediate Synthesis A16

(5-methyl-7-(trifluoromethyl)imidazo[1,2-a]pyridin-2-yl)methanamine

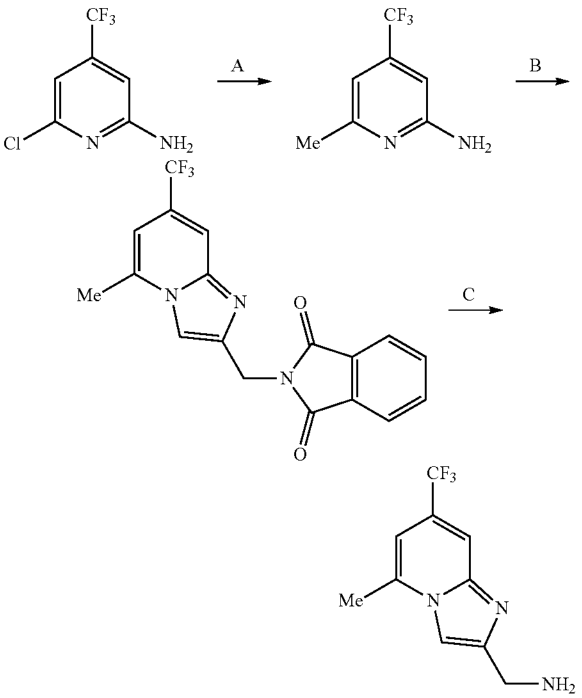

Step A: 6-methyl-4-(trifluoromethyl)pyridin-2-amine

A solution of Cs2CO3 (2.50 g, 7.63 mmol) in water (3.0 mL) was added to a solution of 6-chloro-4-(trifluoromethyl) pyridin-2-amine (500 mg, 2.54 mmol), 2,4,6-trimethyl-1,3,5,2,4,6-trioxatriborinane (1.4 mL, 10.2 mmol) and PdCl2 (dppf)-CH2Cl2adduct (208 mg, 254 μmol) in 1,4-Dioxane (7.0 mL). $N_2$ was bubbled through the reaction mixture for 10 min then the reaction mixture was heated at 100° C. for 1 h. The mixture was concentrated in vacuo. Purification by column (24 g cartridge, 0-10% (0.7 M $NH_3$/MeOH)/DCM) gave the title compound (352 mg, 1.8 mmol, 69%, 88% Purity) as a brown oil.

UPLC/MS (Method 5): m/z 177 (M+H)+, $R_T$ 1.06 min.

Step B: 2-((5-methyl-7-(trifluoromethyl)imidazo[1,2-a]pyridin-2-yl)methyl)isoindoline-1,3-dione 6-Methyl-4-(trifluoromethyl)pyridin-2-amine (238 mg, 1.28 mmol) and 2-(3-bromo-2-oxopropyl)isoindoline-1,3-dione (471 mg, 1.67 mmol) in Ethanol (6.4 mL) were heated under microwave irradiation for 2 h at 80° C. The mixture was cooled to 0° C., MeOH (3.0 mL) was added and the solid was collected by filtration, rinsing with MeOH (2×1.0 mL) to give the title compound (301 mg, 0.82 mmol, 64% yield, 98% purity) as a white solid.

$^1$H NMR in DMSO-d6 was consistent with product structure.

Step C: (5-methyl-7-(trifluoromethyl)imidazo[1,2-a]pyridin-2-yl)methanamine

Hydrazine hydrate (78 μL, 1.61 mmol) was added to a suspension of 2-((5-methyl-7-(trifluoromethyl)imidazo[1,2-a]pyridin-2-yl)methyl)isoindoline-1,3-dione (381 mg, 1.01 mmol) in EtOH (4.0 mL). The suspension was stirred at 65° C. for 1 h. At RT, the suspension was filtered and the solid washed with IPA (5.0 mL). The filtrate was concentrated under reduced pressure. The residue was loaded onto a column of SCX. The column was washed with MeOH (10 mL) and the product eluted with 0.7 M $NH_3$ in MeOH (10 mL). The ammoniacal methanol solution was concentrated in vacuo to give the title compound (128 mg, 0.53 mmol, 53% yield, 95% purity) as a white solid.

UPLC/MS (Method 5): m/z 230 (M+H)+, $R_T$ 0.93 min.

Synthesis 40

(3R,4R)-4-(((3-cyclopropyl-7-(((6-methyl-7-(trifluoromethyl)imidazo[1,2-a]pyridin-2-yl)methyl)amino) pyrazolo[1,5-a]pyrimidin-5-yl)amino)methyl)piperidin-3-ol (H-APPAMP-040)

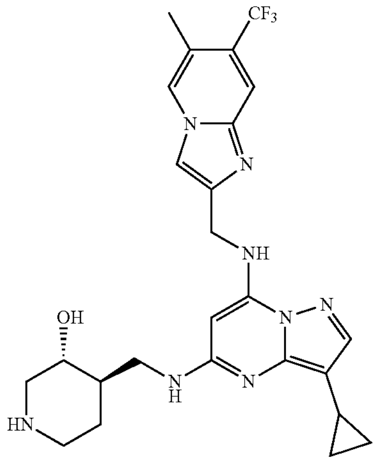 [SMILES: Cc1cn2cc(CNc3cc(NC[C@H]4CCNC[C@@H]4O)nc4c(C5CC5)cnn34)nc2cc1C(F)(F)F]

Step 1: 5-chloro-3-cyclopropyl-N-((6-methyl-7-(trifluoromethyl)imidazo[1,2-a]pyridin-2-yl)methyl) pyrazolo[1,5-a]pyrimidin-7-amine (6-Methyl-7-(trifluoromethyl)imidazo[1,2-a]pyridin-2-yl)methanamine (80 mg, 0.35 mmol) was added to a solution of 5,7-dichloro-3-cyclopropylpyrazolo[1,5-a]pyrimidine (72 mg, 0.31 mmol) and DIPEA (0.36 mL, 2.1 mmol) in EtOH (10 mL). The reaction mixture was heated at 50° C. for 5 h. The reaction mixture was concentrated in vacuo to give the title compound (65 mg, 0.15 mmol, 43% yield, 98% purity) as a yellow solid.

UPLC/MS (Method 5): m/z 421 (M+H)+, $R_T$ 1.61 min

Step 2: tert-butyl (5-chloro-3-cyclopropylpyrazolo[1,5-a]pyrimidin-7-yl)((6-methyl-7-(trifluoromethyl)imidazo[1,2-a]pyridin-2-yl)methyl)carbamate BOC-Anhydride (51 mg, 0.23 mmol) was added to a solution of 5-chloro-3-cyclopropyl-N-((6-methyl-7-(trifluoromethyl)imidazo[1,2-a]pyridin-2-yl)methyl)pyrazolo[1,5-a]pyrimidin-7-amine (65 mg, 0.15 mmol) and DMAP (1.9 mg, 15.0 μmol) in THE (5.0 mL). The reaction mixture was stirred at 35° C. for 2 h. The reaction mixture was concentrated in vacuo. Purification by column chromatography (4 g cartridge, 0-10% MeOH/DCM) gave the title compound (70 mg, 0.13 mmol, 83% yield, 95% purity) as a beige solid.

UPLC/MS (Method 5): m/z 521 (M+H)+, $R_T$ 1.92 min.

Step 3: tert-butyl (3R,4R)-4-(((7-((tert-butoxycarbonyl)((6-methyl-7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((6-methyl-7-(trifluoromethyl)imidazo[1,2-a]pyridin-2-yl)methyl)carbamate (70 mg, 0.13 mmol), (3R,4R)-tert-butyl 4-(aminomethyl)-3-hydroxypiperidine-1-carboxylate (37 mg, 0.16 mmol) and $^{t}$BuBrettPhos Pd G3 (11 mg, 13 μmol) in THE (2.0 mL) was degassed with $N_2$ for 10 min. LiHMDS (1M in THF) (0.17 mL, 0.17 mmol) was added in one portion under bubbling $N_2$. Bubbling was ceased and the reaction mixture heated to 60° C. for 18 h. The reaction mixture was concentrated in vacuo. Purification by column chromatography (4 g cartridge, 0-10% (0.7 M $NH_3$/MeOH)/DCM) gave the title compound (65 mg, 86 μmol, 64% yield, 95% purity) as a white solid.

UPLC/MS (Method 5): m/z 715 (M+H)+, $R_T$ 1.79 min.

Step 4: (3R,4R)-4-(((3-cyclopropyl-7-(((6-methyl-7-(trifluoromethyl)imidazo[1,2-a]pyridin-2-yl)methyl)amino)pyrazolo[1,5-a]pyrimidin-5-yl)amino)methyl)piperidin-3-ol TFA (0.20 mL) was added to a solution of tert-butyl (3R,4R)-4-(((7-((tert-butoxycarbonyl)((6-methyl-7-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (46 mg, 64 μmol) in DCM (0.80 mL). The reaction mixture was stirred at RT for 16 h and concentrated in vacuo. The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (24 mg, 46 μmol, 71% yield, 98% purity) as a yellow solid after trituration from $Et_2O$ and drying overnight at 40° C. under vacuum.

UPLC/MS (Method 5): m/z 515 (M+H)+, $R_T$ 1.28 min.

$^1$H NMR (400 MHz, DMSO-$d_6$) δ 8.54 (s, 1H), 7.93 (s, 1H), 7.88 (s, 1H), 7.70 (t, J=6.2 Hz, 1H), 7.52 (s, 1H), 6.71 (t, J=6.4 Hz, 1H), 5.31 (s, 1H), 5.24 (s, 1H), 4.59 (d, J=6.0 Hz, 2H), 3.56-3.44 (m, 1H), 3.24-3.15 (m, 1H), 3.08-2.97 (m, 1H), 2.90 (dd, J=11.6, 4.5 Hz, 1H), 2.81-2.73 (m, 1H), 2.36-2.23 (m, 4H), 2.15 (dd, J=11.6, 9.9 Hz, 1H), 1.76-1.65 (m, 1H), 1.59-1.50 (m, 1H), 1.37-1.26 (m, 1H), 1.19-1.11 (m, 1H), 0.80-0.73 (m, 2H), 0.70-0.59 (m, 2H). 1H under water.

Intermediate Synthesis A17

(5-methyl-6-(trifluoromethyl)-3aH-indol-2-yl)methanamine

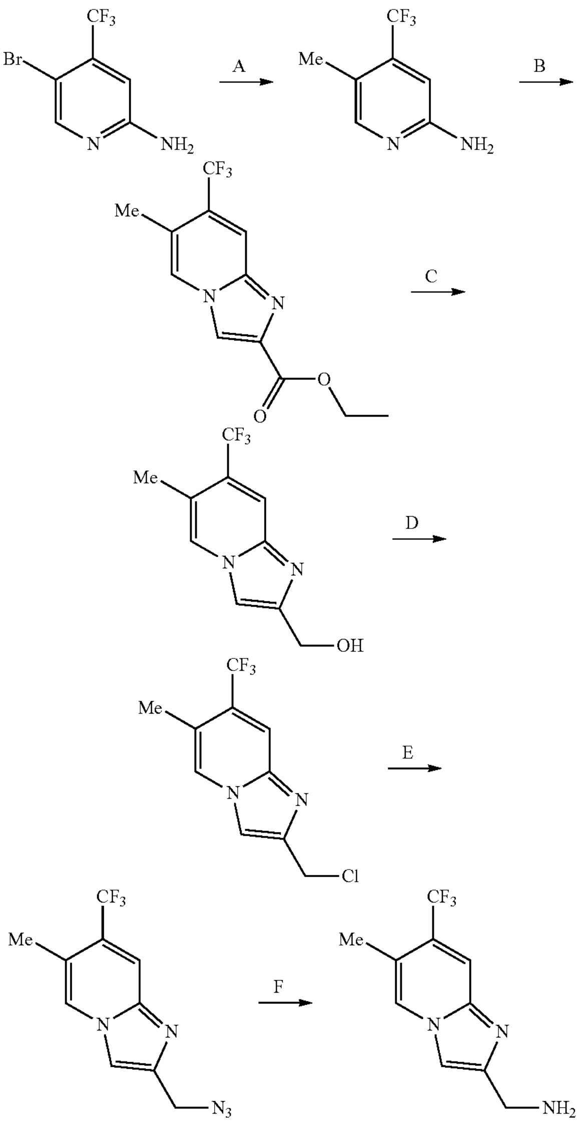

Step A: 5-methyl-4-(trifluoromethyl)pyridin-2-amine

A solution of tripotassium phosphate (2.64 g, 12.45 mmol) in water (3.0 mL) was added to a solution of 5-bromo-4-(trifluoromethyl)pyridin-2-amine (1.00 g, 4.15 mmol), 2,4,6-trimethyl-1,3,5,2,4,6-trioxatriborinane (1.03 g, 8.30 mmol) and (2-Dicyclohexylphosphino-2',6'-dimethoxybiphenyl)[2-(2'-amino-1,1'-biphenyl)]palladium(II) methanesulfonate (291 mg, 332 μmol) in dioxane (30 mL). $N_2$ was bubbled through the reaction mixture for 10 min then the reaction mixture was heated at 60° C. for 4 h. The mixture was concentrated in vacuo. Purification by column (80 g cartridge, 0-10% (0.7 M $NH_3$/MeOH)/DCM) gave the title compound (800 mg, 3.9 mmol, 93% yield, 85% purity) as a brown oil.

UPLC/MS (Method 5): m/z 177 (M+H)+, $R_T$ 1.05 min.

Step B: ethyl 6-methyl-7-(trifluoromethyl)imidazo[1,2-a]pyridine-2-carboxylate

5-Methyl-4-(trifluoromethyl)pyridin-2-amine (800 mg, 4.54 mmol), ethyl 3-bromo-2-oxopropanoate (1.1 mL, 9.08 mmol) and sodium bicarbonate (382 mg, 4.54 mmol) in ethanol (20 mL) were heated at 80° C. overnight. The reaction was concentrated under vacuum. Purification by column (40 g cartridge, 0-10% MeOH/DCM) gave the title compound (535 mg, 1.7 mmol, 37% yield, 85% purity) as a yellow gum.

UPLC/MS (Method 5): m/z 273 (M+H)+, $R_T$ 1.22 min.

Step C: (6-methyl-7-(trifluoromethyl)imidazo[1,2-a]pyridin-2-yl)methanol

Diisobutylaluminum hydride (1M in hexane) (4.0 mL, 4.03 mmol) was added to a solution of ethyl 6-methyl-7-(trifluoromethyl)imidazo[1,2-a]pyridine-2-carboxylate (530 mg, 1.75 mmol) in THE (10 mL) at −40° C. The reaction mixture was allowed to warm to 0° C. over a period of 2 h and stirred at this temperature for 2 h. At 0° C., MeOH (10 mL), followed by water (10 mL) and aq. 1M HCl (10 mL) were added. The mixture was stirred vigorously for 20 min and extracted with ethyl acetate (3×35 mL). The combined organic layers were washed with brine (20 mL), passed through a phase separator, and concentrated in vacuo. Purification by column (24 g cartridge, 0-10% MeOH/DCM) gave the title compound (200 mg, 0.83 mmol, 48% yield, 96% purity) as a white solid.

UPLC/MS (Method 5): m/z 231 (M+H)+, $R_T$ 0.94 min.

Step D: 2-(chloromethyl)-6-methyl-7-(trifluoromethyl)imidazo[1,2-a]pyridine

Thionyl chloride (317 µL, 4.34 mmol) was added dropwise to a solution of (6-methyl-7-(trifluoromethyl)imidazo[1,2-a]pyridin-2-yl)methanol (200 mg, 869 µmol) in DCE (5.0 mL) at RT. The mixture was stirred at 45° C. for 2 h then concentrated to dryness under reduced pressure to give the title compound (215 mg, 0.80 mmol, 92% yield, 92% purity) as a yellow oil.

UPLC/MS (Method 5): m/z 249 (M+H)+, $R_T$ 1.24 min.

Step E: 2-(azidomethyl)-6-methyl-7-(trifluoromethyl)imidazo[1,2-a]pyridine

A solution of 2-(chloromethyl)-6-methyl-7-(trifluoromethyl)imidazo[1,2-a]pyridine (215 mg, 865 µmol) and DIPEA (452 µL, 2.59 mmol) in DMF (5.0 mL) was treated with sodium azide (84 mg, 1.30 mmol). The mixture was heated to 60° C. and stirred for 6 h. The mixture was cooled to RT, diluted with water (100 mL). Extraction with TBME (3×25 mL). The combined organic layers were dried over $MgSO_4$ and concentrated under reduced pressure. Purification by chromatography (12 g cartridge, 0-100% TBME/isohexane) gave the title compound (200 mg, 0.76 mmol, 88% yield, 97% purity) as a brown oil.

UPLC/MS (Method 5): m/z 256 (M+H)+, $R_T$ 1.26 min.

Step F: (5-methyl-6-(trifluoromethyl)-3aH-indol-2-yl)methanamine 2-(Azidomethyl)-6-methyl-7-(trifluoromethyl)imidazo[1,2-a]pyridine (200 mg, 784 µmol), triphenylphosphine (247 mg, 940 µmol) were dissolved in THE (4.5 mL) and water (0.50 mL). The mixture was stirred at RT for 20 h before removal of the solvent in vacuo. The residue was loaded onto a column of SCX. The column was washed with MeOH (150 mL) and the product eluted with 0.7 M $NH_3$ in MeOH (100 mL). The ammoniacal methanol solution was concentrated in vacuo to give the title compound (170 mg, 0.73 mmol, 93% yield, 98% purity) as a white solid.

UPLC/MS (Method 5): m/z 230 (M+H)+, $R_T$ 0.94 min.

Synthesis 41

(3R,4R)-4-(((3-cyclopropyl-7-(((5-isopropoxyimidazo[1,2-a]pyridin-2-yl)methyl)amino)pyrazolo[1,5-a]pyrimidin-5-yl)amino)methyl)piperidin-3-ol (H-APPAMP-041)

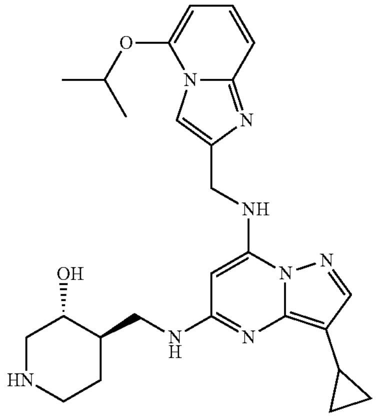 [SMILES: CC(C)Oc1cccc2nc(CNc3cc(NC[C@H]4CCNC[C@@H]4O)nc4c(C5CC5)cnn34)cn12]

Step 1: 5-chloro-3-cyclopropyl-N-((5-isopropoxyimidazo[1,2-a]pyridin-2-yl)methyl)pyrazolo[1,5-a]pyrimidin-7-amine (5-Isopropoxyimidazo[1,2-a]pyridin-2-yl)methanamine (92.0 mg, 448 µmol) was added to a solution of 5,7-dichloro-3-cyclopropylpyrazolo[1,5-a]pyrimidine (102 mg, 448 µmol) and DIPEA (547 µL, 3.14 mmol) in EtOH (4.0 mL). The reaction mixture was heated at 50° C. for 72 h. The reaction mixture was concentrated in vacuo. Purification by column chromatography (12 g cartridge, 0-100% EtOAc/isohexane) gave the title compound (115 mg, 0.28 mmol, 63% yield, 97% purity) as a white solid.

$^1$H NMR consistent with product structure.

Step 2: tert-butyl (5-chloro-3-cyclopropylpyrazolo[1,5-a]pyrimidin-7-yl)((5-isopropoxyimidazo[1,2-a]pyridin-2-yl)methyl)carbamate BOC-Anhydride (74 mg, 337 µmol) was added to a solution of 5-chloro-3-cyclopropyl-N-((5-isopropoxyimidazo[1,2-a]pyridin-2-yl)methyl)pyrazolo[1,5-a]pyrimidin-7-amine (115 mg, 281 µmol) and DMAP (6.9 mg, 56.2 µmol) in THE (3.0 mL). The reaction mixture was stirred at RT for 16 h. The reaction mixture was concentrated under reduced pressure. Purification by column chromatography (12 g cartridge, 0-100% EtOAc/isohexane) gave the title compound (139 mg, 0.25 mmol, 88% yield, 88% purity) as a green oil.

UPLC/MS (Method 5): m/z 497 (M+H)+, $R_T$ 1.85 min.

Step 3: tert-butyl (3R,4R)-4-(((7-((tert-butoxycarbonyl)((5-isopropoxyimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((5-isopropoxyimidazo[1,2-a]pyridin-2-yl)methyl)carbamate (115 mg, 231 μmol), (3R,4R)-tert-butyl 4-(aminomethyl)-3-hydroxypiperidine-1-carboxylate (64 mg, 278 μmol) and $^t$BuBrettPhos Pd G3 (19.8 mg, 23.1 μmol) in THE (2.5 mL) was degassed with $N_2$ for 10 min. LiHMDS (1M in THF) (301 μL, 1 molar, 301 μmol) was added in one portion under bubbling $N_2$. Bubbling was ceased and the reaction mixture heated to 60° C. for 3 h. The reaction mixture was concentrated under reduced pressure. Purification by column chromatography (12 g cartridge, 0-10% MeOH/DCM) followed by further purification on RP Flash C18 (24 g cartridge, 20-80% MeCN/10 mM ammonium bicarbonate) gave the title compound (120 mg, 0.16 mmol, 68% yield, 90% purity) as a white solid.

UPLC/MS (Method 5): m/z 692 (M+H)+, $R_T$ 1.75 min.

Step 4: (3R,4R)-4-(((3-cyclopropyl-7-(((5-isopropoxyimidazo[1,2-a]pyridin-2-yl)methyl)amino)pyrazolo[1,5-a]pyrimidin-5-yl)amino)methyl)piperidin-3-ol TFA (0.50 mL) was added to a solution of tert-butyl tert-butyl (3R,4R)-4-(((7-((tert-butoxycarbonyl)((5-isopropoxyimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (120 mg, 174 μmol) in DCM (2.0 mL). The reaction mixture was stirred at RT for 16 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (38 mg, 77 μmol, 45% yield, 100% purity) as an off-white solid after trituration from MeCN and drying overnight at 40° C. under vacuum.

UPLC/MS (Method 5): m/z 492 (M+H)+, $R_T$ 1.23 min.

$^1$H NMR (400 MHz, DMSO-$d_6$) δ 7.59 (t, J=6.1 Hz, 1H), 7.53 (s, 1H), 7.51 (s, 1H), 7.26 (dd, J=9.0, 7.5 Hz, 1H), 7.11 (d, J=8.9 Hz, 1H), 6.75 (t, J=6.0 Hz, 1H), 6.37 (d, J=7.5 Hz, 1H), 5.33-5.27 (m, 2H), 4.92 (hept, J=6.1 Hz, 1H), 4.53 (d, J=6.0 Hz, 2H), 3.56-3.46 (m, 1H), 3.25-3.18 (m, 1H), 3.08-2.97 (m, 1H), 2.91 (dd, J=11.6, 4.5 Hz, 1H), 2.81-2.73 (m, 1H), 2.36-2.23 (m, 1H), 2.16 (dd, J=11.5, 9.9 Hz, 1H), 1.76-1.66 (m, 1H), 1.60-1.52 (m, 1H), 1.39 (d, J=6.0 Hz, 6H), 1.36-1.27 (m, 1H), 1.21-1.06 (m, 1H), 0.80-0.71 (m, 2H), 0.71-0.59 (m, 2H). 1H under water.

Intermediate Synthesis A18

(5-isopropoxyimidazo[1,2-a]pyridin-2-yl)methanamine

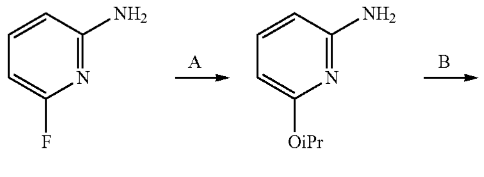

-continued

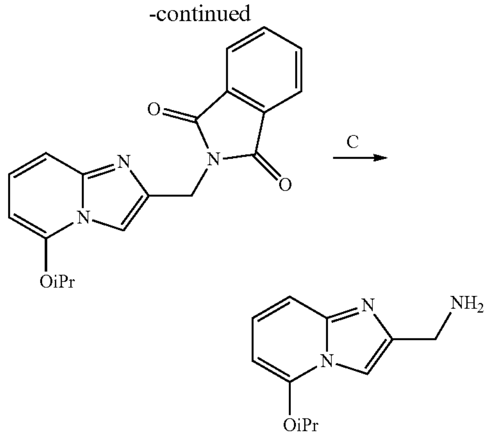

Step A: 6-isopropoxypyridin-2-amine

6-Fluoropyridin-2-amine (500 mg, 4.46 mmol), sodium hydroxide (446 mg, 11.1 mmol) and IPA (3.4 mL, 44 mmol) were heated under microwave irradiation for 5 min at 150° C. The mixture was diluted with water (100 mL) and extracted with DCM (3×30 mL). The combined organic layers were dried over $MgSO_4$, filtered and concentrated in vacuo to give the title compound (510 mg, 3.2 mmol, 71% yield, 95% purity) as a colourless oil.

UPLC/MS (Method 5): m/z 153 (M+H)+, $R_T$ 0.80 min.

Step B: 2-((5-isopropoxyimidazo[1,2-a]pyridin-2-yl)methyl)isoindoline-1,3-dione

6-Isopropoxypyridin-2-amine (300 mg, 1.97 mmol), 2-(3-bromo-2-oxopropyl)isoindoline-1,3-dione (556 mg, 1.97 mmol), sodium bicarbonate (166 mg, 1.97 mmol) in Ethanol (10 mL) were heated under microwave irradiation for 1 h at 80° C.

The mixture was diluted with water (100 mL) and the aq. solution was extracted with DCM (3×30 mL). The combined organic layers were dried over $MgSO_4$, filtered and concentrated under reduced pressure. Purification by column chromatography (24 g cartridge, 0-10% MeOH/DCM) gave the title compound (150 mg, 0.42 mmol, 21% yield, 94% purity) as an off-white solid.

UPLC/MS (Method 5): m/z 336 (M+H)+, $R_T$ 1.30 min.

Step C: (5-isopropoxyimidazo[1,2-a]pyridin-2-yl)methanamine 2-((5-Isopropoxyimidazo[1,2-a]pyridin-2-yl)methyl)isoindoline-1,3-dione (190 mg, 567 μmol), hydrazine (35 wt % in water) (178 μL, 1.98 mmol) and Ethanol (4.0 mL) were stirred for 2 h at 65° C. The reaction was diluted with aq. 2N NaOH (15 mL), water (15 mL) and DCM (15 mL). The layers were separated and the aq. layer was extracted with DCM (2×15 mL) then concentrated in vacuo to afford the title compound (94 mg, 0.41 mmol, 73% yield, 90% purity) as a yellow solid.

$^1$H NMR in DMSO-d6 was consistent with product structure.

Synthesis 42

(3R,4R)-4-(((3-cyclopropyl-7-(((6-cyclopropyl-8-(trifluoromethyl)imidazo[1,2-a]pyridin-2-yl)methyl)amino)pyrazolo[1,5-a]pyrimidin-5-yl)amino)methyl)piperidin-3-ol (H-APPAMP-042)

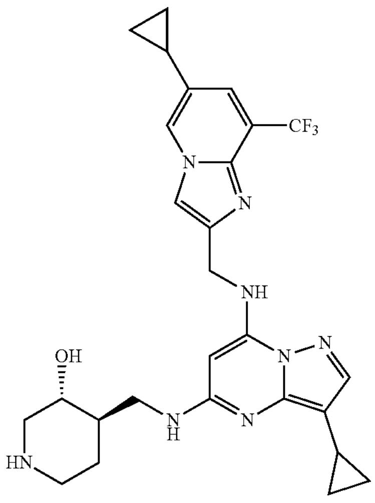 [SMILES: O[C@H]1CNCC[C@@H]1CNc1cc(NCc2cn3cc(C4CC4)cc(C(F)(F)F)c3n2)n2ncc(C3CC3)c2n1]

Step 1: 5-chloro-3-cyclopropyl-N-((6-cyclopropyl-8-(trifluoromethyl)imidazo[1,2-a]pyridin-2-yl)methyl)pyrazolo[1,5-a]pyrimidin-7-amine (6-Cyclopropyl-8-(trifluoromethyl)imidazo[1,2-a]pyridin-2-yl)methanamine (127 mg, 479 μmol) was added to a solution of 5,7-dichloro-3-cyclopropylpyrazolo[1,5-a]pyrimidine (91.0 mg, 399 μmol) and DIPEA (417 μl, 2.39 mmol) in EtOH (1.6 mL). The reaction mixture was heated at 60° C. overnight. The reaction mixture was concentrated in vacuo. Purification by column chromatography (12 g cartridge, 0-10% MeOH/DCM) gave the title compound (170 mg, 0.37 mmol, 92% yield, 97% purity) as an off-white solid.

UPLC/MS (Method 5): m/z 447 (M+H)+, $R_T$ 1.63 min.

Step 2: tert-butyl (5-chloro-3-cyclopropylpyrazolo[1,5-a]pyrimidin-7-yl)((6-cyclopropyl-8-(trifluoromethyl)imidazo[1,2-a]pyridin-2-yl)methyl)carbamate BOC-Anhydride (124 mg, 568 μmol) was added to a solution of 5-chloro-3-cyclopropyl-N-((6-cyclopropyl-8-(trifluoromethyl)imidazo[1,2-a]pyridin-2-yl)methyl)pyrazolo[1,5-a]pyrimidin-7-amine (170 mg, 369 μmol) and DMAP (9.3 mg, 75.9 μmol) in THE (7.5 mL). The reaction mixture was stirred at 65° C. for 1 h.

The reaction mixture was concentrated under reduced pressure and the residue partitioned between DCM (15 mL) and water (30 mL). The aq layer was extracted with DCM (2×30 mL) and the combined organic layers were washed with brine (30 mL), filtered through a phase separator and concentrated under reduced pressure. Purification by column chromatography (12 g cartridge, 0-10% MeOH/DCM) gave the title compound (193 mg, 0.33 mmol, 90% yield, 94% purity) as a yellow solid.

UPLC/MS (Method 5): m/z 547(M+H)+, $R_T$ 1.98 min.

Step 3: tert-butyl (3R,4R)-4-(((7-((tert-butoxycarbonyl)((6-cyclopropyl-8-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((6-cyclopropyl-8-(trifluoromethyl)imidazo[1,2-a]pyridin-2-yl)methyl)carbamate (192 mg, 330 μmol), (3R,4R)-tert-butyl 4-(aminomethyl)-3-hydroxypiperidine-1-carboxylate (91 mg, 396 μmol) and $^t$BuBrettPhos Pd G3 (28.2 mg, 33.0 μmol) in THE (3.3 mL) was degassed with $N_2$ for 10 min. LiHMDS (1M in THF) (396 μL, 396 μmol) was added in one portion under bubbling $N_2$. Bubbling was ceased and the reaction mixture heated to 60° C. for 1 h. The reaction was quenched with water (50 mL) and extracted with EtOAc (3×30 mL). The combined organic layers were dried over $Na_2SO_4$ and concentrated under reduced pressure. Purification by column chromatography (12 g cartridge, 0-100% EtOAc/isohexane) gave a solid which was further purified on RP Flash C18 (24 g cartridge, 30-100% MeCN/10 mM ammonium bicarbonate) to give the title compound (136 mg, 0.18 mmol, 54% yield, 97% purity) as a yellow solid.

UPLC/MS (Method 5): m/z 741 (M+H)+, $R_T$ 1.84 min.

Step 4: (3R,4R)-4-(((3-cyclopropyl-7-(((6-cyclopropyl-8-(trifluoromethyl)imidazo[1,2-a]pyridin-2-yl)methyl)amino)pyrazolo[1,5-a]pyrimidin-5-yl)amino)methyl)piperidin-3-ol Hydrogen chloride (4 M in dioxane) (884 μL, 3.54 mmol) was added to a suspension of tert-butyl (3R,4R)-4-(((7-((tert-butoxycarbonyl)((6-cyclopropyl-8-(trifluoromethyl)imidazo[1,2-a]pyridin-2-yl)methyl)amino)-3-cyclopropylpyrazolo[1,5-a]pyrimidin-5-yl)amino)methyl)-3-hydroxypiperidine-1-carboxylate (135 mg, 177 μmol) in dioxane (2.2 mL). The reaction mixture was stirred at 35° C. for 1 h and concentrated in vacuo. The residue was loaded onto a column of SCX. The column was washed with MeOH (30 mL) and the product eluted with 0.7 M $NH_3$ in MeOH (30 mL). The ammoniacal methanol solution was concentrated in vacuo to give the title compound (65 mg, 0.12 mmol, 67% yield, 98% purity) as a white solid after trituration from $Et_2O$ and drying overnight at 40° C. under vacuum.

UPLC/MS (Method 5): m/z 541 (M+H)+, $R_T$ 1.32 min.

$^1$H NMR (400 MHz, DMSO-$d_6$) δ 8.55 (s, 1H), 7.77 (s, 1H), 7.72 (t, J=6.3 Hz, 1H), 7.53 (s, 1H), 7.46 (s, 1H), 6.70 (t, J=6.1 Hz, 1H), 5.32-5.26 (m, 1H), 5.25 (s, 1H), 4.59 (d, J=6.2 Hz, 2H), 3.56-3.46 (m, 1H), 3.25-3.15 (m, 1H), 3.08-2.98 (m, 1H), 2.90 (dd, J=4.5, 11.7 Hz, 1H), 2.82-2.73 (m, 1H), 2.35-2.28 (m, 1H), 2.21-2.09 (m, 1H), 2.06-1.95 (m, 1H), 1.76-1.68 (m, 1H), 1.59-1.50 (m, 1H), 1.37-1.26 (m, 1H), 1.21-1.04 (m, 1H), 0.99-0.90 (m, 2H), 0.80-0.69 (m, 4H), 0.71-0.58 (m, 2H). 1H under water.

Intermediate Synthesis A19

(6-cyclopropyl-8-(trifluoromethyl)imidazo[1,2-a]pyridin-2-yl)methanamine

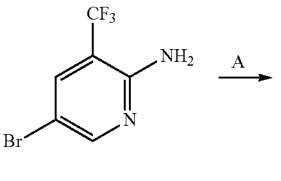

-continued

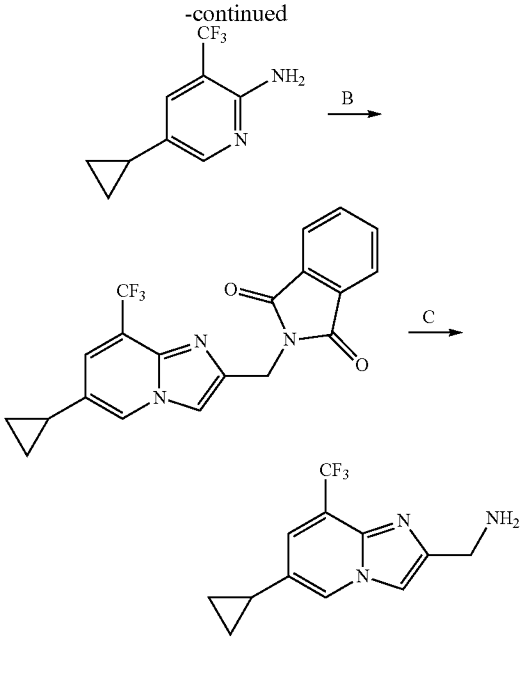

Step A: 5-cyclopropyl-3-(trifluoromethyl)pyridin-2-amine

A solution of tripotassium phosphate (3.96 g, 18.7 mmol) in water (3.8 mL) was added to a solution of 5-bromo-3-(trifluoromethyl)pyridin-2-amine (1.50 g, 6.22 mmol), cyclopropylboronic acid (1.60 g, 18.7 mmol), palladium(II) acetate (210 mg, 934 μmol) and tricyclohexylphosphane (524 mg, 1.87 mmol) in dioxane (15 mL). $N_2$ was bubbled through the reaction mixture for 10 min then the reaction mixture was heated at 100° C. and stirred overnight. The reaction mixture was diluted with EtOAc (10 mL), filtered through celite, rinsing with EtOAc (100 mL). The filtrate was concentrated under reduced pressure. The residue was loaded onto a column of SCX. The column was washed with MeOH (50 mL) and the product eluted with 0.7 M $NH_3$ in MeOH (50 mL). The ammoniacal methanol solution was concentrated in vacuo. Further purification by column (40 g cartridge, 0-10% (0.7 M $NH_3$/MeOH)/DCM) gave the title compound (1.015 g, 4.9 mmol, 78% yield, 97% purity) as an orange solid.

UPLC/MS (Method 3): m/z 203 (M+H)+, $R_T$ 0.94 min.

Step B: 2-((6-cyclopropyl-8-(trifluoromethyl)imidazo[1,2-a]pyridin-2-yl)methyl)isoindoline-1,3-dione 5-Cyclopropyl-3-(trifluoromethyl)pyridin-2-amine (204 mg, 1.01 mmol) and 2-(3-bromo-2-oxopropyl)isoindoline-1,3-dione (285 mg, 1.01 mmol) in Ethanol (5.0 mL) were heated at 80° C. under microwave irradiation for 2.5 hour. sodium bicarbonate (42 mg, 505 μmol) was added and the reaction mixture was heated at 80° C. under microwave irradiation for 1 h. 2-(3-bromo-2-oxopropyl)isoindoline-1,3-dione (85 mg, 303 μmol) was added and the reaction mixture was were heated at 80° C. under microwave irradiation for 1 h. The resultant solid was collected by filtration, rinsing with water (2×3.0 mL). The wet solid was dissolved in DCM (10 mL) and the mixture was filtered through a phase separator. The filtrate was concentrated to give the title compound (256 mg, 0.63 mmol, 63% yield, 95% purity) as a brown solid.

UPLC/MS (Method 5): m/z 386 (M+H)+, $R_T$ 1.47 min.

Step C: (6-cyclopropyl-8-(trifluoromethyl)imidazo[1,2-a]pyridin-2-yl)methanamine Hydrazine hydrate (50 μL, 1.01 mmol) was added to a suspension of 2-((6-cyclopropyl-8-(trifluoromethyl)imidazo[1,2-a]pyridin-2-yl)methyl)isoindoline-1,3-dione (255 mg, 0.629 mmol) in EtOH (3.0 mL). The suspension was stirred at 65° C. for 4 h. At RT, the suspension was filtered and the solid washed with IPA (5.0 mL). The filtrate was concentrated under reduced pressure. Trituration in cold (0° C.) $Et_2O$ (5.0 mL) gave the title compound (126 mg, 0.33 mmol, 53% yield, 68% purity) as a yellow solid.

UPLC/MS (Method 5): m/z 256 (M+H)+, $R_T$ 1.01 min.

Synthesis 43

(3R,4R)-4-(((7-(((5,7-dimethylimidazo[1,2-a]pyrimidin-2-yl)methyl)amino)-3-isopropylpyrazolo[1.5-a]pyrimidin-5-yl)amino)methyl)piperidin-3-ol (H-AP-PAMP-04)

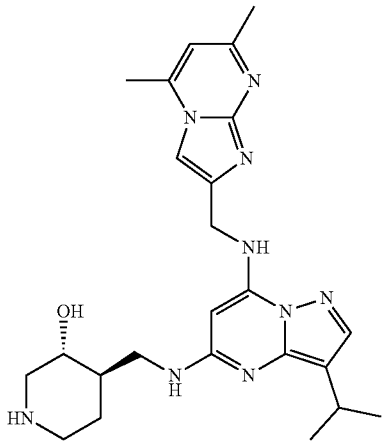 [SMILES: Cc1cc(C)n2cc(CNc3cc(NC[C@H]4CCNC[C@@H]4O)nc4c(C(C)C)cnn34)nc2n1]

Step 1: 5-chloro-3-isopropylpyrazolo[1,5-a]pyrimidin-7-amine

A mixture of 5,7-dichloro-3-isopropylpyrazolo[1,5-a]pyrimidine (1.0 g, 4.35 mmol) in ammonium hydroxide (28% aq.) (10 ml, 71.9 mmol) was stirred at 85° C. overnight. At RT, the resultant solid was collected by filtration, rinsing with water (3×5 mL). The solid was dissolved in TBME (20 mL) and filtered through a phase separator. The filtrate was concentrated in vacuo to give the title compound (900 mg, 4.06 mmol, 93% yield, 95% purity) as an off-white solid.

$^1H$ NMR in DMSO-$d_6$ was consistent with product structure.

Step 2: tert-butyl (5-chloro-3-isopropylpyrazolo[1,5-a]pyrimidin-7-yl)carbamate

BOC-Anhydride (570 mg, 2.61 mmol) was added to a solution of 5-chloro-3-isopropylpyrazolo[1,5-a]pyrimidin-7-amine (500 mg, 2.37 mmol) and DMAP (29 mg, 0.24 mmol) in DCM (12 mL). The reaction mixture was stirred at RT overnight. The reaction mixture was concentrated under reduced pressure and the residue partitioned between DCM (20 mL) and water (20 mL). The aq. layer was extracted with DCM (2×15 mL) and the combined organic layers were filtered through a phase separator then concentrated under reduced pressure. Purification by column chromatography (24 g cartridge, 0-100% EtOAc/isohexane) gave the title compound (600 mg, 1.8 mmol, 77% yield, 95% purity) as a white solid.

Step 3: tert-butyl (5-chloro-3-isopropylpyrazolo[1,5-a]pyrimidin-7-yl)((5,7-dimethylimidazo[1,2-a]pyrimidin-2-yl)methyl)carbamate A mixture of tert-butyl (5-chloro-3-isopropylpyrazolo[1,5-a]pyrimidin-7-yl)carbamate (200 mg, 0.64 mmol), 2-(chloromethyl)-5,7-dimethylimidazo[1,2-a]pyrimidine (164 mg, 0.84 mmol) and $K_2CO_3$ (178 mg, 1.29 mmol) in anhydrous DMF (3.5 mL) was stirred at 70° C. overnight. At RT, EtOAc (20 mL), water (20 mL) and brine (20 mL) were added. The layers were separated then the aq. layer was extracted with EtOAc (3×30 mL). The combined organic layers were washed with brine (3×30 mL), dried over $Na_2SO_4$ and concentrated under reduced pressure.

Purification by column chromatography (12 g cartridge, 0-100% EtOAc/isohexane) gave the title compound (186 mg, 0.38 mmol, 58% yield, 95% purity) as a yellow oil.

UPLC/MS (Method 6): m/z 470 (M+H)+, $R_T$ 0.80 min.

Step 4: tert-butyl (3R,4R)-4-(((7-((tert-butoxycarbonyl)((5,7-dimethylimidazo[1,2-a]pyrimidin-2-yl)methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)((5,7-dimethylimidazo[1,2-a]pyrimidin-2-yl)methyl)carbamate (96 mg, 200 μmol), (3R,4R)-tert-butyl 4-(aminomethyl)-3-hydroxypiperidine-1-carboxylate (52 mg, 220 μmol) and $^t$BuBrettPhos Pd G3 (17 mg, 28.1 μmol) in THE (1.7 mL) was degassed with $N_2$ for 10 min. LiHMDS (1M in THF) (270 μL, 270 μmol) was added in one portion under bubbling $N_2$. Bubbling was ceased and the reaction mixture heated to 60° C. for 2 h. At RT, water (15 mL) and EtOAc (25 mL) were added. The layers were separated and the aq. layer extracted with EtOAc (2×15 mL). The combined organic layers were filtered through a phase separator and concentrated under reduced pressure. Purification by column chromatography (12 g cartridge, 0-100% (3:1 EtOAc/EtOH)/isohexane) gave the title compound (92 mg, 140 μmol, 66% yield, 98% purity) as a yellow oil.

UPLC/MS (Method 4): m/z 664 (M+H)+, $R_T$ 1.61 min.

Step 5: (3R,4R)-4-(((7-(((5,7-dimethylimidazo[1,2-a]pyrimidin-2-yl)methyl)amino)-3-isopropylpyrazolo[1,5-a]pyrimidin-5-yl)amino)methyl)piperidin-3-ol Hydrogen chloride (4M in dioxane) (0.69 mL, 2.8 mmol) was added to a solution of tert-butyl (3R,4R)-4-(((7-((tert-butoxycarbonyl)((5,7-dimethylimidazo[1,2-a]pyrimidin-2-yl)methyl)amino)-3-isopropylpyrazolo[1,5-a]pyrimidin-5-yl)amino)methyl)-3-hydroxypiperidine-1-carboxylate (92 mg, 0.14 mmol) in dioxane (0.5 mL). The reaction mixture was stirred at 35° C. for 1 h and concentrated in vacuo. The residue was loaded onto a column of SCX. The column was washed with MeOH (40 mL) and the product eluted with 0.7 M $NH_3$ in MeOH (40 mL). The ammoniacal methanol solution was concentrated in vacuo to give the title compound (58 mg, 120 μmol, 86% yield, 95% purity) as an off-white solid after trituration from $Et_2O$ and drying overnight at 40° C. under vacuum.

UPLC/MS (Method 4): m/z 464 (M+H)+, $R_T$ 0.94 min.

$^1$H NMR (500 MHz, DMSO-$d_6$) δ 7.63 (s, 1H), 7.62-7.57 (m, 2H), 6.84 (d, J=1.1 Hz, 1H), 6.77-6.71 (m, 1H), 5.37 (s, 1H), 5.31 (s, 1H), 4.57 (d, J=5.7 Hz, 2H), 3.58-3.49 (m, 1H), 3.23-3.17 (m, 1H), 3.09-3.01 (m, 1H), 2.98-2.90 (m, 2H), 2.83-2.77 (m, 1H), 2.57 (s, 3H), 2.48 (s, 3H), 2.36-2.29 (m, 1H), 2.19 (t, J=10.8 Hz, 1H), 1.60-1.54 (m, 1H), 1.39-1.31 (m, 1H), 1.25-1.21 (m, 6H), 1.20-1.13 (m, 1H). 1H under water.

Synthesis 44

(3R,4R)-4-(((7-(((7-cyclopropyl-[1,2,4]triazolo[1,5-a]pyridin-2-yl)methyl)amino)-3-isopropylpyrazolo[1,5-a]pyrimidin-5-yl)amino)methyl)piperidin-3-ol (H-APPAMP-044)

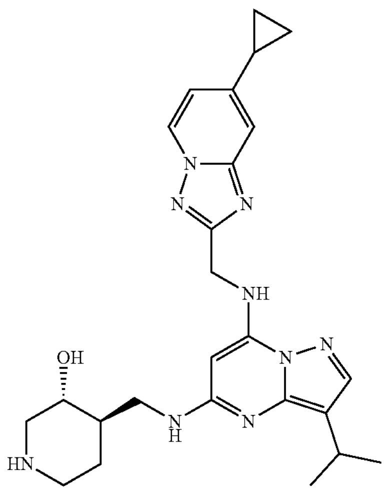 [SMILES: CC(C)c1cnn2c(NCc3nc4cc(C5CC5)ccn4n3)cc(NC[C@H]3CCNC[C@@H]3O)nc12]

Step 1: 5-chloro-N-((7-cyclopropyl-[1,2,4]triazolo[1,5-a]pyridin-2-yl)methyl)-3-isopropylpyrazolo[1,5-a]pyrimidin-7-amine (7-Cyclopropyl-[1,2,4]triazolo[1,5-a]pyridin-2-yl)methanamine (95 mg, 0.45 mmol) was added to a solution of 5,7-dichloro-3-isopropylpyrazolo[1,5-a]pyrimidine (130 mg, 0.55 mmol) and DIPEA (0.55 mL, 3.2 mmol) in EtOH (4.0 mL). The reaction mixture was heated at 50° C. for 16 h. The reaction mixture was concentrated in vacuo. Purification by column chromatography (12 g cartridge, 0-100% EtOAc/isohexane) gave the title compound (138 mg, 0.29 mmol, 64% yield, 81% purity) as a yellow oil.

UPLC/MS (Method 4): m/z 382 (M+H)+, $R_T$ 1.57 min.

Step 2: tert-butyl (5-chloro-3-isopropylpyrazolo[1,5-a]pyrimidin-7-yl)((7-cyclopropyl-[1,2,4]triazolo[1,5-a]pyridin-2-yl)methyl)carbamate BOC-Anhydride (77 mg, 351 μmol) was added to a solution of 5-chloro-N-((7-cyclopropyl-[1,2,4]triazolo[1,5-a]pyridin-2-yl)methyl)-3-isopropylpyrazolo[1,5-a]pyrimidin-7-amine (138 mg, 293 μmol) and DMAP (7.2 mg, 59 μmol) in THE (3.0 mL). The reaction mixture was stirred at RT for 18 h. The reaction mixture was concentrated under reduced pressure. Purification by column chromatography (12 g cartridge, 0-10% MeOH/DCM) gave the title compound (154 mg, 281 μmol, 96% yield, 88% purity) as a yellow oil.

UPLC/MS (Method 3): m/z 482 (M+H)+, $R_T$ 1.87 min.

Step 3: tert-butyl (3R,4R)-4-(((7-((tert-butoxycarbonyl)((7-cyclopropyl-[1,2,4]triazolo[1,5-a]pyridin-2-yl)methyl)amino)-3-isopropylpyrazolo[1,5-a]pyrimidin-5-yl)amino)methyl)-3-hydroxypiperidine-1-carboxylate A solution of tert-butyl (5-chloro-3-isopropylpyrazolo[1,5-a]pyrimidin-7-yl)((7-cyclopropyl-[1,2,4]triazolo[1,5-a]pyridin-2-yl)methyl)carbamate (154 mg, 281 μmol), (3R,4R)-tert-butyl 4-(aminomethyl)-3-hydroxypiperidine-1-carboxylate (71.2 mg, 309 μmol) and $^t$BuBrettPhos Pd G3 (24.0 mg, 28.1 μmol) in THE (3.0 mL) was degassed with $N_2$ for 10 min. LiHMDS (1M in THF) (366 μL, 366 μmol) was added in one portion under bubbling $N_2$. Bubbling was ceased and the reaction mixture heated to 60° C. for 2 h. The reaction mixture was concentrated under reduced pressure. Purification by column chromatography (12 g cartridge, 0-100% EtOAc/isohexane) gave the title compound (139 mg, 187 μmol, 67% yield, 91% purity) as a yellow solid.

UPLC/MS (Method 4): m/z 676 (M+H)+, $R_T$ 2.23 min.

Step 4: (3R,4R)-4-(((7-(((7-cyclopropyl-[1,2,4]triazolo[1,5-a]pyridin-2-yl)methyl)amino)-3-isopropylpyrazolo[1,5-a]pyrimidin-5-yl)amino)methyl)piperidin-3-ol TFA (0.5 mL) was added to a solution of tert-butyl (3R,4R)-4-(((7-((tert-butoxycarbonyl)((7-cyclopropyl-[1,2,4]triazolo[1,5-a]pyridin-2-yl)methyl)amino)-3-isopropylpyrazolo[1,5-a]pyrimidin-5-yl)amino)methyl)-3-hydroxypiperidine-1-carboxylate (139 mg, 187 μmol) in DCM (1.5 mL). The reaction mixture was stirred at RT for 18 h and concentrated in vacuo. The residue was loaded onto a column of SCX. The column was washed with MeOH (50 mL) and the product eluted with 0.7 M $NH_3$ in MeOH (50 mL). The ammoniacal methanol solution was concentrated in vacuo to give the title compound (75 mg, 150 μmol, 80% yield, 95% purity) as a tan solid after trituration from $Et_2O$ and drying overnight at 40° C. under vacuum.

UPLC/MS (Method 3): m/z 476 (M+H)+, $R_T$ 0.73 min.

$^1$H NMR (400 MHz, DMSO-$d_6$) δ 8.74 (d, J=7.1 Hz, 1H), 7.67-7.58 (m, 2H), 7.47 (d, J=1.8 Hz, 1H), 6.87 (dd, J=7.1, 1.9 Hz, 1H), 6.74 (t, J=6.0 Hz, 1H), 5.35-5.27 (m, 1H), 5.25 (s, 1H), 4.66 (d, J=6.2 Hz, 2H), 3.58-3.46 (m, 1H), 3.24-3.16 (m, 1H), 3.09-3.00 (m, 1H), 3.00-2.89 (m, 2H), 2.82-2.74 (m, 1H), 2.37-2.27 (m, 1H), 2.17 (dd, J=11.7, 9.9 Hz, 1H), 2.13-2.05 (m, 1H), 1.61-1.51 (m, 1H), 1.40-1.29 (m, 1H), 1.24 (dd, J=6.9, 4.8 Hz, 6H), 1.21-1.12 (m, 1H), 1.11-1.02 (m, 2H), 0.88-0.82 (m, 2H). 1H under water.

Intermediate Synthesis A20

(7-cyclopropyl-[1,2,4]triazolo[1,5-a]pyridin-2-yl)methanamine

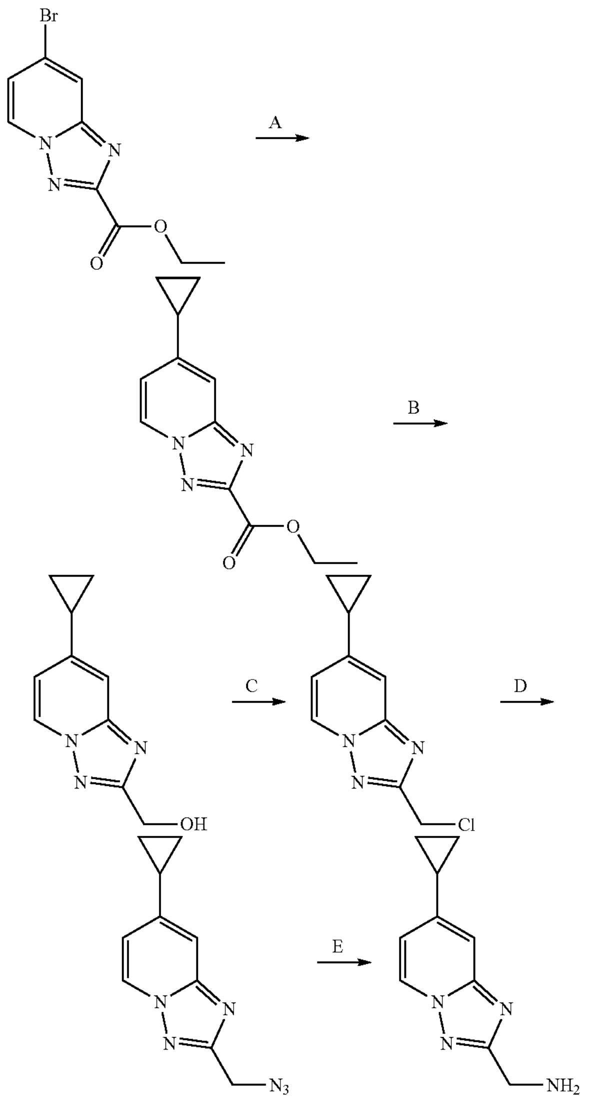

Step A: ethyl 7-cyclopropyl-[1,2,4]triazolo[1,5-a]pyridine-2-carboxylate

A mixture of ethyl 7-bromo-[1,2,4]triazolo[1,5-a]pyridine-2-carboxylate (400 mg, 1.48 mmol), cesium fluoride (675 mg, 4.44 mmol) and cyclopropylboronic acid (382 mg, 4.44 mmol) in Dioxane (15 mL) and sparged with N2 for 10 min. $PdCl_2$(dppf)-$CH_2Cl_2$adduct (242 mg, 296 μmol) was added and $N_2$ was bubbled through the reaction mixture for another 10 min before being heated at 50° C. for 16 h. The mixture was filtered through celite and the filtrate diluted with water (100 mL) then extracted with EtOAc (3×50 mL). The combined organic layers were dried over $MgSO_4$ and concentrated in vacuo. Purification by column chromatography (24 g cartridge, 0-100% EtOAc/isohexane) gave the title compound (274 mg, 1.1 mmol, 75% yield, 94% purity) as a yellow solid.

UPLC/MS (Method 4): m/z 232 (M+H)+, $R_T$ 1.00 min.

Step B: (7-cyclopropyl-[1,2,4]triazolo[1,5-a]pyridin-2-yl)methanol

A mixture of ethyl 7-cyclopropyl-[1,2,4]triazolo[1,5-a] pyridine-2-carboxylate (274 mg, 1.11 mmol) and $NaBH_4$ (42.1 mg, 1.11 mmol) in THF (5.0 mL) was heated to 50° C. and stirred for 17 h. The mixture was quenched with MeOH (5 mL) and stirred for 10 min. Aq. sat. $NH_4Cl$ (aq) (5 mL) was added then the mixture was diluted with aq. sat. $NaHCO_3$ (20 mL) and water (20 mL). The aq. was extracted with DCM (3×20 mL) then the combined organic layers were dried over $MgSO_4$ and concentrated in vacuo. Purification by column chromatography (12 g cartridge, 0-10% MeOH/DCM) gave the title compound (134 mg, 0.67 mmol, 60% yield, 95% purity) as a white solid.

UPLC/MS (Method 4): m/z 190 (M+H)+, $R_T$ 0.70 min.

Step C: 2-(chloromethyl)-7-cyclopropyl-[1,2,4]triazolo[1,5-a]pyridine, HCl

Thionyl chloride (129 μL, 1.77 mmol) was added dropwise to a solution of (7-cyclopropyl-[1,2,4]triazolo[1,5-a] pyridin-2-yl)methanol (134 mg, 0.71 mmol) in DCM (7.0 mL). The mixture was stirred at 0° C. for 2 h. Concentration to dryness under reduced pressure gave the title compound (172 mg, 0.63 mmol, 90% yield, 90% purity) as a white solid.

UPLC/MS (Method 3): m/z 208 (M+H)+, $R_T$ 0.60 min.

Step D: 2-(azidomethyl)-7-cyclopropyl-[1,2,4]triazolo[1,5-a]pyridine

A solution of 2-(chloromethyl)-7-cyclopropyl-[1,2,4]triazolo[1,5-a]pyridin-1-ium chloride (174 mg, 641 μmol) and DIPEA (335 μL, 1.92 mmol) in DMF (3.5 mL) was treated with sodium azide (63 mg, 962 mmol). The mixture was heated to 50° C. and stirred for 3 h. The mixture was concentrated under reduced pressure. Purification by column chromatography (12 g cartridge, 0-100% EtOAc/isohexane) gave the title compound (122 mg, 540 μmol, 84% yield, 95% purity) as a colourless oil.

UPLC/MS (Method 4): m/z 215 (M+H)+, $R_T$ 1.01 min.

Step E: (7-cyclopropyl-[1,2,4]triazolo[1,5-a]pyridin-2-yl)methanamine 2-(Azidomethyl)-7-cyclopropyl-[1,2,4]triazolo[1,5-a] pyridine (122 mg, 569 μmol) and triphenylphosphine (179 mg, 683 μmol) were dissolved in THF (5.0 mL) and water (0.6 mL). The mixture was stirred at 40° C. for 2 h before removal of the solvent in vacuo. The residue was loaded onto a column of SCX. The column was washed with MeOH (40 mL) and the product eluted with 0.7 M $NH_3$ in MeOH (40 mL). The ammoniacal methanol solution was concentrated in vacuo to give the title compound (95 mg, 0.45 mmol, 80% yield, 90% purity) as a white solid.

UPLC/MS (Method 4): m/z 189 (M+H)+, $R_T$ 0.71 min.

Synthesis 45

(3R,4R)-4-(((3-cyclopropyl-7-(((7-phenylimidazo[1,2-a]pyridin-2-yl)methyl)amino)pyrazolo[1,5-a]pyrimidin-5-yl)amino)methyl)piperidin-3-ol (H-AP-PAMP-045)

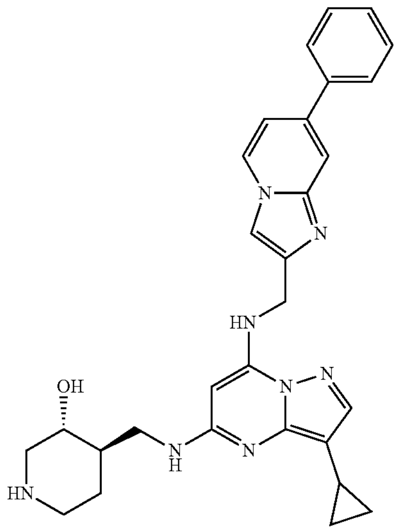 [SMILES: O[C@H]1CNCC[C@@H]1CNc1cc(NCc2cn3ccc(-c4ccccc4)cc3n2)n2ncc(C3CC3)c2n1]

Step 1: 5-chloro-3-cyclopropyl-N-((7-phenylimidazo[1,2-a]pyridin-2-yl)methyl)pyrazolo[1,5-a]pyrimidin-7-amine (7-phenylimidazo[1,2-a]pyridin-2-yl)methanamine (371 mg, 332 μmol) was added to a solution of 5,7-dichloro-3-cyclopropylpyrazolo[1,5-a]pyrimidine (75 mg, 329 μmol) and DIPEA (0.46 mL, 2.63 mmol) in EtOH (2.7 mL). The reaction mixture was heated at 65° C. for 1.5 h. More 5,7-dichloro-3-cyclopropylpyrazolo[1,5-a]pyrimidine (25 mg, 110 μmol) and further stirring at 65° C. for 1.5 h. The reaction mixture was concentrated in vacuo. Purification by column chromatography (24 g cartridge, 0-100% EtOAc/isohexane) gave the title compound (155 mg, 0.36 mmol, 82% yield, 96% purity) as an orange gum.

UPLC/MS (Method 5): m/z 415 (M+H)+, $R_T$ 1.58 min.

Step 2: tert-butyl (5-chloro-3-cyclopropylpyrazolo[1,5-a]pyrimidin-7-yl)((7-phenylimidazo[1,2-a]pyridin-2-yl)methyl)carbamate BOC-Anhydride (144 mg, 660 μmol) was added to a solution of 5-chloro-3-cyclopropyl-N-((7-phenylimidazo[1,2-a]pyridin-2-yl)methyl)pyrazolo[1,5-a]pyrimidin-7-amine (155 mg, 362 μmol) and DMAP (11 mg, 90 μmol) in THF (8.6 mL). The reaction mixture was stirred at 65° C. overnight. The reaction mixture was concentrated under reduced pressure. Purification by column chromatography (12 g cartridge, 0-10% MeOH/DCM) gave the title compound (157 mg, 301 μmol, 82% yield, 98% purity) as a yellow solid.

UPLC/MS (Method 5): m/z 515 (M+H)+, $R_T$ 1.88 min.

Step 3: tert-butyl (3R,4R)-4-(((7-((tert-butoxycarbonyl)((7-phenylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate A solution of tert-butyl (5-chloro-3-cyclopropylpyrazolo[1,5-a]pyrimidin-7-yl)((7-phenylimidazo[1,2-a]pyridin-2-yl)methyl)carbamate (156 mg, 303 μmol), (3R,4R)-tert-butyl 4-(aminomethyl)-3-hydroxypiperidine-1-carboxylate (91 mg, 394 μmol) and $^{t}$BuBrettPhos Pd G3 (52 mg, 61 μmol) in THE (3.0 mL) was degassed with $N_2$ for 10 min. LiHMDS (1 M in THF) (370 μL, 370 μmol) was added in one portion under bubbling $N_2$. Bubbling was ceased and the reaction mixture heated to 60° C. for 1.5 h.

At RT, the reaction mixture was filtered through celite, rinsing with EtOAc (15 mL). The filtrate was diluted with water (10 mL), the layers were separated and the aq. layer further extracted with EtOAc (3×20 mL). The combined organic layer was washed with brine (20 mL), dried over $Na_2SO_4$ and concentrated under reduced pressure. Purification by column chromatography (12 g cartridge, 0-10% (0.7 M $NH_3$/MeOH)/DCM) followed by further purification by RP Flash C18 (12 g cartridge, 15-75% MeCN/10 mM ammonium bicarbonate) gave the title compound (108 mg, 0.14 mmol, 48% yield, 85% purity) as a colourless oil.

UPLC/MS (Method 5): m/z 709 (M+H)+, $R_T$ 1.75 min.

Step 4: (3R,4R)-4-(((7-(((7-cyclopropyl-[1,2,4]triazolo[1,5-a]pyridin-2-yl)methyl)amino)-3-isopropylpyrazolo[1,5-a]pyrimidin-5-yl)amino)methyl)piperidin-3-ol HCl (4M in dioxane) (0.58 mL, 2.31 mmol) was added to a solution of tert-butyl (3R,4R)-4-(((7-((tert-butoxycarbonyl)((7-phenylimidazo[1,2-a]pyridin-2-yl)methyl)amino)-3-cyclopropylpyrazolo[1,5-a]pyrimidin-5-yl)amino)methyl)-3-hydroxypiperidine-1-carboxylate (109 mg, 154 μmol) in dioxane (1.0 mL). The reaction mixture was stirred at 35° C. for 2 h and concentrated in vacuo. The residue was loaded onto a column of SCX. The column was washed with MeOH (20 mL) and the product eluted with 0.7 M $NH_3$ in MeOH (20 mL). The ammoniacal methanol solution was concentrated in vacuo to give the title compound (61 mg, 110 μmol, 74% yield, 95% purity) as an off-white solid after trituration from $Et_2O$ and drying overnight at 40° C. under vacuum.

UPLC/MS (Method 5): m/z 509 (M+H)+, $R_T$ 1.29 min.

$^1$H NMR (400 MHz, DMSO-$d_6$) δ 8.55 (dd, J=7.2, 0.9 Hz, 1H), 7.83-7.76 (m, 4H), 7.65 (t, J=6.2 Hz, 1H), 7.52 (s, 1H), 7.52-7.47 (m, 2H), 7.43-7.38 (m, 1H), 7.26 (dd, J=7.1, 1.9 Hz, 1H), 6.77-6.71 (m, 2H), 5.37-5.31 (m, 1H), 5.29 (s, 1H), 4.58 (d, J=6.0 Hz, 2H), 3.58-3.47 (m, 1H), 3.24-3.16 (m, 1H), 3.09-2.99 (m, 1H), 2.91 (dd, J=11.6, 4.5 Hz, 1H), 2.82-2.74 (m, 1H), 2.35-2.25 (m, 1H), 2.16 (dd, J=11.6, 10.0 Hz, 1H), 1.78-1.68 (m, 1H), 1.60-1.51 (m, 1H), 1.37-1.28 (m, 1H), 1.21-1.11 (m, 1H), 0.81-0.72 (m, 2H), 0.71-0.60 (m, 2H). 1H under water.

Intermediate Synthesis A21

(7-phenylimidazo[1,2-a]pyridin-2-yl)methanamine

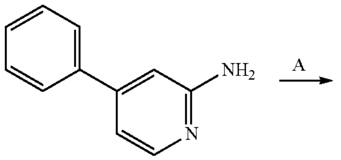

-continued

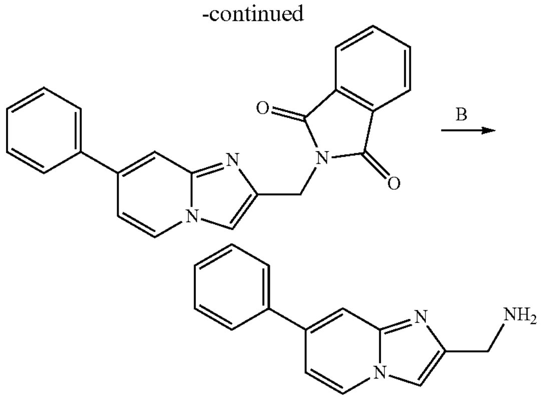

Step A: 2-((7-phenylimidazo[1,2-a]pyridin-2-yl)methyl)isoindoline-1,3-dione

A mixture of 4-phenyl-2-pyridinamine (300 μL, 2.00 mmol), 2-(3-bromo-2-oxopropyl)isoindoline-1,3-dione (564 mg, 2.00 mmol) and sodium carbonate (212 mg, 2.00 mmol) in Ethanol (15 mL) were heated at 80° C. under microwave irradiation for 2 h. More 2-(3-bromo-2-oxopropyl)isoindoline-1,3-dione (226 mg, 800 μmol) and sodium carbonate (85 mg, 800 μmol) were added and the reaction mixture was heated under microwave irradiation at 80° C. for 1 h. At 0° C., water (20 mL) was added. The resultant solid was collected by filtration, rinsing with water (5 mL). The solid was dissolved in DCM (50 mL) then the solution filtered through a phase separator and the filtrate was concentrated under reduced pressure to give a solid. Trituration in $Et_2O$ (5×5 mL) gave the title compound (470 mg, 1.1 mmol, 53% yield, 79% purity) as a green solid.

UPLC/MS (Method 3): m/z 354 (M+H)+, $R_T$ 0.90 min.

Step B: (7-phenylimidazo[1,2-a]pyridin-2-yl)methanamine

Hydrazine hydrate (85 μL, 1.7 mmol) was added to a suspension of 2-((7-phenylimidazo[1,2-a]pyridin-2-yl)methyl)isoindoline-1,3-dione (470 mg, 1.05 mmol) in EtOH (5.2 mL). The suspension was stirred at 65° C. overnight. More hydrazine hydrate (26 μL, 525 μmol) was added and the mixture was stirred at 65° C. for 2 h. The suspension was filtered and the solid washed with EtOH (15 mL). The filtrate was concentrated under reduced pressure. Trituration in cold (0° C.) TBME (2×5 ml) gave the title compound (371 mg, 0.33 mmol, 32% yield, 20% purity) as a brown solid.

UPLC/MS (Method 3): m/z 224 (M+H)+, $R_T$ 0.47 min.

Biological Methods $IC_{50}$ Assay

Materials and solutions:

HEPES-NaOH (Sigma, H-3375)
Sodium orthovanadate (Sigma, S-6508)
DTT (Sigma, D-0632)
$MgCl_2$ (M-3634)
$MnCl_2$ (VWR, 1.05927.1000)
PEG-20000 (SERVA, 33138)
ATP (Sigma, A-7699)
[γ-33P]-ATP (Hartmann Analytic, FF301T)
$H_3PO_4$ (VWR, 1.00563.1000)
NaCl (Merck, 1.06404)

Human CDK12 wt/CycK (ProQinase, 1483-1484-1—Lot 2)

RBER-IRStide (ProQinase, 0863-0000-1—Lot 036)

96-well FlashPlates™ (PerkinElmer, SMP200)

Additionally for the CDK12 Assay:

Human CDK12 wt/CycK (ProQinase, 1483-1484-1—Lot 2)

RBER-IRStide (ProQinase, 0863-0000-1—Lot 036)

Additionally for the CDK7 assay:

Human CDK7/CycH/MAT1 (ProQinase, 0366-0360-4—Lot 2).

RBER-CHKtide (ProQinase, 0581-0000-5—Lot 106).

Assay Procedure:

A radiometric protein kinase assay ($^{33}$PanQinase® Activity Assay) was used for measuring the kinase activity of the two protein kinases (CDK12/CDK7). All kinase assays were performed in 96-well FlashPlates™ from PerkinElmer (Boston, MA, USA) in a 50 μL reaction volume.

The reaction cocktail was pipetted in four steps in the following order:

20 μL of assay buffer (standard buffer)

5 μL of ATP solution (in H2O)

5 μL of test compound (in 10% DMSO)

10 μL of substrate/10 μL of enzyme solution (premixed)

For the CDK7 assay, a reaction mixture (50 μL) containing the following components was prepared:

70 mM HEPES-NaOH (pH 7.5);

sodium orthovanadate (3 μM);

PEG-20000 (50 μg/mL);

DTT (1.2 mM);

$MgCl_2$ (3 mM);

$MnCl_2$ (3 mM);

purified human CDK7/CycH/MAT1 (3.3 nM—Lot 02);

RBER-CHKtide substrate (40 μg/mL—Lot 106);

ATP (3 μM);

[γ-33P]-ATP (approx. $8\times10^5$ cpm per well); and test compound at the appropriate concentration such that the final concentration of DMSO was 10% w/w.

For the CDK7 assay, a reaction mixture (50 μL) containing the following components was prepared:

70 mM HEPES-NaOH (pH 7.5);

sodium orthovanadate (3 μM);

PEG-20000 (50 μg/mL);

DTT (1.2 mM);

$MgCl_2$ (3 mM);

$MnCl_2$ (3 mM);

purified human CDK12 wt/CycK (14.7 nM—Lot 02);

RBER-IRStide substrate (40 μg/mL—Lot 036);

ATP (0.3 μM);

[γ-33P]-ATP (approx. $8\times10^5$ cpm per well); and test compound at the appropriate concentration such that the final concentration of DMSO was 10% w/w.

The reaction mixture was incubated at 30° C. for 60 min and then stopped by the addition of 2% (v/v) $H_3PO_4$. Plates were aspirated and washed two times with 200 μL 0.9% (w/v) NaCl. Incorporation of $^{33}$Pi was determined with a microplate scintillation count (Microbeta, Wallac).

The residual activities for each concentration and the compound $IC_{50}$ values were calculated using Quattro Workflow V3.1.1 (Quattro Research GmbH, Munich, Germany). The fitting model for the $IC_{50}$ determinations was "Sigmoidal response (variable slope)" with parameters "top" fixed at 100% and "bottom" at 0%. The fitting method used was a least-squares fit.

Western Blotting Analysis of Cyclin K Depletion in Cell Culture A673 cells were incubated for 2 hours with of 1 μM compound in presence or in absence of 10 μM proteasome inhibitor MG132 (Sigma Aldrich) or NAE (NEDD8 activating enzyme) inhibitor MLN4942 (Cell Signalling Technologies). Cells were washed 2× with cold Phosphate Buffered Saline (PBS, Sigma Aldrich), followed by the addition of lysis buffer for 15 minutes on ice before harvesting and centrifugation.

Protein content in the cell lysate was assessed by BCA assay (Thermo Fisher). Samples were then prepared with 4× Laemmlli Buffer (Bio-Rad) and heated to 95° C. for 5 minutes. Each sample was loaded onto a Mini-PROTEAN TGX Stain Free Gel (Bio-Rad) at 50 μg protein/well. SDS-PAGE was performed and then protein was transferred onto a PVDF membrane using a Trans-Blot® Turbo™ Midi PVDF Transfer Pack (Bio-Rad. Membranes were blocked in TBS-T (Invitrogen), 5% (w/v) milk powder (Marvel) overnight at 4° C.

Membranes were incubated with anti-CCNK antibody (rabbit) primary antibody (Abcam) and anti-GAPDH antibody (rabbit) in TBS-T for 2 hours. Membranes were then washed three times with TBS-T, before incubation secondary goat anti-rabbit HRP antibody (Cell Signalling Technologies) followed by 3× washing in TBS-T. Blots were imaged using a Chemidoc imager (Bio-Rad). Cyclin K depletion was measured as the observable drop in band intensity in compound treated samples relative to proteasome-inhibitor treated samples, measured by densitometry (Image Lab).

Biological Data

The H-APPAMP compounds were assessed using the biological methods described above.

The following reference compounds were also assessed, for comparison purposes.

REF-001

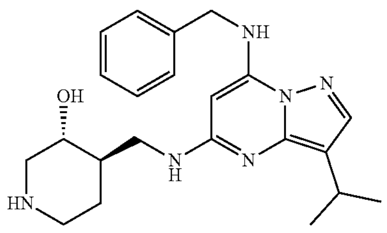

Bondke et al., 2015
(PPDA-001)

REF-002

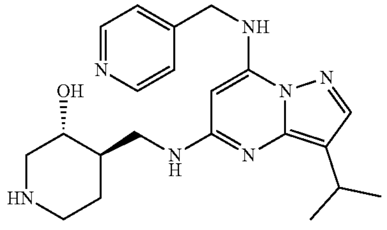

Bondke et al., 2015
(PPDA-003)

-continued

REF-003

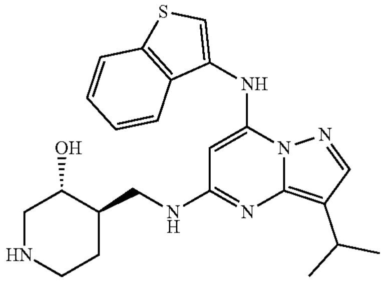

Bondke et al., 2015
(PPDA-008)

The resulting data are summarized in the following table. A ratio of CDK7/CDK12 of greater than 1 indicated selectivity for CDK12.

TABLE 1

Biochemical Assay Data

| Cmpd No. | CDK12 $IC_{50}$ (nM) | CDK7 $IC_{50}$ (nM) | CDK7/ CDK12 |
|---|---|---|---|
| REF-001 | 3200 | 14 | 0.004 |
| REF-002 | 253 | 125 | 0.494 |
| REF-003 | 597 | 11 | 0.018 |
| H-APPAMP-001 | 38.0 | 436 | 11.5 |
| H-APPAMP-002 | 71.5 | 704 | 9.85 |
| H-APPAMP-003 | 50.2 | 411 | 8.19 |
| H-APPAMP-004 | 51.7 | 305 | 5.90 |
| H-APPAMP-005 | 65.0 | 343 | 5.28 |
| H-APPAMP-006 | 26.9 | 127 | 4.72 |
| H-APPAMP-007 | 20.0 | 158 | 7.90 |
| H-APPAMP-008 | 40 | 117 | 2.9 |
| H-APPAMP-009 | 38 | 123 | 3.2 |
| H-APPAMP-010 | 40 | 238 | 6.0 |
| H-APPAMP-011 | 33 | 168 | 5.1 |
| H-APPAMP-012 | 26 | 214 | 8.2 |
| H-APPAMP-013 | 70 | 226 | 3.2 |
| H-APPAMP-014 | 75 | 19 | 0.3 |
| H-APPAMP-015 | 277 | 3 | 0.01 |
| H-APPAMP-016 | 96 | 179 | 1.9 |
| H-APPAMP-017 | 63 | 40 | 0.6 |
| H-APPAMP-018 | 65 | 206 | 3.2 |
| H-APPAMP-019 | 522 | 640 | 1.2 |
| H-APPAMP-020 | 540 | 82 | 0.2 |
| H-APPAMP-021 | 167 | 28 | 0.2 |
| H-APPAMP-022 | 164 | 622 | 3.8 |
| H-APPAMP-023 | 702 | 102 | 0.1 |
| H-APPAMP-024 | 93 | 283 | 3.0 |
| H-APPAMP-025 | 36 | 334 | 9.3 |
| H-APPAMP-026 | 31 | 69 | 2.2 |
| H-APPAMP-027 | 28 | 127 | 4.5 |
| H-APPAMP-028 | 37 | 68 | 1.8 |
| H-APPAMP-029 | 65 | 196 | 3.0 |
| H-APPAMP-030 | 75 | 274 | 3.7 |
| H-APPAMP-031 | 24 | 919 | 38.3 |
| H-APPAMP-032 | 45 | 859 | 19.1 |
| H-APPAMP-033 | 62 | 1060 | 17.1 |
| H-APPAMP-034 | 173 | 152 | 0.9 |
| H-APPAMP-035 | 44 | 1290 | 29.3 |
| H-APPAMP-036 | 287 | 1150 | 4.0 |
| H-APPAMP-037 | 208 | 649 | 3.1 |
| H-APPAMP-038 | 100 | 762 | 7.6 |
| H-APPAMP-039 | 48 | 1830 | 38.1 |
| H-APPAMP-040 | 48 | 1530 | 31.9 |
| H-APPAMP-041 | 46 | 650 | 14.1 |
| H-APPAMP-042 | 100 | 974 | 9.7 |
| H-APPAMP-043 | 21 | 484 | 23 |
| H-APPAMP-044 | 40 | 269 | 6.7 |
| H-APPAMP-045 | 18 | 496 | 27.6 |

The data demonstrated that the H-APPAMP compounds are highly potent inhibitors of CDK12, and, in addition, some also have substantial selectivity for CDK12 as compared to CDK7.

Many of the compounds are also characterised by the ability not only to inhibit CDK12 but also to cause Cyclin K degradation. Cyclin K degradation was evaluated in A673 cells as described above. The data are summarised in the following table. The values reported for THZ-531 were derived from published data in HeLa and A549 cells; see, e.g., Zhang et al., 2016; Słabicki et al., 2020; Lu Lv et al., 2020.

TABLE 2

Cyclin K Degradation and its Relationship to CDK12 Kinase Activity and Cellular Potency

| Compound No. | Biochemical Potency $IC_{50}$ (nM) | Cellular Potency $IC_{50}$ (nM) (in A673 cells) | Ratio of Biochemical Potency: Cellular Potency | Cyclin K Degrader Activity |
|---|---|---|---|---|
| Dinaciclib | 4.1 | 4.9 | 0.83 | – |
| THZ-531 | 160 | 210 | 0.74 | – |
| H-APPAMP-004 | 55 | 8.9 | 6.2 | ++ |
| H-APPAMP-025 | 36 | 1.5 | 23 | +++ |
| H-APPAMP-043 | 21 | 340 | 0.06 | – |
| H-APPAMP-044 | 40 | 44 | 0.91 | + |
| H-APPAMP-045 | 18 | 110 | 0.16 | – |

Legend:
(–): No Cyclin K degradation.
(+): Weak Cyclin K degradation.
(++): Moderate Cyclin K degradation.
(+++): Strong Cyclin K degradation.

The data demonstrate that when the cellular potency in A673 cells is greater than the biochemical potency, then this correlates with cyclin K degradation. Known CDK12/13 inhibitor compounds such as Dinaciclib and THZ-531 are not cyclin K degraders despite being potent in the CDK12 biochemical assay.

The following table summarises the data for a number of the exemplified compounds. Where the ratio of biochemical potency to cellular potency is >0.9, this is an indicator of a compound capable of Cyclin K degradation.

TABLE 3

CDK12 Kinase Activity and Cellular Potency

| Compound No. | Biochemical Potency $IC_{50}$ (nM) | Cellular Potency $IC_{50}$ (nM) (in A673 cells) | Ratio of Biochemical Potency: Cellular Potency |
|---|---|---|---|
| H-APPAMP-001 | 38.0 | 123 | 0.3 |
| H-APPAMP-002 | 71 | 716 | 0.1 |
| H-APPAMP-003 | 50 | 8 | 6.2 |
| H-APPAMP-004 | 51 | 12 | 4.2 |
| H-APPAMP-005 | 65 | 47 | 1.4 |
| H-APPAMP-006 | 27 | 52 | 0.5 |
| H-APPAMP-007 | 20 | 27 | 0.7 |
| H-APPAMP-008 | 40 | 5.7 | 7.0 |
| H-APPAMP-009 | 38 | 14.9 | 2.6 |
| H-APPAMP-010 | 40 | 4.3 | 9.3 |
| H-APPAMP-011 | 33 | 6.3 | 5.2 |
| H-APPAMP-012 | 26 | 21.8 | 1.2 |
| H-APPAMP-013 | 70 | 12.2 | 5.7 |
| H-APPAMP-014 | 75 | 7.3 | 10 |
| H-APPAMP-015 | 277 | 151 | 1.8 |
| H-APPAMP-016 | 96 | 14.8 | 6.5 |
| H-APPAMP-017 | 143 | 8.3 | 17.2 |

TABLE 3-continued

| CDK12 Kinase Activity and Cellular Potency | | | |
|---|---|---|---|
| Compound No. | Biochemical Potency $IC_{50}$ (nM) | Cellular Potency $IC_{50}$ (nM) (in A673 cells) | Ratio of Biochemical Potency: Cellular Potency |
| H-APPAMP-018 | 65 | 16.3 | 4.0 |
| H-APPAMP-019 | 522 | 76.9 | 6.8 |
| H-APPAMP-020 | 540 | 115.5 | 4.7 |
| H-APPAMP-021 | 167 | 2.7 | 62 |
| H-APPAMP-022 | 164 | 10.3 | 16 |
| H-APPAMP-023 | 702 | 296.5 | 2.4 |
| H-APPAMP-024 | 93 | 19.8 | 4.7 |
| H-APPAMP-025 | 36 | 1.5 | 23 |
| H-APPAMP-026 | 31 | 2.5 | 12 |
| H-APPAMP-027 | 28 | 1.6 | 18 |
| H-APPAMP-028 | 37 | 13.1 | 2.8 |
| H-APPAMP-029 | 65 | 18.5 | 3.5 |
| H-APPAMP-030 | 75 | 8.7 | 8.6 |
| H-APPAMP-031 | 24 | 2.2 | 11 |
| H-APPAMP-032 | 45 | 6.1 | 7.4 |
| H-APPAMP-033 | 62 | 5.7 | 11 |
| H-APPAMP-034 | 173 | 12.1 | 14 |
| H-APPAMP-035 | 44 | 17.3 | 2.5 |
| H-APPAMP-036 | 287 | 10.4 | 28 |
| H-APPAMP-037 | 208 | 18.1 | 11 |
| H-APPAMP-038 | 100 | 4.6 | 22 |
| H-APPAMP-039 | 48 | 4.0 | 12 |
| H-APPAMP-040 | 48 | 5.4 | 8.9 |
| H-APPAMP-041 | 46 | 9.8 | 4.7 |
| H-APPAMP-042 | 100 | 30.0 | 3.3 |
| H-APPAMP-043 | 21 | 340 | 0.06 |
| H-APPAMP-044 | 40 | 44 | 0.91 |
| H-APPAMP-045 | 18 | 110 | 0.16 |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below.

Each of these references is incorporated herein by reference in its entirety into the present disclosure, to the same extent as if each individual reference was specifically and individually indicated to be incorporated by reference.

Bahl et al., 2019, International Patent Application Publication No. WO 2019/057825 A1, published 28 Mar. 2019.

Blazek et al., 2011, "The Cyclin K/Cdk12 complex maintains genomic stability via regulation of expression of DNA damage response genes", *Genes Dev*, Vol. 25, No. 20, pp. 2158-2172.

Bondke et al., 2015, International Patent Application Publication No. WO 2015/124941 A1, published 27 Aug. 2015.

Chen et al., 2006, "Identification and Characterization of the CDK12/Cyclin L1 Complex Involved in Alternative Splicing Regulation," *Mol Cell Biol.*, Vol. 26, No. 7, pp. 2736-2745.

Chen et al., 2000, "Activation of Estrogen Receptor α by S118 Phosphorylation Involves a Ligand-Dependent Interaction with TFIIH and Participation of CDK7", *Molecular Cell*, Vol. 6, No. 1, pp. 127-137.

Chen et al., 2002, "Phosphorylation of human estrogen receptor α at serine 118 by two distinct signal transduction pathways revealed by phosphorylation-specific antisera", *Oncogene*, Vol. 21, No. 32, pp. 4921-4931.

Choi et al., 2019, "CDK12 drives breast tumor initiation and trastuzumab resistance via WNT and IRS1-ErbB-PI3K signalling", *EMBO Rep*, Vol. 20, No. 10, e48058.

Cuzick et al., 2010, "Effect of anastrozole and tamoxifen as adjuvant treatment for early-stage breast cancer: 10-year analysis of the ATAC trial", *Lancet Oncol.*, Vol. 11, No. 12, pp. 1135-1141.

Deng et al., 2010, International Patent Application Publication No. WO 2010/118207 A1, published 14 Oct. 2010.

Greifenberg et al., 2016, "Structural and Functional Analysis of the CDK13/Cyclin K Complex," *Cell Rep.*, Vol. 14, No. 2, pp. 320-331.

Gyl et al., 2018, "CDK12: an emerging therapeutic target for cancer", *J Clin Pathol*, Vol. 71, No. 11, pp. 957-962.

Hazel et al., 2017, "Inhibitor Selectivity for Cyclin-Dependent Kinase 7: A Structural, Thermodynamic, and Modelling Study", *Chem Med Chem*, Vol. 12, pp. 372-380.

Iniguez et al., 2018, "EWS/FLI Confers Tumor Cell Synthetic Lethality to CDK12 Inhibition in Ewing Sarcoma", *Cancer Cell*, Vol. 33, No. 2, pp. 202-216.

Johannes et al., 2018, "Structure-Based Design of Selective Noncovalent CDK12 Inhibitors", *Chem Med Chem*, Vol. 13, pp. 231-235.

Johnson et al., 2016, "CDK12 Inhibition Reverses De Novo and Acquired PARP Inhibitor Resistance in BRCA Wild-Type and Mutated Models of Triple-Negative Breast Cancer", *Cell Rep*, Vol. 17, No. 9, pp. 2367-2381.

Johnston et al., 2003, "Aromatase inhibitors for breast cancer: lessons from the laboratory", *Nat. Rev. Cancer*, Vol. 3, pp. 821-831.

Kugel, 2019, International Patent Application Publication No. WO 2019/144149 A2, published 25 Jul. 2019.

Kwiatkowski et al., 2019, International Patent Application Publication No. WO 2019/035866 A1, published 21 Feb. 2019.

Lei et al., 2018, "Cyclin K regulates prereplicative complex assembly to promote mammalian cell proliferation", Nature Communications, Vol. 9, Article 1876.

Li et al., 2016, "CDK12 is a gene-selective RNA polymerase II kinase that regulates a subset of the transcriptome, including Nrf2 target genes", *Sci Rep*, Vol. 6, 21455.

Lord et al., 2016, "BRCAness revisited", *Nat Rev Cancer*, Vol. 16, No. 2, pp. 110-120.

Lu Lv et al., 2020, "Discovery of a molecular glue promoting CDK12-DDB1 interaction to trigger cyclin K degradation", eLife 2020; 9:e59994.

Malumbres et al., 2009, "Cyclin-dependent kinases: a family portrait", *Nature Cell Biology*, Vol. 11, No. 11, pp. 1275-1276.

Morgan, 1995, "Principles of CDK regulation", *Nature*, Vol. 374, pp. 131-134.

Nam et al., 2019, International Patent Application Publication No. WO 2019/197549 A1, published 17 Oct. 2019.

Nam et al., 2019, International Patent Application Publication No. WO 2019/197546 A1, published 17 Oct. 2019.

Patel et al., 2018, "ICEC0942, an Orally Bioavailable Selective Inhibitor of CDK7 for Cancer Treatment", *Mol Cancer Ther*, Vol. 17, No. 6, pp. 1156-1166.

Pines, 1995, "Cyclins and cyclin-dependent kinases: a biochemical view", *Biochem. J.*, Vol. 308, No. 3, pp. 697-711.

Roush et al., 2019, International Patent Application Publication No. WO 2019/217421 A1, published 14 Nov. 2019.
Slabicki et al., 2020, "The CDK inhibitor CR8 acts as a molecular glue degrader that depletes cyclin K", *Nature*, Vol. 585, pp. 293-297.
Zhang et al., 2016, "Covalent targeting of remote cysteine residues to develop CDK12 and CDK13 inhibitors", Nat. Chem. Biol., Vol. 12, No. 10, pp. 876-884.

The invention claimed is:

1. A compound of the following formula:

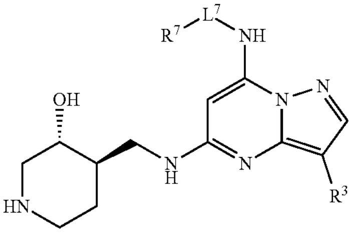

or a pharmaceutically acceptable salt thereof;

wherein:

$R^7$ is a fused bicyclic C8-10heteroaryl group having exactly 1, 2, or 3 ring heteroatoms, wherein each ring heteroatom is N, S, or O;

and wherein $—R^7$ is:

optionally substituted on carbon with one or more groups $—R^{SC}$; and optionally substituted on secondary nitrogen, if present, with a group $—R^{SN}$;

wherein:

each $—R^{SC}$ is independently:

$—R^{TT}$,
—F, —Cl, —Br, —I,
—OH, $—OR^{TT}$,
$-L^T-OH$, $-L^T-OR^{TT}$,
$—CF_3$, $—CHF_2$, $—OCF_3$, $—OCHF_2$,
$—NH_2$, $—NHR^{TT}$, $—NR^{TT}_2$, $—R^{TM}$,
$-L^T-NH_2$, $-L^T-NHR^{TT}$, $-L^T-NR^{TT}_2$, $-L^T-R^{TM}$,
—C(═O)OH, $—C(═O)OR^{TT}$,
$—OC(═O)R^{TT}$,
$—C(═O)NH_2$, $—C(═O)NHR^{TT}$, $—C(═O)NR^{TT}_2$, $—C(═O)R^{TM}$,
$—NHC(═O)R^{TT}$, $—NR^{TN}C(═O)R^{TT}$,
$—NHC(═O)NH_2$, $—NHC(═O)NHR^{TT}$, $—NHC(═O)NR^{TT}_2$, $—NHC(═O)R^{TM}$,
$—NR^{TN}C(═O)NH_2$, $—NR^{TN}C(═O)NHR^{TT}$, $—NR^{TN}C(═O)NR^{TT}_2$, $—NR^{TN}C(═O)R^{TM}$,
$—NHC(═O)OR^{TT}$, $—NR^{TN}C(═O)R^{TT}$,
$—OC(═O)NH_2$, $—OC(═O)NHR^{TT}$, $—OC(═O)NR^{TT}_2$, $—OC(═O)R^{TM}$,
$—C(═O)R^{TT}$,
$—SR^{TT}$, $—S(═O)R^{TT}$, $—S(═O)_2R^{TT}$,
$—S(═O)NH_2$, $—S(═O)NHR^{TT}$, $—S(═O)NR^{TT}_2$, $—S(═O)R^{TM}$,
$—S(═O)_2NH_2$, $—S(═O)_2NHR^{TT}$, $—S(═O)_2NR^{TT}_2$, $—S(═O)_2R^{TM}$,
$—NHS(═O)_2R^{TT}$, $—NR^{TN}S(═O)_2R^{TT}$,
—CN, or $—NO_2$;

each $—R^{SN}$ is independently:

$—R^{TT}$,
$-L^T-OH$, $-L^T-OR^{TT}$,
$-L^T-NH_2$, $-L^T-NHR^{TT}$, $-L^T-NR^{TT}_2$, $-L^T-R^{TM}$,
$—C(═O)R^{TT}$,
$—C(═O)OR^{TT}$,
$—C(═O)NH_2$, $—C(═O)NHR^{TT}$, $—C(═O)NR^{TT}_2$, $—C(═O)R^{TM}$ or
$—S(═O)_2R^{TT}$;

wherein:

each $-L^T-$ is independently linear or branched saturated $C_{1-4}$alkylene;

each $—R^{TT}$ is independently $—R^{TT1}$, $—R^{TT2}$, $-L^{TT}-R^{TT2}$, $—R^{TT3}$, or $-L^{TT}-R^{TT3}$;

each $—R^{TT1}$ is independently linear or branched saturated $C_{1-6}$alkyl, and is optionally substituted with one or more groups selected from —F, —OH, and $—OR^{TTT}$;

each $—R^{TT2}$ is saturated $C_{3-6}$cycloalkyl, and is optionally substituted with one or more groups selected from —F, $—R^{TTT}$, —OH, and $—OR^{TTT}$;

each $—R^{TT3}$ is independently phenyl or naphthyl, and is optionally substituted with one or more groups selected from —F, —Cl, —Br, —I, $—R^{TTT}$, OH, $—OR^{TTT}$, $—OCF_3$, $—NH_2$, $—NHR^{TTT}$ and $—NR^{TTT}_2$;

each $-L^{TT}-$ is independently linear or branched saturated $C_{1-4}$alkylene;

each $—R^{TN}$ is linear or branched saturated $C_{1-4}$alkyl, phenyl, or benzyl;

each $—R^{TM}$ is independently azetidino, pyrrolidino, piperidino, piperazino, morpholino, azepano, or diazepano, and is:

optionally substituted on carbon with one or more groups selected from:$—R^{TMM}$, $—C(═O)R^{TMM}$, $—S(═O)^2R^{TMM}$, —F, $—NH_2$, $—NHR^{TMM}$, $—NR^{TMM}_2$, —OH, and $—OR^{TMM}$; and optionally substituted on secondary nitrogen, if present, with a group selected from: $—R^{TMM}$, $—C(═O)R^{TMM}$, $—C(═O)OR^{TMM}$, and $—S(═O)_2R^{TMM}$, each $—R^{TTT}$ is independently linear or branched saturated $C_{1-4}$alkyl, phenyl, or benzyl; and each $—R^{TMM}$ is independently linear or branched saturated $C_{1-4}$alkyl, phenyl, or benzyl;

and wherein:

$-L^7-$ is independently linear or branched saturated $C_{1-3}$alkylene, and is optionally substituted with one or more groups selected from —F, —OH, and —OMe;

$—R^3$ is independently $—R^{3A}$ or $—R^{3B}$, $—R^{3A}$ is independently linear or branched saturated $C_{1-6}$alkyl, and is optionally substituted with one or more groups selected from —F, —OH, and —OMe; and $—R^{3B}$ is independently saturated $C_{3-7}$cycloalkyl, and is optionally substituted with one or more groups selected from —F, —OH, and —OMe.

2. The compound of claim 1, or a pharmaceutically acceptable salt thereof, wherein:

$—R^3$ is -Me, -Et, -nPr, -iPr, cyclopropyl, or cyclobutyl.

3. The compound of claim 2, or a pharmaceutically acceptable salt thereof, wherein:

$-L^7-$ is $—CH_2—$.

4. The compound of claim 3, or a pharmaceutically acceptable salt thereof, wherein:

$—R^7$ is a fused bicyclic $C_{9-10}$heteroaryl group having exactly 1, 2, or 3 ring heteroatoms, wherein each ring heteroatom is N.

5. The compound of claim 3, or a pharmaceutically acceptable salt thereof, wherein:

$—R^7$ is independently: imidazo [1,2-a]pyridinyl; imidazo [1,2-a]pyrimidinyl; benzimidazolyl; imidazo [1,2-b]

pyridazinyl; [1,2,4]triazolo [1,5-a]pyridinyl; benzofuranyl; imidazo [2,1-b]thiazolyl; or quinolinyl.

6. The compound of claim 5, or a pharmaceutically acceptable salt thereof, wherein:

each —$R^{SC}$, if present, is independently:
—$R^{TT}$,
—F, —Cl, —Br, —I,
—OH, —$OR^{TT}$,
-$L^{T}$-OH, -$L^{T}$-$OR^{TT}$,
—$CF_3$, —$CHF_2$, —$OCF_3$, —$OCHF_2$,
—$NH_2$, —$NHR^{TT}$, —$NR^{TT}{}_2$, —$R^{TM}$,
-$L^{T}$-$NH_2$, -$L^{T}$-$NHR^{TT}$, -$L^{T}$-$NR^{TT}{}_2$, -$L^{T}$-$R^{TM}$,
—C(═O)OH, —C(═O)$OR^{TT}$,
—OC(═O)$R^{TT}$,
—C(═O)$NH_2$, —C(═O)$NHR^{TT}$, —C(═O)$NR^{TT}{}_2$, —C(═O)$R^{TM}$,
—NHC(═O) $R^{TT}$,
—C(═O) $R^{TT}$,
—$S(═O)_2NH_2$, —$S(═O)_2NHR^{TT}$, —$S(═O)_2NR^{TT}{}_2$, —$S(═O)_2R^{TM}$,
—$NHS(═O)_2R^{TT}$,
—CN, or —$NO_2$.

7. The compound of claim 5, or a pharmaceutically acceptable salt thereof, wherein:

each —$R^{SC}$, if present, is independently:
—$R^{TT}$,
—F, —Cl, —Br, —I,
—OH, —$OR^{TT}$,
—$CF_3$, —$CHF_2$, —$OCF_3$, or —$OCHF_2$.

8. The compound of claim 6, or a pharmaceutically acceptable salt thereof, wherein:

each —$R^{SN}$, if present, is independently:
—$R^{TT}$,
—C(═O)$R^{TT}$, or
—C(═O)$OR^{TT}$.

9. The compound of claim 7, or a pharmaceutically acceptable salt thereof, wherein:

each —$R^{SN}$, if present, is independently:
—$R^{TT}$,
—C(═O) $R^{TT}$, or
—C(═O) $OR^{TT}$.

10. The compound of claim 9, or a pharmaceutically acceptable salt thereof, wherein:

each -$L^{T}$-, if present, is —$CH_2$—;
each —$R^{TT1}$, if present, is independently -Me, -Et, -nPr, -iPr, -nBu, -sBu, -iBu, or -tBu;
each —$R^{TT2}$, if present, is independently cyclopropyl, cyclobutyl, cyclopentyl, or cyclohexyl;
each —$R^{TT3}$, if present, is phenyl, and is optionally substituted with one or more groups selected from —F, —Cl, —Br, —I, —$R^{TTT}$, OH, —$OR^{TTT}$, and —$OCF_3$;
each -$L^{TT}$-, if present, is independently —$CH_2$—, —$CH_2CH_2$—, or —$CH_2CH_2CH_2$—;
each —$R^{TN}$, if present, is -Me;
each —$R^{TM}$, if present, is independently pyrrolidino, piperidino, piperazino, or morpholino, and is:
optionally substituted on carbon with one or more groups selected from: —$R^{TMM}$; and
optionally substituted on secondary nitrogen, if present, with a group selected from: —$R^{TMM}$, —C(═O)$R^{TMM}$, and —C(═O)$OR^{TMM}$;
each —$R^{TTT}$, if present, is -Me; and
each —$R^{TMM}$, if present, is -Me.

11. The compound of claim 1, selected from compounds of the following formulae and pharmaceutically acceptable salts thereof:

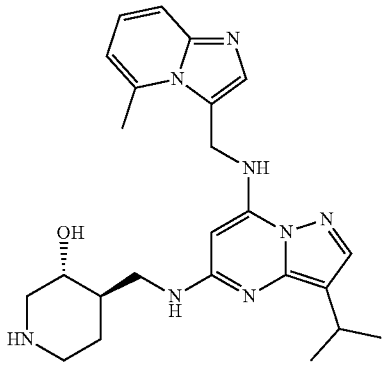
,

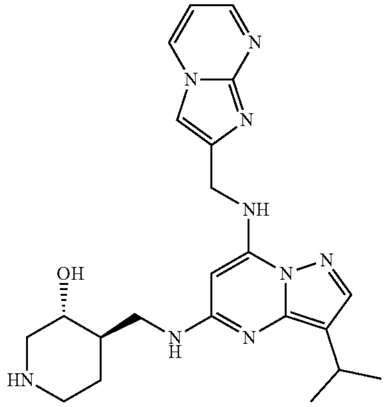
,

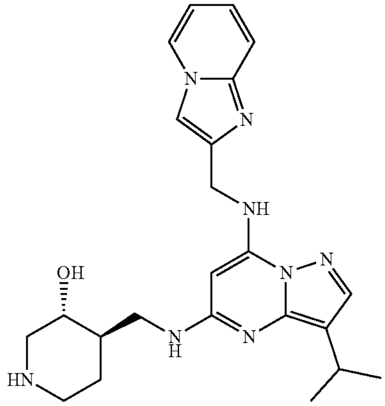
,

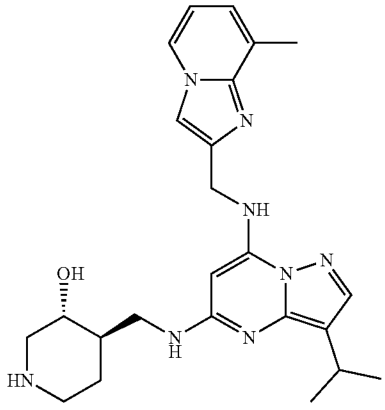
,

-continued
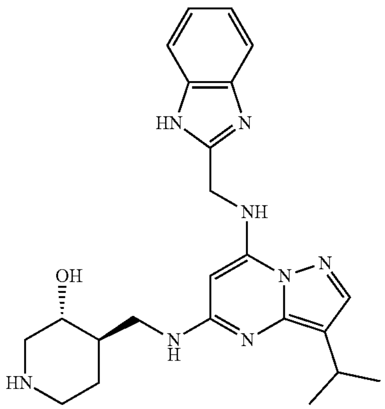
,
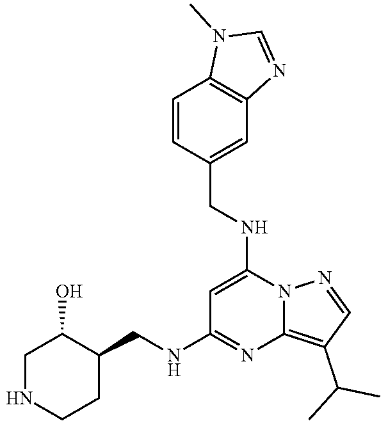
,
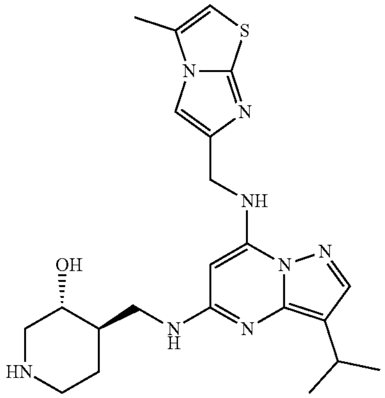
,
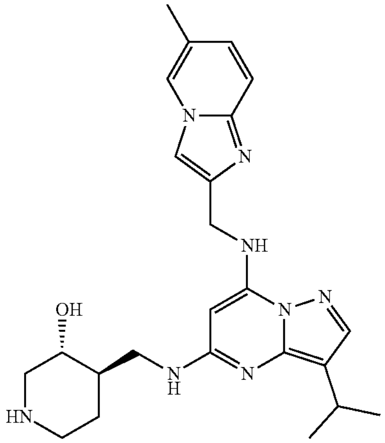
,
-continued
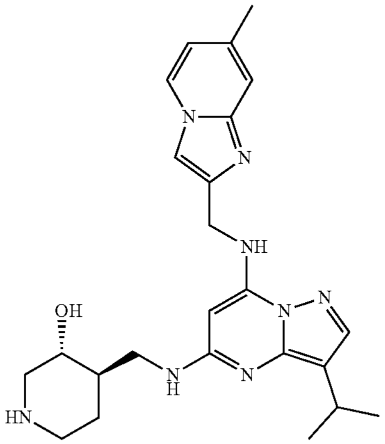
,
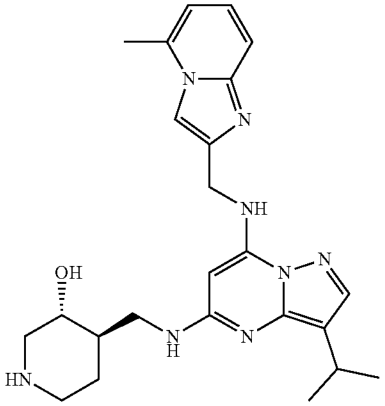
,
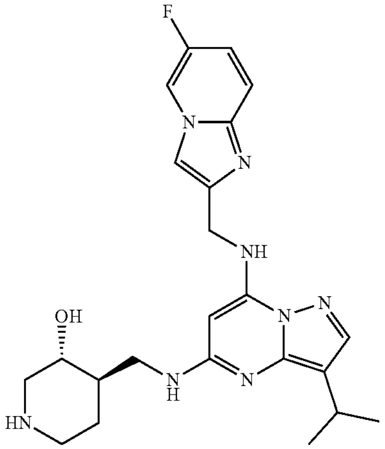
, -continued
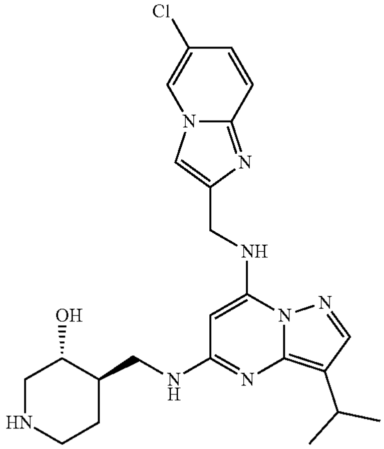
,
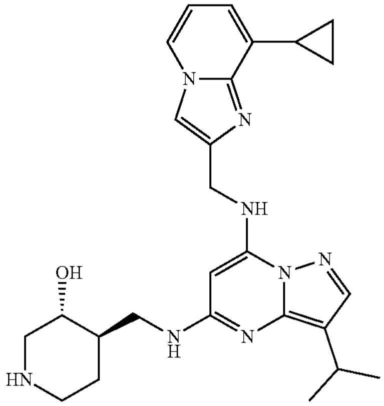
,
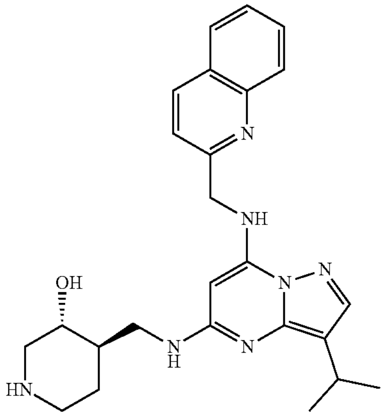
,
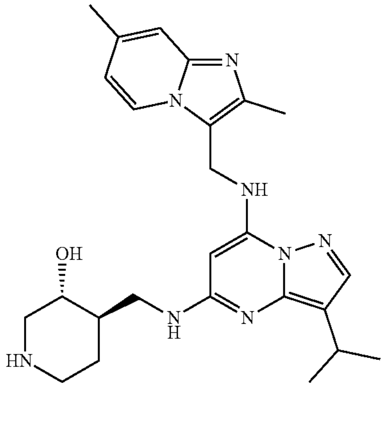
,
-continued
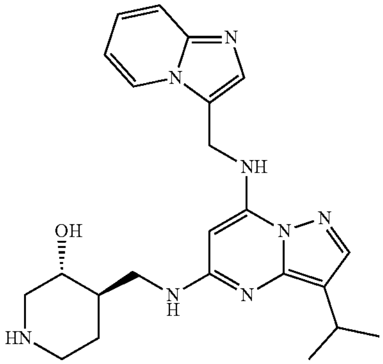
,
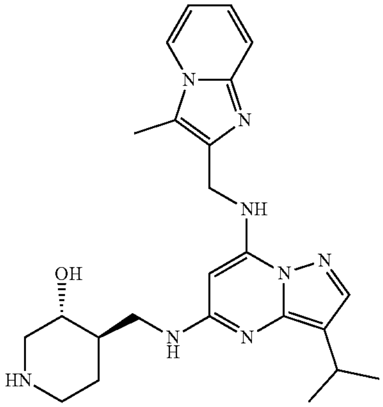
,
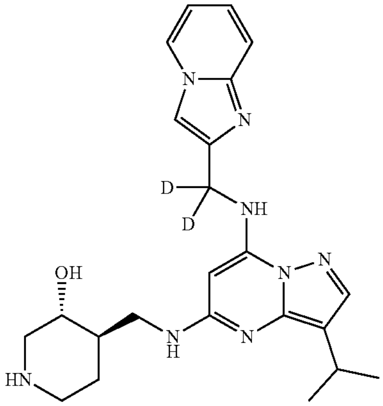
,
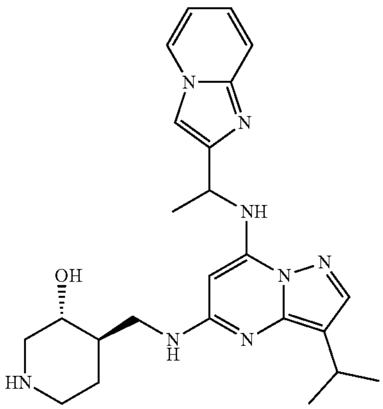
, -continued
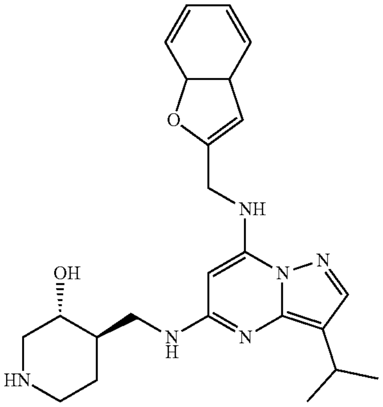
,
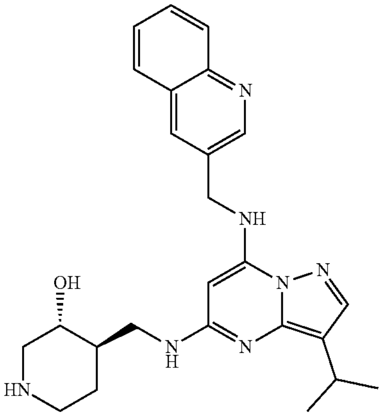
,
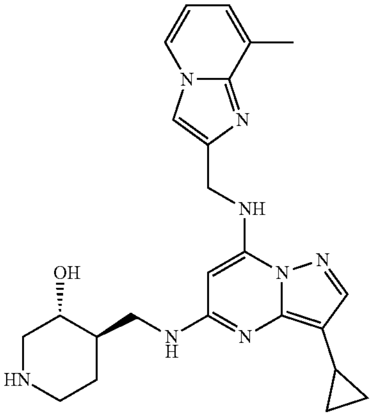
,
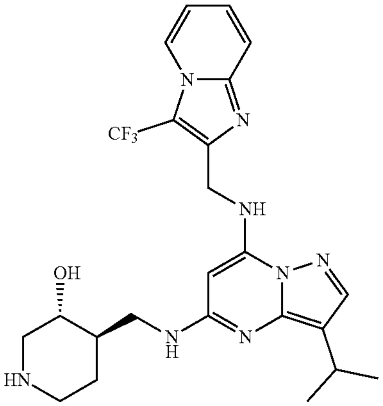
,
-continued
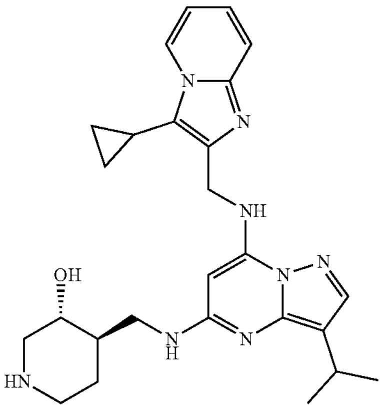
,
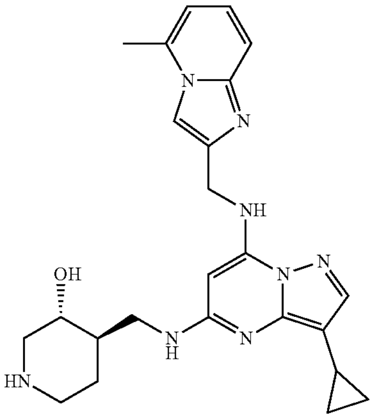
,
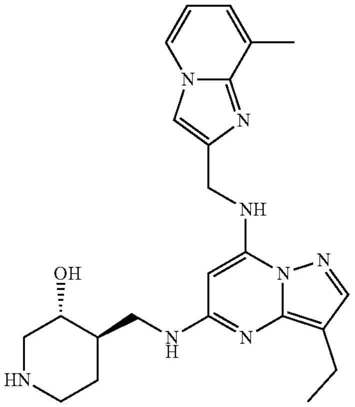
,
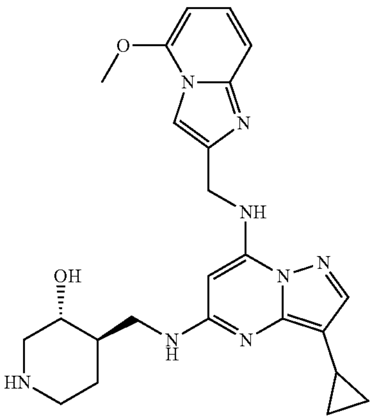
, -continued
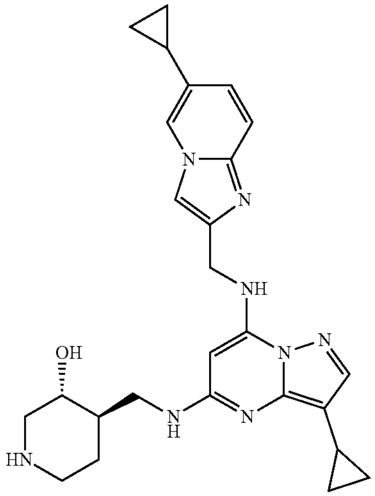
,
,
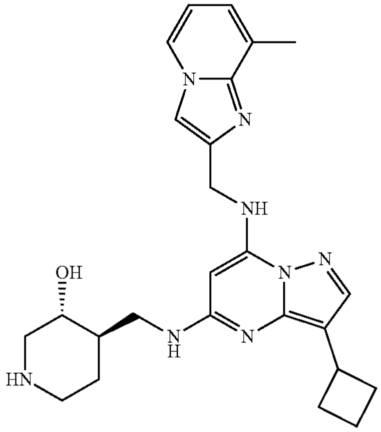
,
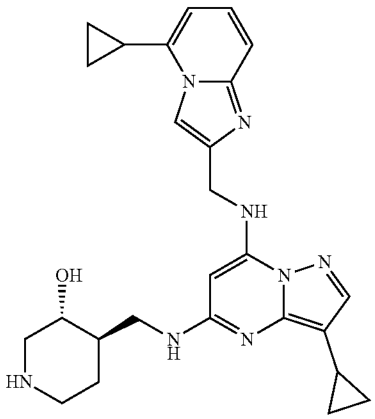
,
-continued
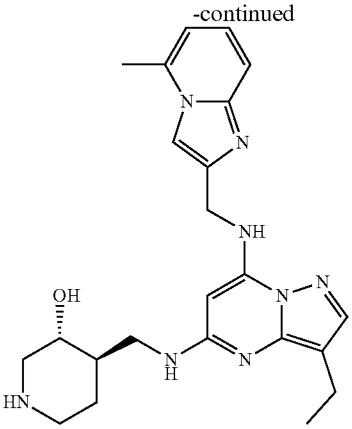
,
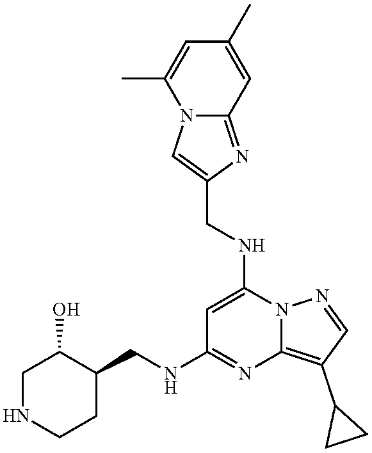
,
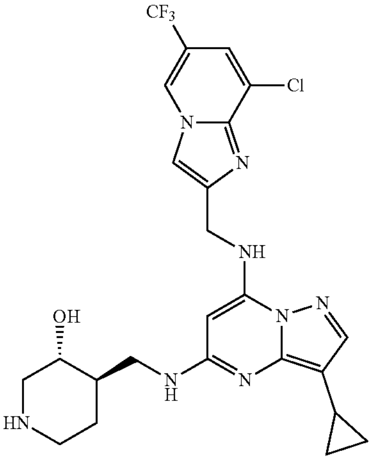
,
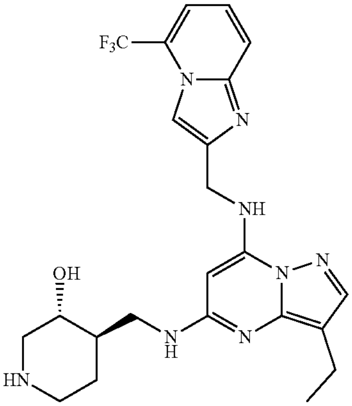
, -continued
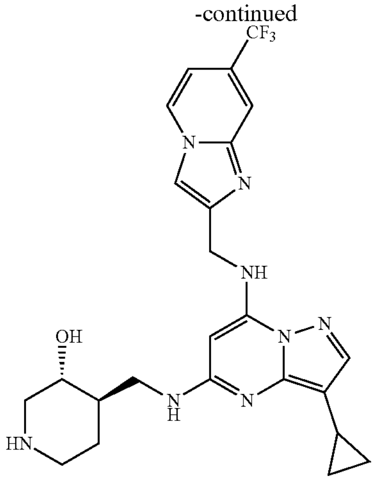
,
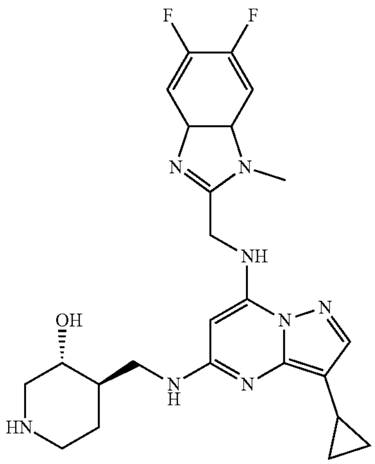
,
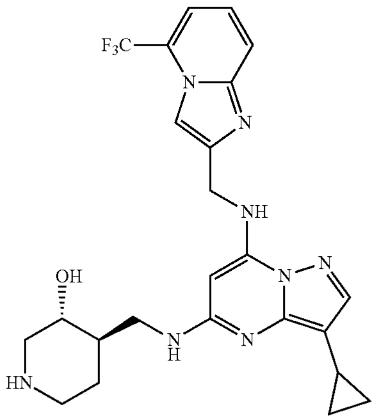
,
-continued
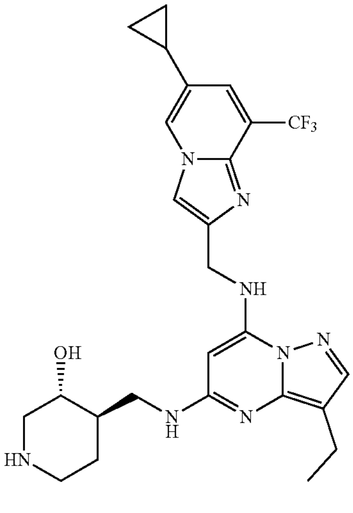
,
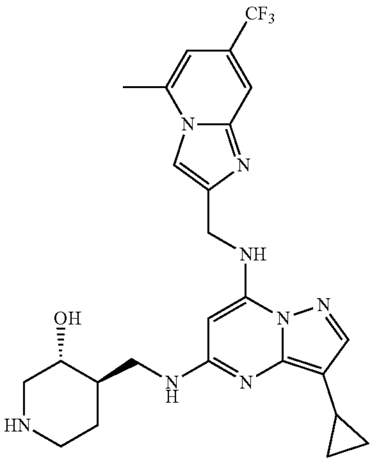
,
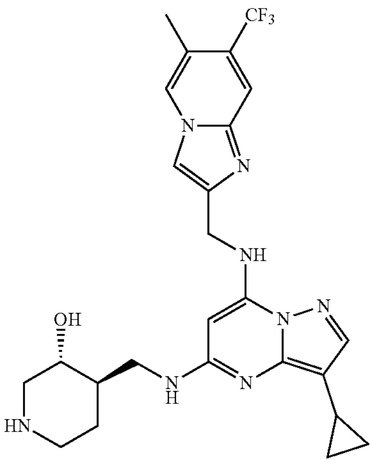
, -continued

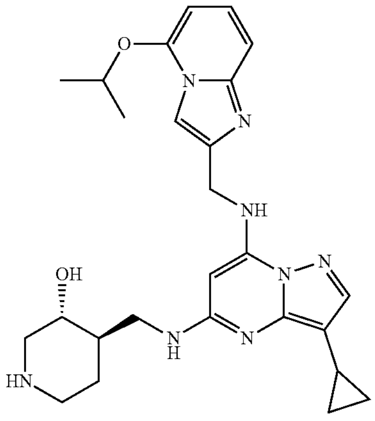

,

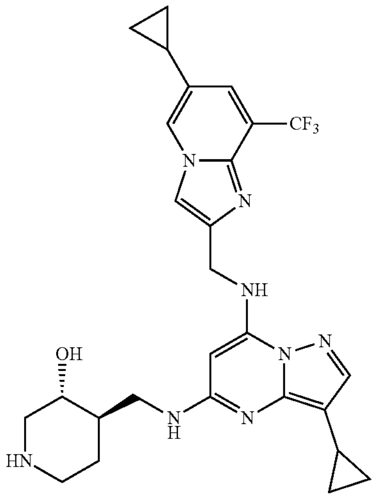

,

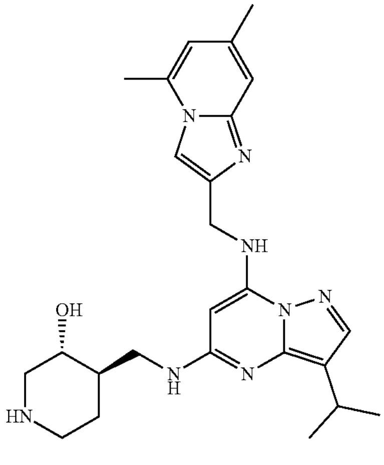

,

-continued

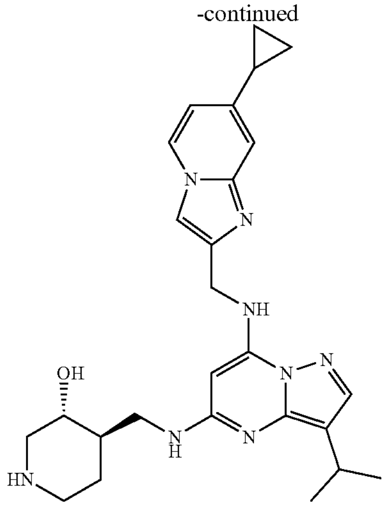

, and

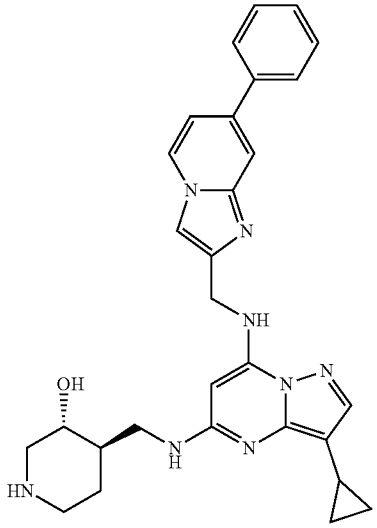

.

12. A composition comprising a compound according to claim 1, or a pharmaceutically acceptable salt thereof, and a pharmaceutically acceptable carrier or diluent.

13. A method of preparing a composition comprising the step of mixing a compound according to claim 1, or a pharmaceutically acceptable salt thereof, and a pharmaceutically acceptable carrier or diluent.

14. A method of inhibiting cyclin-dependent protein kinase (CDK) function in a cell, in vitro or in vivo, comprising contacting the cell with an effective amount of a compound according to claim 1, or a pharmaceutically acceptable salt thereof.

15. A method of inhibiting cell proliferation, inhibiting cell cycle progression, promoting apoptosis, or a combination of one or more these, in vitro or in vivo, comprising contacting a cell with an effective amount of a compound according to claim 1, or a pharmaceutically acceptable salt thereof.

16. A method of treatment of a disorder, comprising administering to a subject in need of treatment a therapeutically-effective amount of a compound according to claim 1, or a pharmaceutically acceptable salt thereof, wherein the disorder is: cancer.

17. The method of claim 16, wherein the treatment further comprises treatment with a further active agent which is:

an aromatase inhibitor;

an anti-estrogen;

an anti-androgen;

a Her2 blocker;

a further cytotoxic chemotherapeutic agent;

an agent stimulating the immune system;

a checkpoint inhibitor; or a DNA repair inhibitor.

18. The method of claim 17, wherein:

the aromatase inhibitor is exemestane, letrozole, or anastrozole;

the anti-estrogen is faslodex, tamoxifen, or hydroxytamoxifen;

the anti-androgen is flutamide, enzalutamide, apalutamide, bicalutamide, or nilutamide;

the Her2 blocker is herceptin, pertuzumab, or lapatinib; and the cytotoxic chemotherapeutic agent is a taxane, paclitaxel, docetaxel, cyclophosphamide, an antimetabolite, carboplatin, capecitabine, gemcitabine, doxorubicin, epirubicin, or 5-fluorouracil.

19. The method of claim 16, wherein the cancer:

is associated with cyclin-dependent protein kinases 12/13 (CDK12/CDK13); results from an inappropriate activity of CDK 12/13; is associated with CDK 12/13 mutation; is associated with CDK 12/13 overexpression; is associated with upstream pathway activation of CDK 12/13; or is ameliorated by the inhibition of CDK 12/13.

20. The method of claim 16, wherein the cancer is selected from: breast cancer, prostate cancer, ovarian cancer, oesophageal cancer, and colorectal cancer.

* * * * *